United States Patent
Paruch et al.

(10) Patent No.: US 11,453,663 B2
(45) Date of Patent: Sep. 27, 2022

(54) SUBSTITUTED PROPANAMIDES AS INHIBITORS OF NUCLEASES

(71) Applicant: MASARYKOVA UNIVERZITA, Brno (CZ)

(72) Inventors: Kamil Paruch, Tisnov (CZ); Benoit Carbain, Brno (CZ); Stepan Havel, Cernozice (CZ); Vit Vsiansky, Brno (CZ); Fedor Nikulenkov, Slapanice (CZ); Lumir Krejci, Brno (CZ)

(73) Assignee: MASARYKOVA UNIVERZITA, Brno (CZ)

( * ) Notice: Subject to any disclaimer, the term of this patent is extended or adjusted under 35 U.S.C. 154(b) by 8 days.

(21) Appl. No.: 17/047,255

(22) PCT Filed: Apr. 15, 2019

(86) PCT No.: PCT/EP2019/059693
§ 371 (c)(1),
(2) Date: Oct. 13, 2020

(87) PCT Pub. No.: WO2019/201867
PCT Pub. Date: Oct. 24, 2019

(65) Prior Publication Data
US 2022/0073507 A1    Mar. 10, 2022

(30) Foreign Application Priority Data
Apr. 17, 2018   (EP) .................. 18167664.4

(51) Int. Cl.
*C07D 417/04*   (2006.01)
*C07D 277/46*   (2006.01)
*C07D 417/12*   (2006.01)

(52) U.S. Cl.
CPC ......... *C07D 417/04* (2013.01); *C07D 277/46* (2013.01); *C07D 417/12* (2013.01)

(58) Field of Classification Search
CPC ... C07D 417/04; C07D 277/46; C07D 417/12
See application file for complete search history.

(56) References Cited

U.S. PATENT DOCUMENTS

| | | | | |
|---|---|---|---|---|
| 6,262,096 B1 * | 7/2001 | Kim | ............... | A61P 21/00 514/369 |
| 7,514,448 B2 * | 4/2009 | Green | ............... | A61P 27/02 546/113 |
| 2022/0002282 A1 * | 1/2022 | Paruch | ............... | C07D 417/12 |

FOREIGN PATENT DOCUMENTS

WO     2010075372 A1     7/2010

OTHER PUBLICATIONS

Chemical Abstracts STN Registry Database, Record for RN 1523103-48-1, "2-Cyano-N-(5,6-dihydro-4H-cyclopentathiazol-2-yl)-2-methylbutanamide", Entered into STN on Jan. 17, 2014. (Year: 2014).*
Dupre; Nature Chemical Biology 2008, 4, 119-125. (Year: 2008).*
Hengel; Cell Chemical Biology 2017, 24, 1101-1119. (Year: 2017).*
Kubben; Nature Reviews Molecular Cell Biology 2017, 18, 595-609. (Year: 2017).*
Shibata; Mol. Cell, 2014, 53, 7-18. (Year: 2014).*
Connelly; Trends in Biochemical Sciences 2002, 27, 410-418. (Year: 2002).*
Chemical Abstracts STN Registry Database, record for RN 1247647-30-8, entered STN Oct. 27, 2010. (Year: 2010).*
International Search Report and Written Opinion for corresponding PCT application No. PCT/EP2019/059693, dated Jun. 7, 2019.

* cited by examiner

*Primary Examiner* — Daniel R Carcanague
(74) *Attorney, Agent, or Firm* — Notaro, Michalos & Zaccaria P.C.

(57) ABSTRACT

Compounds represented by the structural formula (1) where R1, R2, R3, R4, R5, R6 are inhibitors of nucleases, and are useful in particular in a method of treatment and/or prevention of proliferative diseases, neurodegenerative diseases, and other genomic instability associated diseases.

14 Claims, No Drawings
Specification includes a Sequence Listing.

SEQUENCE LISTING

```
<160> NUMBER OF SEQ ID NOS: 2

<210> SEQ ID NO 1
<211> LENGTH: 22
<212> TYPE: DNA
<213> ORGANISM: artificial
<220> FEATURE:
<223> OTHER INFORMATION: oligonucleotide 1 for HTS assay

<400> SEQUENCE: 1
ctaagttcgt caggattcca gc                                              22

<210> SEQ ID NO 2
<211> LENGTH: 40
<212> TYPE: DNA
<213> ORGANISM: artificial
<220> FEATURE:
<223> OTHER INFORMATION: oligonucleotide 2 for HTS assay

<400> SEQUENCE: 2
ctctatcact gttacaatgc tggaatcctg acgaacttag                           40
```

SUBSTITUTED PROPANAMIDES AS INHIBITORS OF NUCLEASES

FIELD OF THE INVENTION

The present invention relates to substituted propanamides as inhibitors of nucleases, especially nuclease MRE11 and MRE11-containing complexes, pharmaceutical compositions containing the compounds, and methods of treatment using the compounds and compositions to treat diseases such as cancer, neurological disorders and other genome instability associated diseases.

BACKGROUND ART

Despite intense development of new anticancer substances, the clinical treatment of most frequently diagnosed solid tumors needs to be improved and for some malignancies reasonably efficient therapies need to be developed, as they are practically non-existent. Early detection followed by surgery remains the main tool that enables significant expansion of life span for majority of patients. In most malignancies it may be necessary to modulate (preferably in a synergistic manner) several relevant biological pathways. Accordingly, the required phenotype (death of tumor cells) can be elicited by synthetic lethal modulation of properly chosen biological processes. Synthetic lethal interactions tend to form clusters; one significant network of such interactions encompasses the biological processes involved in the DNA damage/repair. Selective and efficient activity modulation of selected processes is therefore of significant importance and can lead to a new generation of modern anticancer drugs.

Maintenance of genomic integrity ensured by multifaceted cellular DNA damage response (DDR) is a fundamental biological phenomenon shared by all organisms. On one hand, the DDR network of genome surveillance, checkpoint and repair pathways counterbalances the potentially mutagenic effects of endogenous (oxidative and replicative lesions) and exogenous (e.g. ionizing or UV radiation, cigarette smoke) DNA damaging assaults. On the other hand, modulation of selected components can be exploited in efficient treatment of malignant diseases. It is likely that optimal synthetic lethal treatments will be different for particular tumor sub-populations; this approach is therefore compatible with the concept of personalized medicine.

Amongst the DNA repair processing enzymes, the MRE11-RAD50-NBS1 (MRN) complex plays an important role in preserving genomic integrity by acting as a DNA damage sensor of double strand breaks (DSB) and by promoting repair through non-homologous end-joining (NHEJ) or homologous recombination (*Nature Reviews* 2002, 3, 317; *Trends Biochem. Sciences* 2002, 27, 410.). In response to DSB, MRN activates and recruits ATM (belonging to the phosphatidylinositol-3' kinase-related kinases (PIKKs) family) to damaged DNA sites. ATM initiates a signaling cascade leading to cell cycle arrest and DNA repair. MRE11 is the subunit core of the MRN complex and displays 3'-5'exonuclease activity, single-stranded and DNA-hairpin endonuclease activity. The MRE11-RAD50 complex functions include DNA binding, bridging the ends of DSBs and their processing. NBS1 does not possess any enzymatic activity; its role lies in signaling and interacting with other proteins (*DNA Repair* 2010, 9, 1299; *Cell* 2008, 135, 97.). The significance of MRN complex is underlined by the fact that germline mutations of MRE11, NBS1 and RAD50 cause ataxia-telangiectasia-like disease (ATLD), Nijmegen breakage syndrome (NBS) and NBS-like disorder (NBSLD), respectively (*Cell* 1998, 93, 477; *Cell*, 1999, 99, 577; *Am. J. Hum. Genet.* 2009, 84, 605). ATLD, NBS and NBSLD have similar features as does ataxia-telangiectasia (AT), caused by mutations in the ATM gene, which include hypersensitivity to DSB-inducing agents, chromosome fragility, DNA damage-dependent cell-cycle arrest and high predisposition to cancer (*Cell* 1998, 93, 477; *Oncogene* 2007, 26, 7749; *Cell* 1999, 99, 577; *Am. J. Hum. Genet.* 2009, 84, 605.). In addition, depletion of MRE11 leads to sensitization to poly(ADP-ribose) polymerase (PARP) inhibition (*Cancer Res.* 2011, 71, 2632.). Furthermore, MRE11-deficient cells are also sensitive to topoisomerase poisons, suggesting a role of MRE11 in removal of TOP1/TOP2-lessions and in stimulating an effect of topo inhibitors (*Mol. Cell. Biol.* 2004, 24, 9682.). Indeed, triapine (RNR inhibitor) was recently shown to block MRN-mediated recombination and sensitize ovarian cancer cells to PARP and topo inhibitors (*Mol. Cancer Res.* 2014, 12, 381; *Cancer Res.* 2012, 72, 2814.). Therapeutic importance of MRE11 inhibitors in modern oncology is further supported by recently reported synthetically lethal genetic interactions for MRE11-FEN1 (*PLoS Genet.* 2013, 9, 1, e1003254.) and MRE11-BRCA2 (*Cancer Res.*, 2012, 72, 2814.). Defects in some DNA repair processes also manifest themselves in neuronal tissues and thus can be associated with human neurological disorders (*Cell* 2007, 130, 991.). Mirin and two its structurally closely related analogs PFM01 and PFM03 (*Mol. Cell* 2014, 53, 1; WO 2010/075372) are essentially the only reported examples of (relatively weak) inhibitors of MRE11 nuclease.

DISCLOSURE OF THE INVENTION

The present invention provides substituted propanamide compounds, methods of preparing such compounds, pharmaceutical compositions comprising one or more of such compounds, methods of preparing pharmaceutical formulations comprising one or more of such compounds, and methods of treatment, prevention, inhibition or amelioration of one or more diseases, preferably diseases associated with MRE11 nuclease and/or MRE11-related DNA repair pathways using such compounds or pharmaceutical compositions.

The present invention provides compounds represented by general formula (1):

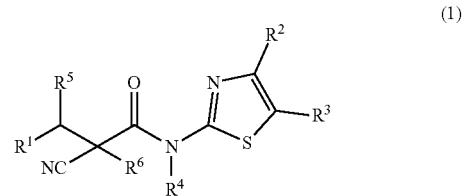

or pharmaceutically acceptable salts, or solvates thereof, which are suitable for use in a method of treatment of cancer, premature aging and/or neurological diseases, more specifically of genome instability-related cancer, genome instability-related premature aging and/or genome instability-related neurological diseases, in particular MRE11-related cancer, MRE11-related premature aging and/or MRE11-related neurological diseases, wherein:

$R^1$ is selected from the group consisting of alkyl; aryl; cycloalkyl; heterocyclyl; and heteroaryl;

wherein each of the alkyl, aryl, cycloalkyl, heterocyclyl, heteroaryl, can be unsubstituted or optionally substituted with one or more moieties which can be the same or different, each moiety being independently selected from the group consisting of F, Cl, Br, I, OH, CN, $N_3$, =O, O($C_1$-$C_6$-alkyl), =S, SH, S($C_1$-$C_6$-alkyl), S(O)$C_1$-$C_6$-alkyl, S(O)$_2$$C_1$-$C_6$-alkyl, $CF_3$, $C_2F_5$, $OCF_3$, $OC_2F_5$, $NH_2$, NH($C_1$-$C_6$-alkyl), N($C_1$-$C_6$-alkyl)$_2$ (such as N(CH$_3$)$_2$), =N—OH, =N—O($C_1$-$C_6$-alkyl), $NO_2$, COOH, COO($C_1$-$C_6$-alkyl), CO($C_1$-$C_6$-alkyl), $CONH_2$, CONH($C_1$-$C_6$-alkyl), CON($C_1$-$C_6$-alkyl)$_2$, ($C_1$-$C_6$-alkyl)-S(O)$_2$—NH—, ($C_1$-$C_6$-alkyl)-S(O)$_2$—N($C_1$-$C_6$-alkyl)-, ($C_1$-$C_6$-alkyl)-NH—(SO)$_2$—, ($C_1$-$C_6$-alkyl)$_2$N—(SO)$_2$—, ($C_1$-$C_6$-alkyl)-CO—NH—, ($C_1$-$C_6$-alkyl)-CO—N($C_1$-$C_6$-alkyl)-, ($C_1$-$C_6$-alkyl)-OCO—NH—, ($C_1$-$C_6$-alkyl)-OCO—N($C_1$-$C_6$-alkyl)-, ($C_1$-$C_6$-alkyl)-CO—NH—CO—, ($C_1$-$C_6$-alkyl)-CO—N($C_1$-$C_6$-alkyl)-CO—, $NH_2$—CO—NH—, ($C_1$-$C_6$-alkyl)-NH—CO—NH—, ($C_1$-$C_6$-alkyl)$_2$N—CO—NH—, $NH_2$—CO—N($C_1$-$C_6$-alkyl)-, ($C_1$-$C_6$-alkyl)-NH—CO—N($C_1$-$C_6$-alkyl)-, ($C_1$-$C_6$-alkyl)$_2$N—CO—N($C_1$-$C_6$-alkyl)-, $NH_2$—S(O)$_2$—NH—, ($C_1$-$C_6$-alkyl)-NH—S(O)$_2$—NH—, ($C_1$-$C_6$-alkyl)$_2$N—S(O)$_2$—NH—, $NH_2$—S(O)$_2$—N($C_1$-$C_6$-alkyl)-, ($C_1$-$C_6$-alkyl)-NH—S(O)$_2$—N($C_1$-$C_6$-alkyl)-, ($C_1$-$C_6$-alkyl)$_2$N—S(O)$_2$—N($C_1$-$C_6$-alkyl)-, $C_1$-$C_6$-alkyl, O—$C_1$-$C_6$-alkyl, O-phenyl, phenyl;

whereas the $C_1$-$C_6$-alkyl, O-phenyl, phenyl in these moieties can optionally be further substituted by one or more substituents selected independently from: F, Cl, Br, I, $C_1$-$C_6$-alkyl, OH, O—$C_1$-$C_6$-alkyl, SH, $SCH_3$, S(O)$C_1$-$C_6$-alkyl, S(O)$_2$$C_1$-$C_6$-alkyl, $CF_3$, $OCF_3$, $NH_2$, NH($C_1$-$C_6$-alkyl), N($C_1$-$C_6$-alkyl)$_2$ (such as N(CH$_3$)$_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, or NHC(O)$NH_2$;

$R^2$ is selected from the group consisting of aryl; heteroaryl; cycloalkyl; heterocyclyl; and alkyl;

wherein each of the alkyl, aryl, cycloalkyl, heterocyclyl, heteroaryl, can be unsubstituted or optionally substituted with one or more moieties which can be the same or different, each moiety being independently selected from the group consisting of F, Cl, Br, I, OH, CN, $N_3$, =O, O($C_1$-$C_6$-alkyl), =S, SH, S($C_1$-$C_6$-alkyl), S(O)$C_1$-$C_6$-alkyl, S(O)$_2$$C_1$-$C_6$-alkyl, $CF_3$, $C_2F_5$, $OCF_3$, $OC_2F_5$, $NH_2$, NH($C_1$-$C_6$-alkyl), N($C_1$-$C_6$-alkyl)$_2$ (such as N(CH$_3$)$_2$), =N—OH, =N—O($C_1$-$C_6$-alkyl), $NO_2$, COOH, COO($C_1$-$C_6$-alkyl), CO($C_1$-$C_6$-alkyl), $CONH_2$, CONH($C_1$-$C_6$-alkyl), CON($C_1$-$C_6$-alkyl)$_2$, ($C_1$-$C_6$-alkyl)-S(O)$_2$—NH—, ($C_1$-$C_6$-alkyl)-S(O)$_2$—N($C_1$-$C_6$-alkyl)-, ($C_1$-$C_6$-alkyl)-NH—(SO)$_2$—, ($C_1$-$C_6$-alkyl)$_2$N—(SO)$_2$—, ($C_1$-$C_6$-alkyl)-CO—NH—, ($C_1$-$C_6$-alkyl)-CO—N($C_1$-$C_6$-alkyl)-, ($C_1$-$C_6$-alkyl)-OCO—NH—, ($C_1$-$C_6$-alkyl)-OCO—N($C_1$-$C_6$-alkyl)-, ($C_1$-$C_6$-alkyl)-CO—NH—CO—, ($C_1$-$C_6$-alkyl)-CO—N($C_1$-$C_6$-alkyl)-CO—, $NH_2$—CO—NH—, ($C_1$-$C_6$-alkyl)-NH—CO—NH—, ($C_1$-$C_6$-alkyl)$_2$N—CO—NH—, $NH_2$—CO—N($C_1$-$C_6$-alkyl)-, ($C_1$-$C_6$-alkyl)-NH—CO—N($C_1$-$C_6$-alkyl)-, ($C_1$-$C_6$-alkyl)$_2$N—CO—N($C_1$-$C_6$-alkyl)-, $NH_2$—S(O)$_2$—NH—, ($C_1$-$C_6$-alkyl)-NH—S(O)$_2$—NH—, ($C_1$-$C_6$-alkyl)$_2$N—S(O)$_2$—NH—, $NH_2$—S(O)$_2$—N($C_1$-$C_6$-alkyl)-, ($C_1$-$C_6$-alkyl)-NH—S(O)$_2$—N($C_1$-$C_6$-alkyl)-, ($C_1$-$C_6$-alkyl)$_2$N—S(O)$_2$—N($C_1$-$C_6$-alkyl)-, $C_1$-$C_6$-alkyl, O—$C_1$-$C_6$-alkyl, O-phenyl, phenyl, heterocyclyl, heteroaryl;

whereas the $C_1$-$C_6$-alkyl, O-phenyl, phenyl, heterocyclyl, heteroaryl in these moieties can optionally be further substituted by one or more substituents selected independently from: F, Cl, Br, $C_1$-$C_6$-alkyl, OH, O—$C_1$-$C_6$-alkyl, SH, $SCH_3$, S(O)$C_1$-$C_6$-alkyl, S(O)$_2$$C_1$-$C_6$-alkyl, $CF_3$, $OCF_3$, $NH_2$, NH($C_1$-$C_6$-alkyl), N($C_1$-$C_6$-alkyl)$_2$ (such as N(CH$_3$)$_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, or NHC(O)$NH_2$, $R^3$ is selected from the group consisting of H; aryl; cycloalkyl; halogen; alkyl; heterocyclyl; and heteroaryl, wherein each of the aryl, cycloalkyl, alkyl or heteroaryl can be unsubstituted or optionally substituted with one or more moieties which can be the same or different, each moiety being independently selected from the group consisting of F, Cl, Br, I, OH, CN, $N_3$, =O, O($C_1$-$C_6$-alkyl), =S, SH, S($C_1$-$C_6$-alkyl), S(O)$C_1$-$C_6$-alkyl, S(O)$_2$$C_1$-$C_6$-alkyl, $CF_3$, $C_2F_5$, $OCF_3$, $OC_2F_5$, $NH_2$, NH($C_1$-$C_6$-alkyl), N($C_1$-$C_6$-alkyl)$_2$ (such as N(CH$_3$)$_2$), =N—OH, =N—O($C_1$-$C_6$-alkyl), $NO_2$, COOH, COO($C_1$-$C_6$-alkyl), CO($C_1$-$C_6$-alkyl), $CONH_2$, CONH($C_1$-$C_6$-alkyl), CON($C_1$-$C_6$-alkyl)$_2$, ($C_1$-$C_6$-alkyl)-S(O)$_2$—NH—, ($C_1$-$C_6$-alkyl)-S(O)$_2$—N($C_1$-$C_6$-alkyl)-, ($C_1$-$C_6$-alkyl)-NH—(SO)$_2$—, ($C_1$-$C_6$-alkyl)$_2$N—(SO)$_2$—, ($C_1$-$C_6$-alkyl)-CO—NH—, ($C_1$-$C_6$-alkyl)-CO—N($C_1$-$C_6$-alkyl)-, ($C_1$-$C_6$-alkyl)-OCO—NH—, ($C_1$-$C_6$-alkyl)-OCO—N($C_1$-$C_6$-alkyl)-, ($C_1$-$C_6$-alkyl)-CO—NH—CO—, ($C_1$-$C_6$-alkyl)-CO—N($C_1$-$C_6$-alkyl)-CO—, $NH_2$—CO—NH—, ($C_1$-$C_6$-alkyl)-NH—CO—NH—, ($C_1$-$C_6$-alkyl)$_2$N—CO—NH—, $NH_2$—CO—N($C_1$-$C_6$-alkyl)-, ($C_1$-$C_6$-alkyl)-NH—CO—N($C_1$-$C_6$-alkyl)-, ($C_1$-$C_6$-alkyl)$_2$N—CO—N($C_1$-$C_6$-alkyl)-, $NH_2$—S(O)$_2$—NH—, ($C_1$-$C_6$-alkyl)-NH—S(O)$_2$—NH—, ($C_1$-$C_6$-alkyl)$_2$N—S(O)$_2$—NH—, $NH_2$—S(O)$_2$—N($C_1$-$C_6$-alkyl)-, ($C_1$-$C_6$-alkyl)-NH—S(O)$_2$—N($C_1$-$C_6$-alkyl)-, ($C_1$-$C_6$-alkyl)$_2$N—S(O)$_2$—N($C_1$-$C_6$-alkyl)-, $C_1$-$C_6$-alkyl, O—$C_1$-$C_6$-alkyl, O-phenyl, phenyl;

whereas the $C_1$-$C_6$-alkyl, O-phenyl, phenyl in these moieties can optionally be further substituted by one or more substituents selected independently from: alkyl, O-phenyl, phenyl being optionally substituted by F, Cl, Br, $C_1$-$C_6$-alkyl, OH, O—$C_1$-$C_6$-alkyl, SH, $SCH_3$, S(O)$C_1$-$C_6$-alkyl, S(O)$_2$$C_1$-$C_6$-alkyl, $CF_3$, $OCF_3$, $NH_2$, NH($C_1$-$C_6$-alkyl), N($C_1$-$C_6$-alkyl)$_2$ (such as N(CH$_3$)$_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, or NHC(O)$NH_2$, $R^2$ and $R^3$ together with the carbon atoms to which they are bound may also form an aliphatic or aromatic ring structure, preferably a monocyclic or polycyclic ring structure having 5-10 ring atoms selected from C, N, O, S;

$R^4$ is selected from the group consisting of H and $C_1$-$C_6$-alkyl;

$R^5$ is selected from the group consisting of H; $C_1$-$C_6$-alkyl; and aryl;

$R^6$ is selected from the group consisting of H and $C_1$-$C_6$-alkyl;

or $R^5$ and $R^6$ together with the $CH_2$—$CH_2$— moiety connecting these two substituents may form a cyclopropyl ring, unsubstituted or optionally substituted with alkyl, O-phenyl, phenyl being optionally substituted by F, Cl, Br, $C_1$-$C_6$-alkyl, OH, O—$C_1$-$C_6$-alkyl, SH, $SCH_3$, S(O)$C_1$-$C_6$-alkyl, S(O)$_2$$C_1$-$C_6$-alkyl, $CF_3$, $OCF_3$, $NH_2$, NH($C_1$-$C_6$-alkyl), N($C_1$-$C_6$-alkyl)$_2$ (such as N(CH$_3$)$_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, or NHC(O)$NH_2$.

In this description and unless indicated otherwise, the generic substituent groups have the following meanings:

"alkyl" means an aliphatic hydrocarbon group which may be straight or branched and contains 1 to 8 carbon atoms, preferably 1 to 6 carbon atoms, even more preferably 1 to 4 carbon atoms, in the chain. Examples of suitable alkyls are methyl, ethyl, propyl, isopropyl, butyl, isobutyl, tert-butyl, pentyl, isopentyl, hexyl;

"aryl" means an aromatic monocyclic or polycyclic ring system containing 6 to 14 carbon atoms, preferably 6 to 10 carbon atoms. Aryls can preferably be monocyclic or bicyclic or tricyclic, condensed or non-condensed. Examples of suitable aryls are phenyl, naphthyl, biphenyl, "cycloalkyl" means an aliphatic monocyclic or polycyclic ring system comprising 3 to 10 carbon atoms, preferably 5 to 7 carbon atoms. Suitable examples include cyclopentyl, cyclohexyl, cycloheptyl, 1-decalinyl, norbornyl, adamantyl;

"heterocyclyl" means an aliphatic monocyclic or polycyclic ring system containing 3 to 10 carbon atoms, preferably 4 to 8 carbon atoms, and at least one heteroatom selected from the group consisting of nitrogen, oxygen and sulfur. Suitable examples include piperazinyl and morpholinyl;

"heteroaryl" means an aromatic monocyclic or polycyclic ring system containing 3 to 14 carbon atoms, preferably 3 to 7 carbon atoms, and at least one heteroatom selected from the group consisting of nitrogen, oxygen and sulfur. Heteroaryls can preferably be monocyclic or bicyclic or tricyclic, condensed or non-condensed. Examples of suitable heteroaryls are pyridyl, pyrimidinyl, pyrazinyl, furanyl, thienyl, pyrazolyl, oxazolyl, thiazolyl, isothiazolyl, isoxazolyl, pyrrolyl, imidazolyl, benzimidazolyl, dihydrobenzimidazolyl, indolyl, indolinolyl, imidazopyridazinyl, benzoxazinyl, dihydrobenzoxazinyl, benzofuranyl. Especially preferred are heteroaryls containing at least one nitrogen atom.

The substituent =O can be present only on aliphatic moieties or in aliphatic parts of moieties.

Pharmaceutically acceptable salts are salts with acids or bases, or acid addition salts. The acids and bases can be inorganic or organic acids and bases commonly used in the art of formulation, such as hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, paratoluenesulfonate, primary, secondary and tertiary amides, ammonia. Solvates are structures containing molecules of a solvent, such as water (hydrates) or any other pharmaceutically acceptable solvent molecules.

$R^1$ is preferably selected from $C_6$-$C_{12}$ aryl and heteroaryl having 5 to 12 ring atoms, wherein said aryl or heteroaryl is monocyclic, bicyclic or tricyclic, and the rings may be condensed or non-condensed. The aryls and heteroaryls include condensed rings wherein one or more rings are aromatic and one or more rings are aliphatic. The aryl or heteroaryl may optionally be substituted by one or more substituents, independently selected from the group consisting of F, Cl, Br, OH, $C_1$-$C_6$ alkyl, $O(C_1$-$C_4$ alkyl), phenyl, O-phenyl, $NH_2$, $N(C_1$-$C_4$ alkyl$)_2$, $NO_2$, $NHCO(C_1$-$C_4$ alkyl), $CF_3$, $OCF_3$, CN, $S(O)_2C_1$-$C_6$-alkyl, $SO_2NH(C_1$-$C_6$-alkyl), $SO_2N(C_1$-$C_6$-alkyl$)_2$.

More preferably, the aryl in R1 is phenyl, biphenyl or naphthyl.

More preferably, the substituents attached to the aryl or heteroaryl in R1 are selected from F, Cl, Br, $C_1$-$C_6$alkyl, $O(C_1$-$C_4$ alkyl), $NO_2$, $NHCO(C_1$-$C_4$ alkyl), $CF_3$, CN, phenyl, OH; or the substituents may be selected from $S(O)_2C_1$-$C_6$-alkyl, $SO_2NH(C_1$-$C_6$-alkyl), $SO_2N(C_1$-$C_6$-alkyl$)_2$.

More preferably, $R^1$ is selected from $C_6$-$C_{12}$ aryl (preferably phenyl) and heteroaryl having 5 to 12 ring atoms, said aryl or heteroaryl is monocyclic, bicyclic or tricyclic, and the rings may be condensed or non-condensed. The aryls and heteroaryls include condensed rings wherein one or more rings are aromatic and one or more rings are aliphatic. The aryl or heteroaryl is substituted with one to three OH groups, preferably with two OH groups or one OH group and one group selected from CN, Cl, Br, F. Preferably, the OH groups are in vicinal positions. The aryl or heteroaryl may optionally be substituted by one or more further substituents, independently selected from the group consisting of F, Cl, Br, $C_1$-$C_6$ alkyl, $O(C_1$-$C_4$ alkyl), phenyl, O-phenyl, $NH_2$, $N(C_1$-$C_4$ alkyl$)_2$, $NO_2$, $NHCO(C_1$-$C_4$ alkyl), $CF_3$, $OCF_3$, CN, $S(O)_2C_1$-$C_6$-alkyl, $SO_2NH(C_1$-$C_6$-alkyl), $SO_2N(C_1$-$C_6$-alkyl$)_2$; in particular selected from F, Cl, Br, $C_1$-$C_6$ alkyl, $O(C_1$-$C_4$ alkyl), $CF_3$, $OCF_3$.

Most preferably, $R^1$ is 3,4-dihydroxyphenyl.

In one embodiment, $R^2$ is preferably selected from aryl, cycloalkyl which may optionally be substituted by one or more substituents, independently selected from the group consisting of F, Cl, Br, OH, $C_1$-$C_6$ alkyl, $S(O)_2C_1$-$C_6$-alkyl, $CF_3$, $OCF_3$, $SO_2NH(C_1$-$C_6$-alkyl), $SO_2N(C_1$-$C_6$-alkyl$)_2$.

In another embodiment, $R^2$ is preferably selected from $C_6$-$C_{12}$ aryl and heteroaryl having 5 to 12 ring atoms, wherein said aryl or heteroaryl is monocyclic, bicyclic or tricyclic, and the rings may be condensed or non-condensed. The aryl or heteroaryl may optionally be substituted by one or more substituents, independently selected from the group consisting of F, Cl, Br, OH, $C_1$-$C_6$ alkyl, O—$C_1$-$C_6$ alkyl, phenyl, O-phenyl, $NH_2$, $N(C_1$-$C_4$ alkyl$)_2$, $NO_2$, $NHCO(C_1$-$C_4$ alkyl), $CF_3$, $OCF_3$, CN, $SO_2NH(C_1$-$C_6$-alkyl), $SO_2N(C_1$-$C_6$-alkyl$)_2$, $S(O)_2C_1$-$C_6$-alkyl.

More preferably, the aryl in $R^2$ is phenyl, biphenyl or naphthyl.

$R^2$ is preferably selected from $C_6$-$C_{12}$ aryl and heteroaryl having 5 to 12 ring atoms, which may optionally be substituted by one or more substituents, independently selected from the group consisting of F, Cl, Br, $C_1$-$C_4$ linear or branched alkyl, phenyl, morpholinyl, $C_3$-$C_5$ cycloalkyl, $O(C_1$-$C_4$ alkyl), phenyl, O-phenyl, $NH_2$, $N(C_1$-$C_4$ alkyl$)_2$, $NO_2$, $NHCO(C_1$-$C_4$ alkyl), $CF_3$, $OCF_3$, CN, $S(O)_2C_1$-$C_6$-alkyl, $SO_2NH(C_1$-$C_6$-alkyl), $SO_2N(C_1$-$C_6$-alkyl$)_2$; in particular selected from F, Cl, Br, $C_1$-$C_6$ alkyl, $O(C_1$-$C_4$ alkyl), $CF_3$, $OCF_3$.

More preferably, $R^2$ is selected from phenyl, naphthyl, benzofuranyl, pyridyl, thiophenyl, pyridazinyl, which are unsubstituted or substituted with one to two substituents selected independently from $O(C_1$-$C_4$ alkyl), phenyl, morpholinyl, OH, $C_1$-$C_4$ linear or branched alkyl, $C_3$-$C_5$ cycloalkyl, F, Br, Cl, $CF_3$, $OCF_3$.

$R^3$ is preferably selected from H, phenyl, methyl, ethyl, propyl, isopropyl, butyl, isobutyl, tert-butyl, F, Cl, Br, cyclopropyl, cyclobutyl, cyclopentyl, cyclohexyl, tetrahydropyranyl, tetrahydrofuranyl, piperidinyl, which are unsubstituted or substituted by one or more substituents, independently selected from the group consisting of F, Cl, Br, OH, $C_1$-$C_6$ alkyl, phenyl, $NH_2$, $N(C_1$-$C_4$ alkyl$)_2$, $NO_2$, $NHCO(C_1$-$C_4$ alkyl), $CF_3$, $OCF_3$, CN, $SO_2NH(C_1$-$C_6$-alkyl), $SO_2N(C_1$-$C_6$-alkyl$)_2$, $S(O)_2C_1$-$C_6$-alkyl.

$R^4$ is preferably selected from H, methyl, ethyl, isopropyl. For example, $R^4$ is H.

$R^5$ is preferably selected from H, phenyl. More preferably, $R^5$ is H.

$R^6$ is preferably selected from H, methyl, ethyl, isopropyl. For example, $R^6$ is H.

In all preferred embodiments, the alkyls, O-phenyls and phenyls may optionally be further substituted by one or more substituents selected from F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, $COO(C_1$-$C_6$-alkyl), $CONH_2$, $CONH(C_1$-$C_6$-alkyl), $CON(C_1$-$C_6$-alkyl)$_2$, $NHC(O)C_1$-$C_6$-alkyl, or $NHC(O)NH_2$.

It should be understood that the preferred and/or specific embodiments of the substituent groups can be combined in any combinations, and they can be combined in any combinations with the most general embodiments of the substituent groups.

In particular, the present invention encompasses the following compounds:

3-(4-acetamidophenyl)-2-cyano-N-(4-phenylthiazol-2-yl)propanamide

N-(4-(4-bromophenyl)thiazol-2-yl)-2-cyano-3-(3,4-dihydroxyphenyl)propanamide 2-cyano-3-(3,4-dihydroxyphenyl)-N-(4-phenylthiazol-2-yl)propanamide 2-cyano-N-(4-(4-cyanophenyl)thiazol-2-yl)-3-(3,4-dihydroxyphenyl)propanamide 2-cyano-3-(3,4-dihydroxyphenyl)-N-(4-(4-(trifluoromethyl)phenyl)thiazol-2-yl)propanamide 2-cyano-3-(3,4-dihydroxyphenyl)-N-(4-(p-tolyl)thiazol-2-yl)propanamide 2-cyano-3-(3,5-dichloro-4-hydroxyphenyl)-N-(4,5-diphenylthiazol-2-yl)propanamide 2-cyano-3-(3,4-dihydroxyphenyl)-N-(4-phenyl-5-(p-tolyl)thiazol-2-yl)propanamide 2-cyano-3-(3,4-dihydroxyphenyl)-N-(4-(4-(trifluoromethoxy)phenyl)thiazol-2-yl)propanamide 2-cyano-3-(3,5-dichloro-4-hydroxyphenyl)-N-(4-(4-(trifluoromethoxy)phenyl)thiazol-2-yl)propanamide N-(4-([1,1'-biphenyl]-3-yl)thiazol-2-yl)-2-cyano-3-(3,4-dihydroxyphenyl)propanamide 2-cyano-3-(3,5-di-tert-butyl-4-hydroxyphenyl)-N-(4-phenylthiazol-2-yl)propanamide N-(4-(4-(tert-butyl)phenyl)thiazol-2-yl)-2-cyano-3-(3,4-dihydroxyphenyl)propanamide 2-(3,4-dihydroxybenzyl)-$N^1$-(4-phenylthiazol-2-yl)malonamide 3-(1H-benzo[d]imidazol-6-yl)-2-cyano-N-(4-phenylthiazol-2-yl)propanamide 2-cyano-3-(3,5-dichloro-4-hydroxyphenyl)-N-(4-(naphthalen-2-yl)thiazol-2-yl)propanamide 2-cyano-3-(3,4-dihydroxyphenyl)-N-(4-(thiophen-3-yl)thiazol-2-yl)propanamide 2-cyano-N-(5-cyclohexyl-4-phenylthiazol-2-yl)-3-(3,4-dihydroxyphenyl)propanamide 2-cyano-3-(4-hydroxy-3,5-dimethylphenyl)-N-(4-phenylthiazol-2-yl)propanamide 3-(2-bromo-3,4-dihydroxyphenyl)-2-cyano-N-(4-phenylthiazol-2-yl)propanamide N-(4-(4-(tert-butyl)phenyl)thiazol-2-yl)-2-cyano-3-(4-hydroxy-3,5-dimethylphenyl)propanamide N-(4-(4-(tert-butyl)phenyl)thiazol-2-yl)-2-cyano-3-(3,5-di-tert-butyl-4-hydroxyphenyl)propanamide 2-cyano-3-(3-cyano-4-hydroxyphenyl)-N-(4-phenylthiazol-2-yl)propanamide 2-cyano-3-(3,4-dihydroxyphenyl)-N-(4-(5-methylthiophen-3-yl)thiazol-2-yl)propanamide 2-cyano-3-(3,4-dihydroxyphenyl)-N-(4-(5,6,7,8-tetrahydronaphthalen-2-yl)thiazol-2-yl)propanamide 2-cyano-N-(4-(4-cyclohexylphenyl)thiazol-2-yl)-3-(3,4-dihydroxyphenyl)propanamide 3-(3-chloro-4-hydroxy-5-methylphenyl)-2-cyano-N-(4-phenylthiazol-2-yl)propanamide 3-(3-chloro-5-fluoro-4-hydroxyphenyl)-2-cyano-N-(4-phenylthiazol-2-yl)propanamide 2-cyano-3-(3,4-dihydroxyphenyl)-N-(4-(pyridin-2-yl)thiazol-2-yl)propanamide 2-cyano-3-(3,4-dihydroxyphenyl)-N-(4-(6-methylpyridin-2-yl)thiazol-2-yl)propanamide 2-cyano-3-(3,4-dihydroxyphenyl)-N-(4-(2-(trifluoromethyl)phenyl)thiazol-2-yl)propanamide 2-cyano-N-(4-(3,4-dichlorophenyl)thiazol-2-yl)-3-(3,4-dihydroxyphenyl)propanamide 2-cyano-3-(3,4-dihydroxyphenyl)-N-(4-(o-tolyl)thiazol-2-yl)propanamide N-(4-(3-chlorophenyl)thiazol-2-yl)-2-cyano-3-(3,4-dihydroxyphenyl)propanamide 3-(3,5-bis(trifluoromethyl)phenyl)-2-cyano-N-(4-phenylthiazol-2-yl)propanamide 2-cyano-3-(3,4-dihydroxyphenyl)-N-(4-(4-methylpyridin-2-yl)thiazol-2-yl)propanamide 2-cyano-3-(3,4-dihydroxyphenyl)-N-(4-(5-methylpyridin-2-yl)thiazol-2-yl)propanamide 2-cyano-3-(3,4-dihydroxyphenyl)-N-(4-(4-isopropylphenyl)thiazol-2-yl)propanamide 2-cyano-3-(3,4-dihydroxyphenyl)-N-(4-(4-methoxypyridin-2-yl)thiazol-2-yl)propanamide 2-cyano-3-(3,4-dihydroxyphenyl)-N-(4-(5-methoxypyridin-2-yl)thiazol-2-yl)propanamide 2-cyano-3-(3,5-di-tert-butyl-4-hydroxyphenyl)-N-(4-(pyridin-2-yl)thiazol-2-yl)propanamide 2-cyano-3-(3,4-dihydroxyphenyl)-N-(4-(6-methoxypyridin-2-yl)thiazol-2-yl)propanamide 2-cyano-N-(4-(2,4-dichlorophenyl)thiazol-2-yl)-3-(3,4-dihydroxyphenyl)propanamide 2-cyano-3-(3,4-dihydroxyphenyl)-N-(4-(3-fluoropyridin-2-yl)thiazol-2-yl)propanamide 2-cyano-3-(3,4-dihydroxyphenyl)-N-(4-(2-fluoro-4-methoxyphenyl)thiazol-2-yl)propanamide 2-cyano-3-(3,4-dihydroxyphenyl)-N-(4-(4-(trifluoromethyl)pyridin-2-yl)thiazol-2-yl)propanamide 2-cyano-N-(4-(2,5-dichlorothiophen-3-yl)thiazol-2-yl)-3-(3,4-dihydroxyphenyl) propanamide 2-cyano-3-(3,4-dihydroxyphenyl)-N-(4-phenylthiazol-2-yl)butanamide 2-cyano-3-(3,4-dihydroxyphenyl)-2-methyl-N-(4-phenylthiazol-2-yl)propanamide In general, the compounds described in this invention can be prepared through the general routes described below in Scheme 1.

Briefly, condensation of appropriate bromoketone (2) with thiourea provides the corresponding aminothiazole (3), which reacts with ethyl cyanoacetate under basic conditions to afford the corresponding amide (4). Alternatively, amide (4) can be prepared in two steps from aminothiazole (3) via reaction with chloroacetyl chloride followed by reaction with potassium cyanide. Subsequent condensation with appropriate aldehyde or ketone compound in the presence of a base followed by reduction provides the target compound (1) (where $R^6$=H). Target compounds (1) with $R^6$=alkyl can be prepared from proper compounds (1) with $R^6$=H by alkylation. Alternatively, properly functionalized cyanoacetate (5) can be condensed with aminothiazole (3) to provide target compounds (1).

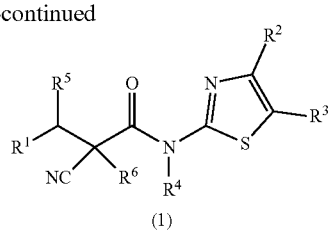

The compounds of Formula (1) act as inhibitors of nuclease MRE11, and are useful in the treatment and prevention of diseases associated with genome instability, e.g. cancer (in particular breast, colon, prostate, lung, head and neck, hepatic, ovarian, colorectal, gastric, melanoma cancers, leukemias, Nijmegen breakage syndrome and Nijme-

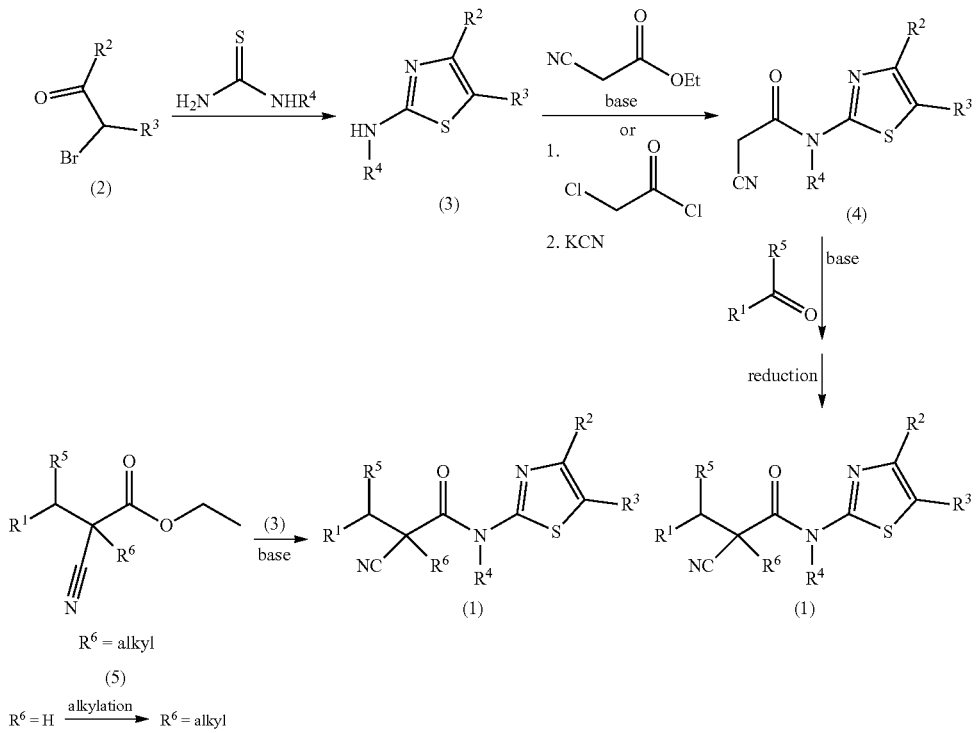

Target compounds (1) with $R^5$=alkyl can be prepared from proper unsaturated precursors via addition of cuprate (Scheme 2).

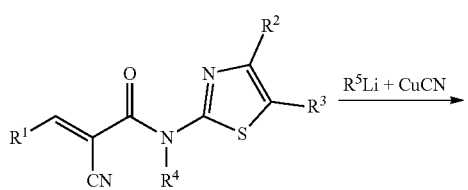

gen breakage-like syndrome, Ataxia-telangiectasia and Ataxia-telangiectasia-like disorder, and Fanconi anemia), premature aging and neurological diseases.

The present invention thus provides the compounds of formula (1) for use as medicaments. More specifically, it provides the compounds of formula (1) for use in the treatment and prevention of conditions selected from genome instability-associated diseases, e.g. cancer (in particular breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia), premature aging and neurological diseases. In one embodiment, the present invention provides the compounds of formula (1) for use in the treatment of solid tumors with mutated BRCA-2. Tests for diagnosing BRCA-2 mutations are commercially available.

The present invention also provides a method for treatment, inhibition, amelioration or prevention of a condition selected from genome instability-associated diseases, e.g. cancer (in particular breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia), premature aging and neurological diseases in a patient suffering from such condition, comprising the step of administering at least one compound of formula (1) to said patient.

The present invention further includes pharmaceutical compositions comprising at least one compound of formula (1) and at least one pharmaceutically acceptable auxiliary compound. The auxiliary compounds may include, e.g., carriers, diluents, fillers, preservatives, stabilisers, binders, wetting agents, emulsifiers, buffers, etc. Suitable auxiliary compounds are well known to those skilled in the art of formulation. The pharmaceutical compositions are prepared by known methods, e.g., mixing, dissolving, etc.

The present invention may also provide novel compounds of general formula (1) as defined above, including the preferred embodiments, with the proviso that if R' is phenyl, then it is not substituted by two alkoxy substituents attached to the phenyl through oxygen atom.

EXAMPLES OF CARRYING OUT THE INVENTION

The present invention provides substituted propanamides which are represented by general formula (1), or pharmaceutically acceptable salts, solvates, esters or prodrugs thereof, wherein the various moieties are as described above.

PREPARATIVE EXAMPLES

Materials and Methods

All commercially available reagents were used as supplied without further purification. The reaction solvents were purchased anhydrous and were stored under nitrogen. Unless noted otherwise, the reactions were carried out in oven-dried glassware under atmosphere of nitrogen. Column chromatography was carried out using silica gel (pore size 60 Å, 230-400 mesh particle size, 40-63 μm particle size). Purification by preparative thin layer chromatography was performed using plates from Merck (PLC Silica gel 60 $F_{254}$, 1 mm). Reverse phase column chromatography was carried out using $C_{18}$-reverse phase silica gel (pore size 90 Å, 230-400 mesh particle size, 40-63 μm particle size). NMR spectra were obtained in indicated deuterated solvents; chemical shifts are quoted in parts per million (δ) referenced to the appropriate deuterated solvent employed. Multiplicities are indicated by s (singlet), d (doublet), t (triplet), q (quartet), p (pentet), sept (septet), m (multiplet) or (br) broad, or combinations thereof. Coupling constant values are given in Hz.

General Procedure A1: Bromination of Acetophenones with Bromine

To a cold solution (0° C.) of the substrate (i.e. appropriate acetophenone derivative) in $CH_2Cl_2$ (14 mL per 1 mmol of the substrate, unless stated otherwise) was added $Br_2$ (1 eq), the resulting mixture was allowed to warm to 25° C. and stirred for 1 h (unless stated otherwise). A saturated aqueous solution of $NaHCO_3$ (3 mL per 1 mmol of the substrate) was added and the mixture was extracted with $CH_2Cl_2$ (3 mL per 1 mmol of the substrate). The combined organic extracts were washed with a 10% aqueous solution of $Na_2S_2O_3$ (2 mL per 1 mmol of the substrate), brine (2 mL per 1 mmol of the substrate), dried over $MgSO_4$, filtered, and the solvent was evaporated in vacuo. The resulting product—the desired bromoketone—was used directly without further purification in the next step.

General Procedure A2: Bromination of Acetophenones with $CuBr_2$

To a solution of the appropriate acetophenone derivative in a mixture of $CHCl_3$ and EtOAc (1:1) (2 mL per 1 mmol of the substrate, unless stated otherwise), was added $CuBr_2$ (2 eq.) and the resulting mixture was refluxed for 2 h. The mixture was filtered through a HPLC filter and evaporated in vacuo. The product was dried under vacuum and put to next step without further purification.

General Procedure A3: Bromination Acetophenones with TMSOTf and NBS:

To a solution of the appropriate acetophenone derivative in $CH_2Cl_2$ (2 mL per 1 mmol of the substrate, unless stated otherwise), were added $NEt_3$ (1.2 eq) and TMFOTf (1.1 eq.) at 0° C. The mixture was allowed to warm to 25° C. and stirred for 16 h. The reaction mixture was then again cooled to 0° C. and NBS (1.1 eq.) was added. The mixture was stirred at 0° C. for 15-30 min. The crude mixture was absorbed on silica and quickly filtered through a pad of silica gel (hexane:EtOAc; 1:1, unless stated otherwise) to provide the desired bromo-acetophenone, which was used directly in the next step.

General Procedure A4: Bromination Acetophenones with $Br_2$ and HBr (47% in $H_2O$):

The appropriate acetophenone (1 eq) was added to the solution of HBr (47% in $H_2O$, 3 eq) and acetic acid (3 mL per 1 mmol of the substrate, unless stated otherwise) at 25° C. Then $Br_2$ (1.1 eq) was added dropwise at 25° C. and the resulting reaction mixture was stirred at 25° C. for 16 h.

Work-Up 1:

Then diethyl ether (5 mL per 1 mmol of the substrate) was added and the reaction mixture was stirred for 30 minutes. The formed precipitate was collected by filtration, washed with diethyl ether (2×2 mL per mmol of the substrate) and dried under vacuum. The crude product was used as such in the next step.

Work-Up 2:

A saturated aqueous solution of $NaHCO_3$ was added until the pH was neutral and the mixture was extracted with EtOAc (3×10 mL per 1 mmol of the substrate). The combined organic extracts were dried over $MgSO_4$, filtered, and the solvent was evaporated in vacuo. The resulting product was used directly without further purification in the next step.

General Procedure B: Condensation of Bromoketones with Thiourea

A mixture of the substrate (i.e. appropriate bromoketone) (1 eq) and thiourea (1.5 eq) in EtOH (3 mL per 1 mmol of bromoketone, unless stated otherwise) was refluxed for 2 h (unless stated otherwise).

Work-Up 1:

A saturated aqueous solution of $NaHCO_3$ (3 mL per 1 mmol of bromoketone) was added to the mixture, which was then extracted with EtOAc (3×5 mL per 1 mmol of bromoketone). The combined organic extracts were washed with brine (3 mL per 1 mmol of bromoketone), dried over $MgSO_4$, filtered, and the solvent was evaporated in vacuo. If necessary, the product was purified by column chromatography on silica gel (unless stated otherwise) to provide the desired aminothiazole.

Work-Up 2:

The solvent was evaporated in vacuo. The resulting solid was triturated with EtOAc (1 mL per 1 mmol of bromoketone) and the mixture was filtered. The solid residue was dissolved in MeOH (1 mL per 1 mmol of bromoketone). A saturated aqueous solution of $NaHCO_3$ (3 mL per 1 mmol of bromoketone) was added and the mixture was extracted with EtOAc (3×5 mL per 1 mmol of bromoketone). The combined organic extracts were washed with brine (3 mL per 1 mmol of bromoketone), dried over $MgSO_4$, filtered, and the solvent was evaporated in vacuo. The product—the desired aminothiazole—was usually sufficiently pure and was used directly without further purification (unless stated otherwise) in the next step.

General Procedure C1: Amide Formation Using NaOEt or NaOMe

To a mixture of the appropriate aminothiazole (1 eq) and ethyl cyanoacetate (1.5 eq) in anhydrous EtOH or MeOH (2 mL per 1 mmol of aminothiazole, unless stated otherwise) was added a solution of NaOEt (21% in EtOH) (1.5 eq, unless stated otherwise) or NaOEt (about 1 mM in EtOH, freshly made from Na and anhydrous EtOH) at 25° C. The mixture was heated to 55° C. for 5 h (unless stated otherwise). A saturated aqueous solution of $NH_4Cl$ (10 mL per 1 mmol of aminothiazole) was added and the mixture was extracted with EtOAc (3×15 mL per 1 mmol of aminothiazole). The organic extracts were washed with water (10 mL per 1 mmol of aminothiazole), brine (10 mL per 1 mmol of aminothiazole), dried over $MgSO_4$, filtered, and the solvent was evaporated in vacuo. The residue was purified by column chromatography on silica gel (unless stated otherwise) to provide the desired amide.

General procedure C2: Amide Formation Via Reaction with Chloroacetyl Chloride in Two Steps Step 1: To a solution of the appropriate aminothiazole (1 eq) in anhydrous acetonitrile (1 mL per 1 mmol), was added $NEt_3$ (1 eq, unless stated otherwise) at 25° C. The mixture was heated to 80° C. and a solution of chloroacetyl chloride (1.5 eq.) in dry acetonitrile (0.5 mL per 1 mmol) was added. The reaction mixture was stirred at 80° C. for 2 h. A saturated aqueous solution of $NH_4Cl$ (10 mL per 1 mmol of aminothiazole) was added and the mixture was extracted with EtOAc (3×15 mL per 1 mmol of aminothiazole). Organic phases were combined and washed with brine (10 mL per 1 mmol of aminothiazole), dried over $MgSO_4$, filtered, and the solvent was evaporated in vacuo. The residue was quickly filtered through a pad of silica gel (hexane:EtOAc; 1:1, unless stated otherwise) to provide the corresponding chloroacetamide.

Step 2: The chloroacetamide was dissolved in anhydrous DMF (1 mL per 1 mmol) and KCN (1 eq, unless stated otherwise) was added and stirred at 25° C. for 6 h. Water (5 ml per 1 mmol) was added and the mixture was extracted with EtOAc (3×15 mL per 1 mmol). The combined organic extracts were dried over $MgSO_4$, filtered, and the solvent was evaporated in vacuo. The residue was purified by column chromatography to provide the desired cyanoacetamide.

General Procedure C3: Amide Formation Using NaH and Ethyl Cyanoacetate

To a solution of the appropriate aminothiazole (1 eq) in anhydrous THF:MeOH (5:1) (6 mL per 1 mmol, unless stated otherwise), was added NaH (1.1 eq, 60% in mineral oil) at 0° C. The mixture was stirred at 55° C. and ethyl cyanoacetate (1.5 eq) was added. After 4 h, additional ethyl cyanoacetate (1.5 eq) was added and the mixture was refluxed for 14 h. The mixture was cooled to 25° C., a saturated aqueous solution of $NH_4Cl$ (20 mL per 1 mmol of aminothiazole) was added and the mixture was extracted with EtOAc (3×20 mL per 1 mmol of aminothiazole). Organic phases were combined and washed with brine (20 mL per 1 mmol of aminothiazole), dried over $MgSO_4$, filtered, and the solvent was evaporated in vacuo. The residue was purified by column chromatography to provide the desired cyanoacetamide.

General Procedure D1: Condensation with Triethylamine as a Base

To a mixture of the appropriate aldehyde (0.95 eq) and cyanoacetamide (1 eq) in absolute EtOH (17 mL per 1 mmol of aldehyde, unless stated otherwise) was added triethylamine (1 eq) and the mixture was stirred at 50° C. for 2 h (unless stated otherwise).

Work-Up 1:

When a precipitate appeared, the solvent was removed by filtration. The solid residue was dissolved in EtOAc (ca. 5 mL per 0.05 mmol of aldehyde) and a saturated aqueous solution of $NH_4Cl$ (5 mL per 0.05 mmol of aldehyde) was added. The mixture was extracted with EtOAc (3×5 mL per 0.05 mmol of aldehyde). The combined organic extracts were washed with water (ca. 4 mL per 0.05 mmol of aldehyde), brine (ca. 4 mL per 0.05 mmol of aldehyde), dried over $MgSO_4$, filtered, and the solvent was evaporated in vacuo. The resulting product—the desired acrylamide—was usually sufficiently pure and was used directly in the next step without further purification (unless stated otherwise).

Work-Up 2:

When no precipitate appeared, a saturated aqueous solution of $NH_4Cl$ (5 mL per 0.05 mmol of aldehyde) was added to the reaction mixture, which was then extracted with EtOAc (3×5 mL per 0.05 mmol of aldehyde). The organic extracts were washed with water (4 mL per 0.05 mmol of aldehyde), brine (4 mL per 0.05 mmol of aldehyde), dried over $MgSO_4$, filtered, and the solvent was evaporated in vacuo. The residue was purified by column chromatography on silica gel and/or by reverse phase column chromatography on $C_{18}$ silica gel to provide the desired acrylamide.

General Procedure D2: Condensation with Piperidine as a Base

To a mixture of the appropriate aldehyde (1 eq) and cyanoacetamide (1 eq) in $CH_2Cl_2$ or $CH_3CN$ (10 mL per 1 mmol of aldehyde, unless stated otherwise) was added piperidine (0.1 eq). The mixture was refluxed for 2 h (unless stated otherwise). A saturated aqueous solution of $NH_4Cl$ (5 mL per 0.1 mmol of aldehyde) was added and the mixture was extracted with EtOAc (3×5 mL per 0.1 mmol of aldehyde). The organic extracts were washed with water (5 mL per 0.1 mmol of aldehyde), brine (5 mL per 0.1 mmol of aldehyde), dried over $MgSO_4$, filtered, and the solvent was evaporated in vacuo. The residue was purified by preparative TLC and/or by column chromatography on silica gel and/or by reverse phase column chromatography on C18 silica gel (unless stated otherwise) to provide the desired acrylamide.

General Procedure E: Reduction with $NaBH_4$

To a solution of the appropriate acrylamide (1 eq) in anhydrous MeOH (20 mL per 1 mmol of acrylamide, unless stated otherwise) was added $NaBH_4$ (2 eq) at 0° C. The mixture was allowed to warm to 25° C. and stirred for 2-16 h. A saturated aqueous solution of $NH_4Cl$ (10 mL per 0.1 mmol of acrylamide) was added and the mixture was extracted with EtOAc (3×10 mL per 0.1 mmol of acrylamide). The organic extracts were washed with water (5 mL per 0.1 mmol of acrylamide), brine (5 mL per 0.1 mmol of acrylamide), dried over MgSO$_4$, filtered, and the solvent was evaporated in vacuo. The residue was purified by preparative TLC and/or by column chromatography on silica gel and/or by reverse phase column chromatography on C$_{18}$ silica gel to provide the desired target compound.

Compounds that contained residual AcOH after reverse phase column chromatography were subjected to treatment with a saturated aqueous solution of NaHCO$_3$ (10 mL per 0.1 mmol of acrylamide) and EtOAc (3×10 mL per 0.1 mmol of acrylamide). The organic extracts were combined, washed with brine (5 mL per 0.1 mmol of acrylamide), dried over MgSO$_4$, and the solvent was evaporated in vacuo.

General Procedure F: Boronate Formation and the Suzuki Coupling n-BuLi (1.6 M in hexane) (2 eq) was added dropwise to a solution of tert-butyl (4-bromothiazol-2-yl)(4-methoxybenzyl)carbamate (1.25 mmol), 2-isopropoxy-4,4,5,5-tetramethyl-1,3,2-dioxaborolane (1.5 eq) and THF (6 mL/mmol) at −78° C. and stirred for 1 h, then the reaction mixture was quenched with a saturated aqueous solution of NH$_4$Cl (8 mL/mmol) at −78° C. The reaction mixture was warmed up to room temperature and extracted with EtOAc (2×40 mL/mmol). The combined organic extracts were washed with brine (16 mL/mmol), dried over MgSO$_4$, filtered, and concentrated under reduced pressure to obtained the crude tert-butyl (4-methoxybenzyl)(4-(4,4,5,5-tetramethyl-1,3,2-dioxaborolan-2-yl)thiazol-2-yl)carbamate, which was used into next step without further purification.

A solution of tert-butyl (4-methoxybenzyl)(4-(4,4,5,5-tetramethyl-1,3,2-dioxaborolan-2-yl)thiazol-2-yl)carbamate (1 eq) in DME (10 mL/mmol) and H$_2$O (2 mL/mmol) was added to a mixture of the appropriate aryl halide (1.1 eq), K$_3$PO$_4$ (3.0 eq) and Pd(dppf)Cl$_2$ (0.1 eq). The reaction mixture was stirred at 80° C. for 3 h, then diluted with water (20 mL/mmol), and extracted with EtOAc (2×40 mL/mmol). The combined organic extracts were washed with brine (15 mL/mmol), dried over MgSO$_4$, filtered, and concentrated under reduced pressure. The residue was purified by column chromatography to provide the desired target compound.

General procedure G: Deprotection with TFA

Trifluoroacetic acid (4 mL/mmol) was added to a tert-butyl (4-methoxybenzyl)(4-substituted thiazol-2-yl)carbamate (1 eq) and stirred at 70° C. for 2 h, then the solvent was evaporated under reduced pressure. The residue was quenched with a saturated aqueous solution of NaHCO$_3$ (30 mL/mmol), and extracted with CH$_2$Cl$_2$ or EtOAc (2×50 mL/mmol). The combined organic extracts were dried over MgSO$_4$, filtered, and concentrated under reduced pressure. The residue was purified by column chromatography to provide the desired target compound.

Preparation of Individual Intermediates and Target Compounds as Examples:

Preparative Example 1

1-([1,1'-biphenyl]-3-yl)ethan-1-one

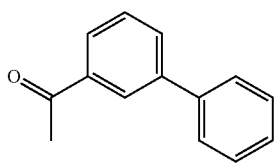

A mixture of dioxane and water (4+1 mL) was added to a mixture of 1-(3-bromophenyl)ethan-1-one (0.75 g, 3.78 mmol, 0.5 mL), phenylboronic acid (0.55 g, 4.5 mmol), K$_2$CO$_3$ (1.04 g, 7.56 mmol) and Pd(dppf)Cl$_2$ (55 mg, 0.1 mmol). The reaction mixture was degassed for 10 min by bubbling argon, then it was stirred at 90° C. for 18 h. The reaction mixture was cooled to 25° C., diluted with EtOAc (15 mL), poured into a saturated aqueous solution of NH$_4$Cl (15 mL), and extracted with EtOAc (2×15 mL). The combined organic extracts were washed with water (15 mL) and brine (15 mL), dried over MgSO$_4$, filtered, and the solvent was evaporated in vacuo. The residue was purified by column chromatography (hexane:EtOAc; 10:1). The product was obtained as a colorless oil (630 mg, 85%).

$^1$H NMR (500 MHz, CDCl$_3$) δ (ppm) 8.19 (t, J=1.8 Hz, 1H), 7.95 (ddd, J=7.7, 1.7, 1.1 Hz, 1H), 7.80 (ddd, J=7.7, 1.9, 1.1 Hz, 1H), 7.66-7.61 (m, 2H), 7.55 (t, J=7.7 Hz, 1H), 7.51-7.46 (m, 2H), 7.43-7.37 (m, 1H), 2.67 (s, 3H);

$^{13}$C NMR (126 MHz, CDCl$_3$) δ (ppm) 198.3, 142.0, 140.4, 137.9, 132.0, 129.3, 129.2, 128.0, 127.4, 127.4, 127.2, 27.0;

Preparative Example 2

3,4-bis((2-(trimethylsilyl)ethoxy)methoxy)benzaldehyde

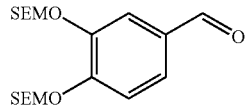

3,4-dihydroxybenzaldehyde (2 g, 14.48 mmol) was dissolved in CH$_2$Cl$_2$ (100 mL) and DIPEA (11.83 g, 15.1 mL, 86.88 mmol) was added. The mixture was cooled to 0° C. and SEMCl (7.24 g, 7.7 mL, 43.44 mmol) was added. The mixture was left to warm up slowly to 25° C. and stirred for 16 h. The mixture was poured in a saturated aqueous solution of NH$_4$Cl (100 mL) and the phases were separated. The organic phase was washed with an aqueous solution of citric acid (5% in water, 2×100 mL), dried over MgSO$_4$, filtered, and evaporated in-vacuo. The product, purified by column chromatography (hexane:EtOAc; 20:1 to 5:1), was obtained as a colorless oil (4.328 g, 75%).

$^1$H NMR (500 MHz, CDCl$_3$) δ (ppm) 9.87 (s, 1H), 7.70 (d, J=2.0 Hz, 1H), 7.53-7.47 (m, 1H), 7.31 (d, J=8.4 Hz, 1H), 5.36 (s, 2H), 5.34 (s, 2H), 3.84-3.77 (m, 4H), 1.02-0.91 (m, 4H), −0.01 (d, J=1.3 Hz, 18H);

$^{13}$C NMR (126 MHz, CDCl$_3$) δ (ppm) 191.0, 153.0, 147.8, 131.1, 126.1, 116.0, 115.4, 93.9, 93.6, 67.0, 66.8, 18.2, 18.2, −1.3.

Preparative Example 3 ethyl (E)-3-(3,4-bis((2-(trimethylsilyl)ethoxy)methoxy)phenyl)-2-cyanoacrylate

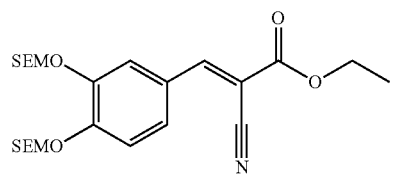

The compound was prepared according to General procedure D2 with 3,4-bis((2-(trimethylsilyl)ethoxy)methoxy)benzaldehyde (2.136 g, 5.36 mmol), ethylcyanoacetate (758 mg, 0.71 mL, 6.7 mmol), and piperidine (46 mg, 53 µL, 0.536 mmol) in anhydrous CH$_2$Cl$_2$ (25 mL) at reflux for 4 h. Ethylcyanoacetate (121 mg, 0.114 mL, 1.07 mmol) was added and the mixture stirred at reflux for 2 additional hh. The same addition of ethylcyanoacetate followed by reflux for 2 h was repeated two more times. The mixture was poured in a saturated aqueous solution of NH$_4$Cl (50 mL) and the phases were separated. The organic phase was washed with brine (50 mL), dried over MgSO$_4$, filtered, and the solvent was evaporated in vacuo. The residue was purified by column chromatography (hexane:EtOAc; 1:0 to 10:1) to give a pale yellow oil (2.403 g, 91%).

$^1$H NMR (500 MHz, CDCl$_3$) δ (ppm) 8.15 (s, 1H), 7.86 (d, J=2.1 Hz, 1H), 7.68 (dd, J=8.6, 2.2 Hz, 1H), 7.28 (d, J=8.5 Hz, 1H), 5.36 (s, 2H), 5.32 (s, 2H), 4.37 (q, J=7.2 Hz, 2H), 3.86-3.76 (m, 4H), 1.39 (t, J=7.1 Hz, 3H), 1.03-0.92 (m, 4H), 0.00 (s, 18H);

$^{13}$C NMR (126 MHz, CDCl$_3$) δ (ppm) 163.2, 154.6, 152.2, 147.5, 127.0, 125.7, 119.0, 115.9, 100.6, 94.2, 93.6, 67.1, 66.9, 62.6, 18.2, 18.2, 14.4, −1.3.

Preparative Example 4

Ethyl 3-(3,4-bis((2-(trimethylsilyl)ethoxy)methoxy)phenyl)-2-cyanopropanoate

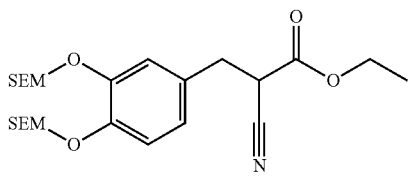 [SMILES: CCOC(=O)C(C#N)Cc1ccc(OCOCC[Si](C)(C)C)c(OCOCC[Si](C)(C)C)c1]

Ethyl (E)-3-(3,4-bis((2-(trimethylsilyl)ethoxy)methoxy)phenyl)-2-cyanoacrylate (540 mg, 1.09 mmol) was dissolved in anhydrous THE (5 mL) and cooled to 0° C. A solution of LiEt$_3$BH (1 M in THF, 1.3 mL, 1.3 mmol) was added and the mixture was stirred for 30 min at 0° C. Mixture was poured into a saturated aqueous solution of NH$_4$Cl (25 mL) and extracted with EtOAc (3×15 mL). The organic fractions were combined washed with brine (25 mL), dried over MgSO$_4$, filtered and evaporated. The product, purified by column chromatography (hexane:EtOAc; 10:1), was obtained as a colorless oil (430 mg, 80%).

$^1$H NMR (500 MHz, CDCl$_3$) δ (ppm) 7.16 (d, J=8.3 Hz, 1H), 7.11 (d, J=2.1 Hz, 1H), 6.87 (dd, J=8.3, 2.2 Hz, 1H), 5.29 (d, J=1.2 Hz, 2H), 5.27 (s, 2H), 4.27 (q, J=7.1 Hz, 2H), 3.86-3.78 (m, 4H), 3.69 (dd, J=8.5, 5.9 Hz, 1H), 3.29-3.09 (m, 2H), 1.31 (t, J=7.1 Hz, 3H), 1.04-0.95 (m, 4H), 0.03 (s, 9H), 0.02 (s, 9H);

$^{13}$C NMR (126 MHz, CDCl$_3$) δ (ppm) 165.8, 147.9, 147.3, 129.5, 123.0, 117.4, 116.9, 116.4, 94.2, 94.1, 66.7, 66.6, 63.1, 40.1, 35.6, 18.3, 18.3, 14.2, −1.2;

HRMS calcd for C$_{24}$H$_{40}$NO$_6$Si$_2$ [M−H]$^-$ 494.2400, found 494.2385.

Preparative Example 5

Ethyl 3-(3,4-bis((2-(trimethylsilyl)ethoxy)methoxy)phenyl)-2-cyano-2-methylpropanoate

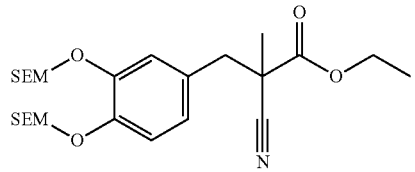 [SMILES: CCOC(=O)C(C)(C#N)Cc1ccc(OCOCC[Si](C)(C)C)c(OCOCC[Si](C)(C)C)c1]

To a solution of ethyl 3-(3,4-bis((2-(trimethylsilyl)ethoxy)methoxy)phenyl)-2-cyanopropanoate (290 mg, 0.58 mmol) in anhydrous THE at 0° C., was added NaH (60% in mineral oil, 28 mg, 0.7 mmol) and the mixture was stirred at 25° C. for 15 min. Then, dimethyl sulfate (95 mg, 72 µL, 0.75 mmol) was added and the mixture was stirred at 25° C. for 16 h. The mixture was poured into water (10 mL) and extracted with EtOAc (3×15 mL). The organic fractions were combined and washed with brine (25 mL), dried over MgSO$_4$, filtered, and the solvent was evaporated in vacuo. The product, purified by column chromatography (hexane:EtOAc; 10:1), was obtained as a colorless oil (220 mg, 75%).

$^1$H NMR (500 MHz, CDCl$_3$) δ (ppm) 7.12 (d, J=8.3 Hz, 1H), 7.11 (d, J=2.1 Hz, 1H), 6.85 (dd, J=8.3, 2.2 Hz, 1H), 5.29-5.24 (m, 4H), 4.22 (q, J=7.1 Hz, 2H), 3.88-3.73 (m, 4H), 3.07 (dd, J=96.2, 13.6 Hz, 2H), 1.59 (s, 3H), 1.26 (t, J=7.2 Hz, 3H), 1.04-0.90 (m, 4H), 0.00 (s, 18H);

$^{13}$C NMR (126 MHz, CDCl$_3$) δ (ppm) 170.4, 148.7, 148.6, 129.5, 125.2, 121.2, 119.8, 117.8, 95.4, 95.3, 67.8, 64.2, 46.8, 44.6, 24.4, 19.5, 19.5, 15.3, 0.0;

HRMS calcd for C$_{25}$H$_{47}$N$_2$O$_6$Si$_2$ [M+NH$_4$]$^+$ 527.2967, found 527.2880.

Preparative Example 6

2-bromo-3-hydroxy-4-methoxybenzaldehyde

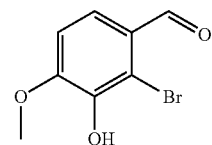

Isovanillin (2 g, 13 mmol) was dissolved in dioxane (16.7 mL) and water (6.7 mL), cooled to 0° C. NBS (2.39 g, 13.4 mmol) was added in portions over 30 min. The solution was allowed to warm to 25° C. and stirred for 2 h. Water (30 mL) was added, the precipitate was collected by filtration and dried under vacuum. The product was obtained as a white solid (2.74 g, 91%).

$^1$H NMR (500 MHz, DMSO-d$_6$) δ (ppm) 10.11 (s, 1H), 9.89 (s, 1H), 7.41 (d, J=8.3 Hz, 1H), 7.15 (d, J=8.5 Hz, 1H), 3.93 (s, 3H);

$^{13}$C NMR (126 MHz, DMSO-d$_6$) δ (ppm) 190.8, 153.3, 144.0, 126.7, 122.0, 113.3, 110.4, 56.4.

Preparative Example 7

2-bromo-3,4-dihydroxybenzaldehyde

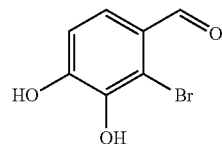

To a solution of 2-bromo-3-hydroxy-4-methoxybenzaldehyde (0.5 g, 2.16 mmol) in anhydrous CH$_2$Cl$_2$ (10 mL) at −78° C. was added BBr$_3$ (1M in CH$_2$Cl$_2$, 8.7 mL, 8.7 mmol). The mixture was warmed up to 25° C. and stirred for 16 h. Then the solution was cooled down to −78° C. and MeOH (5 mL) was added. The mixture was poured into water (25 mL) and extracted with EtOAc (3×10 mL). Combined organic fractions were washed with brine (25 mL), dried over MgSO$_4$, filtered, and the solvent was evaporated. The residue was purified by column chromatography (hexane: EtOAc; 3:2). The product was obtained as a white solid (280 mg, 60%).

$^1$H NMR (500 MHz, DMSO-d$_6$) δ (ppm) 10.06 (s, 1H), 7.30 (d, J=8.4 Hz, 1H), 6.91 (d, J=8.3 Hz, 1H);

$^{13}$C NMR (126 MHz, DMSO-d$_6$) δ (ppm) 190.5, 152.3, 143.2, 125.5, 122.3, 114.4, 114.0;

HRMS calcd for C$_7$H$_4$NBrO$_3$ [M−H]$^-$ 214.9349, found 214.9353.

Preparative Example 8

3-chloro-4-hydroxy-5-methylbenzaldehyde

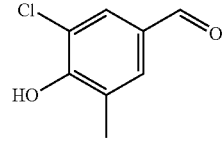

2-chloro-6-methylphenol (0.5 mg, 3.5 mmol) and hexamethylenetetramine (0.5 g, 3.5 mmol) were dissolved in TFA (3 mL) and stirred 30 min at 60° C. The mixture was poured into ice-water (20 mL) and extracted with Et$_2$O (3×20 mL). The organic fractions were combined, washed with brine (25 mL), dried over MgSO$_4$, filtered, and the solvent was evaporated. The product, purified by column chromatography (hexane:EtOAc; 7:3), was obtained as a white solid (220 mg, 40%).

$^1$H NMR (500 MHz, CDCl$_3$) δ (ppm) 9.82 (s, 1H), 7.74 (d, J=1.9 Hz, 1H), 7.64-7.59 (m, 1H), 6.18 (s, 1H), 2.36 (s, 3H);

$^{13}$C NMR (126 MHz, CDCl$_3$) δ (ppm) 190.0, 155.0, 131.6, 130.2, 128.6, 127.0, 120.8, 16.5;

HRMS calcd for C$_8$H$_6$ClO$_2$ [M−H]$^-$ 169.0062, found 169.0060.

Preparative Example 9

3-chloro-5-fluoro-4-hydroxybenzaldehyde

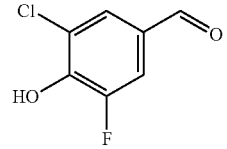 [SMILES: O=Cc1cc(F)c(O)c(Cl)c1]

2-fluoro-6-chlorophenol (0.5 mg, 3.5 mmol) and hexamethylenetetramine (0.5 g, 3.5 mmol) were dissolved in TFA (3 mL) and stirred at 60° C. for 16 h. The mixture was poured into ice-water (20 mL) and extracted with Et$_2$O (3×20 mL). The organic fractions were combined, washed with brine (25 mL), dried over MgSO$_4$, filtered, and the solvent was evaporated. The product, purified by column chromatography (hexane:EtOAc; 7:3), was obtained as a white solid (250 mg, 40%).

$^1$H NMR (500 MHz, CDCl$_3$) δ (ppm) 9.83 (d, J=2.1 Hz, 1H), 7.74-7.71 (m, 1H), 7.59 (dd, J=9.6, 1.8 Hz, 1H), 6.12 (s, 1H);

$^{13}$C NMR (126 MHz, CDCl$_3$) δ (ppm) 188.8, 151.6 (d, J=248.2 Hz), 146.2 (d, J=15.3 Hz), 129.7 (d, J=5.4 Hz), 127.5 (d, J=3.1 Hz), 122.7, 115.4 (d, J=18.5 Hz);

$^{19}$F NMR (471 MHz, CDCl$_3$) δ (ppm) −132.12;

HRMS calcd for C$_7$H$_3$ClFO$_2$ [M−H]$^-$ 172.9811, found 172.9809.

Preparative Example 10

Ethyl 3-(3,4-bis((2-(trimethylsilyl)ethoxy)methoxy) phenyl)-2-cyanopropanoate

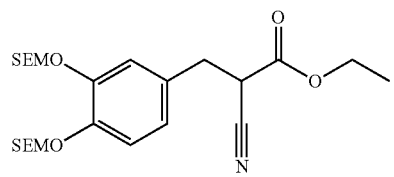

Ethyl (E)-3-(3,4-bis((2-(trimethylsilyl)ethoxy)methoxy) phenyl)-2-cyanoacrylate (540 mg, 1.09 mmol) was dissolved in dry THF (5 mL) and cooled to 0° C. A solution of LiEt$_3$BH (1 M in THF 1.3 mL, 1.3 mmol) was added and the resulting mixture was stirred at 0° C. for 30 min. The mixture was poured into a saturated aqueous solution of NH$_4$Cl (25 mL) and extracted with EtOAc (3×15 mL). The organic fractions were combined, washed with brine (25 mL), dried under MgSO$_4$, and the solvent was and evaporated. The product, purified on column chromatography (hexane:EtOAc; 10:1), was obtained as a colorless oil (430 mg, 80%).

$^1$H NMR (500 MHz, CDCl$_3$) δ (ppm) 7.16 (d, J=8.3 Hz, 1H), 7.11 (d, J=2.1 Hz, 1H), 6.87 (dd, J=8.3, 2.2 Hz, 1H), 5.29 (d, J=1.2 Hz, 2H), 5.27 (s, 2H), 4.27 (q, J=7.1 Hz, 2H), 3.86-3.78 (m, 4H), 3.69 (dd, J=8.5, 5.9 Hz, 1H), 3.29-3.09 (m, 2H), 1.31 (t, J=7.1 Hz, 3H), 1.04-0.95 (m, 4H), 0.03 (s, 9H), 0.02 (s, 9H);

$^{13}$C NMR (126 MHz, CDCl$_3$) δ (ppm) 165.8, 147.9, 147.3, 129.5, 123.0, 117.4, 116.9, 116.4, 94.2, 94.1, 66.7, 66.6, 63.1, 40.1, 35.6, 18.3, 18.3, 14.2, −1.2.

Preparative Example 11

Ethyl 3-(3,4-bis((2-(trimethylsilyl)ethoxy)methoxy)phenyl)-2-cyano-2-methylpropanoate

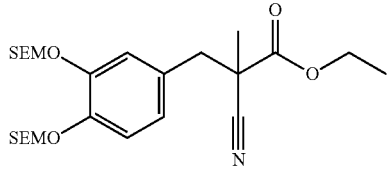

Ethyl 3-(3,4-bis((2-(trimethylsilyl)ethoxy)methoxy)phenyl)-2-cyanopropanoate (290 mg, 0.58 mmol) was dissolved in THF (3 mL), the solution was cooled to 0° C., NaH (60% in mineral oil, 28 mg, 0.7 mmol) was added and the mixture was stirred at 25° C. for 15 min. Dimethyl sulfate (95 mg, 72 µL, 0.75 mmol) was added and the mixture was stirred at 25° C. for 16 h. The mixture was poured into water (10 mL) and extracted with EtOAc (3×15 mL). The organic fractions were combined, washed with brine (25 mL), dried over MgSO$_4$, filtered, and the solvent was evaporated in vacuo. The product, purified by column chromatography (hexane:EtOAc; 10:1), was obtained as a colorless oil (220 mg, 75%).

$^1$H NMR (500 MHz, CDCl$_3$) δ (ppm) 7.12 (d, J=8.3 Hz, 1H), 7.11 (d, J=2.1 Hz, 1H), 6.85 (dd, J=8.3, 2.2 Hz, 1H), 5.29-5.24 (m, 4H), 4.22 (q, J=7.1 Hz, 2H), 3.88-3.73 (m, 4H), 3.07 (dd, J=96.2, 13.6 Hz, 2H), 1.59 (s, 3H), 1.26 (t, J=7.2 Hz, 3H), 1.04-0.90 (m, 4H), 0.00 (s, 18H);

$^{13}$C NMR (126 MHz, CDCl$_3$) δ (ppm) 170.4, 148.7, 148.6, 129.5, 125.2, 121.2, 119.8, 117.8, 95.4, 95.3, 67.8, 64.2, 46.8, 44.6, 24.4, 19.5, 19.5, 15.3, 0.0;

HRMS calcd for C$_{25}$H$_{47}$N$_2$O$_6$Si$_2$ [M+NH$_4$]$^+$ 527.2967, found 527.2880.

Preparative Example 12 tert-butyl (4-bromothiazol-2-yl)carbamate

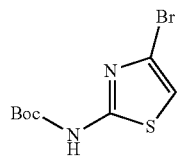

Di-tert-butyl dicarbonate (2.43 g, 11.17 mmol) was added to a mixture of 4-bromothiazol-2-amine (2.00 g, 11.17 mmol) and DMAP (136 mg, 1.11 mmol) in CH$_2$Cl$_2$ (25 mL) and the mixture was stirred at 25° C. for 24 h. The resulting solution was quenched with a saturated aqueous solution of NaHCO$_3$ (100 mL) and the mixture was extracted with CH$_2$Cl$_2$ (2×200 mL). The organic extracts were combined, dried over MgSO$_4$, filtered, and concentrated under reduced pressure. The residue was purified by column chromatography (hexane:EtOAc; 1:0 to 9.5:0.5) to afford the product (2.50 g, 80%) as a white solid.

$^1$H NMR (500 MHz, CDCl$_3$) δ (ppm) 8.83 (s, 1H), 6.79 (s, 1H), 1.54 (s, 9H);

$^{13}$C NMR (126 MHz, CDCl$_3$) δ (ppm) 160.7, 152.1, 120.6, 110.5, 83.5, 28.3;

HRMS calcd for C$_8$H$_{12}$BrN$_2$O$_2$S [M+H]$^+$ 280.9777, found 280.9774.

Preparative Example 13 tert-butyl (4-bromothiazol-2-yl)(4-methoxybenzyl)carbamate

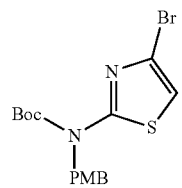

4-Methoxybenzyl chloride (2.72 mL, 20.09 mmol) was added to a solution of tert-butyl (4-bromothiazol-2-yl)carbamate (5.10 g, 18.26 mmol) and Cs$_2$CO$_3$ (11.90 g, 36.53 mmol) in DMF (40 mL) and the mixture was stirred at 80° C. for 1 h. The reaction mixture was cooled to 25° C., quenched with water (100 mL), and extracted with EtOAc (3×300 mL). The organic extracts were dried over MgSO$_4$, filtered, and concentrated under reduced pressure. The residue was purified by column chromatography (hexane:EtOAc; 1:0 to 9.5:0.5) to afford the product (7.20 g, 99%) as a pale yellow wax.

$^1$H NMR (500 MHz, CDCl$_3$) δ (ppm) 7.36-7.31 (m, 2H), 6.85-6.81 (m, 2H), 6.81 (s, 1H), 5.21 (s, 2H), 3.78 (s, 3H), 1.52 (s, 9H);

$^{13}$C NMR (126 MHz, CDCl$_3$) δ (ppm) 161.9, 159.1, 153.0, 129.7, 129.6, 120.5, 113.8, 112.1, 84.1, 55.4, 49.7, 28.3;

HRMS calcd for C$_{16}$H$_{20}$BrN$_2$O$_3$S [M+H]$^+$ 401.0353, found 401.0359.

Preparative Example 14 tert-butyl (4-methoxybenzyl)(4-(4-(trifluoromethyl)pyridin-2-yl)thiazol-2-yl)carbamate

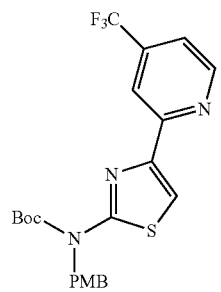

According to General procedure F, tert-butyl (4-methoxybenzyl)(4-(4,4,5,5-tetramethyl-1,3,2-dioxaborolan-2-yl)thiazol-2-yl)carbamate was prepared from n-BuLi (1.6 M in hexane, 0.82 mL, 2.50 mmol), tert-butyl (4-bromothiazol-2-yl)(4-methoxybenzyl)carbamate (0.500 g, 1.25 mmol), and 2-isopropoxy-4,4,5,5-tetramethyl-1,3,2-dioxaborolane (0.383 mL, 1.87 mmol) in THF (8 mL); the reaction time was 1 h at −78° C. The crude product was obtained as a pale-yellow wax (0.558 g, 1.25 mmol) and used as such in the next step.

tert-butyl (4-methoxybenzyl)(4-(4-(trifluoromethyl)pyridin-2-yl)thiazol-2-yl)carbamate was prepared from tert-butyl (4-methoxybenzyl)(4-(4,4,5,5-tetramethyl-1,3,2-dioxaborolan-2-yl)thiazol-2-yl)carbamate (0.558 g, 1.25 mmol), 2-bromo-4-(trifluoromethyl)pyridine (0.310 g, 1.37 mmol), K$_3$PO$_4$ (0.796 g, 3.75 mmol), Pd(dppf)Cl$_2$ (0.91 g, 0.125 mmol) and DME/H$_2$O (12 and 3 mL respectively); the reaction time was 3 h at 80° C. The product, purified by column chromatography (hexane:EtOAc; 1:0 to 9:1), was obtained as a colorless wax (0.350 g, 60%).

$^1$H NMR (500 MHz, CDCl$_3$) δ (ppm) 8.74 (d, J=5.04 Hz, 1H), 8.25 (d, J=1.57 Hz, 1H), 7.81 (s, 1H), 7.42-7.36 (m, 3H), 6.87-6.82 (m, 2H), 5.34 (s, 2H), 3.78 (s, 3H), 1.57 (s, 9H);

$^{13}$C NMR (126 MHz, CDCl$_3$) δ (ppm) 161.7, 159.1, 154.4, 150.3, 148.3, 139.2, 130.1, 129.6, 124.2 (q, $^1J_{C-F}$=272.6 Hz), 122.1, 117.7 (d, J=3.64 Hz), 116.6, 114.3, 113.9, 83.9, 55.4, 50.1, 28.4;

$^{19}$F NMR (471 MHz, CDCl$_3$) δ (ppm) −64.96;

HRMS calcd for C$_{22}$H$_{23}$F$_3$N$_3$O$_3$S [M+H]$^+$ 466.1407, found 466.1409.

Preparative Example 15

4-phenylthiazol-2-amine

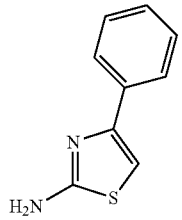

The compound was prepared according to General procedure B from 2-bromoacetophenone (3.21 g, 16.15 mmol) and thiourea (1.84 g, 24.22 mmol) in EtOH (20 mL). Work-up 2 of General procedure B.

The product was obtained as a white solid (2.82 g, 99%).

$^1$H NMR (500 MHz, DMSO-d$_6$) δ (ppm) 7.79 (d, J=7.3 Hz, 2H), 7.40-7.31 (m, 2H), 7.29-7.21 (m, 1H), 7.01 (s, 2H), 6.99 (s, 1H).

Preparative Example 16

5-bromo-4-phenylthiazol-2-amine

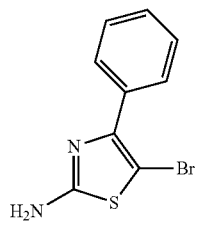 [SMILES: Nc1nc(-c2ccccc2)c(Br)s1]

A solution of NBS (1.062 g, 5.97 mmol) in CH$_2$Cl$_2$ (15 mL) was added to a solution of 4-phenylthiazol-2-amine (1.052 g, 5.97 mmol) in CH$_2$Cl$_2$ (50 mL) and the mixture was stirred at 25° C. for 2 h. A saturated aqueous solution of NH$_4$Cl (25 mL) was added to the mixture, the organic phase was separated, washed with water (25 mL), brine (25 mL), dried over MgSO$_4$, filtered, and the solvent was evaporated in vacuo. The residue was purified by column chromatography (hexane:EtOAc; 1:0 to 1:1). The product was obtained as a pale purple solid (1.211 g, 80%).

$^1$H NMR (500 MHz, DMSO-d$_6$) δ (ppm) 7.83-7.78 (m, 2H), 7.45-7.39 (m, 2H), 7.38-7.32 (m, 1H), 7.28 (s, 2H);

$^{13}$C NMR (126 MHz, DMSO-d$_6$) δ (ppm) 166.9, 147.2, 133.7, 128.1, 127.9, 87.0;

HRMS calcd for C$_9$H$_8$BrN$_2$S [M+H]$^+$ 256.9565, found 256.9565.

Preparative Example 17

4-(4-bromophenyl)thiazol-2-amine

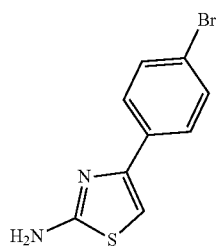 [SMILES: Nc1nc(-c2ccc(Br)cc2)cs1]

The compound was prepared according to General procedure B from 2,4'-dibromoacetophenone (2.07 g, 7.45 mmol) and thiourea (0.85 g, 11.17 mmol) in EtOH (20 mL). Work-up 1 of General procedure B. The product, obtained as a yellow solid (1.895 g, 100%), did not require any further purification.

$^1$H NMR (500 MHz, DMSO-d$_6$) δ (ppm) 7.78-7.70 (m, 2H), 7.58-7.50 (m, 2H), 7.07 (s, 1H), 7.06 (s, 1H);

$^{13}$C NMR (126 MHz, DMSO-d$_6$) δ (ppm) 168.3, 148.6, 134.1, 131.3, 127.5, 120.0, 102.4;

HRMS calcd for C$_9$H$_8$BrN$_2$S [M+H]$^+$ 256.9565, found 256.9565.

Preparative Example 18

4-(2-aminothiazol-4-yl)benzonitrile

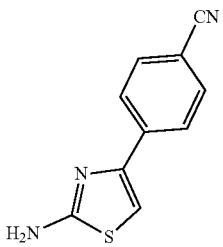 [SMILES: N#Cc1ccc(-c2csc(N)n2)cc1]

The compound was prepared according to General procedure B from 4-(2-bromoacetyl)benzonitrile (0.5 g, 2.23 mmol) and thiourea (190 mg, 4.45 mmol) in EtOH (3 ml).

Work-up 2 of General procedure B. The product was obtained as a white solid (375 mg, 84%).

¹H NMR (500 MHz, DMSO-d₆) δ (ppm) 8.00-7.93 (m, 2H), 7.83-7.78 (m, 2H), 7.32 (s, 1H), 7.16 (s, 2H);

¹³C NMR (126 MHz, DMSO-d₆) δ (ppm) 168.4, 148.1, 138.9, 132.5, 126.1, 119.0, 109.1, 105.5;

HRMS calcd for $C_{10}H_8N_3S$ [M+H]⁺ 202.0433, found 202.0432.

Preparative Example 19

4-(4-(trifluoromethyl)phenyl)thiazol-2-amine

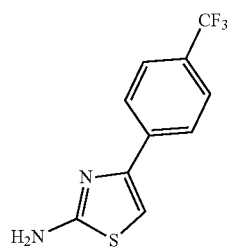 [SMILES: Nc1nc(-c2ccc(C(F)(F)F)cc2)cs1]

The compound was prepared according to General procedure B from 2-bromo-4'-(trifluoromethyl)acetophenone (0.302 g, 1.131 mmol) and thiourea (0.129 g, 1.7 mmol) in EtOH (5 mL). Work-up 1 of General procedure B. The product, obtained as a white solid (0.267 g, 97%), did not require any further purification.

¹H NMR (500 MHz, DMSO-d₆) δ (ppm) 8.00 (d, J=8.1 Hz, 2H), 7.71 (d, J=8.4 Hz, 2H), 7.24 (s, 1H), 7.13 (s, 2H);

¹³C NMR (126 MHz, DMSO-d₆) δ (ppm) 168.4, 148.3, 138.5, 127.1 (q, J=31.8 Hz), 126.0, 125.4 (q, J=4.0 Hz), 124.4 (q, J=271.6 Hz), 104.3;

¹⁹F NMR (471 MHz, DMSO-d₆) δ (ppm) −60.83;

HRMS calcd for $C_{10}H_8F_3N_2S$ [M+H]⁺ 245.0355, found 245.0354.

Preparative Example 20

4-(p-tolyl)thiazol-2-amine

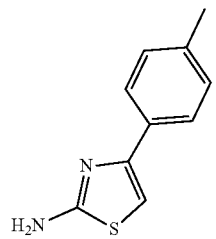

The compound was prepared according to General procedure B from 2-bromo-4'-methylacetophenone (0.598 g, 2.8 mmol) and thiourea (0.32 g, 4.21 mmol) in EtOH (6 mL). Work-up 1 of General procedure B. The product, obtained as a pale yellow solid (0.534 g, 100%), did not require any further purification.

¹H NMR (500 MHz, DMSO-d₆) δ (ppm) 7.68 (d, J=8.3 Hz, 2H), 7.16 (d, J=8.2 Hz, 2H), 6.98 (s, 2H), 6.90 (s, 1H), 2.30 (s, 3H);

¹³C NMR (126 MHz, DMSO-d₆) δ (ppm) 168.0, 149.9, 136.3, 132.3, 129.0, 125.4, 101.0, 20.7;

HRMS calcd for $C_{10}H_{11}N_2S$ [M+H]⁺ 191.0637, found 191.0636.

Preparative Example 21

4-phenyl-5-(p-tolyl)thiazol-2-amine

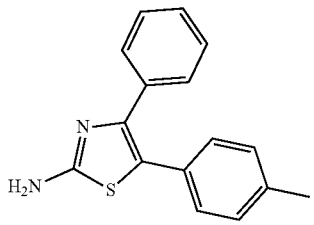 [SMILES: Cc1ccc(-c2sc(N)nc2-c2ccccc2)cc1]

2-bromo-1-phenyl-2-(p-tolyl)ethan-1-one was prepared according to General procedure A1 from 1-phenyl-2-(p-tolyl)ethan-1-one (1.00 g, 4.76 mmol) and Br₂ (0.76 g, 240 µL, 4.76 mmol) in CH₂Cl₂ (10 mL). The crude intermediate (2-bromo-1-phenyl-2-(p-tolyl)ethan-1-one) was obtained as a white solid (1.32 g, 99%) and used as such in the next step.

4-phenyl-5-(p-tolyl)thiazol-2-amine was prepared according to General procedure B from 2-bromo-1-phenyl-2-(p-tolyl)ethan-1-one (1.00 g, 3.57 mmol) and thiourea (0.54 g, 7.14 mmol) in EtOH (10 mL). Work-up 2 of General procedure B. The product was obtained as a white solid (1.06 g, 85%).

¹H NMR (500 MHz, DMSO-d₆) δ (ppm) 7.40-7.36 (m, 2H), 7.28-7.18 (m, 3H), 7.10 (s, 4H), 7.05 (s, 2H), 2.28 (s, 3H);

¹³C NMR (126 MHz, DMSO-d₆) δ (ppm) 165.8, 144.4, 136.3, 135.5, 129.8, 129.2, 128.8, 128.3, 127.9, 127.1, 119.2, 20.7;

HRMS calcd for $C_{16}H_{15}N_2S$ [M+H]⁺ 267.0950, found 267.0951.

Preparative Example 22

4-(4-(trifluoromethoxy)phenyl)thiazol-2-amine

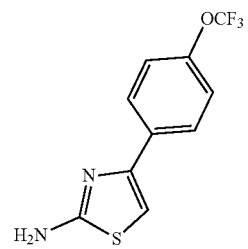 [SMILES: Nc1nc(-c2ccc(OC(F)(F)F)cc2)cs1]

The compound was prepared according to General procedure B from 2-bromo-4'-(trifluoromethoxy)acetophenone (0.26 g, 0.918 mmol) and thiourea (0.105 g, 1.38 mmol) in EtOH (6 mL). Work-up 1 of General procedure B. The product, obtained as a white solid (0.227 g, 95%), did not require any further purification.

¹H NMR (500 MHz, DMSO-d₆) δ (ppm) 7.91 (d, J=8.9 Hz, 2H), 7.39-7.31 (m, 2H), 7.14-7.03 (m, 3H);

$^{13}$C NMR (126 MHz, DMSO-d$_6$) δ (ppm) 168.4, 148.4, 147.2, 134.2, 127.2, 121.0, 120.1 (q, J=255.7 Hz), 102.5;
$^{19}$F NMR (471 MHz, DMSO-d$_6$) δ (ppm) −56.74;
HRMS calcd for C$_{10}$H$_8$F$_3$N$_2$OS [M+H]$^+$ 261.0304, found 261.0303.

Preparative Example 23

4-([1,1'-biphenyl]-3-yl)thiazol-2-amine

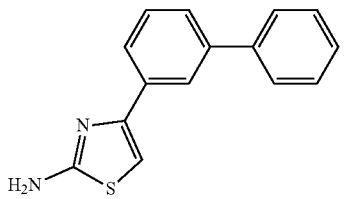 [SMILES: Nc1nc(-c2cccc(-c3ccccc3)c2)cs1]

1-([1,1'-biphenyl]-3-yl)-2-bromoethan-1-one was prepared according to General procedure A1 from 1-([1,1'-biphenyl]-3-yl)ethan-1-one (0.5 g, 3.16 mmol) and Br$_2$ (0.50 g, 160 μL, 3.16 mmol) in CH$_2$Cl$_2$ (10 mL). The crude intermediate (1-([1,1'-biphenyl]-3-yl)-2-bromoethan-1-one) was obtained as a white solid (870 mg, 100%) and used as such in the next step.

4-([1,1'-biphenyl]-3-yl)thiazol-2-amine was prepared according to General procedure B from 1-([1,1'-biphenyl]-3-yl)-2-bromoethan-1-one (870 mg, 3.16 mmol) and thiourea (360 mg, 4.74 mmol) in EtOH (10 mL). Work-up 2 of General procedure B. The product was obtained as a pale yellow wax (0.60 g, 75%).

$^1$H NMR (500 MHz, DMSO-d$_6$) δ (ppm) 8.10-8.08 (m, 1H), 7.80-7.77 (m, 1H), 7.72-7.65 (m, 2H), 7.56-7.53 (m, 1H), 7.51-7.44 (m, 3H), 7.41-7.36 (m, 1H), 7.14 (s, 1H), 7.06 (s, 2H);
$^{13}$C NMR (126 MHz, DMSO-d$_6$) δ (ppm) 168.2, 149.7, 140.4, 140.2, 135.5, 129.1, 128.9, 127.5, 126.7, 125.5, 124.9, 123.9, 102.0;
HRMS calcd for C$_{15}$H$_{13}$N$_2$S [M+H]$^+$ 253.0794, found 253.0795.

Preparative Example 24

4,5-diphenylthiazol-2-amine

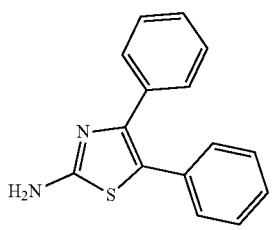 [SMILES: Nc1nc(-c2ccccc2)c(-c2ccccc2)s1]

A mixture of dioxane and water (2.0+0.5 mL) was added to a mixture of 5-bromo-4-phenylthiazol-2-amine (0.116 g, 0.455 mmol), phenylboronic acid (0.069 g, 0.568 mmol), K$_2$CO$_3$ (0.251 g, 1.82 mmol) and Pd(PPh$_3$)$_4$ (0.026 g, 0.023 mmol). The reaction mixture was degassed by bubbling N$_2$ for 5 min, then it was stirred at 55° C. for 5 h and then at 75° C. for 16 h. The mixture was cooled to 25° C., diluted with EtOAc (5 mL), poured into a saturated aqueous solution of NH$_4$Cl (20 mL) and extracted with EtOAc (3×25 mL). The combined organic extracts were washed with water (20 mL) and brine (20 mL), dried over MgSO$_4$, filtered, and the solvent was evaporated in vacuo. The residue was purified by column chromatography (hexane:EtOAc; 1:0 to 1:1) to afford the product as a white solid (0.035 g, 30%).

$^1$H NMR (500 MHz, DMSO-d$_6$) δ (ppm) 7.39-7.35 (m, 2H), 7.31-7.18 (m, 8H), 7.09 (s, 2H);
$^{13}$C NMR (126 MHz, DMSO-d$_6$) δ (ppm) 166.0, 144.9, 135.4, 132.8, 128.9, 128.6, 128.4, 128.0, 127.2, 127.0, 119.0;
HRMS calcd for C$_{15}$H$_{13}$N$_2$S [M+H]$^+$ 253.0794, found 253.0793.

Preparative Example 25

4-(4-(tert-butyl)phenyl)thiazol-2-amine

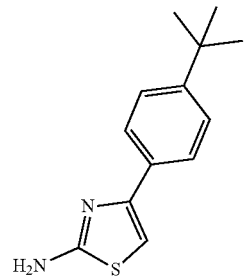 [SMILES: CC(C)(C)c1ccc(-c2csc(N)n2)cc1]

The compound was prepared according to General procedure B from 1-(4-tert-butylphenyl)-2-chloroethane (0.230 g, 1.092 mmol), thiourea (0.125 g, 1.637 mmol) in EtOH (4 mL). Work-up 1 of General procedure B. The residue was purified by column chromatography (hexane:EtOAc; 1:0 to 2:1) to afford the product as a colorless solid (0.227 g, 89%).

$^1$H NMR (500 MHz, DMSO-d$_6$) δ (ppm) 7.73-7.68 (m, 2H), 7.40-7.34 (m, 2H), 6.99 (s, 2H), 6.90 (s, 1H), 1.29 (s, 9H);
$^{13}$C NMR (126 MHz, DMSO-d$_6$) δ (ppm) 168.1, 149.9, 149.5, 132.3, 125.2, 125.1, 100.6, 34.2, 31.1;
HRMS calcd for C$_{13}$H$_{17}$N$_2$S [M+H]$^+$ 233.1107, found 233.1107.

Preparative Example 26

4-(naphthalen-2-yl)thiazol-2-amine

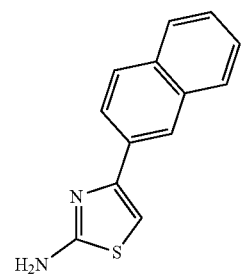 [SMILES: Nc1nc(-c2ccc3ccccc3c2)cs1]

The compound was prepared according to General procedure B from 2-bromo-2'-acetophenone (0.967 g, 3.88 mmol) and thiourea (0.443 g, 5.82 mmol) in EtOH (5 mL). Work-up 1 of General procedure B. The product was obtained as a pale pink solid (0.747 g, 85%) and did not require any additional purification.

$^1$H NMR (500 MHz, DMSO-d$_6$) δ (ppm) 8.32 (d, J=1.8 Hz, 1H), 7.99-7.84 (m, 4H), 7.55-7.43 (m, 2H), 7.16 (s, 1H), 7.09 (s, 2H);

$^{13}$C NMR (126 MHz, DMSO-d$_6$) δ (ppm) 168.2, 149.8, 133.2, 132.3, 132.2, 128.0, 127.8, 127.5, 126.3, 125.7, 124.0, 124.0, 102.4;

HRMS calcd for $C_{13}H_{11}N_2S$ [M+H]$^+$ 227.0637, found 227.0636.

Preparative Example 27

4-(thiophen-3-yl)thiazol-2-amine

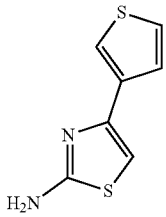

The compound was prepared according to General procedure B from 2-bromo-1-(thiophen-3-yl)ethan-1-one (0.31 g, 1.5 mmol) and thiourea (170 mg, 2.25 mmol) in EtOH (3 mL). Workup 2 of General procedure B. The product was obtained as a white solid (246 mg, 90%).

$^1$H NMR (500 MHz, DMSO-d$_6$) δ (ppm) 7.61 (dd, J=3.0, 1.3 Hz, 1H), 7.51 (dd, J=5.0, 3.0 Hz, 1H), 7.45 (dd, J=5.0, 1.2 Hz, 1H), 7.00 (s, 2H), 6.83 (s, 1H);

$^{13}$C NMR (126 MHz, DMSO-d$_6$) δ (ppm) 168.1, 146.3, 137.3, 126.4, 125.8, 120.7, 101.0;

HRMS calcd for $C_7H_7N_2S_2$[M+H]$^+$ 183.0045, found 183.0045.

Preparative Example 28

5-cyclohexyl-4-phenylthiazol-2-amine

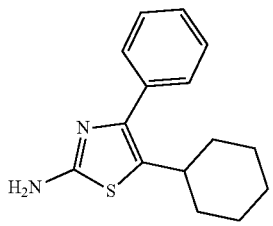 [SMILES: Nc1nc(-c2ccccc2)c(C2CCCCC2)s1]

2-bromo-2-cyclohexyl-1-phenylethan-1-one: the compound was prepared according to General procedure A1 from 2-bromo-2-cyclohexyl-1-phenylethan-1-one (0.6 g, 2.97 mmol) and Br$_2$ (0.47 g, 150 µL, 2.97 mmol) in CH$_2$Cl$_2$ (10 mL). The crude product (2-bromo-2-cyclohexyl-1-phenylethan-1-one) was obtained as a yellow solid (670 mg, 80%) and used as such in the next step.

5-cyclohexyl-4-phenylthiazol-2-amine was prepared according to General procedure B with 2-bromo-2-cyclohexyl-1-phenylethan-1-one (560 mg, 2.0 mmol), thiourea (340 mg, 4.46 mmol) in EtOH (10 mL). Work-up 2 of General procedure B. The product was obtained as a white solid (250 mg, 33%).

$^1$H NMR (500 MHz, DMSO-d$_6$) δ (ppm) 7.47-7.43 (m, 2H), 7.42-7.37 (m, 2H), 7.33-7.27 (m, 1H), 6.84 (s, 2H), 2.90-2.81 (m, 1H), 1.93-1.84 (m, 2H), 1.76-1.68 (m, 2H), 1.64 (d, J=11.7 Hz, 1H), 1.37-1.13 (m, 5H);

$^{13}$C NMR (126 MHz, DMSO-d$_6$) δ (ppm) 164.7, 135.6, 128.2, 128.1, 127.9, 127.0, 115.7, 36.5, 35.9, 26.0, 25.2;

HRMS calcd for $C_{15}H_{19}N_2S$ [M+H]$^+$ 259.1263, found 259.1263.

Preparative Example 29

4-(4-methylthiophen-3-yl)thiazol-2-amine

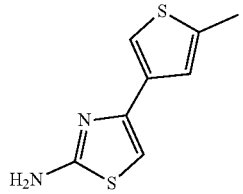

2-bromo-1-(4-methylthiophen-3-yl)ethan-1-one was prepared according to General procedure A2 from 1-(4-methylthiophen-3-yl)ethan-1-one (0.325 g, 2.32 mmol) and CuBr$_2$ (1.04 g, 4.64 mmol) in CHCl$_3$ (2 mL) and EtOAc (2 mL). The crude intermediate was used as such in the next step.

4-(4-methylthiophen-3-yl)thiazol-2-amine was prepared according to General procedure B from 2-bromo-1-(4-methylthiophen-3-yl)ethan-1-one (508 mg, 2.32 mmol) and thiourea (270 mg, 3.48 mmol) in EtOH (5 mL). Work-up 2 of General procedure B. The product was obtained as a white solid (320 mg, 70%).

$^1$H NMR (500 MHz, DMSO-d$_6$) δ (ppm) 7.18 (s, 1H), 7.08 (s, 2H), 6.96 (s, 1H), 6.77 (s, 1H), 2.19 (s, 3H);

$^{13}$C NMR (126 MHz, DMSO-d$_6$) δ (ppm) 168.1, 144.6, 138.8, 137.5, 124.8, 119.9, 99.4, 15.4;

HRMS calcd for $C_8H_9N_2S_2$ [M+H]$^+$ 197.0202, found 197.0198.

Preparative Example 30

4-(5,6,7,8-tetrahydronaphthalen-2-yl)thiazol-2-amine

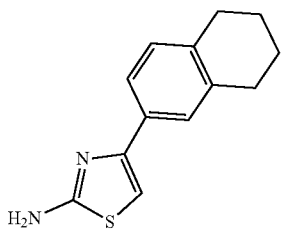 [SMILES: Nc1nc(-c2ccc3c(c2)CCCC3)cs1]

2-bromo-1-(4-cyclohexylphenyl)ethan-1-one was prepared according to General procedure A2 from 1-(4-cyclohexylphenyl)ethan-1-one (0.53 g, 2.6 mmol) and CuBr$_2$ (1.2 g, 5.25 mmol) in CHCl$_3$ (3 mL) and EtOAc (3 mL). The crude intermediate was used as such in the next step.

4-(4-cyclohexylphenyl)thiazol-2-amine was prepared according to General procedure B from 2-bromo-1-(4-cyclohexylphenyl)ethan-1-one (730 mg, 2.6 mmol) and thiourea (300 mg, 3.9 mmol) in EtOH (5 mL). Work-up 2 of General procedure B. The product was obtained as a white solid (420 mg, 60%), and did not require any further purification.

$^1$H NMR (500 MHz, DMSO-d$_6$) δ (ppm) 7.72-7.66 (m, 2H), 7.23-7.17 (m, 2H), 6.98 (s, 2H), 6.89 (s, 1H), 2.47 (d, J=7.9 Hz, 1H), 1.85-1.75 (m, 5H), 1.48-1.30 (m, 5H);

$^{13}$C NMR (126 MHz, DMSO-d$_6$) δ (ppm) 168.0, 149.9, 146.5, 132.7, 126.6, 125.5, 100.5, 43.4, 33.8, 26.3, 25.6;

HRMS calcd for C$_{13}$H$_{15}$N$_2$[M+H]$^+$ 231.0950, found 231.0946.

Preparative Example 31

4-(4-cyclohexylphenyl)thiazol-2-amine

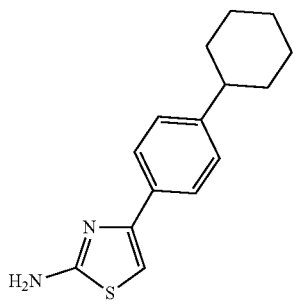 [SMILES: Nc1nc(-c2ccc(C3CCCCC3)cc2)cs1]

2-bromo-1-(4-cyclohexylphenyl)ethan-1-one was prepared according to General procedure A2 from 1-(4-cyclohexylphenyl)ethan-1-one (0.53 g, 2.6 mmol) and CuBr$_2$ (1.2 g, 5.25 mmol) in CHCl$_3$ (3 mL) and EtOAc (3 mL). The crude intermediate was used as such in the next step.

4-(4-cyclohexylphenyl)thiazol-2-amine was prepared according to General procedure B from 2-bromo-1-(4-cyclohexylphenyl)ethan-1-one (730 mg, 2.6 mmol) and thiourea (300 mg, 3.9 mmol) in EtOH (5 mL). Work-up 2 of General procedure B. The product was obtained as a white solid (420 mg, 60%) and did not require any further purification.

$^1$H NMR (500 MHz, DMSO-d$_6$) δ (ppm) 7.72-7.66 (m, 2H), 7.23-7.17 (m, 2H), 6.98 (s, 2H), 6.89 (s, 1H), 2.47 (d, J=7.9 Hz, 1H), 1.85-1.75 (m, 5H), 1.48-1.30 (m, 5H);

$^{13}$C NMR (126 MHz, DMSO-d$_6$) δ (ppm) 168.0, 149.9, 146.5, 132.7, 126.6, 125.5, 100.5, 43.4, 33.8, 26.3, 25.6;

HRMS calcd for C$_{15}$H$_{19}$N$_2$S [M+H]$^+$ 259.1263, found 259.1258.

Preparative Example 32

4-(pyridin-2-yl)thiazol-2-amine

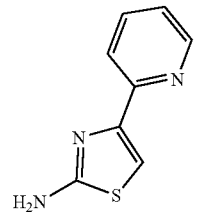 [SMILES: Nc1nc(-c2ccccn2)cs1]

2-bromo-1-(pyridin-2-yl)ethan-1-one was prepared according to General procedure A4 from 2-acetylpyridine (1.0 g, 8.25 mmol), HBr (47% in H$_2$O, 4.26 mL, 24.7 mmol), Br$_2$ (0.636 mL, 12.38 mmol) in acetic acid (20.0 mL); the reaction time was 16 h. Work-up 1 of General procedure A4. The crude product was obtained as a pale yellow solid (1.25 g, 6.24 mmol, 76%) and used as such in the next step.

4-(pyridin-2-yl)thiazol-2-amine was prepared according to General procedure B from 2-bromo-1-(pyridin-2-yl)ethan-1-one (1.22 g, 4.34 mmol) and thiourea (0.495 g, 6.51 mmol) in EtOH (18 ml). Work-up 1 of General procedure B. The product, purified by column chromatography (hexane:EtOAc; 1:1 to 0:1), was obtained as a light green solid (0.3 g, 39%).

$^1$H NMR (500 MHz, DMSO-d$_6$) δ (ppm) 8.53 (dt, J=4.69, 1.38 Hz, 1H), 7.85-7.77 (m, 2H), 7.28-7.22 (m, 2H), 7.08 (s, 2H);

$^{13}$C NMR (126 MHz, DMSO-d$_6$) δ (ppm) 168.4, 152.4, 150.1, 149.2, 136.9, 122.1, 120.0, 105.3;

HRMS calcd for C$_8$H$_8$N$_3$S [M+H]$^+$ 178.0433, found 178.0435.

Preparative Example 33

4-(6-methylpyridin-2-yl)thiazol-2-amine

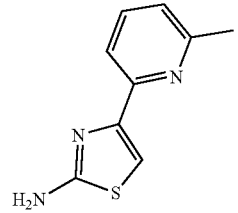

2-bromo-1-(6-methylpyridin-2-yl)ethan-1-one was prepared according to General procedure A4 from 2-acetyl-6-methylpyridine (0.350 g, 2.58 mmol), HBr (47% in H$_2$O, 0.897 mL, 7.76 mmol), and Br$_2$ (0.20 mL, 3.886 mmol) in acetic acid (8 mL); the reaction time was 24 h. Work-up 2 of General procedure A4. The crude intermediate 2-bromo-1-(6-methylpyridin-2-yl)ethan-1-one was obtained as a yellow solid (800 mg, 3.737 mmol) and used as such in the next step.

4-(6-methylpyridin-2-yl)thiazol-2-amine was prepared according to General procedure B from 2-bromo-1-(6-methylpyridin-2-yl)ethan-1-one (800 mg, 3.73 mmol) and thiourea (426 mg, 5.60 mmol) in EtOH (15 mL). Work-up 1 of General procedure B. The product, purified by column chromatography (hexane:EtOAc; 1:1 to 0:1), was obtained as a light green solid (260 mg, 53%).

$^1$H NMR (500 MHz, DMSO-d$_6$) δ (ppm) 7.68 (t, J=7.65 Hz, 1H), 7.62 (d, J=7.60 Hz, 1H), 7.18 (s, 1H), 7.11 (dd, J=7.54, 1.08 Hz, 1H), 7.04 (s, 2H), 2.47 (s, 3H);

$^{13}$C NMR (126 MHz, DMSO-d$_6$) δ (ppm) 168.2, 157.3, 151.8, 150.2, 137.0, 121.5, 117.2, 105.0, 24.2;

HRMS calcd for C$_9$H$_{10}$N$_3$S [M+H]$^+$ 192.0590, found 192.0592.

Preparative Example 34

4-(2-(trifluoromethyl)phenyl)thiazol-2-amine

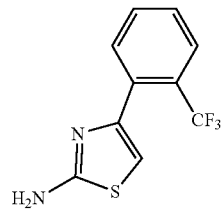 [SMILES: Nc1nc(-c2ccccc2C(F)(F)F)cs1]

2-bromo-1-(2-(trifluoromethyl)phenyl)ethan-1-one was prepared according to General procedure A2 from 1-(2-(trifluoromethyl)phenyl)ethan-1-one (0.54 g, 2.87 mmol) and CuBr$_2$ (1.3 g, 5.74 mmol) in CHCl$_3$ (3 mL) and EtOAc (3 mL). The crude product was used as such in the next step.

4-(2-(trifluoromethyl)phenyl)thiazol-2-amine was prepared according to General procedure B from 2-bromo-1-(2-(trifluoromethyl)phenyl)ethan-1-one (766 mg, 2.87 mmol) and thiourea (330 mg, 4.3 mmol) in EtOH (3 mL). Work-up 1 of General procedure B. The product, purified by column chromatography (hexane:EtOAc; 7:3), was obtained as a white solid (550 mg, 80%).

$^1$H NMR (500 MHz, DMSO-d$_6$) δ (ppm) 7.79-7.74 (m, 1H), 7.69-7.64 (m, 1H), 7.60 (d, J=8.3 Hz, 1H), 7.57-7.50 (m, 1H), 6.99 (s, 2H), 6.57 (s, 1H);

$^{13}$C NMR (126 MHz, DMSO-d$_6$) δ (ppm) 167.6, 147.4, 135.1, 132.0, 131.8, 128.0, 126.6 (q, J=29.9 Hz), 126.1 (q, J=5.5 Hz), 124.1 (q, J=273.4 Hz), 104.9 (q, J=5.9, 2.6 Hz);

$^{19}$F NMR (471 MHz, DMSO-d$_6$) δ (ppm) −56.35;

HRMS calcd for C$_{10}$H$_8$F$_3$N$_2$S [M+H]$^+$ 245.0355, found 245.0353.

Preparative Example 35

4-(3,4-dichlorophenyl)thiazol-2-amine

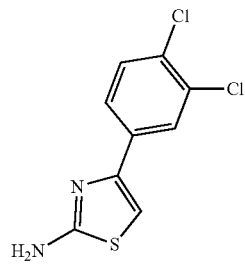 [SMILES: Nc1nc(-c2ccc(Cl)c(Cl)c2)cs1]

2-bromo-1-(3,4-dichlorophenyl)ethan-1-one was prepared according to General procedure A2 from 1-(3,4-dichlorophenyl)ethan-1-one (0.5 g, 2.6 mmol) and CuBr$_2$ (1.2 g, 5.2 mmol) in CHCl$_3$ (3 mL) and EtOAc (3 mL). The crude product was used as such in the next step.

4-(3,4-dichlorophenyl)thiazol-2-amine was prepared according to General procedure B from 2-bromo-1-(3,4-dichlorophenyl)ethan-1-one (700 mg, 2.6 mmol) and thiourea (300 mg, 3.9 mmol) in EtOH (3 mL). Work-up 2 of General procedure B. The product was obtained as a white solid (326 mg, 50%) and did not require any further purification.

$^1$H NMR (500 MHz, DMSO-d$_6$) δ (ppm) 8.01 (d, J=2.0 Hz, 1H), 7.77 (dd, J=8.4, 2.0 Hz, 1H), 7.64-7.58 (m, 1H), 7.21 (d, J=1.4 Hz, 1H), 7.12 (s, 2H);

$^{13}$C NMR (126 MHz, DMSO-d$_6$) δ (ppm) 168.4, 147.2, 135.4, 131.2, 130.6, 129.2, 127.1, 125.5, 103.7;

HRMS calcd for C$_9$H$_5$Cl$_2$N$_2$S [M−H]$^-$ 242.9556, found 242.9553.

Preparative Example 36

4-(o-tolyl)thiazol-2-amine

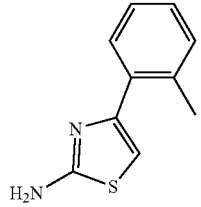

2-bromo-1-(o-tolyl)ethan-1-one was prepared according to General procedure A2 from 1-(o-tolyl)ethan-1-one (0.514 g, 3.83 mmol) and CuBr$_2$ (1.7 g, 7.66 mmol) in CHCl$_3$ (3 mL) and EtOAc (3 mL). The crude product was used as such in the next step.

4-(o-tolyl)thiazol-2-amine was prepared according to General procedure B from 2-bromo-1-(o-tolyl)ethan-1-one (815 mg, 3.83 mmol) and thiourea (440 mg, 5.7 mmol) in EtOH (3 mL). Work-up 2 of General procedure B. The product was obtained as a white solid (534 mg, 75%) and did not require any further purification.

$^1$H NMR (500 MHz, DMSO-d$_6$) δ (ppm) 7.59-7.52 (m, 1H), 7.25-7.15 (m, 3H), 6.94 (s, 2H), 6.59 (s, 1H), 2.41 (s, 3H);

$^{13}$C NMR (126 MHz, DMSO-d$_6$) δ (ppm) 167.2, 150.2, 135.1, 135.1, 130.6, 129.1, 127.1, 125.5, 104.1, 21.1;

HRMS calcd for C$_{10}$H$_{11}$N$_2$S [M+H]$^+$ 191.0637, found 191.0640.

Preparative Example 37

4-(3-chlorophenyl)thiazol-2-amine

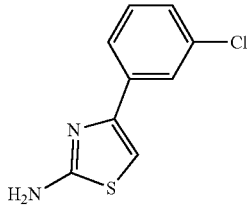 [SMILES: Nc1nc(-c2cccc(Cl)c2)cs1]

4-(3-chlorophenyl)thiazol-2-amine was prepared according to general procedure B from 2-bromo-1-(3-chlorophenyl)ethanone (300 mg, 1.285 mmol), thiourea (147 mg, 1.928 mmol) in EtOH (5 mL). Work-up 2 of General procedure B. The product was obtained as an off-white solid (238 mg, 88% yield).

$^1$H NMR (500 MHz, DMSO-d$_6$) δ (ppm) 7.83 (t, J=1.9 Hz, 1H), 7.75 (dt, J=7.8, 1.3 Hz, 1H), 7.39 (t, J=7.9 Hz, 1H), 7.30 (ddd, J=7.9, 2.1, 1.1 Hz, 1H), 7.16 (s, 1H), 7.08 (s, 2H);

$^{13}$C NMR (126 MHz, DMSO-d$_6$) δ (ppm) 168.3, 148.2, 136.9, 133.3, 130.3, 126.8, 125.2, 123.9, 103.1;

HRMS calcd for C$_9$H$_8$ClN$_2$S [M+H]$^+$ 211.0091, found 211.0090.

Preparative Example 38

4-(4-methylpyridin-2-yl)thiazol-2-amine

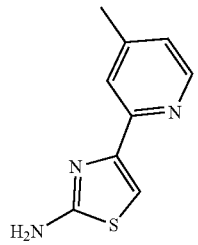

2-bromo-1-(4-methylpyridin-2-yl)ethan-1-one was prepared according to General procedure A3 from 1-(4-methylpyridin-2-yl)ethan-1-one (0.26 g, 1.93 mmol), Et$_3$N (0.23 g, 0.33 mL, 2.3 mmol), TMSOTf (0.47 g, 0.39 mL, 2.13 mmol) and NBS (0.4 g, 2.3 mmol) in CH$_2$Cl$_2$ (2 mL). The crude product was used as such in the next step.

4-(4-methylpyridin-2-yl)thiazol-2-amine was prepared according to General procedure B from 2-bromo-1-(4-methylpyridin-2-yl)ethan-1-one (413 mg, 1.93 mmol) and thiourea (220 mg, 2.8 mmol) in EtOH (3 mL). Work-up 2 of General procedure B. The product was obtained as a brown solid (170 mg, 50%).

$^1$H NMR (500 MHz, DMSO-d$_6$) δ (ppm) 8.37 (d, J=5.0 Hz, 1H), 7.67 (d, J=1.6 Hz, 1H), 7.21 (s, 1H), 7.08 (dd, J=5.0, 1.5 Hz, 1H), 7.05 (s, 2H), 2.33 (s, 3H);

$^{13}$C NMR (126 MHz, DMSO-d$_6$) δ (ppm) 168.3, 152.3, 150.2, 149.0, 147.4, 122.9, 120.9, 105.2, 20.6;

HRMS calcd for C$_9$H$_{10}$N$_3$S [M+H]$^+$ 192.0590, found 192.0593.

Preparative Example 39

4-(5-methylpyridin-2-yl)thiazol-2-amine

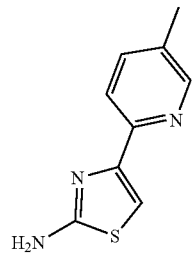

2-bromo-1-(5-methylpyridin-2-yl)ethan-1-one was prepared according to General procedure A3 from 1-(5-methylpyridin-2-yl)ethan-1-one (0.32 g, 2.33 mmol), Et$_3$N (0.26 g, 0.36 mL, 2.6 mmol), TMSOTf (0.57 g, 0.46 mL, 2.56 mmol) and NBS (0.46 g, 2.56 mmol) in CH$_2$Cl$_2$ (3 mL). The crude product was used as such in the next step.

4-(5-methylpyridin-2-yl)thiazol-2-amine was prepared according to General procedure B from 2-bromo-1-(5-methylpyridin-2-yl)ethan-1-one (0.5 g, 2.33 mmol) and thiourea (265 mg, 3.5 mmol) in EtOH (3 mL). Work-up 2 of General procedure B. The product was obtained as an orange solid (300 mg, 70%).

$^1$H NMR (500 MHz, DMSO-d$_6$) δ (ppm) 8.39-8.35 (m, 1H), 7.72 (d, J=7.9 Hz, 1H), 7.61 (dd, J=8.1, 2.2 Hz, 1H), 7.17 (s, 1H), 7.04 (s, 2H), 2.29 (s, 3H);

$^{13}$C NMR (126 MHz, DMSO-d$_6$) δ (ppm) 168.3, 150.2, 150.1, 149.5, 137.1, 131.3, 119.6, 104.3, 17.7;

HRMS calcd for C$_9$H$_{10}$N$_3$S [M+H]$^+$ 192.0590, found 192.0588.

Preparative Example 40

4-(4-isopropylphenyl)thiazol-2-amine

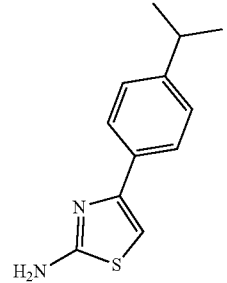

4-(4-isopropylphenyl)thiazol-2-amine was prepared according to General procedure B from 2-bromo-1-(4-isopropylphenyl)ethanone (360 mg, 1.492 mmol) and thiourea (171 mg, 2.240 mmol) in absolute EtOH (6 mL). Work-up 1 of General procedure B. The product, purified by column chromatography (hexane:EtOAc, 5:1 to 1:2), followed by another column chromatography (CH$_2$Cl$_2$:EtOAc, 10:1 to 8:1), was obtained as a brown solid (296 mg, 91% yield).

$^1$H NMR (500 MHz, DMSO-d$_6$) δ (ppm) 7.72-7.69 (m, 2H), 7.25-7.20 (m, 2H), 7.00 (s, 2H), 6.90 (s, 1H), 2.88 (hept, J=6.9 Hz, 1H), 1.21 (d, J=6.9 Hz, 6H);

$^{13}$C NMR (126 MHz, DMSO-d$_6$) δ (ppm) 168.0, 149.9, 147.3, 132.6, 126.3, 125.5, 100.6, 33.1, 23.8;

HRMS calcd for C$_{12}$H$_{15}$N$_2$S [M+H]$^+$ 219.0950, found 219.0948.

Preparative Example 41

4-(4-methoxypyridin-2-yl)thiazol-2-amine

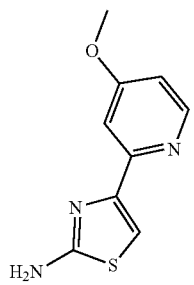

2-bromo-1-(4-methoxypyridin-2-yl)ethan-1-one was prepared according to General procedure A3 from 1-(4-methoxypyridin-2-yl)ethan-1-one (0.3 g, 2.0 mmol), Et$_3$N (0.25 g, 350 µL, 2.5 mmol), TMSOTf (0.51 g, 0.42 mL, 2.5 mmol) and NBS (0.45 g, 2.5 mmol) in CH$_2$Cl$_2$ (3 mL). The crude product was used as such in the next step.

4-(4-methoxypyridin-2-yl)thiazol-2-amine was prepared according to General procedure B from 2-bromo-1-(4-methoxypyridin-2-yl)ethan-1-one (0.46 g, 2.0 mmol) and thiourea (270 mg, 3.4 mmol) in EtOH (3 mL). Work-up 2 of General procedure B. The product was obtained as a white solid (260 mg, 65%).

$^1$H NMR (500 MHz, DMSO-d$_6$) δ (ppm) 8.34 (d, J=5.6 Hz, 1H), 7.37 (d, J=2.6 Hz, 1H), 7.23 (s, 1H), 7.10 (s, 2H), 6.83 (dd, J=5.6, 2.6 Hz, 1H), 3.84 (s, 3H);

$^{13}$C NMR (126 MHz, DMSO-d$_6$) δ (ppm) 168.3, 165.9, 154.1, 150.5, 150.0, 108.5, 105.7, 105.6, 55.1;

HRMS calcd for C$_9$H$_{10}$N$_3$OS [M+H]$^+$ 208.0539, found 208.0534.

Preparative Example 42

4-(5-methoxypyridin-2-yl)thiazol-2-amine

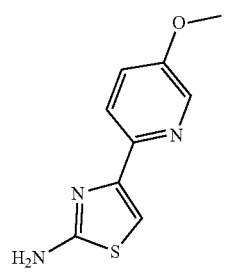

2-bromo-1-(5-methoxypyridin-2-yl)ethan-1-one was prepared according to General procedure A3 from 1-(5-methoxypyridin-2-yl)ethan-1-one (0.3 g, 2.0 mmol), Et$_3$N (0.24 g, 330 µL, 2.4 mmol), TMSOTf (0.53 g, 0.43 mL, 2.4 mmol) and NBS (0.43 g, 2.4 mmol) in CH$_2$Cl$_2$ (3 mL). The crude product was used as such in the next step.

4-(5-methoxypyridin-2-yl)thiazol-2-amine was prepared according to General procedure B from 2-bromo-1-(5-methoxypyridin-2-yl)ethan-1-one (0.46 g, 2.0 mmol) and thiourea (230 mg, 3.0 mmol) in EtOH (3 mL). Work-up 2 of General procedure B. The product was obtained as a white solid (200 mg, 50%).

$^1$H NMR (500 MHz, DMSO-d$_6$) δ (ppm) 8.25 (d, J=3.0 Hz, 1H), 7.77 (d, J=8.6 Hz, 1H), 7.40 (dd, J=8.7, 3.1 Hz, 1H), 7.04 (s, 1H), 7.02 (s, 2H), 3.84 (s, 3H);

$^{13}$C NMR (126 MHz, DMSO-d$_6$) δ (ppm) 168.9, 154.9, 150.4, 146.1, 137.7, 121.1, 103.4, 56.0;

HRMS calcd for C$_9$H$_{10}$N$_3$OS [M+H]$^+$ 208.0539, found 208.0536.

Preparative Example 43

4-(6-methoxypyridin-2-yl)thiazol-2-amine

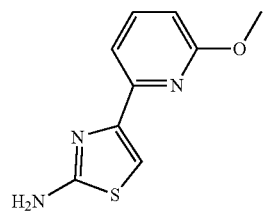

2-bromo-1-(6-methoxypyridin-2-yl)ethan-1-one was prepared according to General procedure A3 from 1-(6-methoxypyridin-2-yl)ethan-1-one (0.3 g, 2 mmol), Et$_3$N (0.25 g, 0.35 mL, 2.51 mmol), TMSOTf (0.51 g, 0.42 mL, 2.31 mmol) and NBS (0.45 g, 2.51 mmol) in CH$_2$Cl$_2$ (3 mL). The crude intermediate was used as such in the next step.

4-(6-methoxypyridin-2-yl)thiazol-2-amine was prepared according to General procedure B from 2-bromo-1-(6-methoxypyridin-2-yl)ethan-1-one (460 mg, 2 mmol) and thiourea (270 mg, 3.43 mmol) in EtOH (3 mL). Work-up 2 of General procedure B. The product was obtained as a pale yellow solid (320 mg, 80%).

$^1$H NMR (500 MHz, CDCl$_3$) δ (ppm) 7.61 (dd, J=8.2, 7.4 Hz, 1H), 7.49 (dd, J=7.4, 0.9 Hz, 1H), 7.34 (s, 1H), 6.66 (dd, J=8.2, 0.8 Hz, 1H), 5.09 (s, 2H), 4.00 (s, 3H);

$^{13}$C NMR (126 MHz, CDCl$_3$) δ (ppm) 167.4, 163.74 151.4, 150.2, 139.5, 113.6, 110.0, 107.5, 53.3;

HRMS calcd for C$_9$H$_{10}$N$_3$OS [M+H]$^+$ 208.0539, found 208.0549.

Preparative Example 44

4-(2,4-dichlorophenyl)thiazol-2-amine

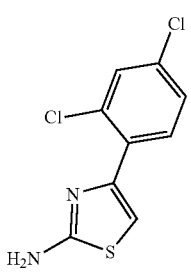 [SMILES: Nc1nc(-c2ccc(Cl)cc2Cl)cs1]

2-bromo-1-(2,4-dichlorophenyl)ethan-1-one was prepared according to General procedure A1 from 1-(2,4-dichlorophenyl)ethan-1-one (2.41 g, 12.75 mmol) and Br$_2$ (2.3 g, 735 µL, 12.75 mmol) in CH$_2$Cl$_2$ (15 ml). The crude product 2-bromo-1-(2,4-dichlorophenyl)ethan-1-one was obtained as a white solid and used as such in the next step.

4-(2,4-dichlorophenyl)thiazol-2-amine was prepared according to General procedure B from 2-bromo-1-(2,4-dichlorophenyl)ethan-1-one (3.4 g, 12.75 mmol) and thiourea (1.4 g, 19 mmol) in EtOH (15 mL). Work-up 2 of General procedure B. The product was obtained as a white solid (2.26 g, 75%).

$^{1}$H NMR (500 MHz, DMSO-d$_6$) δ (ppm) 7.88 (d, J=8.5 Hz, 1H), 7.64-7.60 (m, 1H), 7.48-7.41 (m, 1H), 7.10 (s, 1H), 7.08 (s, 2H);

$^{13}$C NMR (126 MHz, DMSO-d$_6$) δ (ppm) 167.2, 145.1, 132.3, 132.2, 132.0, 131.3, 129.6, 127.3, 106.9;

HRMS calcd for C$_9$H$_7$Cl$_2$N$_2$S [M+H]$^+$ 244.9702, found 244.9705.

Preparative Example 45

4-(3-fluoropyridin-2-yl)thiazol-2-amine

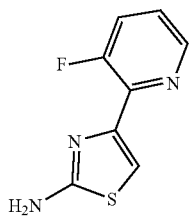

2-bromo-1-(3-fluoropyridin-2-yl)ethan-1-one was prepared according to General procedure A3 from 1-(3-fluoropyridin-2-yl)ethan-1-one (0.3 g, 2.15 mmol), Et$_3$N (0.26 g, 360 µL, 2.6 mmol), TMSOTf (0.53 g, 0.43 mL, 2.4 mmol) and NBS (0.46 g, 2.6 mmol) in CH$_2$Cl$_2$ (3 mL). The crude product was used as such in the next step.

4-(3-fluoropyridin-2-yl)thiazol-2-amine was prepared according to General procedure B from 2-bromo-1-(3-fluoropyridin-2-yl)ethan-1-one (0.47 g, 2.15 mmol) and thiourea (245 mg, 3.2 mmol) in EtOH (3 mL). Work-up 2 of General procedure B. The product was obtained as a white solid (260 mg, 60%).

$^{1}$H NMR (500 MHz, DMSO-d$_6$) δ (ppm) 8.44-8.38 (m, 1H), 7.72 (ddd, J=11.7, 8.3, 1.4 Hz, 1H), 7.41-7.35 (m, 1H), 7.19 (d, J=1.1 Hz, 1H), 7.09 (s, 2H);

$^{13}$C NMR (126 MHz, DMSO-d$_6$) δ (ppm) 167.9, 156.1 (d, J=262.4 Hz), 146.1 (d, J=7.3 Hz), 145.1 (d, J=5.3 Hz), 140.8 (d, J=9.9 Hz), 124.4 (d, J=20.0 Hz), 123.9 (d, J=4.3 Hz), 108.7 (d, J=7.1 Hz);

$^{19}$F NMR (282 MHz, DMSO-d$_6$) δ (ppm) −120.51;

HRMS calcd for C$_8$H$_7$FN$_3$OS [M+H]$^+$ 196.0339, found 196.0333.

Preparative Example 46

4-(2-fluoro-4-methoxyphenyl)thiazol-2-amine

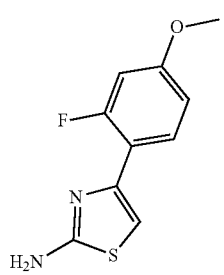

2-bromo-1-(2-fluoro-4-methoxyphenyl)ethan-1-one was prepared according to General procedure A1 from 1-(2-fluoro-4-methoxyphenyl)ethan-1-one (1 g, 6 mmol) and Br$_2$ (0.95 g, 300 µL, 6 mmol) in CH$_2$Cl$_2$ (5 mL). The crude product (2-bromo-1-(2-fluoro-4-methoxyphenyl)ethan-1-one) was obtained as a white solid and used as such in the next step.

4-(2-fluoro-4-methoxyphenyl)thiazol-2-amine was prepared according to General procedure B from 2-bromo-1-(2-fluoro-4-methoxyphenyl)ethan-1-one (1.5 g, 6 mmol) and thiourea (680 mg, 9 mmol) in EtOH (5 mL). Work-up 2 of General procedure B. The product was obtained as a white solid (740 mg, 55%).

$^{1}$H NMR (500 MHz, CDCl$_3$) δ (ppm) 7.97-7.90 (m, 1H), 6.87 (d, J=2.3 Hz, 1H), 6.75 (dd, J=8.7, 2.3 Hz, 1H), 6.68 (dd, J=13.3, 2.6 Hz, 1H), 5.20 (s, 2H), 3.83 (s, 3H);

$^{13}$C NMR (126 MHz, CDCl$_3$) δ (ppm) 166.6, 161.0 (d, J=250.3 Hz), 160.2 (d, J=11.7 Hz), 144.9 (d, J=2.7 Hz), 130.5 (d, J=4.9 Hz), 115.5 (d, J=11.8 Hz), 110.1 (d, J=3.0 Hz), 105.9 (d, J=14.4 Hz), 102.2 (d, J=26.3 Hz), 55.8;

$^{19}$F NMR (471 MHz, CDCl$_3$) δ (ppm) −111.94;

HRMS calcd for C$_{10}$H$_{10}$FN$_2$OS [M+H]$^+$ 225.0492, found 225.0495.

Preparative Example 47

4-(4-(trifluoromethyl)pyridin-2-yl)thiazol-2-amine

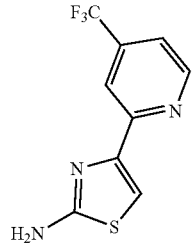 [SMILES: Nc1nc(-c2cc(C(F)(F)F)ccn2)cs1]

The compound was prepared according to General procedure G from tert-butyl (4-methoxybenzyl)(4-(4-(trifluoromethyl)pyridin-2-yl)thiazol-2-yl)carbamate (0.450 g, 0.966 mmol) and trifluoroacetic acid (4.0 mL); the reaction time was 2 h at 70° C. The product, purified by column chromatography (CH$_2$Cl$_2$:MeOH; 1:0 to 15:1); was obtained as a light yellow solid (0.230 g, 92%).

$^{1}$H NMR (500 MHz, DMSO-d$_6$) δ (ppm) 8.81 (d, J=5.03 Hz, 1H), 8.03 (s, 1H), 7.63 (dd, J=5.00, 1.72 Hz, 1H), 7.41 (s, 1H), 7.23 (s, 2H);

$^{13}$C NMR (126 MHz, DMSO-d$_6$) δ (ppm) 168.8, 153.6, 151.0, 148.4, 137.5, 124.1 (q, J=273.5 Hz), 117.6-117.0 (m), 115.8-114.4 (m), 107.3;

$^{19}$F NMR (471 MHz, DMSO-d$_6$) δ (ppm) −63.81;

HRMS calcd for C$_9$H$_7$F$_3$N$_3$S [M+H]$^+$ 246.0307, found 246.0310.

Preparative Example 48

4-(2,5-dichlorothiophen-3-yl)thiazol-2-amine

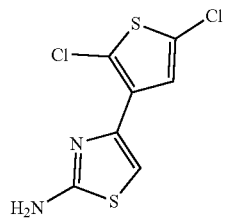 [SMILES: Nc1nc(-c2cc(Cl)sc2Cl)cs1]

2-bromo-1-(2,5-dichlorothiophen-3-yl)ethan-1-one was prepared according to General procedure A2 from 1-(2,5-dichlorothiophen-3-yl)ethan-1-one (0.500 g, 2.56 mmol) and copper (II) bromide (1.14 g, 5.12 mmol) in chloroform (8 mL) and ethyl acetate (8 mL); the reaction time was 2 h. The crude intermediate (2-bromo-1-(2,5-dichlorothiophen-3-yl)ethan-1-one) was obtained as a yellow solid (700 mg, 2.55 mmol) and used as such in the next step.

4-(5-bromothiophen-2-yl)thiazol-2-amine was prepared according to General procedure B from 2-bromo-1-(2,5-dichlorothiophen-3-yl)ethan-1-one (600 mg, 2.19 mmol) and thiourea (250 mg, 3.28 mmol) in EtOH (15 mL). Work-up 1 of General procedure B. The product, purified by column chromatography (hexane:EtOAc; 1:0 to 6.5:3.5), was obtained as a pale yellow solid (340 mg, 53%).

$^1$H NMR (500 MHz, CDCl$_3$) δ (ppm) 7.25 (s, 1H), 7.04 (s, 1H), 5.06 (s, 2H);

$^{13}$C NMR (126 MHz, CDCl$_3$) δ (ppm) 166.4, 143.5, 132.3, 127.6, 126.2, 121.7, 106.9;

HRMS calcd for C$_7$H$_5$Cl$_2$N$_2$S$_2$ [M+H]$^+$ 250.9266, found 250.9269.

Preparative Example 49

2-cyano-N-(4-phenylthiazol-2-yl)acetamide

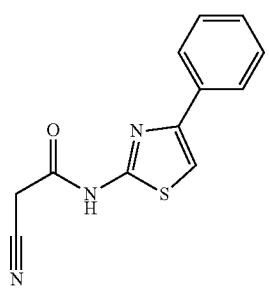 [SMILES: N#CCC(=O)Nc1nc(-c2ccccc2)cs1]

The compound was prepared according to General procedure C1 from 2-amino-4-phenylthiazole (0.5 g, 2.837 mmol), ethyl cyanoacetate (0.453 mL, 4.255 mmol) and NaOEt (21% in EtOH, 1.59 mL, 4.255 mmol) in EtOH (10 mL); the reaction time was 3 h at reflux. The product, purified by column chromatography (toluene:EtOAc; 5:1 to 1:1), was obtained as an off-white solid (0.586 g, 85%).

IR (cm$^{-1}$) 3207, 3081, 2944, 2913, 2211, 1660, 1554, 1480, 1445, 1389, 1265, 1180, 945, 781, 733;

$^1$H NMR (500 MHz, DMSO-d$_6$) δ (ppm) 12.59 (s, 1H), 7.93-7.85 (m, 2H), 7.69 (s, 1H), 7.43 (dd, J=8.3, 7.0 Hz, 2H), 7.36-7.29 (m, 1H), 4.06 (s, 2H);

$^{13}$C NMR (126 MHz, DMSO-d$_6$) δ (ppm) 161.8, 157.3, 149.0, 134.0, 128.7, 127.9, 125.6, 115.1, 108.6, 25.9;

HRMS calcd for C$_{12}$H$_{10}$N$_3$OS [M+H]$^+$ 244.0539, found 244.0538.

Preparative Example 50

N-(4-(4-bromophenyl)thiazol-2-yl)-2-cyanoacetamide

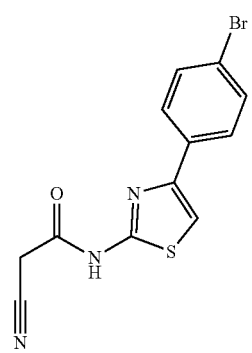 [SMILES: N#CCC(=O)Nc1nc(-c2ccc(Br)cc2)cs1]

The compound was prepared according to General procedure C1 from 4-(4-bromophenyl)thiazol-2-amine (540 mg, 2.12 mmol), ethyl cyanoacetate (250 µL, 2.33 mmol) and NaOEt (21% in EtOH, 0.80 mL, 2.12 mmol). The product, purified by column chromatography (toluene:EtOAc; 1:1), was obtained as a white solid (425 mg, 65%).

$^1$H NMR (500 MHz, DMSO-d$_6$) δ (ppm) 12.60 (s, 1H), 7.87-7.81 (m, 2H), 7.76 (s, 1H), 7.66-7.60 (m, 2H), 4.06 (s, 2H);

$^{13}$C NMR (126 MHz, DMSO-d$_6$) δ (ppm) 161.9, 157.5, 147.8, 133.2, 131.7, 127.6, 120.9, 115.1, 109.4, 25.9;

HRMS calcd for C$_{12}$H$_7$BrN$_3$OS [M−H]$^-$ 321.9478, found 321.9479.

Preparative Example 51

2-cyano-N-(4-(4-cyanophenyl)thiazol-2-yl)acetamide

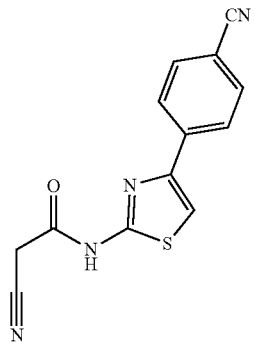 [SMILES: N#CCC(=O)Nc1nc(-c2ccc(C#N)cc2)cs1]

The compound was prepared according to General procedure C1 from 4-(2-aminothiazol-4-yl)benzonitrile (205 mg, 1.02 mmol), ethyl cyanoacetate (170 µL, 1.53 mmol) and NaOEt (21% in EtOH, 380 µL, 1.02 mmol). The product, purified by column chromatography (hexane:EtOAc; 1:1), was obtained as a white solid (260 mg, 96%).

¹H NMR (500 MHz, DMSO-d₆) δ (ppm) 12.66 (s, 1H), 8.07 (d, J=8.2 Hz, 2H), 7.98 (d, J=1.2 Hz, 1H), 7.90 (d, J=8.1 Hz, 2H), 4.07 (s, 2H);
¹³C NMR (126 MHz, DMSO-d₆) δ (ppm) 162.1, 157.8, 147.2, 138.1, 132.8, 126.3, 118.2, 115.1, 112.1, 110.1, 25.9;
HRMS calcd for $C_{13}H_7N_4OS$ [M−H]⁻ 267.0346, found 267.0346.

Preparative Example 52

2-cyano-N-(4-(4-(trifluoromethyl)phenyl)thiazol-2-yl)acetamide

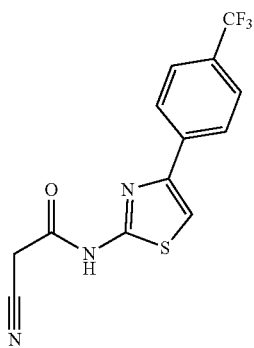 [SMILES: N#CCC(=O)Nc1nc(-c2ccc(C(F)(F)F)cc2)cs1]

The compound was prepared according to General procedure C1 from 4-(4-(trifluoromethyl)phenyl)thiazol-2-amine (200 mg, 0.81 mmol), ethyl cyanoacetate (130 µL, 1.22 mmol) and NaOEt (21% in EtOH, 300 µL, 0.81 mmol). The product, purified by column chromatography (hexane:EtOAc; 2:1), was obtained as a white solid (210 mg, 85%).
¹H NMR (500 MHz, DMSO-d₆) δ (ppm) 12.67 (s, 1H), 8.10 (d, J=8.1 Hz, 2H), 7.91 (s, 1H), 7.79 (d, J=8.1 Hz, 2H), 4.07 (s, 2H);
¹³C NMR (126 MHz, DMSO-d₆) δ (ppm) 162.0, 157.7, 147.4, 137.7, 127.9 (q, J=32.1 Hz), 126.2, 125.7 (q, J=4.0 Hz), 124.8 (d, J=81.2, 271.9 Hz), 115.1, 111.2, 25.9;
¹⁹F NMR (471 MHz, DMSO-d₆) δ (ppm) −60.97;
HRMS calcd for $C_{13}H_7F_3N_3OS$ [M−H]⁻ 310.0267, found 310.0267.

Preparative Example 53

2-cyano-N-(4-(p-tolyl)thiazol-2-yl)acetamide

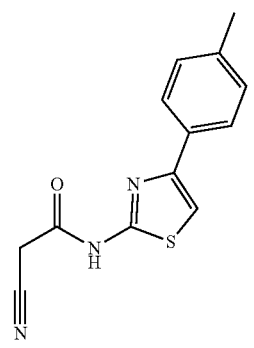 [SMILES: Cc1ccc(-c2csc(NC(=O)CC#N)n2)cc1]

The compound was prepared according to General procedure C1 from 4-(p-tolyl)thiazol-2-amine (0.259 g, 1.36 mmol), ethyl cyanoacetate (217 µL, 2.04 mmol) and NaOEt (21% in EtOH, 763 µL, 2.04 mmol) in EtOH (2 mL). The reaction mixture was stirred at 55° C. for 6 h. The product, purified by column chromatography (hexane:EtOAc; 1:0 to 1:1), was obtained as a pale yellow solid (0.284 g, 81%).
¹H NMR (500 MHz, DMSO-d₆) δ (ppm) 12.56 (s, 1H), 7.78 (d, J=8.4 Hz, 2H), 7.60 (s, 1H), 7.24 (d, J=8.1 Hz, 2H), 4.05 (s, 2H), 2.32 (s, 3H);
¹³C NMR (126 MHz, DMSO-d₆) δ (ppm) 161.8, 157.2, 149.1, 137.2, 131.4, 129.3, 125.6, 115.1, 107.7, 25.9, 20.8;
HRMS calcd for $C_{13}H_{12}N_3OS$ [M+H]⁺ 258.0696 found 258.0696.

Preparative Example 54

2-cyano-N-(4-phenyl-5-(p-tolyl)thiazol-2-yl)acetamide

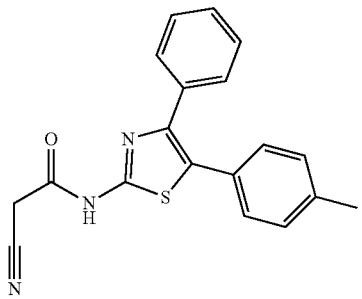 [SMILES: Cc1ccc(-c2sc(NC(=O)CC#N)nc2-c2ccccc2)cc1]

The compound was prepared according to General procedure C1 from 4-phenyl-5-(p-tolyl)thiazol-2-amine (0.4 g, 1.5 mmol) in EtOH (5 mL), ethyl cyanoacetate (240 µL, 2.25 mmol) and NaOEt (21% in EtOH, 560 µL, 1.5 mmol). The product, purified by column chromatography (hexane:EtOAc; 1:1), was obtained as a white solid (240 mg, 50%).
¹H NMR (500 MHz, DMSO-d₆) δ (ppm) 12.62 (s, 1H), 7.46-7.39 (m, 2H), 7.35-7.27 (m, 3H), 7.23-7.17 (m, 4H), 4.07 (s, 2H), 2.32 (s, 3H);
¹³C NMR (126 MHz, DMSO-d₆) δ (ppm) 161.9, 154.9, 143.6, 137.6, 134.5, 129.5, 129.1, 128.5, 128.3, 128.3, 127.7, 126.1, 115.1, 25.8, 20.7;
HRMS calcd for $C_{19}H_{14}N_3OS$ [M−H]⁻ 332.0863, found 332.0862.

Preparative Example 55

2-cyano-N-(4-(4-(trifluoromethoxy)phenyl)thiazol-2-yl)acetamide

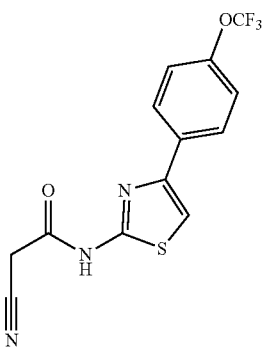 [SMILES: N#CCC(=O)Nc1nc(-c2ccc(OC(F)(F)F)cc2)cs1]

The compound was prepared according to General procedure C1 from 4-(4-(trifluoromethoxy)phenyl)thiazol-2-amine (0.2 g, 0.77 mmol), ethyl cyanoacetate (123 µL, 1.15 mmol) and NaOEt (21% in EtOH, 430 µL, 1.15 mmol) in EtOH (2 mL). The mixture was stirred at 55° C. for 6 h. The product, purified by column chromatography (hexane:EtOAc; 1:0 to 1:1), was obtained as an off-white solid (0.216 g, 85%).

$^1$H NMR (500 MHz, DMSO-$d_6$) δ (ppm) 12.62 (s, 1H), 8.00 (d, J=8.7 Hz, 2H), 7.77 (s, 1H), 7.43 (d, J=8.7 Hz, 2H), 4.06 (s, 2H);

$^{13}$C NMR (126 MHz, DMSO-$d_6$) δ (ppm) 162.5, 158.1, 148.3, 148.0, 133.8, 128.0, 121.8, 120.6 (q, J=256.2 Hz), 115.6, 110.1, 26.4;

$^{19}$F NMR (471 MHz, DMSO-$d_6$) δ (ppm) −56.73;

HRMS calcd for $C_{13}H_9F_3N_3O_2S$ [M+H]$^+$ 328.0362, found 328.0360.

Preparative Example 56

N-(4-([1,1'-biphenyl]-3-yl)thiazol-2-yl)-2-cyanoacetamide

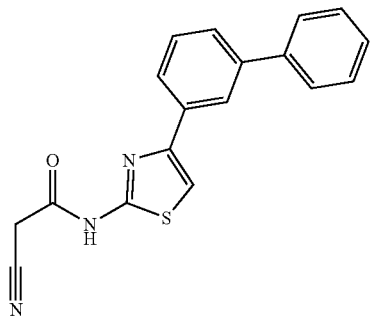 [SMILES: N#CCC(=O)Nc1nc(-c2cccc(-c3ccccc3)c2)cs1]

The compound was prepared according to General procedure C1 from 4-([1,1'-biphenyl]-3-yl)thiazol-2-amine (250 mg, 1.0 mmol) in EtOH (3 mL), ethyl cyanoacetate (130 µL, 1.5 mmol) and NaOEt (21% in EtOH, 370 µL, 1.0 mmol). The product, purified by column chromatography (hexane:EtOAc; 3:2), was obtained as a white solid (300 mg, 65%).

$^1$H NMR (500 MHz, CDCl$_3$) δ (ppm) 8.05-8.02 (m, 1H), 7.78-7.74 (m, 1H), 7.68-7.63 (m, 2H), 7.56-7.52 (m, 1H), 7.49-7.44 (m, 3H), 7.40-7.34 (m, 1H), 6.79 (s, 1H);

$^{13}$C NMR (126 MHz, CDCl$_3$) δ (ppm) 167.5, 151.5, 141.9, 141.3, 135.3, 129.2, 128.9, 127.56, 127.5, 126.8, 125.2, 125.2, 103.4;

HRMS calcd for $C_{18}H_{12}N_3OS$ [M−H]$^−$ 318.0707, found 318.0707.

Preparative Example 57

2-cyano-N-(4,5-diphenylthiazol-2-yl)acetamide

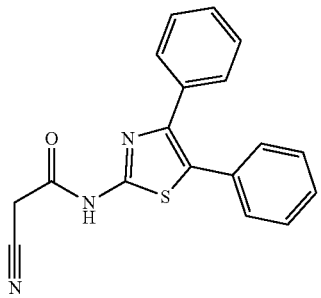 [SMILES: N#CCC(=O)Nc1nc(-c2ccccc2)c(-c2ccccc2)s1]

The compound was prepared according to General procedure C1 from 4,5-diphenylthiazol-2-amine (0.079 g, 0.313 mmol), ethyl cyanoacetate (50 µL, 0.47 mmol) and NaOEt (21% in EtOH, 175 µL, 0.47 mmol) in EtOH (2 mL). The reaction mixture was stirred at 55° C. for 3 h. The crude product was triturated with CH$_2$Cl$_2$:EtOAc (1 mL+1 mL), and the solid was collected by filtration and dried under vacuum. The product was obtained as a white solid (0.059 g, 59%).

$^1$H NMR (500 MHz, DMSO-$d_6$) δ (ppm) 12.66 (s, 1H), 7.47-7.36 (m, 5H), 7.36-7.27 (m, 5H), 4.08 (s, 2H);

$^{13}$C NMR (126 MHz, DMSO-$d_6$) δ (ppm) 162.0, 155.3, 143.9, 134.4, 131.6, 129.3, 128.9, 128.4, 128.3, 128.1, 127.8, 125.9, 115.1, 25.9;

HRMS calcd for $C_{18}H_{12}N_3OS$ [M−H]$^−$ 318.0707, found 318.0709.

Preparative Example 58

N-(4-(4-(tert-butyl)phenyl)thiazol-2-yl)-2-cyanoacetamide

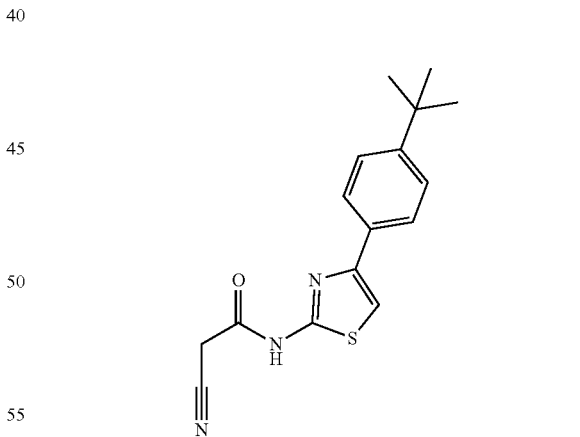

The compound was prepared according to General procedure C1 from 4-(4-(tert-butyl)phenyl)thiazol-2-amine (0.63 g, 2.69 mmol), ethyl cyanoacetate (430 µL, 4.04 mmol) and NaOEt (21% in EtOH, 1.51 mL, 4.04 mmol) in EtOH (6 mL). The product, purified by column chromatography (hexane:EtOAc; 10:1 to 4:1), was obtained as an off-white solid (0.575 g, 71%).

$^1$H NMR (500 MHz, DMSO-$d_6$) δ (ppm) 12.58 (s, 1H), 7.82 (d, J=8.5 Hz, 2H), 7.60 (s, 1H), 7.45 (d, J=8.6 Hz, 2H), 4.05 (s, 2H), 1.30 (s, 9H);

¹³C NMR (126 MHz, DMSO-d₆) δ (ppm) 161.8, 157.2, 150.4, 149.0, 131.4, 125.5, 125.4, 115.1, 107.8, 34.3, 31.0, 25.9;

HRMS calcd for $C_{16}H_{18}N_3OS$ [M+H]⁺ 300.1165, found 300.1168.

Preparative Example 59

2-cyano-N-(4-(naphthalen-2-yl)thiazol-2-yl)acetamide

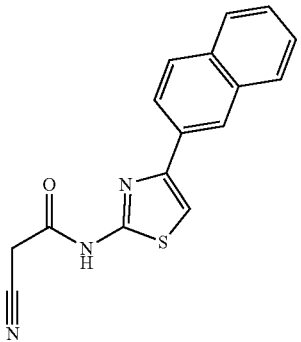 [SMILES: N#CCC(=O)Nc1nc(-c2ccc3ccccc3c2)cs1]

The compound was prepared according to General procedure C1 from 4-(naphthalen-2-yl)thiazol-2-amine (0.207 g, 0.915 mmol), ethylcyanoacetate (146 µL, 1.37 mmol) and NaOEt (21% in EtOH, 512 µL, 1.37 mmol) in EtOH (2 mL). The mixture was heated at 50° C. for 21 h. Solvent was evaporated in vacuo, the solid residue was mixed with a saturated aqueous solution of NH₄Cl (20 mL), and the mixture was extracted with EtOAc (3×25 mL). The combined organic phases were washed with brine, dried over MgSO₄, filtered, and the solvent was evaporated in vacuo. The obtained product did not require any further purification. The product was obtained as a pale pink solid (0.161 g, 60%).

¹H NMR (500 MHz, DMSO-d₆) δ (ppm) 12.68 (s, 1H), 8.42 (s, 1H), 8.05 (d, J=8.5, 1.7 Hz, 1H), 8.00-7.90 (m, 3H), 7.83 (d, J=1.5 Hz, 1H), 7.59-7.47 (m, 2H), 4.08 (s, 2H);

¹³C NMR (126 MHz, DMSO-d₆) δ (ppm) 161.9, 157.4, 148.9, 133.1, 132.5, 131.5, 128.3, 128.1, 127.6, 126.5, 126.2, 124.3, 123.9, 115.1, 109.2, 25.9;

HRMS calcd for $C_{16}H_{12}N_3OS$ [M+H]⁺ 294.0696, found 294.0695.

Preparative Example 60

2-cyano-N-(4-(thiophen-3-yl)thiazol-2-yl)acetamide

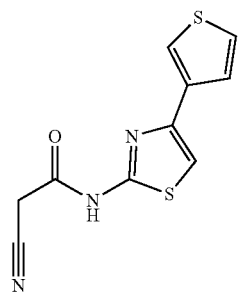 [SMILES: N#CCC(=O)Nc1nc(-c2ccsc2)cs1]

The compound was prepared according to General procedure C1 from 4-(thiophen-3-yl)thiazol-2-amine (135 mg, 0.74 mmol), ethyl cyanoacetate (90 µL, 0.81 mmol), and NaOEt (21% in EtOH, 280 µL, 0.74 mmol). The product, purified by column chromatography (hexane:EtOAc; 1:1), was obtained as a white solid (77 mg, 40%).

¹H NMR (500 MHz, DMSO-d₆) δ (ppm) 12.59 (s, 1H), 7.80-7.76 (m, 1H), 7.60 (dd, J=5.1, 3.0 Hz, 1H), 7.55 (dd, J=5.0, 1.2 Hz, 1H), 7.52 (s, 1H), 4.04 (s, 2H);

¹³C NMR (126 MHz, DMSO-d₆) δ (ppm) 161.8, 157.2, 145.4, 136.4, 127.0, 125.9, 121.6, 115.1, 108.0, 25.8;

HRMS calcd for $C_{10}H_6N_3OS_2$ [M−H]⁻ 247.9958, found 247.9959.

Preparative Example 61

2-cyano-N-(5-cyclohexyl-4-phenylthiazol-2-yl)acetamide

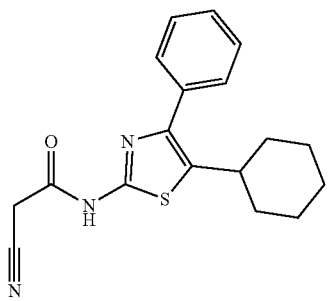 [SMILES: N#CCC(=O)Nc1nc(-c2ccccc2)c(C2CCCCC2)s1]

The compound was prepared according to General procedure C1 from 5-cyclohexyl-4-phenylthiazol-2-amine (0.1 g, 0.39 mmol), ethylcyanoacetate (62 µL, 0.6 mmol), and NaOEt (21% in EtOH, 150 µL, 0.38 mmol) in EtOH (3 mL). The product, purified by column chromatography (hexane:EtOAc; 1:1), was obtained as a white solid (50 mg, 40%).

¹H NMR (500 MHz, DMSO-d₆) δ (ppm) 12.41 (s, 1H), 7.55-7.50 (m, 2H), 7.49-7.43 (m, 2H), 7.40-7.35 (m, 1H), 4.01 (s, 2H), 3.09-2.91 (m, 1H), 1.98-1.92 (m, 2H), 1.80-1.73 (m, 2H), 1.70-1.65 (m, 1H), 1.41 (q, J=12.0 Hz, 2H), 1.35-1.23 (m, 3H);

¹³C NMR (126 MHz, DMSO-d₆) δ (ppm) 161.4, 153.7, 143.3, 135.0, 134.4, 128.5, 128.2, 128.0, 127.5, 115.2, 36.4, 35.9, 26.1, 25.1;

HRMS calcd for $C_{18}H_{18}N_3OS$ [M−H]⁻ 324.1176, found 324.1176.

Preparative Example 62

2-cyano-N-(4-(4-methylthiophen-3-yl)thiazol-2-yl)acetamide

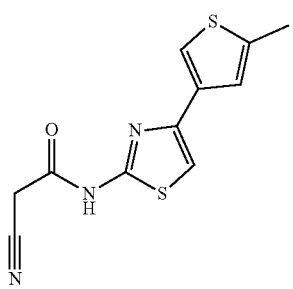 [SMILES: Cc1cc(-c2csc(NC(=O)CC#N)n2)cs1]

The compound was prepared according to General procedure C2:

Step 1: from 4-(4-methylthiophen-3-yl)thiazol-2-amine (150 mg, 0.78 mmol), chloroacetyl chloride (131 mg, 92 μL, 1.12 mmol), Et₃N (113 mg, 155 μL, 1.12 mmol) in CH₃CN (2.5 mL). After the work-up, the residue was purified by column chromatography (hexane:EtOAc; 7:3); the corresponding 2-chloroacetamide was obtained as a white solid (100 mg, 0.37 mmol).

Step 2: from KCN (50 mg, 0.78 mmol) in DMF (2 mL). The product, purified by column chromatography (hexane:EtOAc; 7:3), was obtained as an off-white solid (95 mg, 45%).

$^1$H NMR (500 MHz, DMSO-d$_6$) δ (ppm) 12.66 (s, 1H), 7.47 (s, 1H), 7.34 (s, 1H), 7.07 (s, 1H), 4.03 (s, 2H), 2.22 (s, 3H);

$^{13}$C NMR (126 MHz, DMSO-d$_6$) δ (ppm) 162.4, 157.8, 144.4, 138.4, 138.3, 126.5, 121.4, 115.6, 107.1, 26.4, 15.9;

HRMS calcd for C$_{11}$H$_{10}$N$_3$OS$_2$ [M+H]$^+$ 264.0260, found 264.0256.

Preparative Example 63

2-cyano-N-(4-(5,6,7,8-tetrahydronaphthalen-2-yl)thiazol-2-yl)acetamide

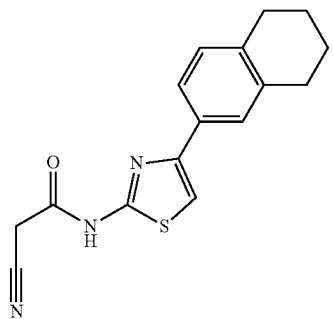 [SMILES: N#CCC(=O)Nc1nc(-c2ccc3c(c2)CCCC3)cs1]

The compound was prepared according to General procedure C2:

Step 1: from 4-(4-cyclohexylphenyl)thiazol-2-amine (360 mg, 1.4 mmol), chloroacetyl chloride (234 mg, 165 μL, 2.1 mmol), and Et₃N (140 mg, 194 μL, 1.4 mmol) in CH₃CN (7 mL). After the work-up, the residue was purified by column chromatography (hexane:EtOAc; 7:3) to afford the corresponding 2-chloroacetamide as a white solid (430 mg, 1.4 mmol).

Step 2: from KCN (190 mg, 2.8 mmol) in DMF (1 mL). The product, purified by column chromatography (hexane:EtOAc; 7:3), was obtained as an off-white solid (265 mg, 60%).

$^1$H NMR (500 MHz, DMSO-d$_6$) δ12.56 (s, 1H), 7.60-7.56 (m, 3H), 7.10 (d, J=8.2 Hz, 1H), 4.08-4.01 (m, 2H), 2.74 (dt, J=17.1, 5.1 Hz, 4H), 1.81-1.70 (m, 4H);

$^{13}$C NMR (126 MHz, DMSO) δ 161.7, 157.0, 149.2, 136.8, 136.5, 131.3, 129.2, 126.2, 122.8, 115.1, 107.4, 28.8, 28.5, 25.8, 22.7.

Preparative Example 64

2-cyano-N-(4-(4-cyclohexylphenyl)thiazol-2-yl)acetamide

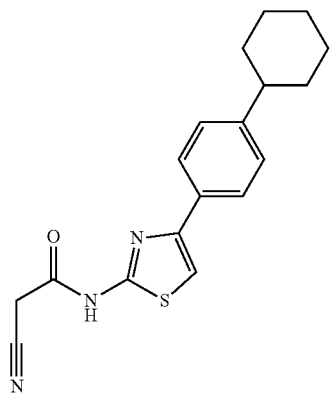 [SMILES: N#CCC(=O)Nc1nc(-c2ccc(C3CCCCC3)cc2)cs1]

The compound was prepared according to General procedure C2:

Step 1: from 4-(4-cyclohexylphenyl)thiazol-2-amine (360 mg, 1.4 mmol), chloroacetyl chloride (234 mg, 165 μL, 2.1 mmol), and Et₃N (140 mg, 194 μL, 1.4 mmol) in CH₃CN (7 mL). After the work-up, the residue was purified by column chromatography (hexane:EtOAc; 7:3), to afford the corresponding 2-chloroacetamide as a white solid (450 mg, 1.4 mmol).

Step 2: from KCN (190 mg, 2.8 mmol) in DMF (1 mL). The product, purified by column chromatography (hexane:EtOAc; 7:3), was obtained as a pale yellow solid (265 mg, 60%,).

$^1$H NMR (500 MHz, DMSO-d$_6$) δ (ppm) 12.50 (s, 1H), 7.75-7.70 (m, 2H), 7.53 (s, 1H), 7.24-7.18 (m, 2H), 3.98 (s, 2H), 2.47 (d, J=2.8 Hz, 1H), 1.78-1.69 (m, 5H), 1.42-1.25 (m, 5H).

$^{13}$C NMR (126 MHz, CDCl$_3$) δ (ppm) 170.3, 161.8, 157.1, 149.1, 147.3, 131.8, 125.6, 115.1, 107.6, 43.5, 33.8, 26.3, 25.5, 20.7.

HRMS calcd for C$_{18}$H$_{20}$N$_3$OS [M+H]$^+$ 326.1322, found 326.1320.

Preparative Example 65

2-cyano-N-(4-(pyridin-2-yl)thiazol-2-yl)acetamide

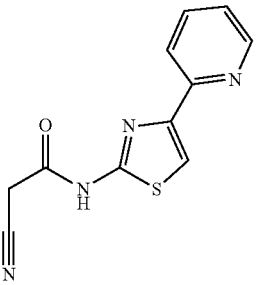 [SMILES: N#CCC(=O)Nc1nc(-c2ccccn2)cs1]

The compound was prepared according to General procedure C3 from 4-(pyridin-2-yl)thiazol-2-amine (0.285 g, 1.60 mmol), ethyl cyanoacetate (0.256 mL, 2.41 mmol) and NaH (60% in mineral oil, 0.077 mg, 1.92 mmol)) in MeOH (5 mL); the reaction time was 4 h at 60° C. The product, purified by column chromatography (hexane:EtOAc; 1:1 to 0:1), was obtained as a yellow solid (0.245 g, 62%).

$^1$H NMR (500 MHz, DMSO-$d_6$) δ (ppm) 12.63 (s, 1H), 8.61 (dt, J=4.66, 1.47 Hz, 1H), 7.95-7.86 (m, 3H), 7.36-7.32 (m, 1H), 4.07 (s, 2H);

$^{13}$C NMR (126 MHz, DMSO-$d_6$) δ (ppm) 161.9, 157.5, 151.8, 149.5, 149.1, 137.3, 122.9, 119.9, 115.1, 112.1, 25.9;

HRMS calcd for $C_{11}H_9N_4OS$ [M+H]$^+$ 245.0492, found 245.0497.

Preparative Example 66

2-cyano-N-(4-(6-methylpyridin-2-yl)thiazol-2-yl)acetamide

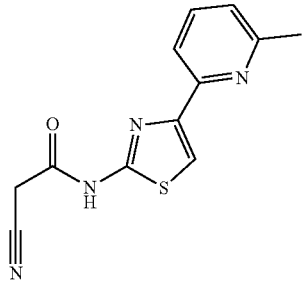 [SMILES: Cc1cccc(-c2csc(NC(=O)CC#N)n2)n1]

The compound was prepared according to General procedure C3 from 4-(6-methylpyridin-2-yl)thiazol-2-amine (0.250 g, 1.30 mmol), ethyl cyanoacetate (0.208 mL, 1.96 mmol) and NaH (60% in mineral oil, 0.057 mg, 1.44 mmol)) in MeOH (5 mL); the reaction time was 4 h at 60° C. The product, purified by column chromatography (hexane:EtOAc; 1:1 to 0:1), was obtained as an off-white solid (0.290 g, 86%).

$^1$H NMR (500 MHz, DMSO-$d_6$) δ (ppm) 12.62 (s, 1H), 7.82 (s, 1H), 7.79-7.71 (m, 2H), 7.20 (dd, J=7.34, 1.26 Hz, 1H), 4.06 (s, 2H), 2.51 (s, 3H);

$^{13}$C NMR (126 MHz, DMSO-$d_6$) δ (ppm) 161.9, 157.8, 157.4, 151.1, 149.3, 137.4, 122.3, 117.1, 115.1, 111.8, 25.9, 24.1;

HRMS calcd for $C_{12}H_{11}N_4OS$ [M+H]$^+$ 259.0648, found 259.0650.

Preparative Example 67

2-cyano-N-(4-(2-(trifluoromethyl)phenyl)thiazol-2-yl)acetamide

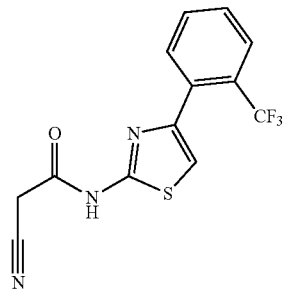 [SMILES: N#CCC(=O)Nc1nc(-c2ccccc2C(F)(F)F)cs1]

The compound was prepared according to General procedure C1 from 4-(2-(trifluoromethyl)phenyl)thiazol-2-amine (300 mg, 1.22 mmol), ethyl cyanoacetate (206 mg, 195 μL, 1.8 mmol), and Na (28 mg, 1.22 mmol) in EtOH (2 mL). The product, purified by column chromatography (hexane:EtOAc; 7:3), was obtained as a white solid (211 mg, 55%).

$^1$H NMR (500 MHz, DMSO-$d_6$) δ (ppm) 12.54 (s, 1H), 7.86-7.81 (m, 1H), 7.77-7.71 (m, 1H), 7.66-7.59 (m, 2H), 7.33 (s, 1H), 4.06 (s, 2H);

$^{13}$C NMR (126 MHz, DMSO-$d_6$) δ (ppm) 162.0, 156.6, 146.8, 134.2, 132.3, 132.0, 128.7, 127.0 (q, J=30.0 Hz), 126.3 (q, J=5.4 Hz), 124.0 (q, J=273.4 Hz), 115.1, 112.5, 25.9;

$^{19}$F NMR (471 MHz, DMSO-$d_6$) δ (ppm) −56.39;

HRMS calcd for $C_{13}H_9F_3N_3OS$ [M+H]$^+$ 312.0413, found 312.0417.

Preparative Example 68

2-cyano-N-(4-(3,4-dichlorophenyl)thiazol-2-yl)acetamide

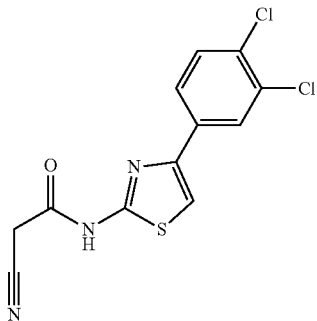 [SMILES: N#CCC(=O)Nc1nc(-c2ccc(Cl)c(Cl)c2)cs1]

The compound was prepared according to General procedure C1 from 4-(3,4-dichlorophenyl)thiazol-2-amine (300 mg, 1.22 mmol), ethyl cyanoacetate (206 mg, 195 μL, 1.8 mmol), and Na (28 mg, 1.22 mmol) in EtOH (2 mL). The product, purified by column chromatography (hexane:EtOAc; 7:3), was obtained as a white solid (280 mg, 75%).

$^1$H NMR (500 MHz, DMSO-$d_6$) δ (ppm) 12.63 (s, 1H), 8.12 (d, J=2.0 Hz, 1H), 7.90 (s, 1H), 7.87 (dd, J=8.4, 2.0 Hz, 1H), 7.70 (dd, J=8.4, 1.0 Hz, 1H), 4.07 (s, 2H);

$^{13}$C NMR (126 MHz, DMSO-$d_6$) δ (ppm) 162.0, 157.6, 146.4, 134.6, 131.5, 131.0, 130.1, 127.3, 125.7, 115.1, 110.6, 25.9;

HRMS calcd for $C_{12}H_6Cl_2N_3OS$ [M−H]$^-$ 309.9614, found 309.9610.

Preparative Example 69

2-cyano-N-(4-(o-tolyl)thiazol-2-yl)acetamide

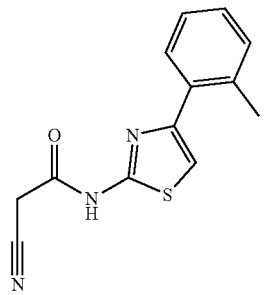 [SMILES: Cc1ccccc1-c1csc(NC(=O)CC#N)n1]

The compound was prepared according to General procedure C1 from 4-(o-tolyl)thiazol-2-amine (285 mg, 1.5 mmol), ethyl cyanoacetate (250 mg, 250 μL, 2.25 mmol), and Na (35 mg, 1.5 mmol) in EtOH (1.5 mL). The product, purified by column chromatography (hexane:EtOAc; 7:3), was obtained as a white solid (310 mg, 80%).

$^1$H NMR (500 MHz, DMSO-d$_6$) δ (ppm) 12.52 (s, 1H), 7.60-7.53 (m, 1H), 7.33 (s, 1H), 7.31-7.22 (m, 3H), 4.05 (s, 2H), 2.42 (s, 3H);

$^{13}$C NMR (126 MHz, DMSO-d$_6$) δ (ppm) 161.7, 156.3, 149.2, 135.4, 134.2, 130.8, 129.2, 127.8, 125.8, 115.2, 111.4, 25.9, 20.9;

HRMS calcd for C$_{13}$H$_{12}$N$_3$OS [M+H]$^+$ 258.0696, found 258.0699.

Preparative Example 70

N-(4-(3-chlorophenyl)thiazol-2-yl)-2-cyanoacetamide

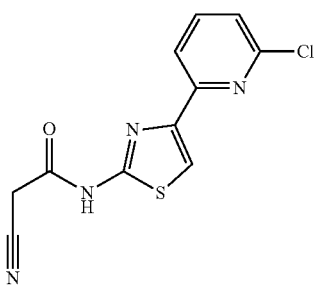 [SMILES: N#CCC(=O)Nc1nc(-c2cccc(Cl)n2)cs1]

The compound was prepared according to General procedure C3 from 4-(3-chlorophenyl)thiazol-2-amine (150 mg, 0.712 mmol), ethyl cyanoacetate (114 μL, 1.068 mmol) and NaH (60% in mineral oil, 30 mg, 0.783 mmol) in MeOH (1 mL) and THF (3 mL); the reaction time was 6 h at 50° C. The product, purified by column chromatography on silica gel (hexane:EtOAc; 10:1 to 2:1), was obtained as a white solid (171 mg, 87%).

$^1$H NMR (500 MHz, DMSO-d$_6$) δ (ppm) 12.62 (s, 1H), 7.94 (t, J=1.9 Hz, 1H), 7.88-7.85 (m, 1H), 7.84 (s, 1H), 7.47 (t, J=7.9 Hz, 1H), 7.41-7.37 (m, 1H), 4.06 (s, 2H);

$^{13}$C NMR (126 MHz, DMSO-d$_6$) δ (ppm) 162.0, 157.5, 147.3, 136.0, 133.6, 130.7, 127.6, 125.3, 124.2, 115.1, 110.1, 25.9;

HRMS calcd for C$_{12}$H$_9$ClN$_3$OS [M+H]$^1$ 278.0149, found 278.0147.

Preparative Example 71

2-cyano-N-(4-(4-methylpyridin-2-yl)thiazol-2-yl)acetamide

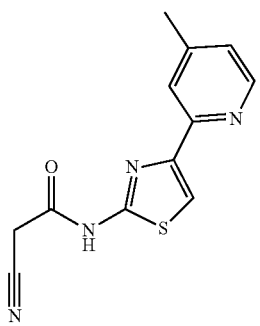 [SMILES: Cc1ccnc(-c2csc(NC(=O)CC#N)n2)c1]

The compound was prepared according to General procedure C3 from 4-(4-methylpyridin-2-yl)thiazol-2-amine (160 mg, 0.84 mmol), ethylcyanoacetate (140 mg, 130 μL, 1.3 mmol), NaH (60% in mineral oil, 34 mg, 0.84 mmol) in THF (2 mL) and MeOH (0.1 mL). The product, purified by column chromatography (EtOAc:MeOH; 1:0 to 10:1), was obtained as a white solid (125 mg, 60%).

$^1$H NMR (500 MHz, DMSO-d$_6$) δ (ppm) 12.62 (s, 1H), 8.45 (d, J=4.9 Hz, 1H), 7.85 (s, 1H), 7.76 (s, 1H), 7.17 (d, J=5.0 Hz, 1H), 4.07 (s, 2H), 2.37 (s, 3H);

$^{13}$C NMR (126 MHz, DMSO-d$_6$) δ (ppm) 161.9, 157.5, 151.7, 149.3, 149.2, 147.8, 123.6, 120.8, 115.1, 112.0, 25.9, 20.7;

HRMS calcd for C$_{12}$H$_{11}$N$_4$OS [M+H]$^+$ 259.0648, found 259.0646.

Preparative Example 72

2-cyano-N-(4-(5-methylpyridin-2-yl)thiazol-2-yl)acetamide

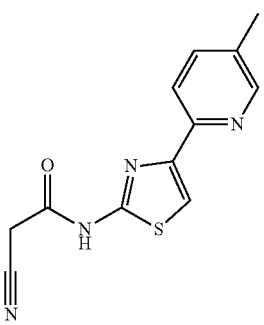 [SMILES: Cc1ccc(-c2csc(NC(=O)CC#N)n2)nc1]

The compound was prepared according to General procedure C3 from 4-(5-methylpyridin-2-yl)thiazol-2-amine (280 mg, 1.47 mmol), ethyl cyanoacetate (260 mg, 245 μL, 2.2 mmol), and NaH (60% in mineral oil, 59 mg, 1.47 mmol) in THF (3 mL) and MeOH (0.1 mL). The product, purified by column chromatography (CH$_2$Cl$_2$:MeOH; 10:1), was obtained as a pink solid (280 mg, 75%).

¹H NMR (500 MHz, DMSO-d₆) δ (ppm) 12.60 (s, 1H), 8.44 (d, J=2.1 Hz, 1H), 7.82 (d, J=8.1 Hz, 1H), 7.80 (s, 1H), 7.69 (dd, J=8.0, 2.2 Hz, 1H), 4.06 (s, 2H), 2.32 (s, 3H);

¹³C NMR (126 MHz, DMSO-d₆) δ (ppm) 161.9, 157.5, 149.8, 149.4, 149.3, 137.5, 132.2, 119.5, 115.1, 111.2, 25.9, 17.7;

HRMS calcd for $C_{12}H_{11}N_4OS$ [M+H]⁺ 259.0648, found 259.0645.

Preparative Example 73

2-cyano-N-(4-(4-isopropylphenyl)thiazol-2-yl)acetamide

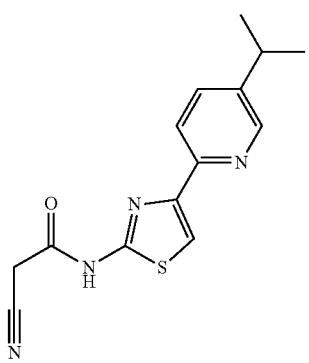 [SMILES: CC(C)c1ccc(-c2csc(NC(=O)CC#N)n2)nc1]

The compound was prepared according to General procedure C3 from 4-(4-isopropylphenyl)thiazol-2-amine (250 mg, 1.145 mmol), ethyl cyanoacetate (244 μL, 2.290 mmol), and NaH (60% in mineral oil, 50 mg, 1.260 mmol) in MeOH (1 mL) and THF (3 mL). The mixture was stirred at 50° C. for 4 h. The product, purified by column chromatography on silica gel (hexane:EtOAc, 10:1 to 2:1), was obtained as a white solid (227 mg, 69%).

¹H NMR (500 MHz, DMSO-d₆) δ (ppm) 12.57 (s, 1H), 7.80 (d, J=8.4 Hz, 2H), 7.60 (s, 1H), 7.30 (d, J=8.5 Hz, 2H), 4.05 (s, 2H), 2.91 (hept, J=6.7 Hz, 1H), 1.22 (d, J=7.0 Hz, 6H);

¹³C NMR (126 MHz, DMSO-d₆) δ (ppm) 161.8, 157.2, 149.1, 148.1, 131.8, 126.6, 125.7, 115.1, 107.7, 33.1, 25.9, 23.7;

HRMS calcd for $C_{15}H_{16}N_3OS$ [M+H]⁺ 286.1009, found 286.1010.

Preparative Example 74

2-cyano-N-(4-(4-methoxypyridin-2-yl)thiazol-2-yl)acetamide

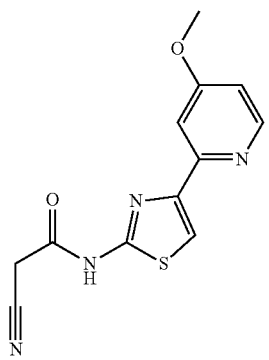 [SMILES: COc1ccnc(-c2csc(NC(=O)CC#N)n2)c1]

The compound was prepared according to General procedure C3 from 4-(4-methoxypyridin-2-yl)thiazol-2-amine (212 mg, 1.0 mmol), ethyl cyanoacetate (170 mg, 150 μL, 1.5 mmol), and NaH (60% in mineral oil, 44 mg, 1.1 mmol) in THF (2 mL) and MeOH (0.1 mL). The product, purified by column chromatography (hexane:EtOAc; 1:1 to 0:1), was obtained as an white solid (130 mg, 50%).

¹H NMR (500 MHz, DMSO-d₆) δ (ppm) 12.64 (s, 1H), 8.42 (d, J=5.6 Hz, 1H), 7.86 (s, 1H), 7.46 (d, J=2.5 Hz, 1H), 6.93 (dd, J=5.7, 2.6 Hz, 1H), 4.06 (s, 2H), 3.87 (s, 3H);

¹³C NMR (126 MHz, DMSO-d₆) δ (ppm) 166.1, 162.0, 157.5, 153.4, 151.0, 149.0, 115.1, 112.4, 109.2, 105.8, 55.3, 25.9;

HRMS calcd for $C_{12}H_{11}N_4O_2S$ [M+H]⁺ 275.0597, found 275.0595.

Preparative Example 75

2-cyano-N-(4-(5-methoxypyridin-2-yl)thiazol-2-yl)acetamide

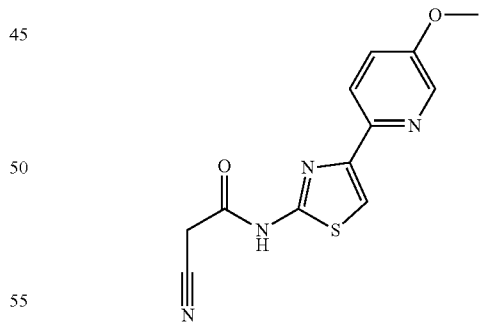

The compound was prepared according to General procedure C3 from 4-(5-methoxypyridin-2-yl)thiazol-2-amine (180 mg, 1.13 mmol), ethyl cyanoacetate (170 mg, 165 μL, 1.3 mmol), and NaH (60% in mineral oil, 35 mg, 0.88 mmol) in THF (3 mL) and MeOH (0.1 mL). The product, purified by column chromatography (hexane:EtOAc; 1:1 to 0:1), was obtained as a white solid (110 mg, 45%).

¹H NMR (500 MHz, DMSO-d₆) δ (ppm) 12.58 (s, 1H), 8.32 (dd, J=3.0, 0.6 Hz, 1H), 7.87 (d, J=8.7 Hz, 1H), 7.69 (s, 1H), 7.48 (dd, J=8.7, 3.0 Hz, 1H), 4.06 (s, 2H), 3.86 (s, 3H);

$^{13}$C NMR (126 MHz, DMSO-d$_6$) δ (ppm) 161.8, 157.4, 154.8, 149.0, 144.8, 137.5, 121.0, 120.6, 115.1, 109.9, 55.6, 25.9;

HRMS calcd for C$_{12}$H$_{11}$N$_4$O$_2$S [M+H]$^+$ 275.0597, found 275.0599.

Preparative Example 76

2-cyano-N-(4-(6-methoxypyridin-2-yl)thiazol-2-yl) acetamide

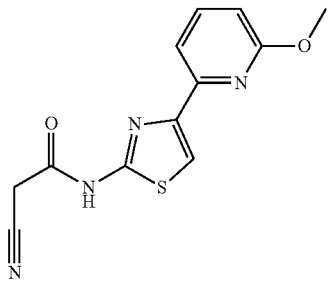 [SMILES: COc1cccc(-c2csc(NC(=O)CC#N)n2)n1]

The compound was prepared according to General procedure C3 from 4-(6-methoxypyridin-2-yl)thiazol-2-amine (270 mg, 1.3 mmol), ethyl cyanoacetate (220 mg, 0.2 mL, 1.95 mmol), and NaH (60% in mineral oil, 60 mg, 1.43 mmol) in THF (2 mL) and MeOH (0.1 mL). The reaction mixture was poured into a saturated aqueous solution of NH$_4$Cl (15 mL). The precipitate was collected by filtration, washed with water (3 mL) and EtOAc (5 mL), and dried under vacuum. The product was obtained as a white solid (270 mg, 75%).

$^1$H NMR (500 MHz, DMSO-d$_6$) δ (ppm) 12.61 (s, 1H), 7.86 (s, 1H), 7.78 (dd, J=8.2, 7.4 Hz, 1H), 7.51 (d, J=7.3 Hz, 1H), 6.77 (d, J=8.1 Hz, 1H), 4.06 (s, 2H), 3.94 (s, 3H);

$^{13}$C NMR (126 MHz, DMSO-d$_6$) δ (ppm) 163.1, 162.0, 157.5, 149.4, 149.0, 140.0, 115.1, 112.9, 112.2, 109.9, 52.8, 25.9;

HRMS calcd for C$_{12}$H$_{11}$N$_4$O$_2$S [M+H]$^+$ 275.0597, found 275.0594.

Preparative Example 77

2-cyano-N-(4-(2,4-dichlorophenyl)thiazol-2-yl)acetamide

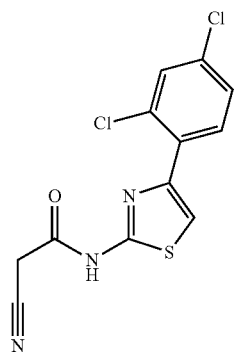 [SMILES: N#CCC(=O)Nc1nc(-c2ccc(Cl)cc2Cl)cs1]

The compound was prepared according to General procedure C3 from 4-(2,4-dichlorophenyl)thiazol-2-amine (1.0 g, 4.0 mmol), ethyl cyanoacetate (0.8 g, 750 µL, 6.0 mmol), and NaH (60% in mineral oil, 163 mg, 4.0 mmol) in THF (5 mL) and MeOH (0.3 mL). The product, purified by column chromatography (hexane:EtOAc; 5:1), was obtained as a white solid (850 mg, 70%).

$^1$H NMR (500 MHz, DMSO-d$_6$) δ (ppm) 12.64 (s, 1H), 7.84 (d, J=8.5 Hz, 1H), 7.72 (s, 1H), 7.72 (d, J=2.3 Hz, 1H), 7.53 (dd, J=8.4, 2.2 Hz, 1H), 4.06 (s, 2H);

$^{13}$C NMR (126 MHz, DMSO-d$_6$) δ (ppm) 162.0, 161.7, 156.7, 144.6, 133.0, 132.2, 131.8, 129.8, 127.6, 115.1, 113.9, 25.9;

HRMS calcd for C$_{12}$H$_8$Cl$_2$N$_3$OS [M+H]$^+$ 311.9760, found 311.9762.

Preparative Example 78

2-cyano-N-(4-(3-fluoropyridin-2-yl)thiazol-2-yl) acetamide

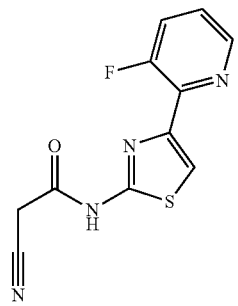 [SMILES: N#CCC(=O)Nc1nc(-c2ncccc2F)cs1]

The compound was prepared according to General procedure C3 from 4-(3-fluoropyridin-2-yl)thiazol-2-amine (250 mg, 1.28 mmol), ethyl cyanoacetate (216 mg, 205 µL, 1.92 mmol), and NaH (60% in mineral oil, 51 mg, 1.28 mmol) in THF (3 mL) and MeOH (0.1 mL). The reaction mixture was poured into a saturated aqueous solution of NH$_4$Cl (10 mL). The precipitate was collected by filtration, washed with EtOAc:MeOH (1:0.1, 5.5 mL) and Et$_2$O (2 mL), and dried under vacuum. The product was obtained as a white solid (230 mg, 70%).

$^1$H NMR (500 MHz, DMSO-d$_6$) δ (ppm) 12.77 (s, 1H), 8.52-8.46 (m, 1H), 7.85 (s, 1H), 7.84-7.77 (m, 1H), 7.51-7.43 (m, 1H), 4.07 (s, 2H);

$^{13}$C NMR (126 MHz, DMSO-d$_6$) δ (ppm) 162.0, 157.1, 156.3 (d, J=262.5 Hz), 145.4 (d, J=5.3 Hz), 145.2 (d, J=6.2 Hz), 140.0 (d, J=9.8 Hz), 124.8 (d, J=15.0 Hz), 124.7, 115.5 (d, J=6.4 Hz), 115.1, 25.9;

$^{19}$F NMR (471 MHz, DMSO-d$_6$) δ -121.09;

HRMS calcd for C$_{11}$H$_8$FN$_3$OS [M+H]$^+$ 263.0397, found 263.0399.

Preparative Example 79

2-cyano-N-(4-(2-fluoro-4-methoxyphenyl)thiazol-2-yl)acetamide

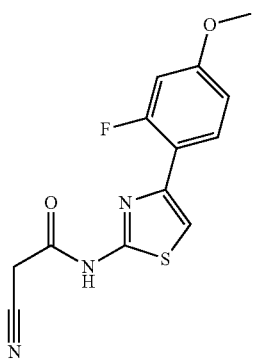 [SMILES: COc1ccc(-c2csc(NC(=O)CC#N)n2)c(F)c1]

The compound was prepared according to General procedure C3 from 4-(2-fluoro-4-methoxyphenyl)thiazol-2-amine (640 mg, 2.85 mmol), ethyl cyanoacetate (480 mg, 450 µL, 3.14 mmol), and NaH (60% in mineral oil, 126 mg, 3.14 mmol) in THF (3 mL) and MeOH (0.1 mL). The product, purified by column chromatography (hexane:EtOAc; 5:1), was obtained as a white solid (630 mg, 75%).

$^1$H NMR (500 MHz, DMSO-d$_6$) δ (ppm) 12.57 (s, 1H), 7.96-7.85 (m, 1H), 7.41 (d, J=2.5 Hz, 1H), 6.93 (dd, J=13.6, 2.6 Hz, 1H), 6.89 (dd, J=8.7, 2.6 Hz, 1H), 4.05 (s, 2H), 3.81 (s, 3H);

$^{13}$C NMR (126 MHz, DMSO-d$_6$) δ (ppm) 161.9, 160.2 (d, J=248.8 Hz), 160.1 (d, J=11.1 Hz), 156.7, 142.9, 129.7 (d, J=4.8 Hz), 115.1, 114.4 (d, J=12.0 Hz), 110.7, 110.7 (d, J=10.7 Hz), 102.1 (d, J=25.9 Hz), 55.7, 25.9;

$^{19}$F NMR (471 MHz, DMSO-d$_6$) δ (ppm) -112.16;

HRMS calcd for C$_{13}$H$_{11}$FN$_3$O$_2$S [M+H]$^+$ 292.0551, found 292.0551.

Preparative Example 80

2-cyano-N-(4-(4-(trifluoromethyl)pyridin-2-yl)thiazol-2-yl)acetamide

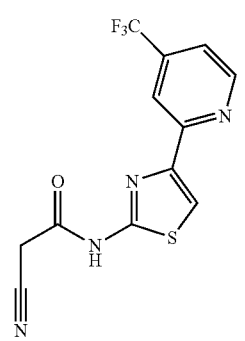 [SMILES: N#CCC(=O)Nc1nc(-c2cc(C(F)(F)F)ccn2)cs1]

The compound was prepared according to General procedure C3 from 4-(4-(trifluoromethyl)pyridin-2-yl)thiazol-2-amine (220 mg, 0.897 mmol), ethyl cyanoacetate (0.143 mL, 1.34 mmol) and NaH (60% in mineral oil, 0.047 mg, 1.16 mmol) in MeOH (6 mL); the reaction time was 20 h at 60° C. The product, purified by column chromatography (CH$_2$Cl$_2$:MeOH; 1:0 to 9.5:0.5), was obtained as a white solid (110 mg, 39%).

$^1$H NMR (500 MHz, DMSO-d$_6$) δ (ppm) 12.72 (s, 1H), 8.90 (d, J=5.08 Hz, 1H), 8.14 (s, 1H), 8.04 (s, 1H), 7.73 (dd, J=5.06, 1.76 Hz, 1H), 4.08 (s, 2H);

$^{13}$C NMR (126 MHz, DMSO-d$_6$) δ (ppm) 162.1, 158.0, 153.1, 151.3, 147.5, 137.8, 137.5, 124.0 (q, $^1J_{C-F}$=272.8 Hz), 118.2 (d, J=3.69 Hz), 115.2-114.8 (m), 114.0, 25.9;

$^{19}$F NMR (471 MHz, DMSO-d$_6$) δ (ppm) -63.83;

HRMS calcd for C$_{12}$H$_8$F$_3$N$_4$OS [M+H]$^+$ 313.0365, found 313.0369.

Preparative Example 81

2-cyano-N-(4-(2,5-dichlorothiophen-3-yl)thiazol-2-yl)acetamide

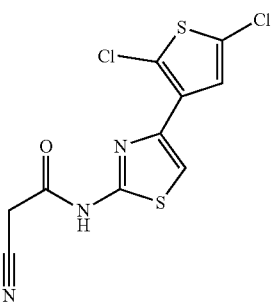 [SMILES: N#CCC(=O)Nc1nc(-c2cc(Cl)sc2Cl)cs1]

The compound was prepared according to General procedure C3 from 4-(2,5-dichlorothiophen-3-yl)thiazol-2-amine (330 mg, 1.31 mmol), ethyl cyanoacetate (0.209 mL, 1.97 mmol) and NaH (60% in mineral oil, 0.057 mg, 1.44 mmol) in MeOH (8 mL); the reaction time was 14 h at 60° C. The product, purified by column chromatography (hexane:EtOAc; 1:0 to 3:1), was obtained as a yellow solid (328 mg, 78%).

$^1$H NMR (500 MHz, DMSO-d$_6$) δ (ppm) 12.60 (s, 1H), 7.73 (s, 1H), 7.41 (s, 1H), 4.06 (s, 2H);

$^{13}$C NMR (126 MHz, DMSO-d$_6$) δ (ppm) 162.1, 157.0, 141.5, 132.2, 127.4, 125.2, 121.0, 115.0, 112.4, 25.9;

HRMS calcd for C$_{10}$H$_6$Cl$_2$N$_3$OS$_2$ [M+H]$^+$ 317.9324, found 317.9323.

Preparative Example 82

(E)-3-(4-acetamidophenyl)-2-cyano-N-(4-phenylthiazol-2-yl)acrylamide

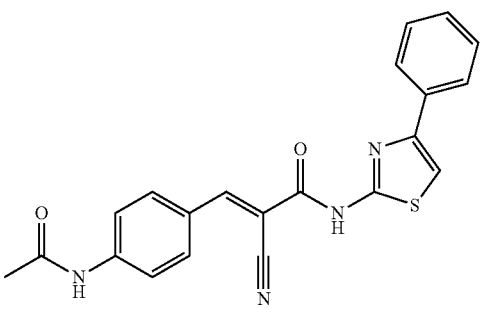 [SMILES: CC(=O)Nc1ccc(/C=C(\C#N)C(=O)Nc2nc(-c3ccccc3)cs2)cc1]

The compound was prepared according to General procedure D1 from 2-cyano-N-(4-phenylthiazol-2-yl)acetamide (54 mg, 0.22 mmol), 4-acetamidobenzaldehyde (34 mg, 0.211 mmol), and NEt₃ (31 μL, 0.22 mmol) in EtOH (1 mL); the reaction time was 3 h. The solvent was evaporated in vacuo and the residue was purified by column chromatography (hexane:EtOAc; 1:0 to 1:2). The product was obtained as a yellow solid (76 mg, 94%).

$^1$H NMR (500 MHz, DMSO-d$_6$) δ (ppm) 12.80 (s, 1H), 10.40 (s, 1H), 8.43 (s, 1H), 8.00 (d, J=8.9 Hz, 2H), 7.94 (d, J=7.5 Hz, 2H), 7.81 (d, J=8.9 Hz, 2H), 7.70 (s, 1H), 7.45 (t, J=7.7 Hz, 2H), 7.35 (t, J=7.5 Hz, 1H), 2.11 (s, 3H);

$^{13}$C NMR (126 MHz, DMSO-d$_6$) δ (ppm) 169.1, 161.4, 151.4, 149.2, 143.6, 134.0, 131.9, 128.7, 127.9, 126.0, 125.7, 118.9, 116.1, 108.8, 24.2;

HRMS calcd for C$_{21}$H$_{15}$N$_4$O$_2$S [M−H]⁻ 387.0921, found 387.0921.

Preparative Example 83

(E)-N-(4-(4-bromophenyl)thiazol-2-yl)-2-cyano-3-(3,4-dihydroxyphenyl)acrylamide

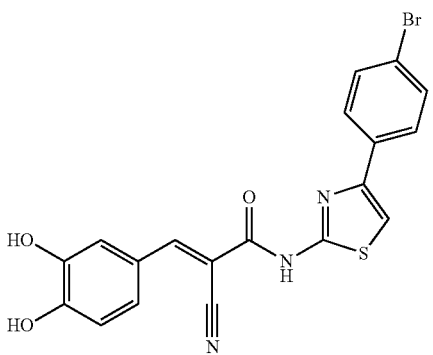 [SMILES: N#C/C(=C\c1ccc(O)c(O)c1)C(=O)Nc1nc(-c2ccc(Br)cc2)cs1]

The compound was prepared according to General procedure D1 from N-(4-(4-bromophenyl)thiazol-2-yl)-2-cyanoacetamide (150 mg, 0.46 mmol), 3,4-dihydroxybenzaldehyde (61 mg, 0.44 mmol) and NEt₃ (65 μL, 0.46 mmol) in EtOH (3 mL); the reaction time was 4 h. Work-up 1 of General procedure D1. The product was obtained as a yellow solid (80 mg, 40%).

$^1$H NMR (500 MHz, DMSO-d$_6$) δ (ppm) 12.68 (s, 1H), 10.29 (s, 1H), 9.65 (s, 1H), 8.31 (s, 1H), 7.89 (d, J=8.4 Hz, 2H), 7.77 (s, 1H), 7.65 (d, J=8.4 Hz, 2H), 7.61 (d, J=2.1 Hz, 1H), 7.38 (dd, J=8.4, 2.2 Hz, 1H), 6.94 (d, J=8.3 Hz, 1H);

$^{13}$C NMR (126 MHz, DMSO-d$_6$) δ (ppm) 161.8, 152.1, 158.1, 151.5, 147.9, 145.8, 133.3, 131.7, 127.7, 125.9, 123.1, 120.9, 116.5, 116.4, 116.1, 109.5;

HRMS calcd for C$_{19}$H$_{12}$BrN$_3$O$_3$S [M−H]⁻ 441.9691, found 441.9691.

Preparative Example 84

(E)-2-cyano-3-(3,4-dihydroxyphenyl)-N-(4-phenylthiazol-2-yl)acrylamide

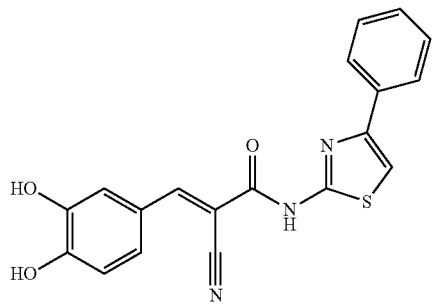 [SMILES: N#C/C(=C\c1ccc(O)c(O)c1)C(=O)Nc1nc(-c2ccccc2)cs1]

The compound was prepared according to General procedure D2 from 2-cyano-N-(4-phenylthiazol-2-yl)acetamide (775 mg, 3.19 mmol), 3,4-dihydroxybenzaldehyde (440 mg, 3.19 mmol), and piperidine (31 L, 0.319 mmol) in CH$_2$Cl$_2$ (20 mL); the reaction time was 3 h. The crude product was purified by column chromatography (toluene:EtOAc; 1:1). The combined fractions containing the product were concentrated in vacuo to the volume of 10 mL. EtOAc (1 mL) was added and the precipitated solid was collected by filtration, washed on filter with a mixture of toluene and EtOAc (2.7 mL+0.3 mL), and dried under vacuum. The product was obtained as a yellow solid (780 mg, 67%).

$^1$H NMR (500 MHz, DMSO-d$_6$) δ (ppm) 12.64 (s, 1H), 10.21 (s, 1H), 9.70 (s, 1H), 8.32 (s, 1H), 7.94 (d, J=7.0 Hz, 2H), 7.68 (s, 1H), 7.62 (d, J=2.3 Hz, 1H), 7.45 (m, J=7.7 Hz, 2H), 7.39 (dd, J=8.4, 2.3 Hz, 1H), 7.38-7.31 (m, 1H), 6.94 (d, J=8.2 Hz, 1H);

$^{13}$C NMR (126 MHz, DMSO-d$_6$) δ (ppm) 161.9, 158.2, 152.1, 151.5, 149.1, 145.8, 134.1, 128.7, 127.9, 125.9, 125.7, 123.1, 116.5, 116.1, 108.7, 99.7;

HRMS calcd for C$_{19}$H$_{12}$N$_3$O$_3$S [M−H]⁻ 362.0605, found 362.0608.

Preparative Example 85

(E)-2-cyano-N-(4-(4-cyanophenyl)thiazol-2-yl)-3-(3,4-dihydroxyphenyl)acrylamide

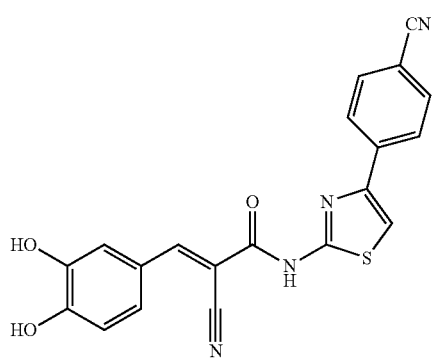

The compound was prepared according to General procedure D1 from 2-cyano-N-(4-(4-cyanophenyl)thiazol-2-yl)

acetamide (90 mg, 0.33 mmol), 3,4-dihydroxybenzaldehyde (42 mg, 0.30 mmol) and NEt₃ (46 μL, 0.33 mmol) in EtOH (3 mL). The reaction time was 4 h at 50° C. and then 16 h at 25° C. Work-up 2 of General procedure D1. The crude product was purified by column chromatography (hexane: EtOAc:MeOH; 1:1:0 to 0:50:1). The fractions containing the product were concentrated in vacuo to the residual volume of 5 mL. The precipitate was collected by filtration and dried under vacuum. The product was obtained as a yellow solid (35 mg, 30%).

¹H NMR (500 MHz, DMSO-d₆) δ (ppm) 12.74 (s, 1H), 10.30 (s, 1H), 9.66 (s, 1H), 8.32 (s, 1H), 8.16-8.07 (m, 2H), 8.00 (s, 1H), 7.96-7.84 (m, 2H), 7.62 (d, J=2.3 Hz, 1H), 7.39 (dd, J=8.4, 2.2 Hz, 1H), 6.94 (d, J=8.2 Hz, 11H);

¹³C NMR (126 MHz, DMSO-d₆) δ (ppm) 162.0, 158.6, 152.3, 151.6, 147.3, 145.8, 138.3, 132.8, 126.3, 126.0, 123.1, 118.8, 116.5, 116.3, 116.1, 112.3, 110.0;

HRMS calcd for C₂₀H₁₁N₄O₃S [M−H]⁻ 387.0557, found 387.0558.

Preparative Example 86

(E)-2-cyano-3-(3,4-dihydroxyphenyl)-N-(4-(4-(trifluoromethyl)phenyl)thiazol-2-yl)acrylamide

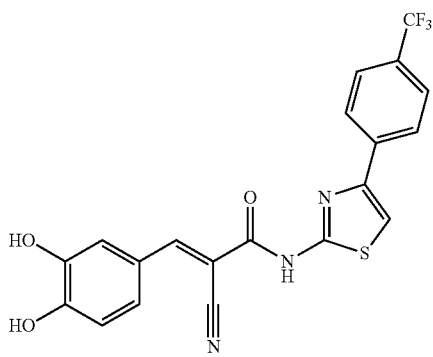 [SMILES: N#C/C(=C\c1ccc(O)c(O)c1)C(=O)Nc1nc(-c2ccc(C(F)(F)F)cc2)cs1]

The compound was prepared according to General procedure D1 from 2-cyano-N-(4-(4-trifluoromethylphenyl)thiazol-2-yl)acetamide (80 mg, 0.33 mmol), 3,4-dihydroxybenzaldehyde (32 mg, 0.30 mmol) and NEt₃ (36 μL, 0.26 mmol) in EtOH (3 mL); the reaction time was 4 h at 50° C. and then 16 h at 25° C. Work-up 1 of General procedure D1. The product was obtained as a yellow solid (42 mg, 40%).

¹H NMR (500 MHz, DMSO-d₆) δ (ppm) 12.64 (s, 1H), 9.74 (s, 2H), 8.32 (s, 1H), 8.16 (d, J=8.3 Hz, 2H), 7.92 (s, 1H), 7.82 (d, J=8.2 Hz, 2H), 7.63 (d, J=2.3 Hz, 1H), 7.39 (dd, J=8.4, 2.3 Hz, 1H), 6.94 (d, J=8.3 Hz, 1H);

¹³C NMR (126 MHz, DMSO-d₆) δ (ppm) 162.2, 159.0, 152.5, 152.1, 147.2, 146.3, 138.4, 128.4 (q, J=31.8 Hz), 126.8, 126.2 (q, J=4.5 Hz), 126.2 (q, J=70.8 Hz), 124.8 (q, J=272.2 Hz), 123.6, 117.0, 116.6, 111.7;

HRMS calcd for C₂₀H₁₁F₃N₃O₃S [M−H]⁻ 430.0479, found 430.0481.

Preparative Example 87

(E)-2-cyano-3-(3,4-dihydroxyphenyl)-N-(4-(p-tolyl)thiazol-2-yl)acrylamide

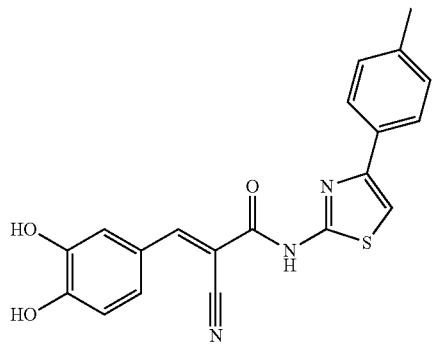 [SMILES: Cc1ccc(-c2csc(NC(=O)/C(C#N)=C/c3ccc(O)c(O)c3)n2)cc1]

The compound was prepared according to General procedure D1 from 2-cyano-N-(4-(p-tolyl)thiazol-2-yl)acetamide (60 mg, 0.233 mmol), 3,4-dihydroxybenzaldehyde (31 mg, 0.222 mmol) and NEt₃ (32 μL, 0.233 mmol) in EtOH (1 mL); the reaction time was 1.5 h. The solvent was evaporated in vacuo and the residue was stirred in a mixture of CH₂Cl₂ and CH₃CN (1.5 mL+1.5 mL) at 25° C. for 2 h. The solid was collected by filtration, washed on filter with EtOH (1 mL), diethyl ether (1 mL), and dried under vacuum. The product was obtained as an orange solid (33 mg, 38%).

¹H NMR (500 MHz, DMSO-d₆) δ (ppm) 10.69 (s, 2H), 8.28 (s, 1H), 7.83 (d, J=7.9 Hz, 2H), 7.61 (d, J=2.3 Hz, 1H), 7.57 (s, 1H), 7.38 (dd, J=8.4, 2.3 Hz, 1H), 7.26 (d, J=8.2 Hz, 2H), 6.92 (d, J=8.2 Hz, 1H), 2.34 (s, 3H);

¹³C NMR (126 MHz, DMSO-d₆) δ (ppm) 162.4, 159.4, 151.8, 151.6, 145.8, 137.1, 131.4, 129.3, 125.9, 125.7, 123.0, 116.7, 116.3, 116.1, 107.6, 20.8;

HRMS calcd for C₂₀H₁₄N₃O₃S [M−H]⁻ 376.0761, found 376.0761.

Preparative Example 88

(E)-2-cyano-3-(3,5-dichloro-4-hydroxyphenyl)-N-(4,5-diphenylthiazol-2-yl)acrylamide

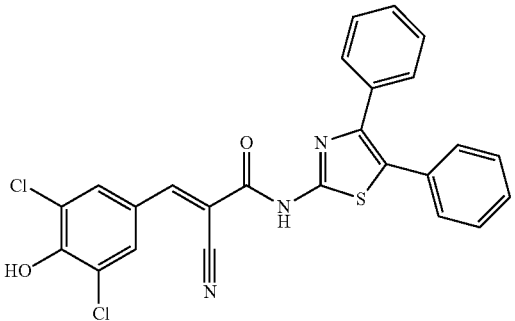 [SMILES: N#C/C(=C\c1cc(Cl)c(O)c(Cl)c1)C(=O)Nc1nc(-c2ccccc2)c(-c2ccccc2)s1]

The compound was prepared according to General procedure D1 from 2-cyano-N-(4,5-diphenylthiazol-2-yl)acetamide (70 mg, 0.22 mmol), 3,5-dichloro-4-hydroxybenzaldehyde (40 mg, 0.21 mmol) and NEt₃ (30 μL, 0.22 mmol) in EtOH (3 mL); the reaction time was 4 h. Work-up 2 of General procedure D1. The product, purified by reverse phase column chromatography (H$_2$O:MeOH:AcOH; 45:55:0.05 to 5:95:0.05), was obtained as a pale yellow solid (65 mg, 60%).

$^1$H NMR (500 MHz, DMSO-d$_6$) δ (ppm) 12.86 (s, 1H), 8.32 (s, 1H), 8.05 (s, 2H), 7.47-7.43 (m, 2H), 7.41-7.31 (m, 8H);

$^{13}$C NMR (126 MHz, DMSO-d$_6$) δ (ppm) 149.8, 132.0, 131.5, 129.7, 129.5, 129.1, 128.9, 128.6, 123.5, 116.8;

HRMS calcd for C$_{25}$H$_{14}$Cl$_2$N$_3$O$_2$S [M−H]$^-$ 490.0189, found 490.0190.

Preparative Example 89

(E)-2-cyano-3-(3,4-dihydroxyphenyl)-N-(4-phenyl-5-(p-tolyl)thiazol-2-yl)acrylamide

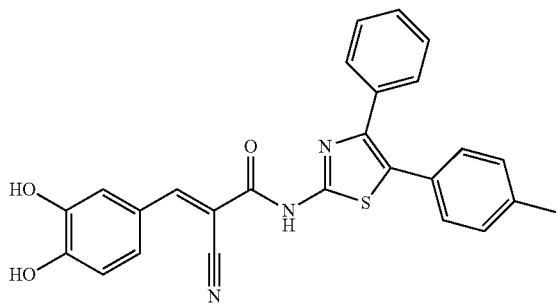 [SMILES: Cc1ccc(-c2sc(NC(=O)/C(C#N)=C/c3ccc(O)c(O)c3)nc2-c2ccccc2)cc1]

The compound was prepared according to General procedure D1 from 2-cyano-N-(4-phenyl-5-(p-tolyl)thiazol-2-yl)acetamide (90 mg, 0.27 mmol), 3,4-dihydroxybenzaldehyde (35 mg, 0.26 mmol) and NEt$_3$ (38 μL, 0.27 mmol) in EtOH (3 mL); the reaction time was 4 h. Work-up 2 of General procedure D1. The product, purified by reverse phase column chromatography (H$_2$O:MeOH:AcOH; 40:60:0.05 to 15:85:0.05), was obtained as a yellow solid (40 mg, 40%).

$^1$H NMR (500 MHz, DMSO-d$_6$) δ (ppm) 12.70 (s, 1H), 10.26 (s, 1H), 9.66 (s, 1H), 8.31 (s, 1H), 7.61 (d, J=2.3 Hz, 1H), 7.49-7.44 (m, 2H), 7.38 (dd, J=8.4, 2.3 Hz, 1H), 7.36-7.30 (m, 3H), 7.25-7.17 (m, 4H), 6.93 (d, J=8.4 Hz, 1H), 2.32 (s, 3H);

$^{13}$C NMR (126 MHz, DMSO-d$_6$) δ (ppm) 152.0, 151.5, 145.8, 137.5, 129.5, 129.1, 128.6, 128.5, 128.3, 127.8, 125.9, 123.1, 116.5, 116.1, 20.7;

HRMS calcd for C$_{26}$H$_{18}$N$_3$O$_3$S [M−H]$^-$ 452.1074, found 452.1075.

Preparative Example 90

(E)-2-cyano-3-(3,4-dihydroxyphenyl)-N-(4-(4-(trifluoromethoxy)phenyl)thiazol-2-yl)acrylamide

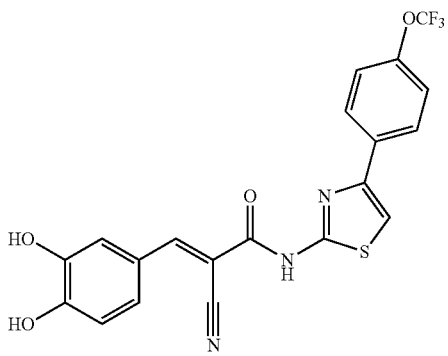 [SMILES: N#C/C(=C\c1ccc(O)c(O)c1)C(=O)Nc1nc(-c2ccc(OC(F)(F)F)cc2)cs1]

The compound was prepared according to General procedure D1 from 2-cyano-N-(4-(4-(trifluoromethoxy)phenyl)thiazol-2-yl)acetamide (55 mg, 0.168 mmol), 3,4-dihydroxybenzaldehyde (22 mg, 0.16 mmol) and NEt$_3$ (23 μL, 0.168 mmol) in EtOH (1 mL); the reaction time was 2 h. The solvent was evaporated in vacuo and the residue was purified by preparative TLC (hexane:EtOAc, 1:1), followed by reverse phase column chromatography (H$_2$O:MeOH:AcOH; 70:30:0.05 to 20:80:0.05). The product was obtained as an orange-brown solid (15 mg, 20%).

$^1$H NMR (500 MHz, DMSO-d$_6$) δ (ppm) 8.29 (s, 1H), 8.08-8.02 (m, 2H), 7.75 (s, 1H), 7.61 (d, J=2.1 Hz, 1H), 7.44 (d, J=7.9 Hz, 2H), 7.38 (dd, J=8.4, 2.3 Hz, 1H), 6.93 (d, J=8.2 Hz, 1H); $^{13}$C NMR (126 MHz, DMSO-d$_6$) δ (ppm) 152.4, 152.2, 148.3, 146.3, 134.0, 128.0, 126.4, 123.6, 121.8, 120.6 (q, J=256.2 Hz), 117.1, 117.0, 116.6, 110.1;

$^{19}$F NMR (471 MHz, DMSO-d$_6$) δ (ppm) −56.68;

HRMS calcd for C$_{20}$H$_{11}$F$_3$N$_3$O$_4$S [M−H]$^-$ 446.0428, found 446.0428.

Preparative Example 91

(E)-2-cyano-3-(3,5-dichloro-4-hydroxyphenyl)-N-(4-(4-(trifluoromethoxy)phenyl)thiazol-2-yl)acrylamide

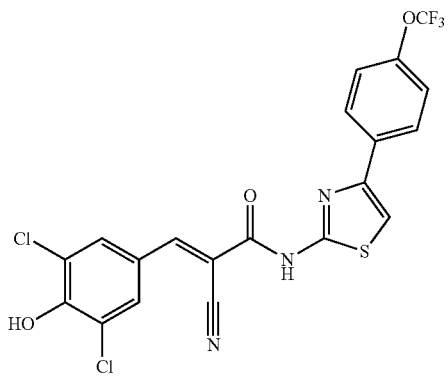 [SMILES: N#C/C(=C\c1cc(Cl)c(O)c(Cl)c1)C(=O)Nc1nc(-c2ccc(OC(F)(F)F)cc2)cs1]

The compound was prepared according to General procedure D1 from 2-cyano-N-(4-(4-(trifluoromethoxy)phenyl)

thiazol-2-yl)acetamide (50 mg, 0.15 mmol), 4-hydroxy-3,5-dichlorobenzaldehyde (28 mg, 0.14 mmol) and NEt$_3$ (21 µL, 0.15 mmol) in EtOH (3 mL); the reaction time was 4 h. Work-up 2 of General procedure D1. The product, purified by column chromatography (hexane:EtOAc:MeOH; 1:1:0 to 0:10:1), was obtained as a yellow solid (35 mg, 45%).

$^1$H NMR (500 MHz, DMSO-d$_6$) δ (ppm) 12.84 (s, 1H), 8.36 (s, 1H), 8.06-8.04 (m, 4H), 7.80 (s, 1H), 7.45 (d, J=8.3 Hz, 2H);

$^{13}$C NMR (126 MHz, DMSO-d$_6$) δ (ppm) 161.1, 153.6, 149.4, 147.9, 130.8, 127.5, 122.7, 121.3, 121.1, 120.1 (q, J=256.2 Hz), 119.0, 115.8, 109.9;

$^{19}$F NMR (471 MHz, DMSO-d$_6$) δ (ppm) −56.69;

HRMS calcd for C$_{20}$H$_9$F$_3$N$_3$O$_3$S [M−H]$^-$ 497.9699, found 497.9697.

Preparative Example 92

(E)-N-(4-([1,1'-biphenyl]-3-yl)thiazol-2-yl)-2-cyano-3-(3,4-dihydroxyphenyl)acrylamide

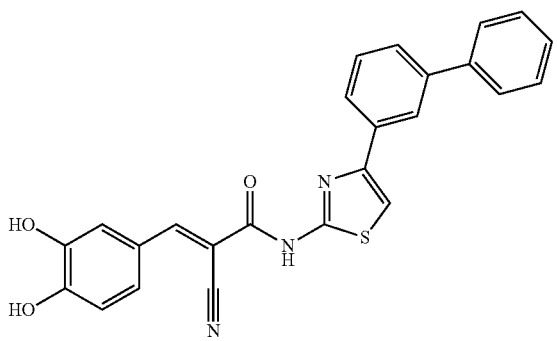 [SMILES: N#C/C(=C\c1ccc(O)c(O)c1)C(=O)Nc1nc(-c2cccc(-c3ccccc3)c2)cs1]

The compound was prepared according to General procedure D2 from N-(4-([1,1'-biphenyl]-3-yl)thiazol-2-yl)-2-cyanoacetamide (200 mg, 0.6 mmol), 3,4-dihydroxybenzaldehyde (85 mg, 0.6 mmol) and piperidine (6.0 µL, 0.06 mmol) in CH$_2$Cl$_2$ (3 mL); the reaction time was 4 h at reflux and then 16 h at 25° C. The product, purified by reverse phase column chromatography (H$_2$O:MeOH:AcOH; 45:55:0.05 to 10:90:0.05), was obtained as a yellow solid (80 mg, 30%).

$^1$H NMR (500 MHz, DMSO-d$_6$) δ (ppm) 12.61 (s, 1H), 9.81 (s, 2H), 8.32 (s, 1H), 8.24 (s, 1H), 7.94 (d, J=7.7 Hz, 1H), 7.83 (s, 1H), 7.74 (d, J=7.6 Hz, 2H), 7.64 (d, J=7.9 Hz, 1H), 7.62 (d, J=2.2 Hz, 1H), 7.56-7.53 (m, 1H), 7.52-7.50 (m, 1H), 7.43-7.37 (m, 2H), 6.94 (d, J=8.3 Hz, 1H);

$^{13}$C NMR (126 MHz, DMSO-d$_6$) δ (ppm) 161.9, 152.0, 151.6, 145.8, 140.7, 140.0, 134.5, 129.4, 128.9, 127.6, 126.7, 126.2, 125.7, 124.8, 124.1, 123.1, 116.5, 116.1;

HRMS calcd for C$_{25}$H$_{16}$N$_3$O$_3$S [M−H]$^-$ 438.0918, found 438.0918.

Preparative Example 93

(E)-2-cyano-3-(3,5-di-tert-butyl-4-hydroxyphenyl)-N-(4-phenylthiazol-2-yl)acrylamide

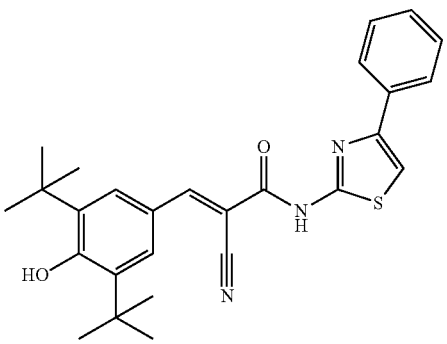 [SMILES: CC(C)(C)c1cc(/C=C(\C#N)C(=O)Nc2nc(-c3ccccc3)cs2)cc(C(C)(C)C)c1O]

The compound was prepared according to General procedure D1 from 2-cyano-N-(4-phenylthiazol-2-yl)acetamide (50 mg, 0.21 mmol), 3,5-di-tert-butyl-4-hydroxybenzaldehyde hemihydrate (50 mg, 0.21 mmol), and piperidine (2.0 µL, 0.027 mmol) in CH$_2$Cl$_2$ (2 mL); the reaction time was 2 h at reflux. The solvent was evaporated in vacuo and the residue was purified by column chromatography (hexane:EtOAc; 10:1 to 3:1). The product was obtained as a yellow solid (72 mg, 76%).

$^1$H NMR (500 MHz, DMSO-d$_6$) δ (ppm) 12.66 (s, 1H), 8.49 (s, 1H), 8.16 (s, 1H), 8.00-7.89 (m, 4H), 7.69 (s, 1H), 7.49-7.41 (m, 2H), 7.39-7.31 (m, 1H), 1.43 (s, 18H);

$^{13}$C NMR (126 MHz, DMSO-d$_6$) δ (ppm) 159.2, 152.9, 139.0, 134.1, 128.7, 128.7, 127.9, 125.7, 122.9, 116.6, 108.7, 34.7, 29.9;

HRMS calcd for C$_{27}$H$_{28}$N$_3$O$_2$S [M−H]$^-$ 458.1908, found 458.1908.

Preparative Example 94

(E)-N-(4-(4-(tert-butyl)phenyl)thiazol-2-yl)-2-cyano-3-(3,4-dihydroxyphenyl)acrylamide

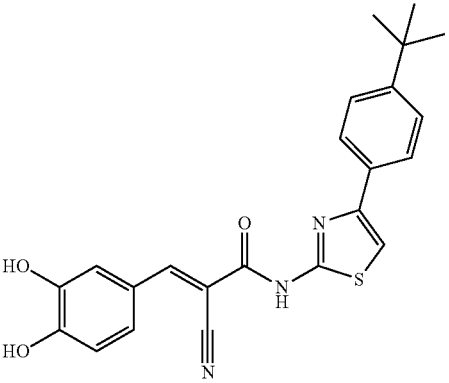 [SMILES: CC(C)(C)c1ccc(-c2csc(NC(=O)/C(C#N)=C/c3ccc(O)c(O)c3)n2)cc1]

The compound was prepared according to General procedure D2 from N-(4-(4-(tert-butyl)phenyl)thiazol-2-yl)-2-cyanoacetamide (80 mg, 0.267 mmol), 3,4-dihydroxybenzaldehyde (37 mg, 0.267 mmol) and piperidine (3.0 µL, 0.027 mmol) in CH$_2$Cl$_2$ (6 mL); the reaction time was 2 h at reflux and then 16 h at 25° C. The product, purified by reverse phase column chromatography (H$_2$O:MeOH:AcOH; 40:60:0.05 to 6:94:0.05), was obtained as a yellow solid (110 mg, 89%).

$^1$H NMR (500 MHz, DMSO-d$_6$) δ (ppm) 8.29 (s, 1H), 7.89-7.82 (m, 2H), 7.65-7.56 (m, 2H), 7.46 (d, J=8.5 Hz, 2H), 7.38 (d, J=8.4 Hz, 1H), 6.92 (d, J=8.2 Hz, 1H), 1.31 (s, 9H);

$^{13}$C NMR (126 MHz, DMSO-d$_6$) δ (ppm) 162.3, 151.8, 151.7, 150.4, 145.8, 131.2, 125.9, 125.5, 125.4, 123.1, 116.4, 116.1, 107.8, 34.3, 31.0;

HRMS calcd for C$_{23}$H$_{22}$N$_3$O$_3$S [M+H]$^+$ 420.1376, found 420.1377.

Preparative Example 95

(E)-2-cyano-3-(3,5-dichloro-4-hydroxyphenyl)-N-(4-(naphthalen-2-yl)thiazol-2-yl)acrylamide

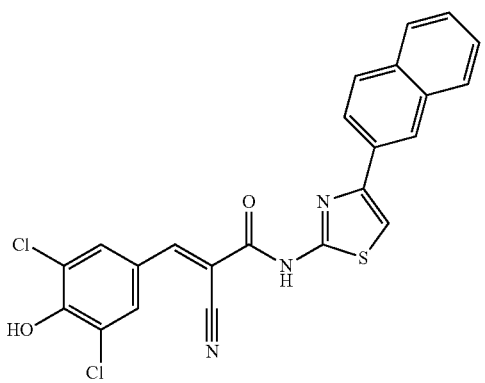 [SMILES: N#C/C(=C\c1cc(Cl)c(O)c(Cl)c1)C(=O)Nc1nc(-c2ccc3ccccc3c2)cs1]

The compound was prepared according to General procedure D1 from 2-cyano-N-(4-(naphthalen-2-yl)thiazol-2-yl)acetamide (50 mg, 0.17 mmol), 3,5-dichloro-4-hydroxybenzaldehyde (31 mg, 0.16 mmol) and NEt$_3$ (24 μL, 0.17 mmol) in EtOH (1.5 mL); the reaction time was 4 h. Work-up 2 of General procedure D1. The product, purified by column chromatography (CH$_2$Cl$_2$:MeOH; 10:1), was obtained as a pale yellow solid (30 mg, 40%).

$^1$H NMR (500 MHz, DMSO-d$_6$) δ (ppm) 12.86 (s, 1H), 8.49 (d, J=1.6 Hz, 1H), 8.39 (s, 1H), 8.07 (s, 3H), 7.99 (d, J=8.7 Hz, 1H), 7.97-7.92 (m, 2H), 7.86 (s, 1H), 7.61-7.49 (m, 2H);

$^{13}$C NMR (126 MHz, DMSO-d$_6$) δ (ppm) 161.0, 153.4, 149.3, 133.1, 132.6, 131.4, 130.8, 128.3, 128.1, 128.0, 127.6, 126.6, 126.3, 124.4, 123.9, 122.7, 115.7;

HRMS calcd for C$_{23}$H$_{12}$Cl$_2$N$_3$O$_2$S [M−H]$^−$ 464.0033, found 464.0032.

Preparative Example 96

(E)-2-cyano-3-(3,4-dihydroxyphenyl)-N-(4-(thiophen-3-yl)thiazol-2-yl)acrylamide

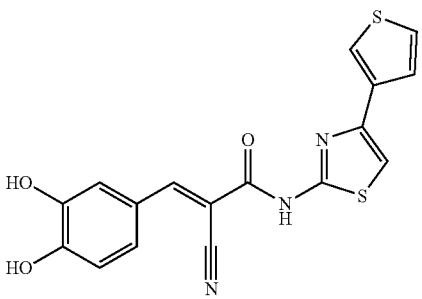 [SMILES: N#C/C(=C\c1ccc(O)c(O)c1)C(=O)Nc1nc(-c2ccsc2)cs1]

The compound was prepared according to General procedure D1 from 2-cyano-N-(4-(thiophen-3-yl)thiazol-2-yl)acetamide (67 mg, 0.27 mmol), 3,4-dihydroxybenzaldehyde (35 mg, 0.25 mmol) and NEt$_3$ (40 μL, 0.27 mmol) in EtOH (3 mL); the reaction time was 2.5 h at 50° C. and then 16 h at 25° C. Work-up 1 of General procedure D1. The product was obtained as a yellow solid (55 mg, 55%).

$^1$H NMR (500 MHz, DMSO-d$_6$) δ (ppm) 12.55 (s, 1H), 9.85 (s, 2H), 8.29 (s, 1H), 7.85 (s, 1H), 7.66-7.57 (m, 3H), 7.51 (s, 1H), 7.37 (dd, J=8.4, 2.1 Hz, 1H), 6.93 (d, J=8.3 Hz, 1H);

$^{13}$C NMR (126 MHz, DMSO-d$_6$) δ (ppm) 162.3, 151.8, 151.5, 145.8, 135.9, 127.0, 126.0, 125.8, 123.1, 121.6, 116.6, 116.5, 116.0, 107.9;

HRMS calcd for C$_{17}$H$_{10}$N$_3$O$_3$S$_2$ [M−H]$^−$ 368.0169, found 368.0169.

Preparative Example 97

(E)-2-cyano-N-(5-cyclohexyl-4-phenylthiazol-2-yl)-3-(3,4-dihydroxyphenyl)acrylamide

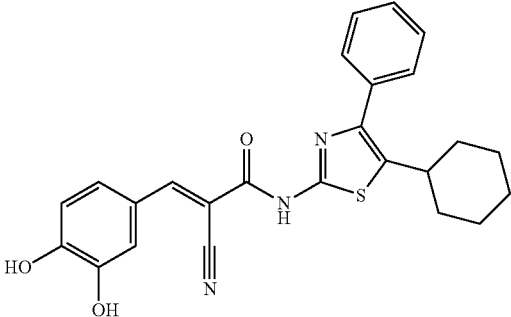 [SMILES: N#C/C(=C\c1ccc(O)c(O)c1)C(=O)Nc1nc(-c2ccccc2)c(C2CCCCC2)s1]

The compound was prepared according to General procedure D2 from 2-cyano-N-(5-cyclohexyl-4-phenylthiazol-2-yl)acetamide (50 mg, 0.15 mmol), 3,4-dihydroxybenzaldehyde (31 mg, 0.15 mmol) and piperidine (2 μL, 0.02 mmol) in CH$_2$Cl$_2$ (2 mL); the reaction time was 4 h at 50° C. and then 16 h at 25° C. The product, purified by reverse phase column chromatography (H$_2$O:MeOH:AcOH; 45:55:0.5 to 10:90:0.5), was obtained as a yellow solid (30 mg, 45%).

¹H NMR (500 MHz, DMSO-d₆) δ (ppm) 12.51 (s, 1H), 10.13 (s, 1H), 9.70 (s, 1H), 8.24 (s, 1H), 7.60 (d, J=2.3 Hz, 1H), 7.55 (d, J=7.3 Hz, 2H), 7.48 (dd, J=8.6, 6.8 Hz, 2H), 7.40 (t, J=7.3 Hz, 1H), 7.35 (dd, J=8.4, 2.3 Hz, 1H), 6.92 (d, J=8.3 Hz, 1H), 3.05-2.91 (m, 1H), 2.02-1.90 (m, 2H), 1.83-1.74 (m, 2H), 1.72-1.63 (m, 1H), 1.51-1.37 (m, 2H), 1.36-1.22 (m, 3H);

¹³C NMR (126 MHz, DMSO-d₆) δ (ppm) 151.6, 151.3, 145.8, 135.0, 128.5, 128.9, 127.7, 125.7, 123.2, 116.5, 116.0, 36.4, 35.7, 26.1, 25.2;

HRMS calcd for $C_{25}H_{22}N_3O_3S$ [M−H]⁻ 444.1387, found 444.1387.

Preparative Example 98

(E)-2-cyano-3-(4-hydroxy-3,5-dimethylphenyl)-N-(4-phenylthiazol-2-yl)acrylamide

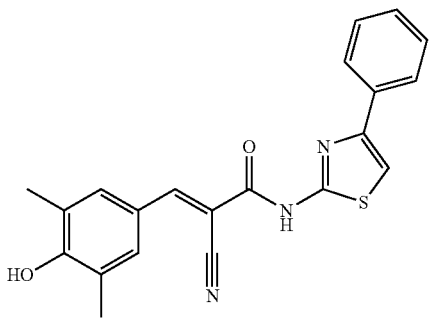 [SMILES: Cc1cc(/C=C(\C#N)C(=O)Nc2nc(-c3ccccc3)cs2)cc(C)c1O]

The compound was prepared according to General procedure D1 from 2-cyano-N-(4-phenylthiazol-2-yl)acetamide (80 mg, 0.33 mmol), 4-hydroxy-3,5-dimethylbenzaldehyde (47 mg, 0.31 mmol) and NEt₃ (46 μL, 0.33 mmol) in EtOH (3 mL); the reaction time was 4 h. Work-up 1 of General procedure D1. The product was obtained as a yellow solid (50 mg, 50%).

¹H NMR (500 MHz, DMSO-d₆) δ (ppm) 12.67 (s, 1H), 9.60 (s, 1H), 8.34 (s, 1H), 7.98-7.89 (m, 2H), 7.76-7.67 (m, 3H), 7.46-7.44 (m, 2H), 7.38-7.31 (m, 1H), 2.24 (s, 6H);

¹³C NMR (126 MHz, DMSO-d₆) δ (ppm) 162.0, 158.7, 151.9, 134.0, 131.9, 128.7, 127.9, 125.7, 125.1, 122.7, 116.5, 108.6, 100.1, 16.6;

HRMS calcd for $C_{21}H_{16}N_3O_2S$ [M−H]⁻ 374.0969, found 374.0969.

Preparative Example 99

(E)-3-(2-bromo-3,4-dihydroxyphenyl)-2-cyano-N-(4-phenylthiazol-2-yl)acrylamide

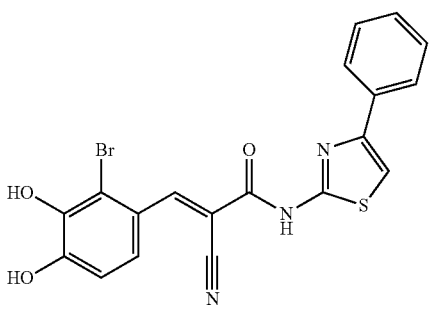 [SMILES: N#C/C(=C\c1ccc(O)c(O)c1Br)C(=O)Nc1nc(-c2ccccc2)cs1]

The compound was prepared according to General procedure D2 from 2-cyano-N-(4-phenylthiazol-2-yl)acetamide (90 mg, 0.42 mmol), 2-bromo-3,4-dihydroxybenzaldehyde (73 mg, 0.42 mmol) and piperidine (3 μL, 0.027 mmol) in CH₂Cl₂ (3 mL). The reaction time was 2 h at reflux. The product, purified by reverse phase column chromatography (H₂O:MeOH:AcOH; 60:40:0.05 to 5:95:0.05), was obtained as a yellow solid (150 mg, 80%).

¹H NMR (500 MHz, DMSO-d₆) δ (ppm) 8.41 (s, 1H), 7.95-7.91 (m, 2H), 7.85 (d, J=8.7 Hz, 1H), 7.57 (s, 1H), 7.48-7.39 (m, 2H), 7.36-7.28 (m, 1H), 6.66 (d, J=8.7 Hz, 1H);

¹³C NMR (126 MHz, DMSO-d₆) δ (ppm) 163.1, 161.0, 149.2, 148.1, 145.2, 134.3, 128.6, 127.6, 125.7, 123.5, 118.1, 114.4, 112.8, 108.1;

HRMS calcd for $C_{19}H_{13}BrN_3O_3S$ [M+H]⁺ 443.9836, found 443.9840.

Preparative Example 100

(E)-N-(4-(4-(tert-butyl)phenyl)thiazol-2-yl)-2-cyano-3-(4-hydroxy-3,5-dimethylphenyl)acrylamide

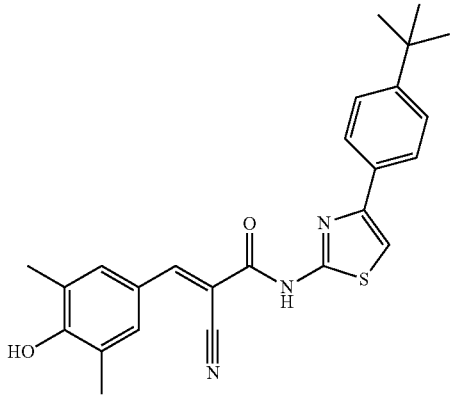 [SMILES: Cc1cc(/C=C(\C#N)C(=O)Nc2nc(-c3ccc(C(C)(C)C)cc3)cs2)cc(C)c1O]

The compound was prepared according to General procedure D2 from N-(4-(4-(tert-butyl)phenyl)thiazol-2-yl)-2-cyanoacetamide (75 mg, 0.251 mmol), 4-hydroxy-3,5-dimethylbenzaldehyde (38 mg, 0.251 mmol), and piperidine (1.8 mg, 2 μL, 0.025 mmol) in CH₂Cl₂ (4 mL); the reaction time was 3 h at reflux. The residue was purified by column chromatography (hexane:EtOAc; 10:1 to 2:1) to give the product as a yellow solid (101 mg, 93%).

¹H NMR (500 MHz, DMSO-d₆) δ (ppm) 12.63 (s, 1H), 9.61 (s, 1H), 8.33 (s, 1H), 7.86 (d, J=8.4 Hz, 2H), 7.71 (s, 2H), 7.62 (s, 1H), 7.47 (d, J=8.5 Hz, 2H), 2.24 (s, 6H), 1.31 (s, 9H);

¹³C NMR (126 MHz, DMSO-d₆) δ (ppm) 161.8, 158.7, 157.9, 151.8, 150.4, 131.9, 125.5, 125.1, 122.7, 116.5, 108.0, 99.9, 34.5, 34.3, 31.1, 31.0, 16.6;

HRMS calcd for $C_{25}H_{26}N_3O_2S$ [M+H]⁺ 432.1740, found 432.1738.

Preparative Example 101

(E)-N-(4-(4-(tert-butyl)phenyl)thiazol-2-yl)-2-cyano-3-(3,5-di-tert-butyl-4-hydroxyphenyl)acrylamide

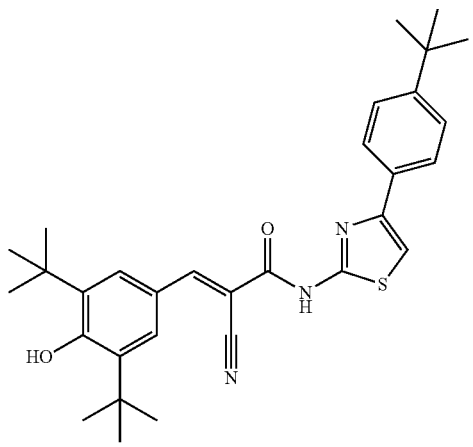 [SMILES: CC(C)(C)c1ccc(-c2csc(NC(=O)/C(C#N)=C/c3cc(C(C)(C)C)c(O)c(C(C)(C)C)c3)n2)cc1]

The compound was prepared according to General procedure D2 from N-(4-(4-(tert-butyl)phenyl)thiazol-2-yl)-2-cyanoacetamide (75 mg, 0.251 mmol), 3,5-di-tert-butyl-4-hydroxybenzaldehyde (59 mg, 0.251 mmol), and piperidine (2 μL, 0.025 mmol) in $CH_2Cl_2$ (4 mL); the reaction time was 3 h at reflux. The residue was purified by column chromatography (hexane:EtOAc, 10:1 to 6:1) to give the product as a yellow solid (124 mg, 96% yield).

$^1$H NMR (500 MHz, DMSO-$d_6$) δ (ppm) 12.65 (s, 1H), 8.49 (s, 1H), 8.16 (s, 1H), 7.94 (s, 2H), 7.86 (d, J=8.4 Hz, 2H), 7.62 (s, 1H), 7.47 (d, J=8.5 Hz, 2H), 1.43 (s, 18H), 1.31 (s, 9H);

$^{13}$C NMR (126 MHz, DMSO-$d_6$) δ (ppm) 159.7, 159.4, 157.0, 156.2, 151.5, 150.7, 137.3, 131.6, 129.9, 126.0, 125.9, 123.7, 117.2, 108.1, 97.5, 34.8, 34.8, 31.4, 30.2;

HRMS calcd for $C_{31}H_{37}N_3O_2S$ $[M+H]^+$ 516.2679, found 516.2678.

Preparative Example 102

(E)-2-cyano-3-(3-cyano-4-hydroxyphenyl)-N-(4-phenylthiazol-2-yl)acrylamide

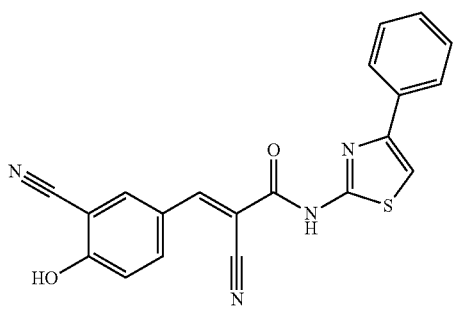 [SMILES: N#C/C(=C\c1ccc(O)c(C#N)c1)C(=O)Nc1nc(-c2ccccc2)cs1]

The compound was prepared according to General procedure D2 from 2-cyano-N-(4-phenylthiazol-2-yl)acetamide (47 mg, 0.20 mmol), 5-formyl-2-hydroxybenzonitrile (30 mg, 0.20 mmol) and piperidine (3 L, 0.027 mmol) in $CH_2Cl_2$ (2 mL). The reaction time was 2 h at reflux. The precipitate was collected by filtration, washed with $CH_2Cl_2$ (3 mL) and dried under vacuum. The product was obtained as a yellow solid (50 mg, 70%).

$^1$H NMR (500 MHz, DMSO-$d_6$) δ (ppm) 8.14 (s, 1H), 8.01-7.97 (m, 1H), 7.96-7.90 (m, 3H), 7.62 (s, 1H), 7.48-7.41 (m, 2H), 7.37-7.30 (m, 1H), 6.45 (d, J=9.4 Hz, 1H);

$^{13}$C NMR (126 MHz, DMSO-$d_6$) δ (ppm) 174.9, 163.0, 158.9, 149.9, 148.6, 140.8, 135.0, 134.2, 128.7, 127.7, 125.7, 122.0, 119.3, 118.2, 114.1, 108.2, 102.0;

HRMS calcd for $C_{20}H_{13}N_4O_2S$ $[M+H]^+$ 373.0754, found 373.0750.

Preparative Example 103

(E)-2-cyano-3-(3,4-dihydroxyphenyl)-N-(4-(4-methylthiophen-3-yl)thiazol-2-yl)acrylamide

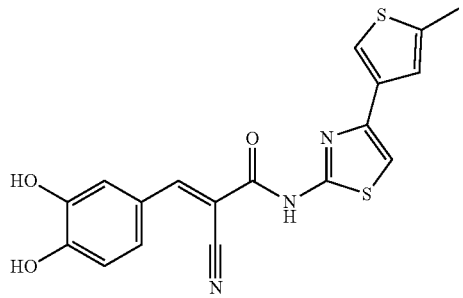 [SMILES: Cc1cc(-c2csc(NC(=O)/C(C#N)=C/c3ccc(O)c(O)c3)n2)cs1]

The compound was prepared according to General procedure D2 from 2-cyano-N-(4-(4-methylthiophen-3-yl)thiazol-2-yl)acetamide (50 mg, 0.19 mmol), 3,4-dihydroxybenzaldehyde (26 mg, 0.19 mmol) and piperidine (3 μL, 0.027 mmol) in $CH_2Cl_2$ (2 mL). The reaction time was 2 h at reflux. The product, purified by reverse phase column chromatography ($H_2O$:MeOH:AcOH; 60:40:0.05 to 5:95:0.05), was obtained as a yellow solid (55 mg, 75%).

$^1$H NMR (500 MHz, DMSO-$d_6$) δ (ppm) 10.01 (s, 2H), 8.30 (s, 1H), 7.60 (d, J=2.3 Hz, 1H), 7.40 (s, 1H), 7.37 (dd, J=8.5, 2.3 Hz, 1H), 7.32 (d, J=3.5 Hz, 1H), 6.94 (d, J=8.3 Hz, 1H), 6.79 (dd, J=3.5, 1.3 Hz, 1H), 2.46 (s, 3H);

$^{13}$C NMR (126 MHz, DMSO-$d_6$) δ (ppm) 162.1, 158.4, 151.9, 151.6, 145.8, 144.0, 138.9, 135.9, 126.3, 125.8, 123.8, 123.1, 116.6, 116.5, 116.1, 106.2, 15.0;

HRMS calcd for $C_{18}H_{14}N_3O_3S_2$ $[M+H]^+$ 384.0471, found 384.0468.

Preparative Example 104

(E)-2-cyano-3-(3,4-dihydroxyphenyl)-N-(4-(5,6,7,8-tetrahydronaphthalen-2-yl)thiazol-2-yl)acrylamide

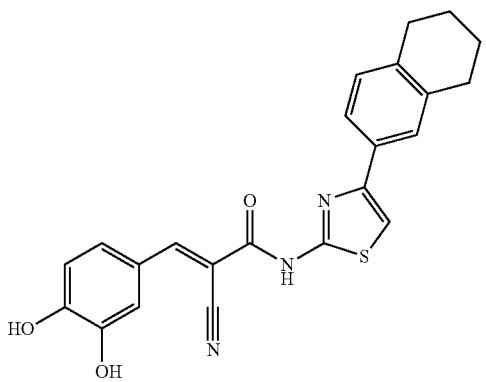 [SMILES: N#C/C(=C\c1ccc(O)c(O)c1)C(=O)Nc1nc(-c2ccc3c(c2)CCCC3)cs1]

The compound was prepared according to General procedure D2 from 2-cyano-N-(4-(4-cyclohexylphenyl)thiazol-2-yl)acetamide (75 mg, 0.23 mmol), 3,4-dihydroxybenzaldehyde (32 mg, 0.23 mmol), and piperidine (3 μL, 0.027 mmol) in $CH_2Cl_2$ (3 mL). The reaction time was 2 h at reflux. The product, purified by reverse phase column chromatography ($H_2O$:MeOH:AcOH; 60:40:0.05 to 5:95:0.05), was obtained as a yellow solid (70 mg, 70%).

$^1$H NMR (500 MHz, DMSO-$d_6$) δ (ppm) 12.51 (s, 1H), 9.98 (s, 2H), 8.30 (s, 1H), 7.66-7.59 (m, 3H), 7.55 (s, 1H), 7.38 (dd, J=8.4, 2.3 Hz, 1H), 7.11 (d, J=7.9 Hz, 1H), 6.93 (d, J=8.3 Hz, 1H), 2.84-2.66 (m, 4H), 1.81-1.71 (m, 4H);

$^{13}$C NMR (126 MHz, DMSO-$d_6$) δ (ppm) 162.3, 158.7, 151.8, 151.7, 148.2, 145.8, 136.8, 136.5, 131.2, 129.2, 126.3, 125.9, 123.1, 122.9, 116.6, 116.4, 116.1, 107.4, 30.6, 28.8, 28.6, 22.7;

HRMS calcd for $C_{23}H_{20}N_3O_3S$ $[M+H]^+$ 418.1220, found 418.1220.

Preparative Example 105

(E)-2-cyano-N-(4-(4-cyclohexylphenyl)thiazol-2-yl)-3-(3,4-dihydroxyphenyl)acrylamide

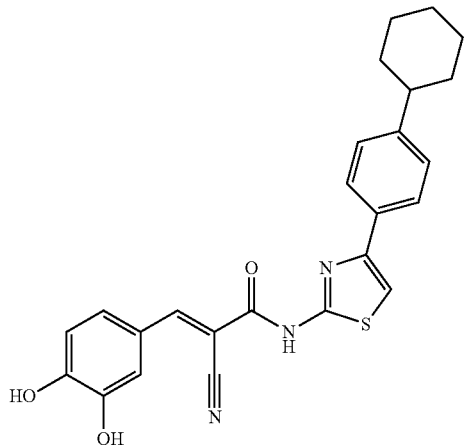 [SMILES: N#C/C(=C\c1ccc(O)c(O)c1)C(=O)Nc1nc(-c2ccc(C3CCCCC3)cc2)cs1]

The compound was prepared according to General procedure D2 from 2-cyano-N-(4-(4-cyclohexylphenyl)thiazol-2-yl)acetamide (75 mg, 0.23 mmol), 3,4-dihydroxybenzaldehyde (32 mg, 0.23 mmol), and piperidine (3 μL, 0.027 mmol) in $CH_2Cl_2$ (3 mL). The reaction time was 2 h at reflux. The product, purified by reverse phase column chromatography ($H_2O$:MeOH:AcOH; 60:40:0.05 to 5:95:0.05), was obtained as a yellow solid (70 mg, 70%).

$^1$H NMR (500 MHz, DMSO-$d_6$) δ (ppm) 12.63 (s, 1H), 10.25 (s, 1H), 9.65 (s, 1H), 8.30 (s, 1H), 7.84 (d, J=7.9 Hz, 2H), 7.66-7.55 (m, 2H), 7.38 (dd, J=8.4, 2.3 Hz, 1H), 7.29 (d, J=8.2 Hz, 2H), 6.93 (d, J=8.3 Hz, 1H), 2.57-2.53 (m, 1H), 1.86-1.75 (m, 4H), 1.74-1.68 (m, 1H), 1.48-1.33 (m, 4H), 1.31-1.20 (m, 1H);

$^{13}$C NMR (126 MHz, DMSO-$d_6$) δ (ppm) 161.9, 152.0, 151.5, 149.2, 147.3, 145.8, 131.9, 127.0, 125.8, 125.7, 123.1, 116.5, 116.0, 107.9, 43.5, 33.8, 26.3, 25.6;

HRMS calcd for $C_{25}H_{22}N_3O_3S$ $[M-H]^-$ 444.1387, found 444.1381.

Preparative Example 106

(E)-3-(3-chloro-4-hydroxy-5-methylphenyl)-2-cyano-N-(4-phenylthiazol-2-yl)acrylamide

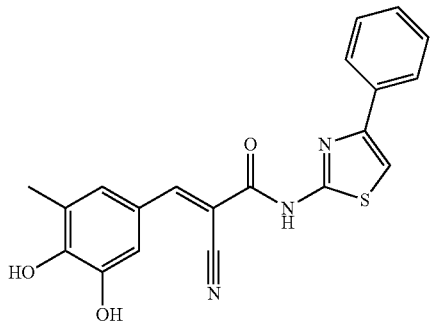 [SMILES: Cc1cc(/C=C(\C#N)C(=O)Nc2nc(-c3ccccc3)cs2)cc(O)c1O]

The compound was prepared according to General procedure D2 from 2-cyano-N-(4-phenylthiazol-2-yl)acetamide (93 mg, 0.38 mmol), 3-chloro-4-hydroxy-5-methylbenzaldehyde (65 mg, 0.38 mmol), and piperidine (3 μL, 0.027 mmol) in $CH_2Cl_2$ (3 mL). The reaction time was 2 h at reflux. The precipitate was collected by filtration, washed with $CH_2Cl_2$ (3 mL) and dried under vacuum. The product was obtained as a yellow solid (130 mg, 85%).

$^1$H NMR (500 MHz, DMSO-$d_6$) δ (ppm) 12.78 (s, 1H), 10.50 (s, 1H), 8.34 (s, 1H), 7.97 (d, J=2.2 Hz, 1H), 7.95-7.92 (m, 2H), 7.79-7.74 (m, 1H), 7.69 (s, 1H), 7.49-7.42 (m, 2H), 7.39-7.32 (m, 1H), 2.28 (s, 3H);

$^{13}$C NMR (126 MHz, DMSO-$d_6$) δ (ppm) 161.7, 155.7, 150.5, 133.7, 132.3, 129.8, 128.7, 128.0, 127.6, 125.7, 123.5, 121.0, 116.1, 108.7, 16.8;

HRMS calcd for $C_{20}H_{15}ClN_3O_2S$ $[M+H]^+$ 396.0568, found 396.0564.

Preparative Example 107

(E)-3-(3-chloro-5-fluoro-4-hydroxyphenyl)-2-cyano-N-(4-phenylthiazol-2-yl)acrylamide

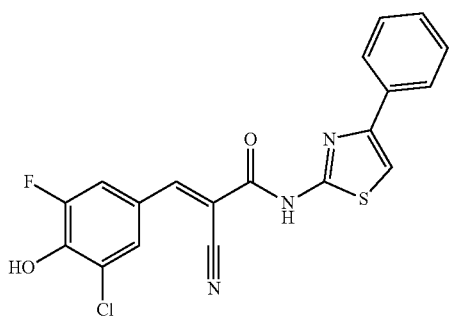 [SMILES: N#C/C(=C\c1cc(F)c(O)c(Cl)c1)C(=O)Nc1nc(-c2ccccc2)cs1]

The compound was prepared according to General procedure D2 from 2-cyano-N-(4-phenylthiazol-2-yl)acetamide (143 mg, 0.58 mmol), 3-chloro-5-fluoro-4-hydroxybenzaldehyde (100 mg, 0.58 mmol), and piperidine (3 µL, 0.027 mmol) in CH$_2$Cl$_2$ (3 mL). The reaction time was 2 h at reflux. The precipitate was collected by filtration, washed with CH$_2$Cl$_2$ (3 mL) and dried under vacuum. The product was obtained as a yellow solid (130 mg, 55%).

$^1$H NMR (500 MHz, DMSO-d$_6$) δ (ppm) 12.88 (s, 1H), 11.84 (s, 1H), 8.36 (s, 1H), 7.95-7.90 (m, 3H), 7.87 (dd, J=11.6, 2.2 Hz, 1H), 7.70 (s, 1H), 7.49-7.43 (m, 2H), 7.39-7.33 (m, 1H);

$^{13}$C NMR (126 MHz, DMSO-d$_6$) δ (ppm) 151.5 (d, J=243.4 Hz), 149.6, 146.7 (d, J=17.8 Hz), 133.5, 128.7, 128.3 (d, J=69.2 Hz), 125.7, 122.7 (d, J=5.3 Hz), 122.4, 116.3 (d, J=20.2 Hz), 115.9, 108.8;

$^{19}$F NMR (471 MHz, DMSO-d$_6$) δ (ppm) −129.93;

HRMS calcd for C$_{19}$H$_{12}$ClFN$_3$O$_2$S [M+H]$^+$ 400.0317, found 400.0314.

Preparative Example 108

(E)-2-cyano-3-(3,4-dihydroxyphenyl)-N-(4-(pyridin-2-yl)thiazol-2-yl)acrylamide

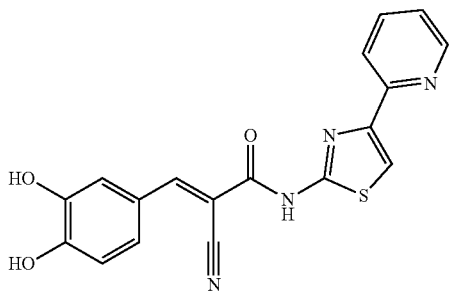 [SMILES: N#C/C(=C\c1ccc(O)c(O)c1)C(=O)Nc1nc(-c2ccccn2)cs1]

The compound was prepared according to General procedure D2 from 2-cyano-N-(4-(pyridin-2-yl)thiazol-2-yl)acetamide (110 mg, 0.450 mmol), 3,4-dihydroxybenzaldehyde (62 mg, 0.450 mmol), and piperidine (4.4 µL, 0.045 mmol) in CH$_2$Cl$_2$ (6 mL); the reaction time was 3 h. The solvent was evaporated and the solid residue was triturated with EtOAc (8 mL). The solid was collected by filtration, washed with MeOH (5 mL) and dried under vacuum to afford the pure product as a pale yellow solid (90 mg, 55%).

$^1$H NMR (500 MHz, DMSO-d$_6$) δ (ppm) 12.67 (brs, 1H), 10.30 (brs, 1H), 9.70 (brs, 1H), 8.66-8.56 (m, 1H), 8.32 (s, 1H), 8.00 (d, J=7.85 Hz, 1H), 7.94-7.86 (m, 2H), 7.62 (d, J=2.26 Hz, 1H), 7.43-7.32 (m, 2H), 6.94 (d, J=8.29 Hz, 1H);

$^{13}$C NMR (126 MHz, DMSO-d$_6$) δ (ppm) 152.1, 151.5, 149.5, 145.8, 137.2, 125.9, 123.1, 122.9, 120.0, 116.5, 116.4, 116.0, 112.2;

HRMS calcd for C$_{18}$H$_{13}$N$_4$O$_3$S [M+H]$^+$ 365.0703, found 365.0697.

Preparative Example 109

(E)-2-cyano-3-(3,4-dihydroxyphenyl)-N-(4-(6-methylpyridin-2-yl)thiazol-2-yl)acrylamide

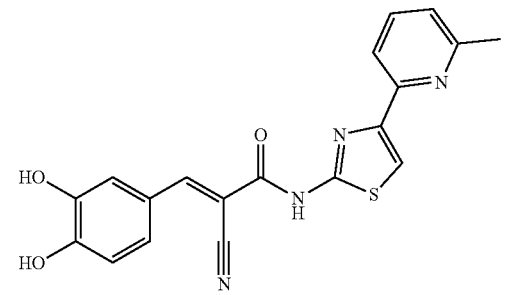 [SMILES: Cc1cccc(-c2csc(NC(=O)/C(C#N)=C/c3ccc(O)c(O)c3)n2)n1]

The compound was prepared according to General procedure D2 from 2-cyano-N-(4-(6-methylpyridin-2-yl)thiazol-2-yl)acetamide (180 mg, 0.696 mmol), 3,4-dihydroxybenzaldehyde (96 mg, 0.696 mmol), and piperidine (6.8 µL, 0.069 mmol) in CH$_2$Cl$_2$ (8 mL); the reaction time was 3 h. The solvent was evaporated and the solid residue was triturated with EtOAc (8 mL). The solid was collected by filtration, washed with MeOH (5 mL) and dried under vacuum to afford the product as a yellow solid (180 mg, 68%).

$^1$H NMR (500 MHz, DMSO-d$_6$) δ (ppm) 12.39 (brs, 1H), 9.77 (brs, 2H), 8.31 (s, 1H), 7.83 (s, 1H), 7.82-7.75 (m, 2H), 7.62 (d, J=2.29 Hz, 1H), 7.38 (dd, J=8.39, 2.29 Hz, 1H), 7.21 (dd, J=7.32, 1.37 Hz, 1H), 6.93 (d, J=8.27 Hz, 1H), 2.52 (s, 3H);

$^{13}$C NMR (126 MHz, DMSO-d$_6$) δ (ppm) 157.8, 152.0, 151.5, 151.1, 145.8, 137.4, 125.8, 123.1, 122.2, 117.2, 116.5, 116.0, 111.9, 24.2;

HRMS calcd for C$_{19}$H$_{15}$N$_4$O$_3$S [M+H]$^+$ 379.0859, found 379.0857.

Preparative Example 110

(E)-2-cyano-3-(3,4-dihydroxyphenyl)-N-(4-(2-(trifluoromethyl)phenyl)thiazol-2-yl)acrylamide

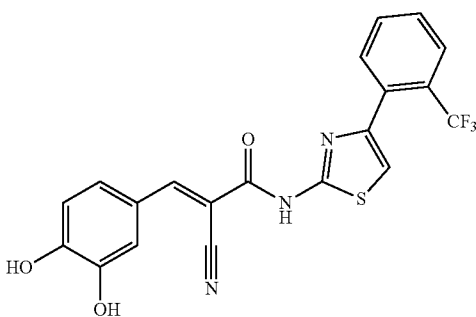 [SMILES: N#C/C(=C\c1ccc(O)c(O)c1)C(=O)Nc1nc(-c2ccccc2C(F)(F)F)cs1]

The compound was prepared according to General procedure D2 from 2-cyano-N-(4-(2-(trifluoromethyl)phenyl)thiazol-2-yl)acetamide (100 mg, 0.32 mmol), 3,4-dihydroxybenzaldehyde (44 mg, 0.32 mmol), and piperidine (3 µL, 0.027 mmol) in CH$_2$Cl$_2$ (3 mL). The reaction time was 2 h at reflux. The product, purified by reverse phase column chromatography (H$_2$O:MeOH:AcOH; 60:40:0.05 to 5:95:0.05), was obtained as a yellow solid (100 mg, 70%).

$^1$H NMR (500 MHz, DMSO-d$_6$) δ (ppm) 12.65 (s, 1H), 10.21 (s, OH), 9.68 (s, 1H), 8.28 (s, 1H), 7.85 (d, J=7.8 Hz, 1H), 7.78-7.72 (m, 1H), 7.69-7.62 (m, 2H), 7.60 (d, J=2.1 Hz, 1H), 7.37 (dd, J=8.4, 2.2 Hz, 1H), 7.30 (s, 1H), 6.93 (d, J=8.3 Hz, 1H);

$^{13}$C NMR (126 MHz, DMSO-d$_6$) δ (ppm) 162.0, 157.4, 152.0, 151.5, 145.8, 132.2, 132.1, 127.0 (q, J=31.8 Hz), 126.2 (q, J=5.4 Hz), 125.8, 124.0 (q, J=274.0 Hz), 123.1, 116.5, 116.1;

$^{19}$F NMR (471 MHz, DMSO-d$_6$) δ (ppm) −56.27;

HRMS calcd for C$_{20}$H$_{13}$F$_3$N$_3$O$_3$S [M+H]$^+$ 432.0624, found 432.0627.

Preparative Example 111

(E)-2-cyano-N-(4-(3,4-dichlorophenyl)thiazol-2-yl)-3-(3,4-dihydroxyphenyl)acrylamide

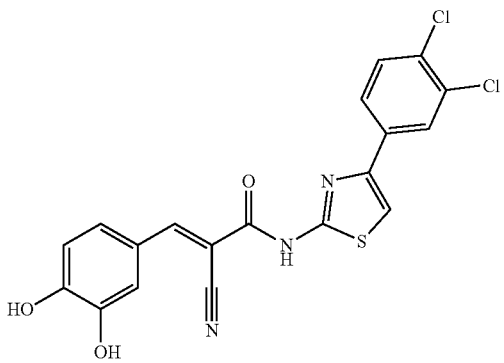 [SMILES: N#C/C(=C\c1ccc(O)c(O)c1)C(=O)Nc1nc(-c2ccc(Cl)c(Cl)c2)cs1]

The compound was prepared according to General procedure D2 from 2-cyano-N-(4-(3,4-dichlorophenyl)thiazol-2-yl)acetamide (100 mg, 0.32 mmol), 3,4-dihydroxybenzaldehyde (44 mg, 0.32 mmol), and piperidine (3 µL, 0.027 mmol) in CH$_2$Cl$_2$ (3 mL). The reaction time was 2 h at reflux. The product, purified by reverse phase column chromatography (H$_2$O:MeOH:AcOH; 60:40:0.05 to 5:95:0.05), was obtained as a yellow solid (50 mg, 40%).

$^1$H NMR (500 MHz, DMSO-d$_6$) δ (ppm) 12.60 (s, 1H), 10.21 (s, 1H), 9.70 (s, 1H), 8.31 (s, 1H), 8.19 (d, J=2.0 Hz, 1H), 7.92 (dd, J=8.4, 2.1 Hz, 1H), 7.90 (s, 1H), 7.71 (d, J=8.4 Hz, 1H), 7.62 (d, J=2.2 Hz, 1H), 7.38 (dd, J=8.4, 2.2 Hz, 1H), 6.94 (d, J=8.3 Hz, 1H);

$^{13}$C NMR (126 MHz, DMSO-d$_6$) δ (ppm) 162.2, 158.9, 152.1, 151.6, 146.3, 145.8, 134.7, 131.6, 131.0, 130.1, 127.4, 125.9, 125.7, 123.1, 116.5, 116.4, 116.1, 110.7;

HRMS calcd for C$_{19}$H$_{12}$Cl$_2$N$_3$O$_3$S [M+H]$^+$ 431.9971, found 431.9968.

Preparative Example 112

(E)-2-cyano-3-(3,4-dihydroxyphenyl)-N-(4-(o-tolyl)thiazol-2-yl)acrylamide

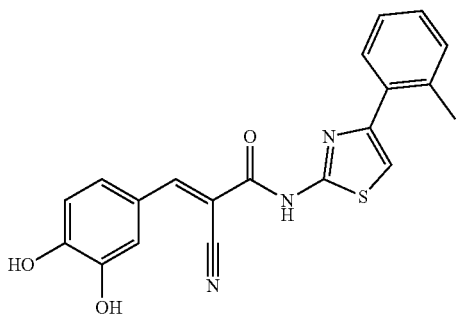 [SMILES: Cc1ccccc1-c1csc(NC(=O)/C(C#N)=C/c2ccc(O)c(O)c2)n1]

The compound was prepared according to General procedure D2 from 2-cyano-N-(4-(o-tolyl)thiazol-2-yl)acetamide (100 mg, 0.39 mmol), 3,4-dihydroxybenzaldehyde (54 mg, 0.39 mmol), and piperidine (3 L, 0.027 mmol) in anhydrous CH$_2$Cl$_2$ (3 mL). The reaction time was 2 h at reflux. The precipitate was collected by filtration, washed with CH$_2$Cl$_2$ (3 mL) and dried under vacuum. Product was obtained as a yellow solid (110 mg, 75%).

$^1$H NMR (500 MHz, DMSO-d$_6$) δ (ppm) 12.61 (s, 1H), 9.89 (s, 2H), 8.28 (s, 1H), 7.61 (d, J=2.2 Hz, 1H), 7.59 (d, J=6.7 Hz, 1H), 7.37 (dd, J=8.4, 2.2 Hz, 1H), 7.28 (ddt, J=9.7, 6.0, 3.4 Hz, 4H), 6.93 (d, J=8.3 Hz, 1H), 2.44 (s, 3H);

$^{13}$C NMR (126 MHz, DMSO-d$_6$) δ (ppm) 162.4, 151.9, 151.4, 145.8, 135.5, 130.7, 129.4, 127.9, 125.8, 123.2, 116.5, 116.0, 111.2, 20.8;

HRMS calcd for C$_{20}$H$_{16}$N$_3$O$_3$S [M+H]$^+$ 378.0907, found 378.0907.

Preparative Example 113

(E)-N-(4-(3-chlorophenyl)thiazol-2-yl)-2-cyano-3-(3,4-dihydroxyphenyl)acrylamide

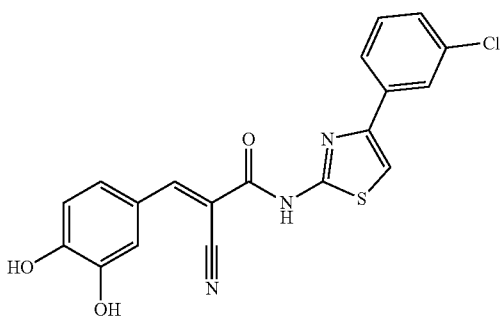 [SMILES: N#C/C(=C\c1ccc(O)c(O)c1)C(=O)Nc1nc(-c2cccc(Cl)c2)cs1]

The compound was prepared according to General procedure D2 from N-(4-(3-chlorophenyl)thiazol-2-yl)-2-cyanoacetamide (150 mg, 0.540 mmol), 3,4-dihydroxybenzaldehyde (75 mg, 0.540 mmol), and piperidine (4 µL, 0.054 mmol) in CH$_2$Cl$_2$ (5 mL); the reaction time was 2 h at reflux. The residue was purified by column chromatography (hexane:EtOAc, 10:1 to 1:3), followed by reverse phase column chromatography (H$_2$O:MeOH:AcOH; 50:50:0.05 to 8:92:0.05) to give the product as an orange solid (164 mg, 0.412 mmol, 76% yield).

$^1$H NMR (500 MHz, DMSO-d$_6$) δ (ppm) 8.21 (s, 1H), 7.99 (t, J=1.9 Hz, 1H), 7.89 (d, J=7.8 Hz, 1H), 7.73 (s, 1H), 7.60 (d, J=2.4 Hz, 1H), 7.46 (t, J=7.9 Hz, 1H), 7.39-7.32 (m, 2H), 6.85 (s, 1H);

$^{13}$C NMR (126 MHz, DMSO-d$_6$) δ (ppm) 164.9, 163.0, 161.0, 150.9, 147.0, 146.1, 136.6, 133.5, 130.6, 127.3, 125.4, 124.1, 117.3, 116.2, 115.7, 109.6, 101.7;

HRMS calcd for C$_{19}$H$_{13}$ClN$_3$O$_3$S [M+H]$^+$ 398.0361, found 398.0362.

Preparative Example 114

(E)-3-(3,5-bis(trifluoromethyl)phenyl)-2-cyano-N-(4-phenylthiazol-2-yl)acrylamide

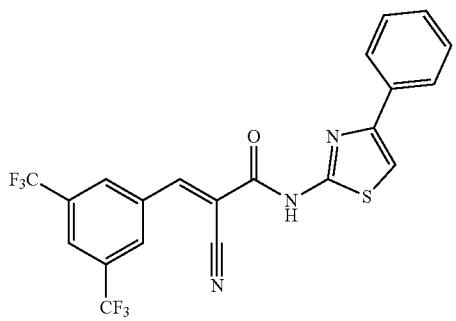 [SMILES: N#C/C(=C\c1cc(C(F)(F)F)cc(C(F)(F)F)c1)C(=O)Nc1nc(-c2ccccc2)cs1]

The compound was prepared according to General procedure D2 from 2-cyano-N-(4-(6-methoxypyridin-2-yl)thiazol-2-yl)acetamide (148 mg, 0.607 mmol), 3,5-bis(trifluoromethyl)benzaldehyde (147 mg, 0.607 mmol), and piperidine (5 mg, 6 µL, 0.061 mmol) in CH$_2$Cl$_2$ (3 mL). The product, purified by column chromatography on silica gel (hexane:EtOAc; 20:1 to 5:1), was obtained as a yellow solid (197 mg, 67%).

$^1$H NMR (500 MHz, DMSO-d$_6$) δ (ppm) 13.03 (s, 1H), 8.69 (s, 1H), 8.61 (s, 2H), 8.39 (s, 1H), 7.93 (d, J=7.5 Hz, 2H), 7.74 (s, 1H), 7.46 (t, J=7.7 Hz, 2H), 7.37 (t, J=7.2 Hz, 1H);

$^{13}$C NMR (126 MHz, DMSO-d$_6$) δ (ppm) 148.9, 134.3, 131.0 (q, J=32.9 Hz), 130.2, 128.8, 128.1, 125.8, 125.4, 124.0 (q, J=273.3 Hz), 109.1;

$^{19}$F NMR (471 MHz, DMSO-d$_6$) δ (ppm) −61.59;

HRMS calcd for C$_{21}$H$_{12}$F$_6$N$_3$OS [M+H]$^+$ 468.0600, found 468.0598.

Preparative Example 115

(E)-2-cyano-3-(3,4-dihydroxyphenyl)-N-(4-(4-methylpyridin-2-yl)thiazol-2-yl)acrylamide

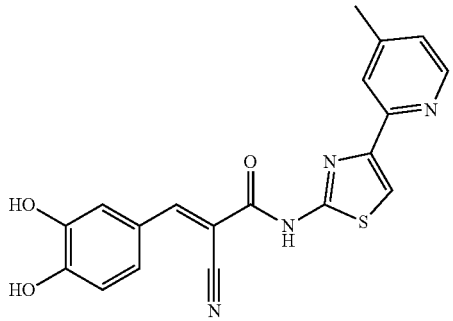 [SMILES: Cc1ccnc(-c2csc(NC(=O)/C(C#N)=C/c3ccc(O)c(O)c3)n2)c1]

The compound was prepared according to General procedure D2 from 2-cyano-N-(4-(4-methylpyridin-2-yl)thiazol-2-yl)acetamide (60 mg, 0.23 mmol), 3,4-dihydroxybenzaldehyde (32 mg, 0.23 mmol), and piperidine (3 µL, 0.027 mmol) in CH$_2$Cl$_2$ (3 mL). The reaction time was 2 h at reflux. The precipitate was collected by filtration, washed with a mixture of CH$_2$Cl$_2$:MeOH (3 mL+0.3 mL) and dried under vacuum. The product was obtained as a yellow solid (80 mg, 95%).

$^1$H NMR (500 MHz, DMSO-d$_6$) δ (ppm) 12.61 (s, 1H), 9.79 (s, 2H), 8.47 (d, J=4.9 Hz, 1H), 8.32 (s, 1H), 7.86 (s, 2H), 7.62 (d, J=2.2 Hz, 1H), 7.39 (dd, J=8.4, 2.2 Hz, 1H), 7.18 (d, J=5.0 Hz, 1H), 6.94 (d, J=8.3 Hz, 1H), 2.39 (s, 3H);

$^{13}$C NMR (126 MHz, DMSO-d$_6$) δ (ppm) 162.1, 158.6, 152.1, 151.6, 149.3, 147.8, 145.8, 125.9, 123.6, 123.1, 120.9, 116.5, 116.4, 116.1, 112.1, 20.7;

HRMS calcd for C$_{19}$H$_{15}$N$_4$O$_3$S [M+H]$^+$ 379.0859, found 379.0863.

Preparative Example 116

(E)-2-cyano-3-(3,4-dihydroxyphenyl)-N-(4-(5-methylpyridin-2-yl)thiazol-2-yl)acrylamide

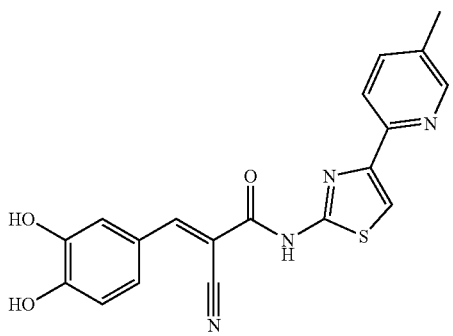 [SMILES: Cc1ccc(-c2csc(NC(=O)/C(C#N)=C/c3ccc(O)c(O)c3)n2)nc1]

The compound was prepared according to General procedure D2 from 2-cyano-N-(4-(5-methylpyridin-2-yl)thiazol-2-yl)acetamide (77 mg, 0.3 mmol), 3,4-dihydroxybenzaldehyde (41 mg, 0.3 mmol), and piperidine (3 µL, 0.027 mmol) in $CH_2Cl_2$ (3 mL). The reaction time was 2 h at reflux. The precipitate was collected by filtration, washed with $CH_2Cl_2$ (5 mL) and dried under vacuum. The product was obtained as a yellow solid (76 mg, 70%).

$^1$H NMR (500 MHz, DMSO-$d_6$) δ (ppm) 10.24 (s, 3H), 8.44 (d, J=2.2 Hz, 1H), 8.22 (s, 1H), 7.90 (d, J=8.0 Hz, 1H), 7.73 (s, 1H), 7.69 (dd, J=8.1, 2.2 Hz, 1H), 7.60 (d, J=2.3 Hz, 1H), 7.35 (dd, J=8.3, 2.3 Hz, 1H), 6.89 (d, J=8.3 Hz, 1H), 2.33 (s, 3H);

$^{13}$C NMR (126 MHz, DMSO-$d_6$) δ (ppm) 162.9, 161.0, 152.0, 150.8, 149.8, 149.7, 148.8, 145.9, 137.4, 131.8, 125.8, 123.0, 119.5, 117.2, 116.0, 110.7, 17.7;

HRMS calcd for $C_{19}H_{15}N_4O_3S$ [M+H]$^+$ 379.0859, found 379.0864.

Preparative Example 117

(E)-2-cyano-3-(3,4-dihydroxyphenyl)-N-(4-(4-isopropylphenyl)thiazol-2-yl)acrylamide

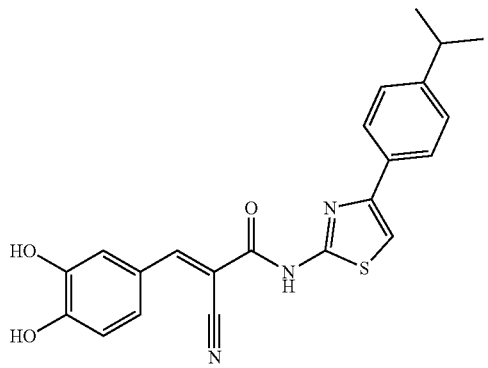 [SMILES: CC(C)c1ccc(-c2csc(NC(=O)/C(C#N)=C/c3ccc(O)c(O)c3)n2)cc1]

The compound was prepared according to General procedure D2 from 2-cyano-N-(4-(4-isopropylphenyl)thiazol-2-yl)acetamide (200 mg, 0.701 mmol), 3,4-dihydroxybenzaldehyde (97 mg, 0.701 mmol), and piperidine (5 µL, 0.070 mmol) in $CH_2Cl_2$ (6 mL). The reaction time was 3 h at reflux. The product, purified by column chromatography (hexane:EtOAc, 10:1 to 1:1) followed by reverse phase column chromatography ($C_{18}$ silica gel, $H_2O$:MeOH:AcOH; 50:50:0.05 to 8:92:0.05), was obtained as a dark yellow solid (195 mg, 69% yield).

$^1$H NMR (500 MHz, DMSO-$d_6$) δ (ppm) 8.22 (s, 1H), 7.85 (d, J=8.5 Hz, 2H), 7.60 (d, J=2.3 Hz, 1H), 7.52 (s, 1H), 7.35 (dd, J=8.4, 2.3 Hz, 1H), 7.32-7.28 (m, 2H), 6.85 (d, J=6.5 Hz, 1H), 2.92 (hept, J=6.8 Hz, 1H), 1.23 (d, J=6.9 Hz, 6H);

$^{13}$C NMR (126 MHz, DMSO-$d_6$) δ (ppm) 167.6, 162.6, 159.5, 151.5, 148.4, 148.1, 146.0, 131.8, 126.6, 125.7, 122.8, 116.9, 116.1, 107.6, 33.1, 23.8;

HRMS calcd for $C_{22}H_{20}N_3O_3S$ [M+H]$^+$ 406.1220, found 406.1222.

Preparative Example 118

(E)-2-cyano-3-(3,4-dihydroxyphenyl)-N-(4-(4-methoxypyridin-2-yl)thiazol-2-yl)acrylamide

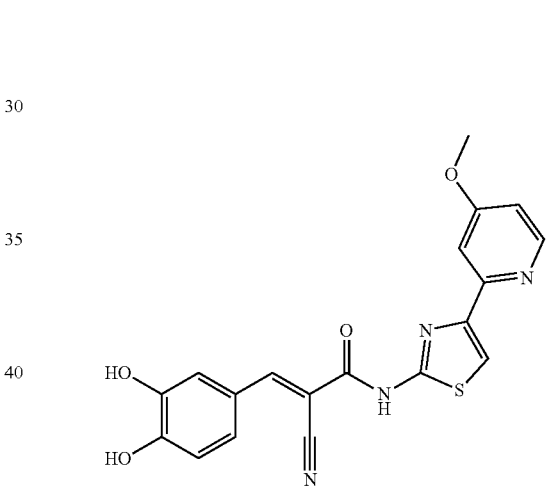

The compound was prepared according to General procedure D2 from 2-cyano-N-(4-(4-methoxypyridin-2-yl)thiazol-2-yl)acetamide (60 mg, 0.22 mmol), 3,4-dihydroxybenzaldehyde (30 mg, 0.22 mmol), and piperidine (3 µL, 0.027 mmol) in $CH_2Cl_2$ (5 mL). The reaction time was 2 h at reflux. The precipitate was collected by filtration, washed with $CH_2Cl_2$ (5 mL) and dried under vacuum. The product was obtained as a yellow solid (50 mg, 60%).

$^1$H NMR (500 MHz, DMSO-$d_6$) δ (ppm) 12.54 (s, 1H), 9.88 (s, 2H), 8.43 (d, J=5.6 Hz, 1H), 8.31 (s, 1H), 7.87 (s, 1H), 7.62 (d, J=2.2 Hz, 1H), 7.57 (d, J=2.5 Hz, 1H), 7.39 (dd, J=8.4, 2.3 Hz, 1H), 6.96-6.92 (m, 2H), 3.89 (s, 3H);

$^{13}$C NMR (126 MHz, DMSO-$d_6$) δ (ppm) 166.1, 162.2, 158.8, 153.4, 152.0, 151.6, 150.8, 148.9, 145.8, 125.9, 123.1, 116.5, 116.1, 112.5, 109.3, 105.7, 55.3;

HRMS calcd for $C_{19}H_{15}N_4O_4S$ [M+H]$^+$ 395.0809, found 395.0808.

Preparative Example 119

(E)-2-cyano-3-(3,4-dihydroxyphenyl)-N-(4-(5-methoxypyridin-2-yl)thiazol-2-yl)acrylamide

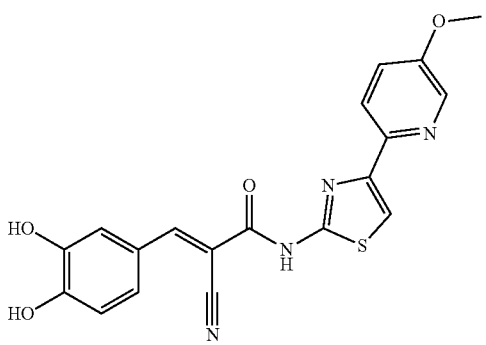 [SMILES: COc1ccc(-c2csc(NC(=O)/C(C#N)=C/c3ccc(O)c(O)c3)n2)nc1]

The compound was prepared according to General procedure D2 from 2-cyano-N-(4-(5-methoxypyridin-2-yl)thiazol-2-yl)acetamide (60 mg, 0.22 mmol), 3,4-dihydroxybenzaldehyde (30 mg, 0.22 mmol), and piperidine (3 μL, 0.027 mmol) in CH$_2$Cl$_2$ (3 mL). The reaction time was 2 h at reflux. The precipitate was collected by filtration, washed with CH$_2$Cl$_2$ (5 mL) and dried under vacuum. The product was obtained as a yellow solid (80 mg, 90%).

$^1$H NMR (500 MHz, DMSO-d$_6$) δ (ppm) 9.70 (s, 2H), 8.30 (d, J=3.0 Hz, 1H), 8.12 (s, 1H), 7.96 (d, J=8.7 Hz, 1H), 7.57 (d, J=2.3 Hz, 1H), 7.52 (s, 1H), 7.46 (dd, J=8.7, 3.0 Hz, 1H), 7.31 (dd, J=8.4, 2.2 Hz, 1H), 6.83 (d, J=8.3 Hz, 1H), 3.86 (s, 3H);

$^{13}$C NMR (126 MHz, DMSO-d$_6$) δ (ppm) 172.3, 163.7, 154.5, 152.5, 149.5, 148.4, 145.9, 145.7, 137.2, 125.8, 122.8, 120.8, 120.5, 118.0, 115.9, 115.4, 108.8, 55.6;

HRMS calcd for C$_{19}$H$_{15}$N$_4$O$_4$S [M+H]$^+$ 395.0809, found 395.0807.

Preparative Example 120

(E)-2-cyano-3-(3,5-di-tert-butyl-4-hydroxyphenyl)-N-(4-(pyridin-2-yl)thiazol-2-yl)acrylamide

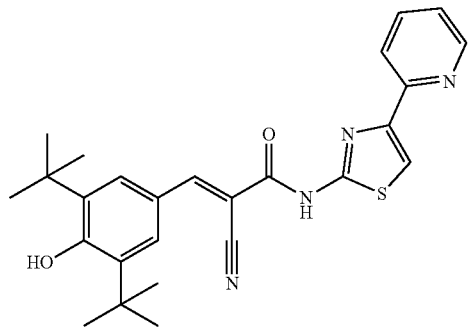 [SMILES: CC(C)(C)c1cc(/C=C(\C#N)C(=O)Nc2nc(-c3ccccn3)cs2)cc(C(C)(C)C)c1O]

The compound was prepared according to General procedure D2 from 2-cyano-N-(4-(pyridin-2-yl)thiazol-2-yl)acetamide (80 mg, 0.33 mmol), 3,5-di-tert-butyl-4-hydroxybenzaldehyde (77 mg, 0.33 mmol), and piperidine (3 μL, 0.027 mmol) in CH$_2$Cl$_2$ (5 mL). The reaction time was 2 h at reflux. The precipitate was collected by filtration, washed with CH$_2$Cl$_2$ (5 mL) and dried under vacuum. The product was obtained as a yellow solid (65 mg, 45%).

$^1$H NMR (500 MHz, DMSO-d$_6$)) δ (ppm) 12.72 (s, 1H), 8.64-8.61 (m, 1H), 8.50 (s, 1H), 8.17 (s, 1H), 8.04-7.99 (m, 1H), 7.95 (s, 2H), 7.93-7.87 (m, 2H), 7.38-7.33 (m, 1H), 1.44 (s, 18H);

$^{13}$C NMR (126 MHz, DMSO-d$_6$) δ (ppm) 162.0, 159.5, 152.9, 151.9, 149.5, 139.0, 137.3, 128.7, 122.9, 122.8, 120.0, 116.6, 112.3, 34.7, 29.9;

HRMS calcd for C$_{26}$H$_{29}$N$_4$O$_2$S [M+H]$^+$ 461.2006, found 461.2004.

Preparative Example 121

(E)-2-cyano-3-(3,4-dihydroxyphenyl)-N-(4-(6-methoxypyridin-2-yl)thiazol-2-yl)acrylamide

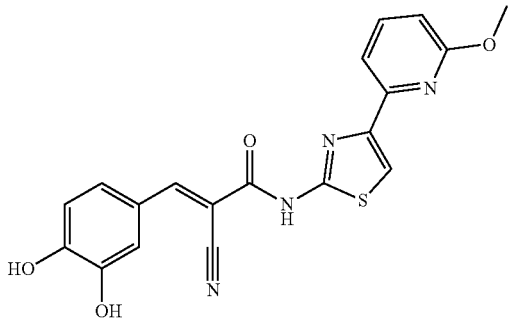 [SMILES: COc1cccc(-c2csc(NC(=O)/C(C#N)=C/c3ccc(O)c(O)c3)n2)n1]

The compound was prepared according to General procedure D2 from 2-cyano-N-(4-(6-methoxypyridin-2-yl)thiazol-2-yl)acetamide (80 mg, 0.3 mmol), 3,4-dihydroxybenzaldehyde (40 mg, 0.3 mmol), and piperidine (3 μL, 0.027 mmol) in CH$_2$Cl$_2$ (3 mL). The reaction time was 2 h at reflux. The precipitate was collected by filtration, washed with CH$_2$Cl$_2$ (3 mL) and dried under vacuum. The product was obtained as a yellow solid (50 mg, 60%).

$^1$H NMR (500 MHz, DMSO-d$_6$) δ (ppm) 12.54 (s, 1H), 9.88 (s, 2H), 8.43 (d, J=5.6 Hz, 1H), 8.31 (s, 1H), 7.87 (s, 1H), 7.62 (d, J=2.2 Hz, 1H), 7.57 (d, J=2.5 Hz, 1H), 7.39 (dd, J=8.4, 2.3 Hz, 1H), 6.96-6.92 (m, 2H), 3.89 (s, 3H);

$^{13}$C NMR (126 MHz, DMSO-d$_6$) δ (ppm) 166.1, 162.2, 158.8, 153.4, 152.0, 151.6, 150.8, 148.9, 145.8, 125.9, 123.1, 116.5, 116.1, 112.5, 109.3, 105.7, 55.3;

HRMS calcd for C$_{19}$H$_{15}$N$_4$O$_4$S [M+H]$^+$ 395.0809, found 395.0810.

Preparative Example 122

(E)-2-cyano-N-(4-(2,4-dichlorophenyl)thiazol-2-yl)-3-(3,4-dihydroxyphenyl)acrylamide

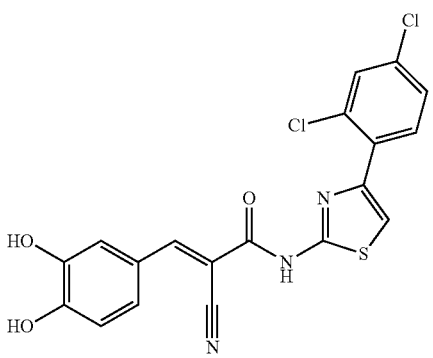 [SMILES: N#C/C(=C\c1ccc(O)c(O)c1)C(=O)Nc1nc(-c2ccc(Cl)cc2Cl)cs1]

The compound was prepared according to General procedure D2 from 2-cyano-N-(4-(2,4-dichlorophenyl)thiazol-2-yl)acetamide (330 mg, 1.1 mmol), 3,4-dihydroxybenzaldehyde (138 mg, 1.1 mmol), and piperidine (3 μL, 0.027 mmol) in $CH_2Cl_2$ (3 mL). The reaction time was 2 h at reflux. The precipitate was collected by filtration, washed with $CH_2Cl_2$ (5 mL) and dried under vacuum. The product was obtained as a yellow solid (360 mg, 85%).

$^1$H NMR (500 MHz, DMSO-$d_6$) δ (ppm) 12.67 (s, 1H), 10.20 (s, 1H), 9.68 (s, 1H), 8.31 (s, 1H), 7.88 (s, 1H), 7.83-7.76 (m, 1H), 7.62 (d, J=2.2 Hz, 1H), 7.59 (d, J=7.3 Hz, 1H), 7.38 (dd, J=8.4, 2.2 Hz, 1H), 6.94 (d, J=8.3 Hz, 1H), 6.78 (d, J=8.1 Hz, 1H);

$^{13}$C NMR (126 MHz, DMSO-$d_6$) δ (ppm) 163.1, 161.9, 152.1, 151.6, 145.8, 140.0, 125.9, 123.1, 116.5, 116.1, 112.9, 112.3, 109.9;

HRMS calcd for $C_{19}H_{12}Cl_2N_3O_3S$ [M+H]$^+$ 431.9971, found 431.9969.

Preparative Example 123

(E)-2-cyano-3-(3,4-dihydroxyphenyl)-N-(4-(3-fluoropyridin-2-yl)thiazol-2-yl)acrylamide

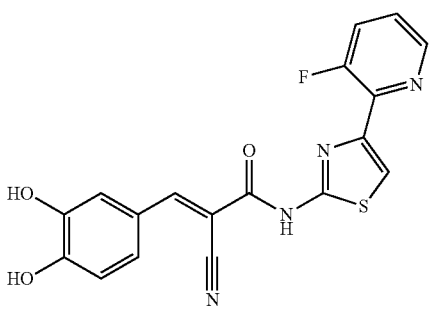 [SMILES: N#C/C(=C\c1ccc(O)c(O)c1)C(=O)Nc1nc(-c2ncccc2F)cs1]

The compound was prepared according to General procedure D2 from 2-cyano-N-(4-(3-fluoropyridin-2-yl)thiazol-2-yl)acetamide (100 mg, 0.39 mmol), 3,4-dihydroxybenzaldehyde (65 mg, 0.39 mmol), and piperidine (3 μL, 0.027 mmol) in $CH_2Cl_2$ (3 mL). The reaction time was 2 h at reflux. The precipitate was collected by filtration, washed with $CH_2Cl_2$ (5 mL) and dried under vacuum. The product was obtained as a yellow solid (100 mg, 70%).

$^1$H NMR (500 MHz, DMSO-$d_6$) δ (ppm) 12.83 (s, 1H), 10.72-9.32 (m, 2H), 8.51 (d, J=4.7, 1.9 Hz, 1H), 8.34 (s, 1H), 7.89-7.79 (m, 2H), 7.64-7.59 (m, 1H), 7.51-7.46 (m, 1H), 7.41-7.36 (m, 1H), 6.95-6.92 (m, 1H);

$^{13}$C NMR (126 MHz, DMSO-$d_6$) δ (ppm) 156.5 (d, J=261.6 Hz), 152.0, 151.6, 145.8, 145.4 (d, J=5.2 Hz), 125.8, 124.7 (d, J=4.3 Hz), 124.6, 123.1, 116.5, 116.1, 115.6;

$^{19}$F NMR (471 MHz, DMSO-$d_6$) δ (ppm) −121.02;

HRMS calcd for $C_{18}H_{10}FN_4O_3S$ [M−H]$^-$ 381.0463, found 381.0458.

Preparative Example 124

(E)-2-cyano-3-(3,4-dihydroxyphenyl)-N-(4-(2-fluoro-4-methoxyphenyl)thiazol-2-yl)acrylamide The compound was prepared according to General procedure D2 from 2-cyano-N-(4-(2-fluoro-4-methoxyphenyl)thiazol-2-yl)acetamide (150 mg, 0.56 mmol), 3,4-dihydroxybenzaldehyde (80 mg, 0.56 mmol), and piperidine (3 μL, 0.027 mmol) in $CH_2Cl_2$ (5 mL). The reaction time was 2 h at reflux. The precipitate was collected by filtration, washed with $CH_2Cl_2$ (5 mL) and dried under vacuum. The product was obtained as a yellow solid (190 mg, 85%).

$^1$H NMR (500 MHz, DMSO-$d_6$) δ (ppm) 10.55 (s, 3H), 8.28 (s, 1H), 8.03-7.96 (m, 1H), 7.61 (d, J=2.3 Hz, 1H), 7.40 (d, J=2.4 Hz, 1H), 7.37 (dd, J=8.4, 2.3 Hz, 1H), 7.01-6.88 (m, 3H), 3.82 (s, 3H);

$^{13}$C NMR (126 MHz, DMSO-$d_6$) δ (ppm) 160.2 (d, J=249.0 Hz), 160.0 (d, J=11.6 Hz), 151.8 (d, J=10.9 Hz), 145.8, 129.8 (d, J=5.3 Hz), 125.9, 123.1, 114.5, 110.7, 110.6, 102.1 (d, J=26.2 Hz), 55.7;

HRMS calcd for $C_{20}H_{15}FN_3O_4S$ [M+H]$^+$ 412.0762, found 412.0765.

Preparative Example 125

(E)-2-cyano-3-(3,4-dihydroxyphenyl)-N-(4-(4-(trifluoromethyl)pyridin-2-yl)thiazol-2-yl)acrylamide

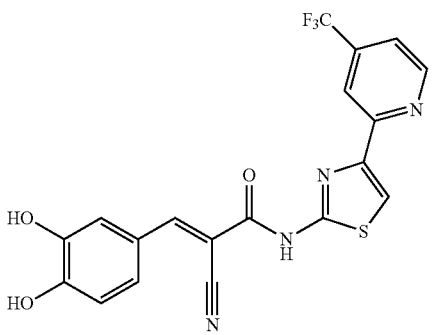 [SMILES: N#C/C(=C\c1ccc(O)c(O)c1)C(=O)Nc1nc(-c2cc(C(F)(F)F)ccn2)cs1]

The compound was prepared according to General procedure D2 from 2-cyano-N-(4-(4-(trifluoromethyl)pyridin-2-yl)thiazol-2-yl)acetamide (110 mg, 0.352 mmol), 3,4-dihydroxybenzaldehyde (48 mg, 0.352 mmol), and piperidine (3.5 µL, 0.035 mmol) in CH$_2$Cl$_2$ (7 mL); the reaction time was 4 h at 45° C. The product, purified by column chromatography (CH$_2$Cl$_2$:MeOH; 1:0 to 9.5:0.5), was obtained as a dark yellow solid (65 mg, 43%).

$^1$H NMR (500 MHz, DMSO-d$_6$) δ (ppm) 12.72 (s, 1H), 10.27 (s, 1H), 9.70 (s, 1H), 8.91 (d, J=5.03 Hz, 1H), 8.33 (s, 1H), 8.25 (s, 1H), 8.06 (s, 1H), 7.74 (dd, J=5.08, 1.72 Hz, 1H), 7.62 (d, J=2.29 Hz, 1H), 7.39 (dd, J=8.39, 2.24 Hz, 1H), 6.94 (d, J=8.24 Hz, 1H);

$^{13}$C NMR (126 MHz, DMSO-d$_6$) δ (ppm) 162.1, 159.2, 152.2, 151.6, 151.3, 147.7, 145.8, 137.8, 137.5, 125.9, 124.0 (q, $^1J_{C-F}$=273.4 Hz), 123.1, 118.1, 116.5, 116.3, 116.1, 115.1, 114.1;

$^{19}$F NMR (471 MHz, DMSO-d$_6$) δ (ppm) −63.73;

HRMS calcd for C$_{19}$H$_{12}$F$_3$N$_4$O$_3$S [M+H]$^+$ 433.0577, found 433.0580.

Preparative Example 126

(E)-2-cyano-N-(4-(2,5-dichlorothiophen-3-yl)thiazol-2-yl)-3-(3,4-dihydroxyphenyl) acrylamide

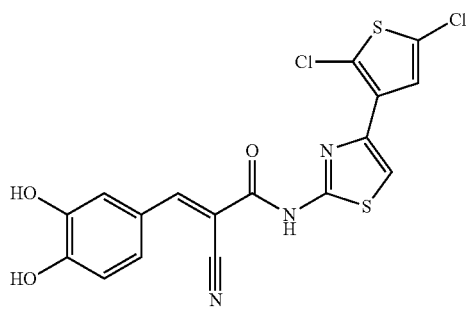 [SMILES: N#C/C(=C\c1ccc(O)c(O)c1)C(=O)Nc1nc(-c2cc(Cl)sc2Cl)cs1]

The compound was prepared according to General procedure D2 from 2-cyano-N-(4-(2,5-dichlorothiophen-3-yl)thiazol-2-yl)acetamide (214 mg, 0.67 mmol), 3,4-dihydroxybenzaldehyde (93 mg, 0.67 mmol), and piperidine (6.6 µL, 0.067 mmol) in CH$_2$Cl$_2$ (10 mL) and THF (3 mL); the reaction time was 3 h. The product, purified by reverse phase column chromatography (H$_2$O:MeOH:AcOH; 50:50:0.05 to 10:90:0.05), was obtained as a dark yellow solid (54 mg, 18%).

$^1$H NMR (500 MHz, DMSO-d$_6$) δ (ppm) 10.23 (brs, 3H), 8.19 (s, 1H), 7.62 (s, 1H), 7.59 (d, J=2.26 Hz, 1H), 7.48 (s, 1H), 7.34 (dd, J=8.37, 2.27 Hz, 1H), 6.88 (d, J=8.30 Hz, 1H);

$^{13}$C NMR (126 MHz, DMSO-d$_6$) δ (ppm) 163.6, 150.8, 145.8, 141.2, 132.8, 127.7, 125.6, 124.9, 120.3, 117.2, 116.0, 111.8;

HRMS calcd for C$_{17}$H$_{10}$Cl$_2$N$_3$O$_3$S$_2$[M+H]$^+$ 437.9535, found 437.9535.

Preparative Example 127

(E)-3-(3,4-bis((triisopropylsilyl)oxy)phenyl)-2-cyano-N-(4-phenylthiazol-2-yl)acrylamide

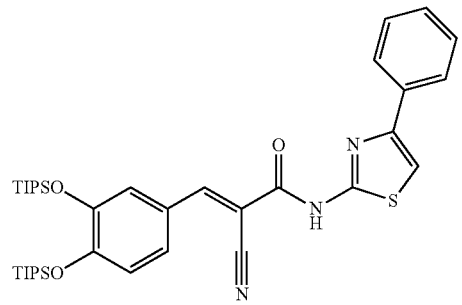

(E)-2-cyano-3-(3,4-dihydroxyphenyl)-N-(4-phenylthiazol-2-yl)acrylamide (0.85 g, 2.33 mmol) was dissolved in anhydrous CH$_2$Cl$_2$ (10 mL). DMAP (14 mg, 0.11 mmol), Et$_3$N (0.6 g, 0.8 mL, 5.8 mmol) and TIPSCl (0.95 g, 1.05 mL, 4.91 mmol) were added and the mixture was stirred for 16 h at 25° C. The product, purified by column chromatography (hexane:EtOAc; 5:1), was obtained as a yellow solid (1.24 g, 80%).

$^1$H NMR (500 MHz, DMSO-d$_6$) δ (ppm) 9.60 (s, 1H), 8.30 (s, 1H), 7.90-7.84 (m, 2H), 7.61-7.57 (m, 1H), 7.56-7.49 (m, 1H), 7.47-7.40 (m, 2H), 7.37-7.31 (m, 1H), 7.24-7.21 (m, 1H), 6.95 (d, J=8.4 Hz, 1H), 1.47-1.31 (m, 6H), 1.16 (d, J=2.6 Hz, 18H), 1.15 (d, J=2.6 Hz, 18H);

$^{13}$C NMR (126 MHz, DMSO-d$_6$) δ (ppm) 159.1, 156.8, 154.7, 153.5, 150.6, 147.9, 134.1, 128.8, 128.2, 126.9, 126.1, 124.7, 121.7, 120.2, 116.8, 108.5, 18.0, 17.9, 13.2, 13.2;

Preparative Example 128

3-(4-acetamidophenyl)-2-cyano-N-(4-phenylthiazol-2-yl)propanamide

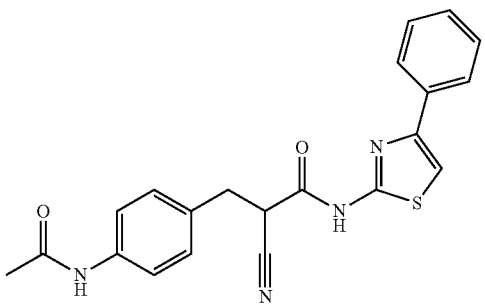 [SMILES: CC(=O)Nc1ccc(CC(C#N)C(=O)Nc2nc(-c3ccccc3)cs2)cc1]

The compound was prepared according to General procedure E from (E)-3-(4-acetamidophenyl)-2-cyano-N-(4-phenylthiazol-2-yl)acrylamide (43 mg, 0.111 mmol) and NaBH$_4$ (9 mg, 0.221 mmol) in MeOH (2 mL); the reaction time was 2 h. The product, purified by column chromatography (CH$_2$Cl$_2$:MeOH; 1:0 to 5:1), was obtained as a pale yellow solid (32 mg, 74%).

$^1$H NMR (500 MHz, DMSO-d$_6$) δ (ppm) 12.79 (s, 1H), 9.90 (s, 1H), 7.90 (dd, J=8.5, 1.3 Hz, 2H), 7.71 (s, 1H), 7.53 (d, J=8.7 Hz, 2H), 7.47-7.41 (m, 2H), 7.37-7.31 (m, 1H), 7.25 (d, J=8.5 Hz, 2H), 4.31 (dd, J=9.5, 6.0 Hz, 1H), 3.29-3.26 (m, 1H), 3.12 (dd, J=13.6, 9.5 Hz, 1H), 2.02 (s, 3H);

$^{13}$C NMR (126 MHz, DMSO-d$_6$) δ (ppm) 168.2, 164.0, 157.2, 149.1, 138.4, 134.0, 130.6, 129.3, 128.8, 127.9, 125.7, 119.0, 117.2, 108.9, 40.4, 34.8, 23.9;

HRMS calcd for C$_{21}$H$_{17}$N$_4$O$_2$S [M–H]$^-$ 389.1078, found 389.1078.

Preparative Example 129

N-(4-(4-bromophenyl)thiazol-2-yl)-2-cyano-3-(3,4-dihydroxyphenyl)propanamide

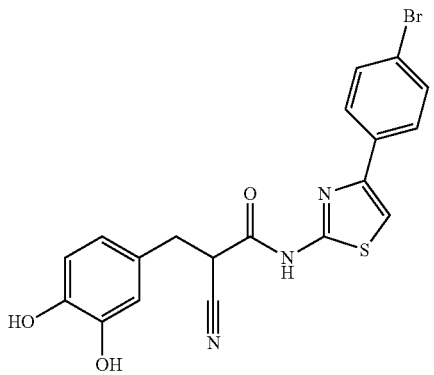 [SMILES: N#CC(Cc1ccc(O)c(O)c1)C(=O)Nc1nc(-c2ccc(Br)cc2)cs1]

The compound was prepared according to General procedure E from (E)-N-(4-(4-bromophenyl)thiazol-2-yl)-2-cyano-3-(3,4-dihydroxyphenyl)acrylamide (110 mg, 0.25 mmol) and NaBH$_4$ (20 mg, 0.5 mmol) in MeOH (3 mL); the reaction time was 16 h. The product, purified by reverse phase column chromatography (H$_2$O:MeOH:AcOH; 45:55:0.05 to 25:75:0.05), was obtained as a pale yellow solid (73 mg, 70%).

$^1$H NMR (500 MHz, DMSO-d$_6$) δ (ppm) 12.78 (s, 1H), 8.84 (s, 2H), 7.90-7.82 (m, 2H), 7.79 (s, 1H), 7.70-7.56 (m, 2H), 6.72 (d, J=2.1 Hz, 1H), 6.67 (d, J=8.0 Hz, 1H), 6.56 (dd, J=8.0, 2.1 Hz, 1H), 4.24 (dd, J=9.4, 5.9 Hz, 1H), 3.23-2.87 (m, 2H);

$^{13}$C NMR (126 MHz, DMSO-d$_6$) δ (ppm) 164.2, 157.4, 147.9, 145.1, 144.5, 133.2, 131.7, 127.7, 126.8, 121.0, 119.8, 117.3, 116.4, 115.5, 109.7, 40.6, 34.9;

HRMS calcd for C$_{19}$H$_{12}$BrN$_3$O$_3$S [M–H]$^-$ 443.9847, found 443.9845.

Preparative Example 130

2-cyano-3-(3,4-dihydroxyphenyl)-N-(4-phenylthiazol-2-yl)propanamide

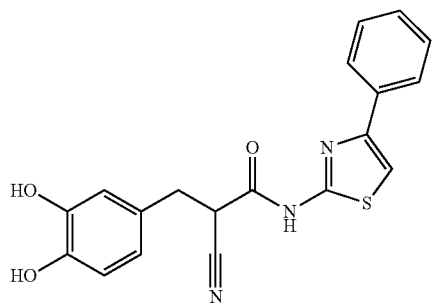 [SMILES: N#CC(Cc1ccc(O)c(O)c1)C(=O)Nc1nc(-c2ccccc2)cs1]

The compound was prepared according to General procedure E from (E)-2-cyano-3-(3,4-dihydroxyphenyl)-N-(4-phenylthiazol-2-yl)acrylamide (150 mg, 0.4 mmol) and NaBH$_4$ (30 mg, 0.8 mmol) in MeOH (2 mL); the reaction time was 4 h. The product, purified by reverse phase column chromatography (H$_2$O:MeOH:AcOH; 45:55:0.05 to 30:70:0.05), was obtained as a pale yellow solid (83 mg, 55%).

$^1$H NMR (500 MHz, CDCl$_3$) δ (ppm) 7.73 (s, 1H), 7.71 (s, 1H), 7.42-7.40 (m, 2H), 7.38-7.36 (m, 1H), 7.16 (s, 1H), 6.64 (d, J=8.0 Hz, 1H), 6.55 (d, J=2.1 Hz, 1H), 6.40 (d, J=8.2 Hz, 1H), 3.36 (t, J=7.0 Hz, 1H), 3.08-2.88 (m, 2H);

$^{13}$C NMR (126 MHz, CDCl$_3$) δ (ppm) 163.2, 158.6, 149.9, 144.1, 143.8, 133.6, 129.5, 129.3, 127.4, 126.6, 121.7, 116.5, 116.3, 116.0, 109.3, 40.8, 35.7;

HRMS calcd for C$_{19}$H$_{14}$N$_3$O$_3$S [M–H]$^-$ 364.0761, found 364.0760.

Preparative Example 131

2-cyano-N-(4-(4-cyanophenyl)thiazol-2-yl)-3-(3,4-dihydroxyphenyl)propanamide

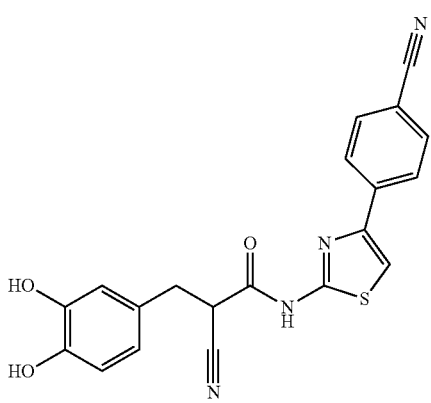 [SMILES: N#Cc1ccc(-c2csc(NC(=O)C(C#N)Cc3ccc(O)c(O)c3)n2)cc1]

The compound was prepared according to General procedure E from (E)-2-cyano-N-(4-(4-cyanophenyl)thiazol-2-yl)-3-(3,4-dihydroxyphenyl)acrylamide (110 mg, 0.28 mmol) and NaBH$_4$ (11 mg, 0.56 mmol) in MeOH (3 mL); the reaction time was 4 h. The product, purified by reverse phase column chromatography (H$_2$O:MeOH:AcOH; 45:55:0.05 to 30:70:0.05), was obtained as a pale yellow solid (40 mg, 36%).

$^1$H NMR (500 MHz, DMSO-d$_6$) δ (ppm) 12.83 (s, 1H), 8.85 (s, 1H), 8.82 (s, 1H), 8.15-8.05 (m, 2H), 8.01 (s, 1H), 7.95-7.87 (m, 2H), 6.72 (d, J=2.1 Hz, 1H), 6.67 (d, J=8.0 Hz, 1H), 6.56 (dd, J=8.1, 2.1 Hz, 1H), 4.25 (dd, J=9.4, 5.9 Hz, 1H), 3.22-2.90 (m, 2H);

$^{13}$C NMR (126 MHz, DMSO-d$_6$) δ (ppm) 164.4, 157.7, 147.3, 145.1, 144.5, 138.1, 132.8, 126.8, 126.3, 119.8, 118.8, 117.2, 116.3, 115.5, 112.4, 110.1, 40.6, 34.9;

HRMS calcd for C$_{20}$H$_{13}$N$_4$O$_3$S [M−H]$^-$ 389.0714, found 389.0715.

Preparative Example 132

2-cyano-3-(3,4-dihydroxyphenyl)-N-(4-(4-(trifluoromethyl)phenyl)thiazol-2-yl)propanamide

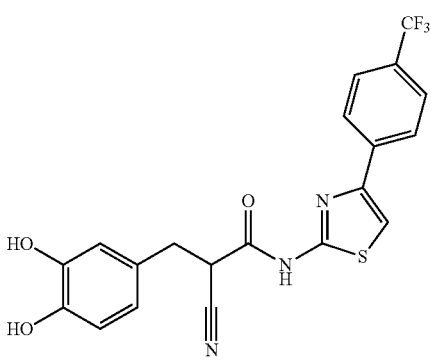 [SMILES: N#CC(Cc1ccc(O)c(O)c1)C(=O)Nc1nc(-c2ccc(C(F)(F)F)cc2)cs1]

The compound was prepared according to General procedure E from (E)-2-cyano-3-(3,4-dihydroxyphenyl)-N-(4-(4-(trifluoromethyl)phenyl)thiazol-2-yl)acrylamide (56 mg, 0.13 mmol) and NaBH$_4$ (10 mg, 0.26 mmol) in MeOH (2 mL); the reaction time was 16 h. The product, purified by reverse phase column chromatography (H$_2$O:MeOH:AcOH; 45:55:0.05 to 20:80:0.05), was obtained as a pale yellow solid (36 mg, 77%).

$^1$H NMR (500 MHz, DMSO-d$_6$) δ (ppm) 12.84 (s, 1H), 8.85 (s, 1H), 8.82 (s, 1H), 8.12 (d, J=8.1 Hz, 2H), 7.95 (s, 1H), 7.81 (d, J=8.3 Hz, 2H), 6.72 (d, J=2.1 Hz, 1H), 6.67 (d, J=8.0 Hz, 1H), 6.56 (dd, J=8.1, 2.1 Hz, 1H), 4.25 (dd, J=9.4, 5.8 Hz, 1H), 3.23-2.90 (m, 2H);

$^{13}$C NMR (126 MHz, DMSO-d$_6$) δ (ppm) 164.3, 157.6, 147.5, 145.1, 144.5, 137.7, 127.9 (q, J=31.1 Hz), 126.8, 126.2, 125.7 (q, J=4.0 Hz), 124.2 (q, J=272.2 Hz), 119.8, 117.3, 116.3, 115.5, 111.4, 40.6, 34.9;

$^{19}$F NMR (471 MHz, DMSO-d$_6$) δ (ppm) −60.95;

HRMS calcd for C$_{20}$H$_{13}$F$_3$N$_3$O$_3$S [M−H]$^-$ 432.0635, found 432.0634.

Preparative Example 133

2-cyano-3-(3,4-dihydroxyphenyl)-N-(4-(p-tolyl)thiazol-2-yl)propanamide

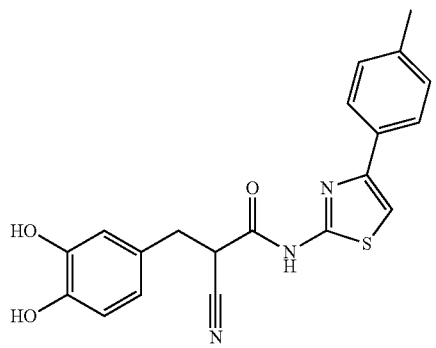 [SMILES: Cc1ccc(-c2csc(NC(=O)C(C#N)Cc3ccc(O)c(O)c3)n2)cc1]

(E)-2-cyano-3-(3,4-dihydroxyphenyl)-N-(4-(p-tolyl)thiazol-2-yl)acrylamide (25 mg, 0.066 mmol) was dissolved in THF (5 mL) and 10-20% Pd(OH)$_2$ on active charcoal (1 mg) was added. The suspension was stirred under atmosphere of H$_2$ (1 bar) at 50° C. for 4 h. The suspension was filtered, the filtrate was concentrated in vacuo and the residue was purified by preparative TLC (hexane:EtOAc; 1:1). The product was obtained as a pale yellow solid (10 mg, 40%).

$^1$H NMR (500 MHz, CDCl$_3$) δ (ppm) 7.59 (s, 1H), 7.57 (s, 1H), 7.22 (d, J=7.8 Hz, 2H), 7.08 (s, 1H), 6.62 (d, J=8.0 Hz, 1H), 6.53 (s, 1H), 6.32 (dd, J=8.0, 1.9 Hz, 1H), 3.23 (t, J=7.3 Hz, 1H), 2.97-2.86 (m, 2H), 2.37 (s, 3H);

$^{13}$C NMR (126 MHz, CDCl$_3$) δ (ppm) 163.5, 158.9, 149.8, 144.0, 143.7, 139.5, 130.8, 130.2, 127.5, 126.6, 121.5, 118.8, 116.5, 116.3, 116.0, 108.6, 40.7, 35.8;

HRMS calcd for C$_{20}$H$_{16}$N$_3$O$_3$S [M−H]$^-$ 378.0918, found 378.0919.

Preparative Example 134

2-cyano-3-(3,5-dichloro-4-hydroxyphenyl)-N-(4,5-diphenylthiazol-2-yl)propanamide

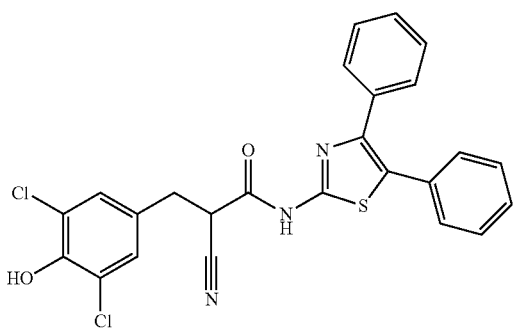 [SMILES: N#CC(Cc1cc(Cl)c(O)c(Cl)c1)C(=O)Nc1nc(-c2ccccc2)c(-c2ccccc2)s1]

The compound was prepared according to General procedure E from (E)-2-cyano-3-(3,5-dichloro-4-hydroxyphenyl)-N-(4,5-diphenylthiazol-2-yl)acrylamide (42 mg, 0.08 mmol) and NaBH$_4$ (6 mg, 0.16 mmol) in MeOH (3 mL); the reaction time was 2 h. The product, purified by preparative TLC (hexane:EtOAc; 2:1), was obtained as a pale yellow solid (25 mg, 65%).

$^1$H NMR (500 MHz, CDCl$_3$) δ (ppm) 7.49-7.45 (m, 2H), 7.39-7.29 (m, 8H), 6.97 (s, 2H), 3.04-2.82 (m, 2H), 2.70 (t, J=7.2 Hz, 1H);

$^{13}$C NMR (126 MHz, CDCl$_3$) δ (ppm) 163.0, 157.5, 147.6, 143.2, 133.8, 131.0, 129.7, 129.3, 129.2, 129.2, 129.2, 129.1, 128.7, 128.6, 121.4, 115.7, 39.5, 34.6;

HRMS calcd for C$_{25}$H$_{16}$Cl$_2$N$_3$O$_2$S [M–H]$^-$ 492.0346, found 492.0345.

Preparative Example 135

2-cyano-3-(3,4-dihydroxyphenyl)-N-(4-phenyl-5-(p-tolyl)thiazol-2-yl)propanamide

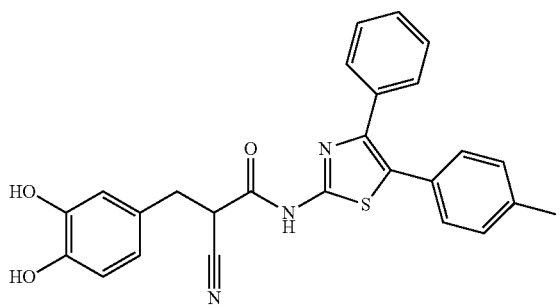 [SMILES: Cc1ccc(-c2sc(NC(=O)C(C#N)Cc3ccc(O)c(O)c3)nc2-c2ccccc2)cc1]

The compound was prepared according to General procedure E from (E)-2-cyano-3-(3,4-dihydroxyphenyl)-N-(4-phenyl-5-(p-tolyl)thiazol-2-yl)acrylamide (70 mg, 0.15 mmol) and NaBH$_4$ (10 mg, 0.3 mmol) in MeOH (3 mL); the reaction time was 16 h. The product, purified by reverse phase column chromatography (H$_2$O:MeOH:AcOH; 45:55:0.05 to 15:85:0.05), was obtained as a pale yellow solid (43 mg, 65%).

$^1$H NMR (500 MHz, DMSO-d$_6$) δ (ppm) 12.80 (s, 1H), 8.86 (s, 1H), 8.83 (s, 1H), 7.48-7.39 (m, 2H), 7.35-7.26 (m, 3H), 7.21-7.15 (m, Hz, 4H), 6.72 (d, J=2.1 Hz, 1H), 6.68 (d, J=8.0 Hz, 1H), 6.57 (dd, J=8.1, 2.1 Hz, 1H), 4.23 (dd, J=9.3, 6.0 Hz, 1H), 3.22-2.92 (m, 2H), 2.32 (s, 3H);

$^{13}$C NMR (126 MHz, DMSO-d$_6$) δ (ppm) 164.2, 145.1, 144.5, 137.6, 134.5, 129.5, 129.1, 128.5, 128.3, 128.3, 127.7, 126.8, 119.8, 117.3, 116.4, 115.5, 40.6, 35.0, 20.7;

HRMS calcd for C$_{26}$H$_{20}$N$_3$O$_3$S [M–H]$^-$ 454.1231, found 454.1233.

Preparative Example 136

2-cyano-3-(3,4-dihydroxyphenyl)-N-(4-(4-(trifluoromethoxy)phenyl)thiazol-2-yl)propanamide

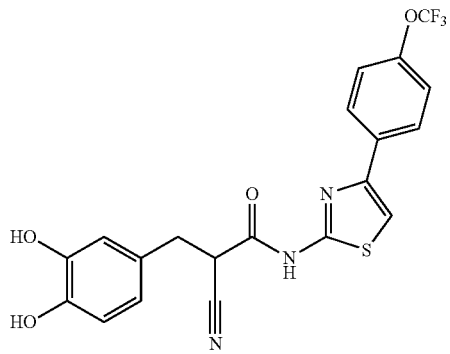 [SMILES: N#CC(Cc1ccc(O)c(O)c1)C(=O)Nc1nc(-c2ccc(OC(F)(F)F)cc2)cs1]

The compound was prepared according to General procedure E from (E)-2-cyano-3-(3,4-dihydroxyphenyl)-N-(4-(4-(trifluoromethoxy)phenyl)thiazol-2-yl)acrylamide (100 mg, 0.22 mmol) and NaBH$_4$ (16 mg, 0.44 mmol) in MeOH (3 mL); the reaction time was 16 h. The product, purified by preparative TLC (hexane:EtOAc; 1:1), was obtained as a pale yellow solid (44 mg, 44%).

$^1$H NMR (500 MHz, DMSO-d$_6$) δ (ppm) 12.80 (s, 1H), 8.84 (s, 2H), 8.05-7.98 (m, 2H), 7.80 (s, 1H), 7.47-7.41 (m, 2H), 6.72 (d, J=2.1 Hz, 1H), 6.67 (d, J=8.0 Hz, 1H), 6.56 (dd, J=8.1, 2.1 Hz, 1H), 4.24 (dd, J=9.4, 5.9 Hz, 1H), 3.21-2.92 (m, 2H);

$^{13}$C NMR (126 MHz, DMSO-d$_6$) δ (ppm) 164.2, 157.5, 147.8, 147.6, 145.1, 144.5, 133.3, 127.5, 126.8, 121.1, 120.1 (q, J=256.2 Hz), 119.8, 117.3, 116.4, 115.5, 109.9, 40.6, 34.9;

HRMS calcd for C$_{20}$H$_{13}$F$_3$N$_3$O$_4$S [M–H]$^-$ 448.0584, found 448.0583.

Preparative Example 137

2-cyano-3-(3,5-dichloro-4-hydroxyphenyl)-N-(4-(4-(trifluoromethoxy)phenyl)thiazol-2-yl)propanamide

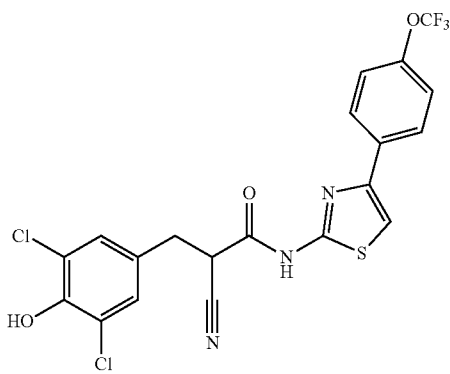 [SMILES: N#CC(Cc1cc(Cl)c(O)c(Cl)c1)C(=O)Nc1nc(-c2ccc(OC(F)(F)F)cc2)cs1]

The compound was prepared according to General procedure E from (E)-2-cyano-3-(3,5-dichloro-4-hydroxyphenyl)-N-(4-(4-(trifluoromethoxy)phenyl)thiazol-2-yl)acrylamide (80 mg, 0.16 mmol) and NaBH$_4$ (12 mg, 0.32 mmol) in MeOH (3 mL); the reaction time was 16 h. The product, purified by reverse phase column chromatography (H$_2$O:MeOH:AcOH; 45:55:0.05 to 10:90:0.05), was obtained as a pale yellow solid (41 mg, 50%).

$^1$H NMR (500 MHz, DMSO-d$_6$) δ (ppm) 12.79 (s, 1H), 10.13 (s, 1H), 8.06-7.99 (m, 2H), 7.81 (s, 1H), 7.47-7.41 (m, 2H), 7.37 (s, 2H), 4.34 (dd, J=9.5, 5.7 Hz, 1H), 3.28-3.02 (m, 2H);

$^{13}$C NMR (126 MHz, DMSO-d$_6$) δ (ppm) 163.8, 157.4, 148.2, 147.8, 147.7, 133.2, 129.2, 129.1, 127.5, 122.1, 121.3, 120.1 (d, J=256.2 Hz), 116.9, 109.9, 40.3, 33.7;

$^{19}$F NMR (471 MHz, DMSO-d$_6$) δ (ppm) −56.71;

HRMS calcd for C$_{20}$H$_{11}$Cl$_2$F$_3$N$_3$O$_3$S [M−H]$^-$ 499.9856, found 499.9855.

Preparative Example 138

N-(4-([1,1'-biphenyl]-3-yl)thiazol-2-yl)-2-cyano-3-(3,4-dihydroxyphenyl)propanamide

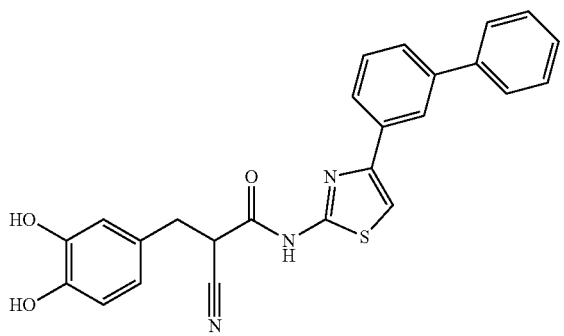 [SMILES: N#CC(Cc1ccc(O)c(O)c1)C(=O)Nc1nc(-c2cccc(-c3ccccc3)c2)cs1]

The compound was prepared according to General procedure E from (E)-N-(4-([1,1'-biphenyl]-3-yl)thiazol-2-yl)-2-cyano-3-(3,4-dihydroxyphenyl)acrylamide (50 mg, 0.11 mmol) and NaBH$_4$ (8 mg, 0.22 mmol) in MeOH (3 mL); the reaction time was 16 h. The product, purified by reverse phase column chromatography (H$_2$O:MeOH:AcOH; 45:55:0.05 to 15:85:0.05), was obtained as a yellow solid (30 mg, 64%).

$^1$H NMR (500 MHz, DMSO-d$_6$) δ (ppm) 12.79 (s, 1H), 8.85 (s, 1H), 8.82 (s, 1H), 8.22-8.16 (m, 1H), 7.95-7.89 (m, 1H), 7.87 (s, 1H), 7.76-7.70 (m, 2H), 7.67-7.61 (m, 1H), 7.55 (d, J=7.8 Hz, 1H), 7.53-7.49 (m, 2H), 7.43-7.38 (m, 1H), 6.73 (d, J=2.1 Hz, 1H), 6.67 (d, J=8.0 Hz, 1H), 6.57 (dd, J=8.0, 2.1 Hz, 1H), 4.24 (dd, J=9.4, 5.8 Hz, 1H), 3.22-2.92 (m, 2H);

$^{13}$C NMR (126 MHz, DMSO-d$_6$) δ (ppm) 164.1, 157.2, 148.9, 145.1, 144.5, 140.7, 140.0, 134.6, 129.4, 128.9, 127.6, 126.8, 126.7, 124.7, 124.1, 119.8, 116.4, 115.5, 109.3, 40.6, 35.0;

HRMS calcd for C$_{25}$H$_{18}$N$_3$O$_3$S [M−H]$^-$ 440.1074, found 440.1073.

Preparative Example 139

2-cyano-3-(3,5-di-tert-butyl-4-hydroxyphenyl)-N-(4-phenylthiazol-2-yl)propanamide

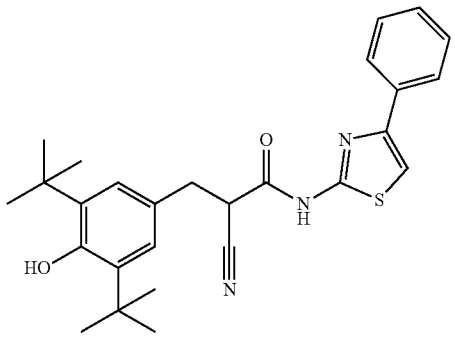 [SMILES: CC(C)(C)c1cc(CC(C#N)C(=O)Nc2nc(-c3ccccc3)cs2)cc(C(C)(C)C)c1O]

The compound was prepared according to General procedure E from (E)-2-cyano-3-(3,5-di-tert-butyl-4-hydroxyphenyl)-N-(4-phenylthiazol-2-yl)acrylamide (50 mg, 0.11 mmol) and NaBH$_4$ (12 mg, 0.32 mmol) in a mixture of MeOH (2 mL) and THF (1 mL); the reaction time was 6 h. The product, purified by reverse phase column chromatography (H$_2$O:MeOH:AcOH; 45:55:0.05 to 5:95:0.05), was obtained as a pale yellow solid (36 mg, 72%).

$^1$H NMR (500 MHz, DMSO-d$_6$) δ (ppm) 12.72 (s, 1H), 7.89 (dd, J=8.3, 1.4 Hz, 2H), 7.71 (s, 1H), 7.44 (t, J=7.7 Hz, 2H), 7.36-7.29 (m, 1H), 7.04 (s, 2H), 6.85 (s, 1H), 4.23 (dd, J=8.5, 6.2 Hz, 1H), 3.20 (dd, J=13.5, 6.2 Hz, 1H), 3.11 (dd, J=13.6, 8.5 Hz, 1H), 1.33 (s, 18H);

$^{13}$C NMR (126 MHz, DMSO-d$_6$) 3164.3, 161.0, 157.2, 153.0, 149.1, 139.1, 134.0, 128.7, 127.9, 126.9, 125.6, 125.4, 117.4, 108.8, 40.8, 35.9, 34.4, 30.2;

HRMS calcd for C$_{27}$H$_{30}$N$_3$O$_2$S [M−H]$^-$ 460.2064, found 460.2065.

Preparative Example 140

N-(4-(4-(tert-butyl)phenyl)thiazol-2-yl)-2-cyano-3-(3,4-dihydroxyphenyl)propanamide

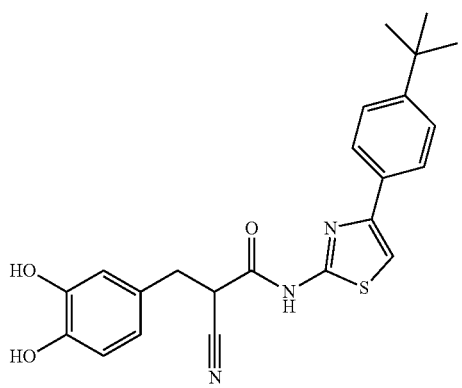 [SMILES: CC(C)(C)c1ccc(-c2csc(NC(=O)C(C#N)Cc3ccc(O)c(O)c3)n2)cc1]

The compound was prepared according to General procedure E from (E)-N-(4-(4-(tert-butyl)phenyl)thiazol-2-yl)-2-cyano-3-(3,4-dihydroxyphenyl)acrylamide (50 mg, 0.192 mmol) and NaBH$_4$ (18 mg, 0.477 mmol) in MeOH (3 mL); the reaction time was 4 h. The product, purified by column chromatography (hexane:EtOAc; 3:1 to 1:2), was obtained as a pale yellow solid (45 mg, 90%).

$^1$H NMR (500 MHz, DMSO-d$_6$) δ (ppm) 12.8 (s, 1H), 8.8 (s, 1H), 8.8 (s, 1H), 7.8 (d, J=8.5 Hz, 2H), 7.6 (s, 1H), 7.5 (d, J=8.5 Hz, 2H), 6.7 (d, J=2.1 Hz, 1H), 6.7 (d, J=7.9 Hz, 1H), 6.6 (dd, J=8.0, 2.2 Hz, 1H), 4.2 (dd, J=9.5, 6.0 Hz, 1H), 3.2 (dd, J=13.7, 5.9 Hz, 1H), 3.0 (dd, J=13.7, 9.5 Hz, 1H), 1.3 (s, 9H);

$^{13}$C NMR (126 MHz, DMSO-d$_6$) δ (ppm) 164.1, 157.1, 150.4, 149.1, 145.1, 144.5, 131.4, 126.9, 125.5, 125.4, 119.8, 117.3, 116.4, 115.5, 108.1, 40.6, 35.0, 34.3, 31.0;

HRMS calcd for C$_{23}$H$_{24}$N$_3$O$_3$S [M+H]$^+$ 422.1533, found 422.1536.

Preparative Example 141

2-(3,4-dihydroxybenzyl)-N$^1$-(4-phenylthiazol-2-1 malonamide

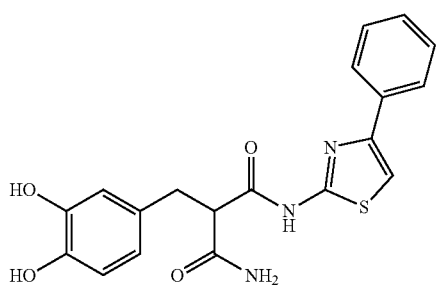 [SMILES: NC(=O)C(Cc1ccc(O)c(O)c1)C(=O)Nc1nc(-c2ccccc2)cs1]

A mixture of 2-cyano-3-(3,4-dihydroxyphenyl)-N-(4-phenylthiazol-2-yl)propanamide (67 mg, 0.183 mmol) and hydride-platinum(II) complex [PtH{(PMe$_2$O)$_2$H}(PMe$_2$OH)] (CAS #173416-05-2) (16 mg, 0.037 mmol) in EtOH (4 mL) and water (1 mL) was stirred at 100° C. for 24 h. The solvent was evaporated and the residue was purified by column chromatography (hexane:EtOAc, 1:1 to 0:1) to afford the product as a white solid (51 mg, 73% yield).

$^1$H NMR (500 MHz, DMSO-d$_6$) δ (ppm) 12.13 (s, 1H), 8.67 (s, 1H), 8.61 (s, 1H), 7.91-7.84 (m, 2H), 7.61 (s, 1H), 7.42 (dd, J=8.6, 7.0 Hz, 2H), 7.36-7.27 (m, 2H), 7.18 (s, 1H), 6.63 (d, J=2.1 Hz, 1H), 6.59 (d, J=8.1 Hz, 1H), 6.47 (dd, J=8.0, 2.1 Hz, 1H), 3.68 (t, J=7.5 Hz, 1H), 3.01-2.90 (m, 2H);

$^{13}$C NMR (126 MHz, DMSO-d$_6$) δ (ppm) 169.4, 167.9, 157.5, 148.8, 144.8, 143.6, 134.2, 129.6, 128.7, 127.7, 125.6, 119.4, 116.3, 115.3, 108.1, 54.7, 33.8;

HRMS calcd for C$_{19}$H$_{18}$N$_3$O$_4$S [M+H]$^+$ 384.1013, found 384.1014.

Preparative Example 142

3-(1H-benzo[d]imidazol-6-yl)-2-cyano-N-(4-phenylthiazol-2-yl)propanamide

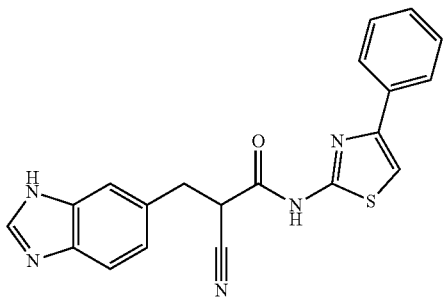 [SMILES: N#CC(Cc1ccc2nc[nH]c2c1)C(=O)Nc1nc(-c2ccccc2)cs1]

(E)-3-(1H-benzo[d]imidazol-6-yl)-2-cyano-N-(4-phenylthiazol-2-yl)acrylamide was prepared according to General procedure D2 from 2-cyano-N-(4-phenylthiazol-2-yl)acetamide (100 mg, 0.411 mmol), 1H-benzimidazol-5-carbaldehyde (60 mg, 0.411 mmol), and piperidine (3.5 mg, 0.041 mmol, 4 μL) in CH$_2$Cl$_2$ (4 mL). The reaction time was 2 h at reflux. The yellow precipitate was collected by filtration, washed with CH$_2$Cl$_2$ (5 mL) and dried under vacuum. The product was obtained as a yellow solid (152 mg, 0.409 mmol, 99%) and used as such in the next step.

HRMS calcd for C$_{20}$H$_{14}$N$_5$OS [M+H]$^+$ 372.0914, found 372.0912.

3-(1H-benzo[d]imidazol-6-yl)-2-cyano-N-(4-phenylthiazol-2-yl)propanamide was prepared according to General procedure E from (E)-3-(1H-benzo[d]imidazol-6-yl)-2-cyano-N-(4-phenylthiazol-2-yl)acrylamide (93 mg, 0.25 mmol) and NaBH$_4$ (39 mg, 1.0 mmol) in MeOH (3 mL); the reaction time was 2 h. The product, purified by column chromatography on silica gel (CH$_2$Cl$_2$:MeOH; 1:0 to 10:1), was obtained as a pale yellow solid (63 mg, 67%).

$^1$H NMR (500 MHz, CDCl$_3$) δ (ppm) 12.82 (s, 1H), 12.43 (s, 1H), 8.19 (s, 1H), 7.94-7.87 (m, 2H), 7.72 (s, 1H), 7.56 (s, 2H), 7.46-7.41 (m, 2H), 7.38-7.30 (m, 1H), 7.18 (d, J=8.2 Hz, 1H), 4.39 (dd, J=9.5, 5.8 Hz, 1H), 3.46 (dd, J=13.5, 5.7 Hz, 1H), 3.30-3.24 (m, 1H);

$^{13}$C NMR (126 MHz, CDCl$_3$) δ (ppm) 164.1, 157.3, 149.1, 142.3, 134.0, 128.7, 127.9, 125.6, 123.1, 119.5, 117.3, 112.0, 108.8, 41.0, 35.6;

HRMS calcd for C$_{20}$H$_{16}$N$_5$OS [M+H]$^+$ 374.1070, found 374.1073.

Preparative Example 143

2-cyano-3-(3,5-dichloro-4-hydroxyphenyl)-N-(4-(naphthalen-2-yl)thiazol-2-yl)propanamide

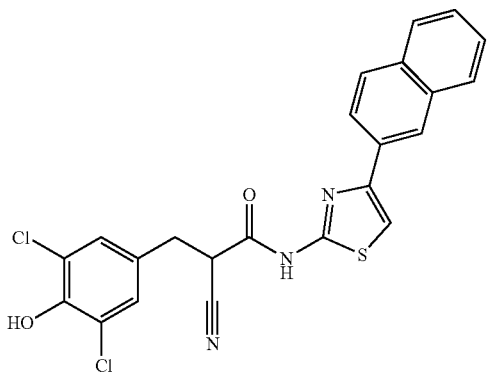 [SMILES: N#CC(Cc1cc(Cl)c(O)c(Cl)c1)C(=O)Nc1nc(-c2ccc3ccccc3c2)cs1]

The compound was prepared according to General procedure E from (E)-2-cyano-3-(3,5-dichloro-4-hydroxyphenyl)-N-(4-(naphthalen-2-yl)thiazol-2-yl)acrylamide (150 mg, 0.322 mmol) and NaBH$_4$ (49 mg, 1.287 mmol) in MeOH (6.5 mL). The mixture was stirred for 4 h. The residue was purified by reverse phase column chromatography (H$_2$O:MeOH:AcOH; 50:50:0.05 to 92:8:0.05) to afford the product as a gray solid (73 mg, 48%).

$^1$H NMR (500 MHz, DMSO-d$_6$) δ (ppm) 12.84 (s, 1H), 10.14 (s, 1H), 8.43 (s, 1H), 8.05 (dd, J=8.5, 1.8 Hz, 1H), 8.00-7.91 (m, 3H), 7.88 (s, 1H), 7.57-7.50 (m, 2H), 7.39 (s, 2H), 4.36 (dd, J=9.5, 5.8 Hz, 1H), 3.29-3.23 (m, 1H), 3.15 (dd, J=13.7, 9.6 Hz, 1H);

$^{13}$C NMR (126 MHz, DMSO-d$_6$) δ (ppm) 163.8, 157.3, 149.0, 148.2, 133.1, 132.6, 131.4, 129.2, 128.3, 128.2, 127.6, 126.5, 126.2, 124.3, 123.9, 122.1, 117.0, 109.6, 40.4, 33.8;

HRMS calcd for C$_{23}$H$_{15}$Cl$_2$N$_3$O$_2$S [M+H]$^+$ 468.0335, found 468.0335.

Preparative Example 144

3-(3,4-bis((2-(trimethylsilyl)ethoxy)methoxy)phenyl)-2-cyano-2-methyl-N-(4-phenylthiazol-2-yl)propanamide

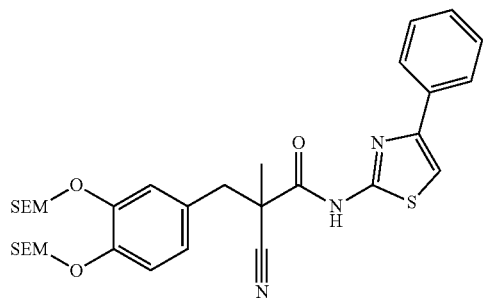 [SMILES: CC(C#N)(Cc1ccc(OCOCC[Si](C)(C)C)c(OCOCC[Si](C)(C)C)c1)C(=O)Nc1nc(-c2ccccc2)cs1]

Ethyl 3-(3,4-bis((2-(trimethylsilyl)ethoxy)methoxy)phenyl)-2-cyano-2-methylpropanoate (74 mg, 0.14 mmol) and 4-phenylthiazol-2-amine (27 mg, 0.15 mmol) were dissolved in THF (2 mL) and the solution was cooled to −10° C. A solution of i-PrMgCl•LiCl (1.3M in THF, 115 μL, 0.15 mmol) was added and the mixture was stirred at 25° C. for 30 min. The mixture was poured into water (10 mL) and extracted with EtOAc (3×10 mL). Organic fractions were combined, washed with brine (20 mL), dried over MgSO$_4$, filtered, and the solvent was evaporated. The residue was purified by column chromatography (hexane:EtOAc; 10:1) to afford the product as a colorless wax (45 mg, 50%).

$^1$H NMR (500 MHz, CDCl$_3$) δ (ppm) 7.85-7.79 (m, 2H), 7.44-7.39 (m, 2H), 7.37-7.31 (m, 1H), 7.19 (s, 1H), 7.13 (s, 1H), 7.12 (d, J=11.0 Hz, 1H), 6.87 (dd, J=8.4, 2.1 Hz, 1H), 5.23 (d, J=1.2 Hz, 2H), 5.23-5.17 (m, 2H), 3.82-3.72 (m, 4H), 3.18 (dd, J=154.7, 13.6 Hz, 2H), 1.76 (s, 3H), 1.02-0.89 (m, 4H), −0.00 (s, 18H);

$^{13}$C NMR (126 MHz, CDCl$_3$) δ (ppm) 166.4, 150.6, 147.6, 134.2, 129.0, 128.4, 128.0, 126.3, 123.8, 120.6, 118.3, 116.7, 108.5, 94.1, 94.0, 66.6, 66.6, 46.8, 43.8, 23.8, 18.2, 18.2, −1.2;

HRMS calcd for C$_{32}$H$_{46}$N$_3$O$_5$SSi$_2$ [M+H]$^+$ 640.2691, found 640.2686.

Preparative Example 145

2-cyano-3-(3,4-dihydroxyphenyl)-N-(4-(thiophen-3-yl)thiazol-2-yl)propanamide

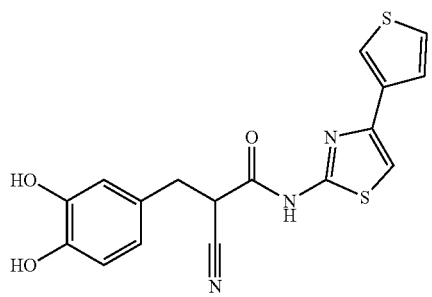 [SMILES: N#CC(Cc1ccc(O)c(O)c1)C(=O)Nc1nc(-c2ccsc2)cs1]

The compound was prepared according to General procedure E from (E)-2-cyano-3-(3,4-dihydroxyphenyl)-N-(4-(thiophen-3-yl)thiazol-2-yl)acrylamide (75 mg, 0.2 mmol) and NaBH$_4$ (15 mg, 0.4 mmol) in MeOH (2 mL); the reaction time was 16 h. The product, purified by reverse phase column chromatography (H$_2$O:MeOH:AcOH; 45:55:0.05 to 20:80:0.05), was obtained as a pale yellow solid (51 mg, 70%).

$^1$H NMR (500 MHz, DMSO-d$_6$) δ (ppm) 12.76 (s, 1H), 8.85 (s, 1H), 8.82 (s, 1H), 7.79 (dd, J=2.9, 1.3 Hz, 1H), 7.61 (dd, J=5.0, 3.0 Hz, 1H), 7.56 (dd, J=5.0, 1.3 Hz, 1H), 7.54 (s, 1H), 6.72 (d, J=2.1 Hz, 1H), 6.67 (d, J=7.9 Hz, 1H), 6.56 (dd, J=8.0, 2.1 Hz, 1H), 4.22 (dd, J=9.4, 5.9 Hz, 1H), 3.23-2.90 (m, 2H);

$^{13}$C NMR (126 MHz, DMSO-d$_6$) δ (ppm) 164.1, 157.1, 145.5, 145.1, 144.5, 136.4, 127.1, 126.8, 126.0, 121.6, 119.8, 117.3, 116.4, 115.5, 108.3, 40.6, 35.0;

HRMS calcd for C$_{17}$H$_{12}$N$_3$O$_3$S$_2$ [M−H]$^-$ 370.0326, found 370.0325.

Preparative Example 146

2-cyano-N-(5-cyclohexyl-4-phenylthiazol-2-yl)-3-(3,4-dihydroxyphenyl)propanamide

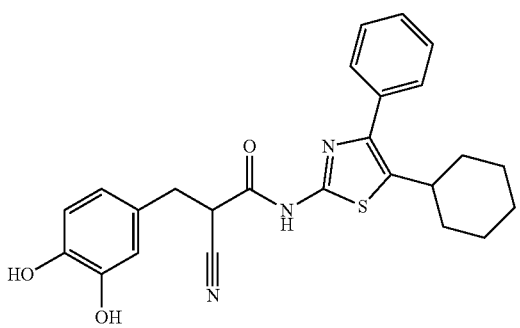 [SMILES: N#CC(Cc1ccc(O)c(O)c1)C(=O)Nc1nc(-c2ccccc2)c(C2CCCCC2)s1]

The compound was prepared according to General procedure E from (E)-2-cyano-N-(5-cyclohexyl-4-phenylthiazol-2-yl)-3-(3,4-dihydroxyphenyl)acrylamide (52 mg, 0.16 mmol) and NaBH$_4$ (22 mg, 0.32 mmol) in EtOH (2 mL); the reaction time was 3 h. The product, purified by reverse phase column chromatography (H$_2$O:MeOH:AcOH; 60:40:0.05 to 5:95:0.05), was obtained as a white solid (40 mg, 75%).

$^1$H NMR (500 MHz, DMSO-d$_6$) δ 12.61 (s, 1H), 8.85 (s, 1H), 8.83 (s, 1H), 7.56-7.51 (m, 2H), 7.47 (dd, J=8.5, 6.8 Hz, 2H), 7.41-7.34 (m, 1H), 6.71 (d, J=2.1 Hz, 1H), 6.67 (d, J=8.0 Hz, 1H), 6.56 (dd, J=8.1, 2.1 Hz, 1H), 4.18 (dd, J=9.3, 6.1 Hz, 1H), 3.19-2.91 (m, 3H), 1.98-1.93 (m, 2H), 1.82-1.73 (m, 2H), 1.68 (s, 1H), 1.50-1.36 (m, 2H), 1.36-1.22 (m, 3H);

$^{13}$C NMR (126 MHz, DMSO-d$_6$) δ 163.7, 153.6, 145.1, 144.5, 143.4, 135.0, 134.6, 128.5, 128.2, 127.6, 126.9, 119.8, 117.4, 116.3, 115.5, 40.4, 36.4, 35.9, 34.9, 26.1, 25.2;

HRMS calcd for C$_{25}$H$_{26}$N$_3$O$_3$S [M+H]$^+$ 448.1689, found 448.1681.

Preparative Example 147

2-cyano-3-(4-hydroxy-3,5-dimethylphenyl)-N-(4-phenylthiazol-2-yl)propanamide

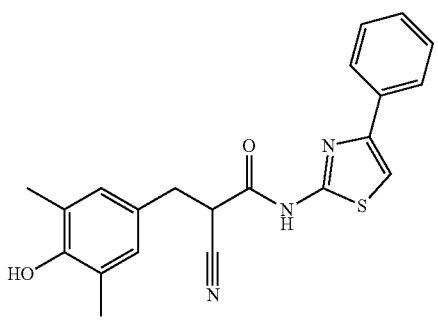 [SMILES: Cc1cc(CC(C#N)C(=O)Nc2nc(-c3ccccc3)cs2)cc(C)c1O]

The compound was prepared according to General procedure E from (E)-2-cyano-3-(4-hydroxy-3,5-dimethylphenyl)-N-(4-phenylthiazol-2-yl)acrylamide (50 mg, 0.133 mmol) and NaBH$_4$ (10 mg, 0.26 mmol) in MeOH (3 mL); the reaction time was 16 h. The product, purified by reverse phase column chromatography (H$_2$O:MeOH:AcOH; 45:55:0.05 to 1:4:0.05), was obtained as a pale yellow solid (30 mg, 60%).

$^1$H NMR (500 MHz, DMSO-d$_6$) δ (ppm) 12.74 (s, 1H), 8.16 (s, 1H), 7.96-7.86 (m, 2H), 7.71 (s, 1H), 7.44-7.42 (m, 2H), 7.37-7.30 (m, 1H), 6.87 (s, 2H), 4.24 (dd, J=9.6, 5.8 Hz, 1H), 3.22-2.92 (m, 2H), 2.13 (s, 6H);

$^{13}$C NMR (126 MHz, DMSO-d$_6$) δ (ppm) 164.2, 157.3, 152.3, 149.1, 134.0, 128.7, 127.9, 126.4, 125.6, 124.2, 117.3, 108.8, 40.7, 34.9, 16.6;

HRMS calcd for C$_{21}$H$_{18}$N$_3$O$_2$S [M−H]$^−$ 376.1125, found 376.1125.

Preparative Example 148

3-(2-bromo-3,4-dihydroxyphenyl)-2-cyano-N-(4-phenylthiazol-2-yl)propanamide

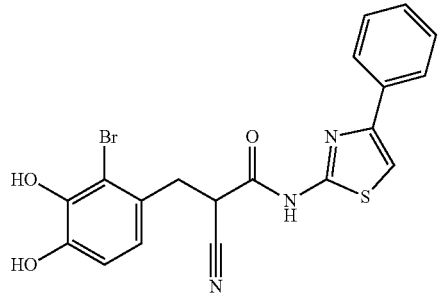 [SMILES: N#CC(Cc1ccc(O)c(O)c1Br)C(=O)Nc1nc(-c2ccccc2)cs1]

The compound was prepared according to General procedure E from (E)-3-(2-bromo-3,4-dihydroxyphenyl)-2-cyano-N-(4-phenylthiazol-2-yl)acrylamide (50 mg, 0.11 mmol) and NaBH$_4$ (8 mg, 0.22 mmol) in EtOH (2 mL); the reaction time was 2 h. The product, purified by reverse phase column chromatography (H$_2$O:MeOH:AcOH; 60:40:0.05 to 5:95:0.05), was obtained as a white solid (30 mg, 60%).

$^1$H NMR (500 MHz, DMSO-d$_6$) δ (ppm) 12.83 (s, 1H), 9.77 (s, 1H), 9.15 (s, 1H), 7.94-7.85 (m, 2H), 7.73 (s, 1H), 7.48-7.40 (m, 2H), 7.37-7.29 (m, 1H), 6.76-6.68 (m, 2H), 4.32 (t, J=7.8 Hz, 1H), 3.31-3.25 (m, 2H);

$^{13}$C NMR (126 MHz, DMSO-d$_6$) δ (ppm) 163.5, 157.0, 149.1, 145.4, 143.1, 134.0, 128.7, 127.9, 125.9, 125.6, 120.8, 116.9, 114.0, 112.4, 109.0, 38.1, 35.0;

HRMS calcd for C$_{19}$H$_{15}$BrN$_3$O$_3$S [M+H]$^+$ 445.9993, found 445.9993.

Preparative Example 149

N-(4-(4-(tert-butyl)phenyl)thiazol-2-yl)-2-cyano-3-(4-hydroxy-3,5-dimethylphenyl)propanamide

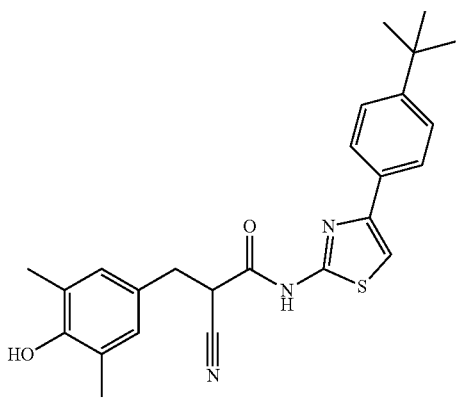 [SMILES: Cc1cc(CC(C#N)C(=O)Nc2nc(-c3ccc(C(C)(C)C)cc3)cs2)cc(C)c1O]

The compound was prepared according to General procedure E from (E)-N-(4-(4-(tert-butyl)phenyl)thiazol-2-yl)-2-cyano-3-(4-hydroxy-3,5-dimethylphenyl)acrylamide (74 mg, 0.17 mmol) and NaBH$_4$ (27 mg, 0.685 mmol) in MeOH (2 mL); the reaction time was 2 h. The product, purified by column chromatography on silica gel (hexane:EtOAc; 1:0 to 3:1), followed by reverse phase column chromatography (H$_2$O:MeOH:AcOH; 70:30:0.05 to 80:20:0.05) was obtained as a white solid (44 mg, 60%).

$^1$H NMR (500 MHz, CDCl$_3$) δ (ppm) 12.73 (s, 1H), 8.15 (s, 1H), 7.82 (d, J=8.6 Hz, 2H), 7.63 (s, 1H), 7.45 (d, J=8.6 Hz, 2H), 6.87 (s, 2H), 4.23 (dd, J=9.6, 6.0 Hz, 11H), 3.16 (dd, J=13.6, 5.8 Hz, 11H), 2.97 (dd, J=13.7, 9.3 Hz, 1H), 2.13 (s, 6H), 1.31 (s, 9H);

$^{13}$C NMR (126 MHz, CDCl$_3$) δ (ppm) 164.2, 152.3, 150.4, 149.1, 131.4, 128.8, 126.4, 125.5, 125.4, 124.2, 117.4, 108.0, 40.7, 34.9, 34.3, 31.0, 16.6;

HRMS calcd for C$_{25}$H$_{28}$N$_3$O$_2$S [M+H]$^{+-}$ 434.1897, found 434.1894.

Preparative Example 150

N-(4-(4-(tert-butyl)phenyl)thiazol-2-yl)-2-cyano-3-(3,5-di-tert-butyl-4-hydroxyphenyl)propanamide

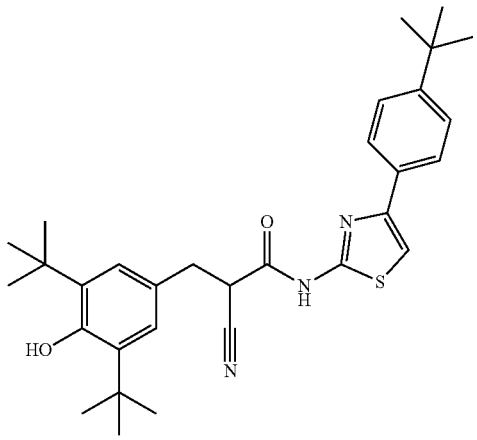 [SMILES: CC(C)(C)c1ccc(-c2csc(NC(=O)C(C#N)Cc3cc(C(C)(C)C)c(O)c(C(C)(C)C)c3)n2)cc1]

The compound was prepare according to General procedure E from (E)-N-(4-(4-(tert-butyl)phenyl)thiazol-2-yl)-2-cyano-3-(3,5-di-tert-butyl-4-hydroxyphenyl)acrylamide (85 mg, 0.165 mmol), NaBH$_4$ (25 mg, 0.660 mmol) in MeOH (4 mL). The reaction mixture was stirred for 3 h. The product, purified by reverse phase column chromatography (MeOH:H$_2$O:AcOH; 60:40:0.05 to 90:10:0.05), was obtained as a white solid (54 mg, 63% yield).

$^1$H NMR (500 MHz, DMSO-d$_6$) δ (ppm) 12.71 (s, 1H), 7.81 (d, J=8.6 Hz, 2H), 7.63 (s, 1H), 7.45 (d, J=8.7 Hz, 2H), 7.04 (s, 2H), 6.85 (s, 1H), 4.22 (dd, J=8.5, 6.0 Hz, 1H), 3.19 (dd, J=13.6, 6.3 Hz, 1H), 3.10 (dd, J=13.5, 8.6 Hz, 1H), 1.33 (s, 18H), 1.30 (s, 9H);

$^{13}$C NMR (126 MHz, DMSO-d$_6$) δ (ppm) 164.2, 157.1, 153.0, 150.4, 149.1, 139.1, 131.4, 126.9, 125.5, 125.4, 125.4, 117.4, 108.0, 40.8, 35.9, 34.4, 34.3, 31.0, 30.3;

HRMS calcd for C$_{31}$H$_{40}$N$_3$O$_2$S [M+H]$^+$ 518.2836, found 518.2833.

Preparative Example 151

2-cyano-3-(3-cyano-4-hydroxyphenyl)-N-(4-phenylthiazol-2-yl)propanamide

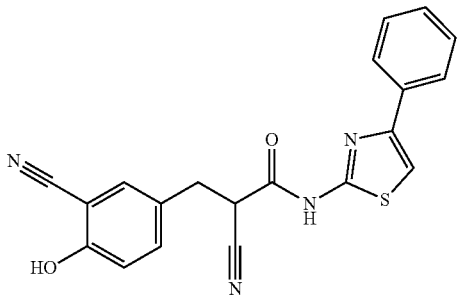 [SMILES: N#Cc1cc(CC(C#N)C(=O)Nc2nc(-c3ccccc3)cs2)ccc1O]

The compound was prepared according to General procedure E from (E)-2-cyano-3-(3-cyano-4-hydroxyphenyl)-N-(4-phenylthiazol-2-yl)acrylamide (20 mg, 0.05 mmol) and NaBH$_4$ (4 mg, 0.1 mmol) in EtOH (2 mL); the reaction time was 2 h. The product, purified by reverse phase column chromatography (H$_2$O:MeOH:AcOH; 60:40:0.05 to 5:95:0.05), was obtained as a white solid (16 mg, 80%).

$^1$H NMR (500 MHz, DMSO-d$_6$) δ (ppm) 12.77 (s, 1H), 11.07 (s, 1H), 7.94-7.85 (m, 2H), 7.72 (s, 1H), 7.59 (d, J=2.4 Hz, 1H), 7.47-7.42 (m, 3H), 7.38-7.32 (m, 1H), 7.03-6.97 (m, 1H), 4.32 (dd, J=9.4, 5.9 Hz, 1H), 3.29-3.07 (m, 2H);

$^{13}$C NMR (126 MHz, DMSO-d$_6$) δ (ppm) 163.8, 159.3, 149.1, 135.5, 134.0, 133.6, 128.7, 127.9, 127.4, 125.6, 117.0, 116.8, 116.3, 109.6, 108.9, 98.8, 40.3, 33.9;

HRMS calcd for C$_{20}$H$_{15}$N$_4$O$_2$S [M+H]$^+$ 375.0910, found 375.0908.

Preparative Example 152

2-cyano-3-(3,4-dihydroxyphenyl)-N-(4-(5-methyl-thiophen-3-yl)thiazol-2-yl)propanamide (SH-1413)

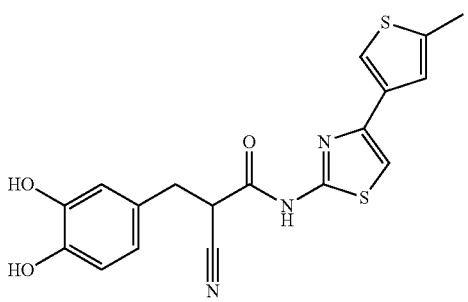 [SMILES: Cc1cc(-c2csc(NC(=O)C(C#N)Cc3ccc(O)c(O)c3)n2)cs1]

The compound was prepared according to General procedure E from (E)-2-cyano-3-(3,4-dihydroxyphenyl)-N-(4-(4-methylthiophen-3-yl)thiazol-2-yl)acrylamide (32 mg, 0.08 mmol) and NaBH$_4$ (6 mg, 0.16 mmol) in EtOH (2 mL); the reaction time was 2 h. The product, purified by reverse phase column chromatography (H$_2$O:MeOH:AcOH; 60:40: 0.05 to 5:95:0.05), was obtained as a white solid (15 mg, 50%).

$^1$H NMR (500 MHz, DMSO-d$_6$) δ (ppm) 12.83 (s, 1H), 8.85 (s, 1H), 8.82 (s, 1H), 7.50 (s, 1H), 7.35 (d, J=1.4 Hz, 1H), 7.08 (d, J=1.3 Hz, 1H), 6.71 (d, J=2.2 Hz, 1H), 6.66 (d, J=8.0 Hz, 1H), 6.55 (dd, J=8.1, 2.1 Hz, 1H), 4.20 (dd, J=9.5, 5.9 Hz, 1H), 3.20-2.91 (m, 2H), 2.23 (d, J=1.1 Hz, 3H);

$^{13}$C NMR (126 MHz, DMSO-d$_6$) δ (ppm) 164.1, 157.2, 145.1, 144.5, 144.0, 137.9, 137.7, 126.8, 126.0, 120.9, 119.8, 117.2, 116.3, 115.5, 106.4, 40.6, 35.0, 15.4;

HRMS calcd for C$_{18}$H$_{16}$N$_3$O$_3$S$_2$[M+H]$^+$ 386.0628, found 386.0625.

Preparative Example 153

2-cyano-3-(3,4-dihydroxyphenyl)-N-(4-(5,6,7,8-tetrahydronaphthalen-2-yl)thiazol-2-yl)propanamide

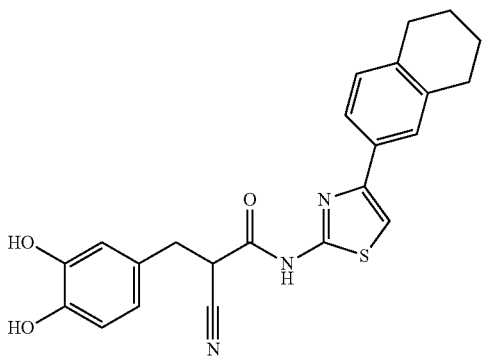 [SMILES: N#CC(Cc1ccc(O)c(O)c1)C(=O)Nc1nc(-c2ccc3c(c2)CCCC3)cs1]

The compound was prepared according to General procedure E from (E)-2-cyano-3-(3,4-dihydroxyphenyl)-N-(4-(5,6,7,8-tetrahydronaphthalen-2-yl)thiazol-2-yl)acrylamide (55 mg, 0.13 mmol) and NaBH$_4$ (10 mg, 0.26 mmol) in EtOH (3 mL); the reaction time was 2 h. The product, purified by reverse phase column chromatography (H$_2$O: MeOH:AcOH; 60:40:0.05 to 5:95:0.05), was obtained as a white solid (33 mg, 60%).

$^1$H NMR (500 MHz, CDCl$_3$) δ (ppm) 7.41 (dd, J=7.8, 1.8 Hz, 1H), 7.38 (s, 1H), 7.11 (d, J=7.9 Hz, 1H), 7.08 (s, 1H), 6.61 (d, J=8.1 Hz, 1H), 6.53-6.48 (m, 1H), 6.32 (dd, J=8.4, 2.0 Hz, 1H), 3.28-3.17 (m, 1H), 2.99-2.86 (m, 2H), 2.77 (dd, J=16.2, 5.5 Hz, 4H), 1.86-1.73 (m, 4H);

$^{13}$C NMR (126 MHz, CDCl$_3$) δ (ppm) 163.61, 158.8, 150.1, 144.0, 143.7, 138.9, 138.5, 130.8, 130.3, 127.5, 127.3, 123.8, 121.5, 116.6, 116.2, 115.9, 108.4, 40.6, 35.9, 29.7, 29.4, 23.2, 23.2;

HRMS calcd for C$_{23}$H$_{22}$N$_3$O$_3$S [M+H]$^+$ 420.1376, found 420.1377.

Preparative Example 154

2-cyano-N-(4-(4-cyclohexylphenyl)thiazol-2-yl)-3-(3,4-dihydroxyphenyl)propanamide

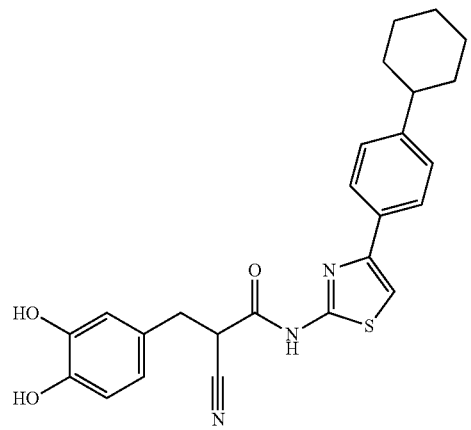 [SMILES: N#CC(Cc1ccc(O)c(O)c1)C(=O)Nc1nc(-c2ccc(C3CCCCC3)cc2)cs1]

The compound was prepared according to General procedure E from (E)-2-cyano-N-(4-(4-cyclohexylphenyl)thiazol-2-yl)-3-(3,4-dihydroxyphenyl)acrylamide (30 mg, 0.07 mmol) and NaBH$_4$ (5 mg, 0.13 mmol) in EtOH (2 mL); the reaction time was 2 h. The product, purified by reverse phase column chromatography (H$_2$O:MeOH:AcOH; 60:40:0.05 to 5:95:0.05), was obtained as a white solid (10 mg, 33%).

$^1$H NMR (500 MHz, CDCl$_3$) δ (ppm) 7.69-7.62 (m, 2H), 7.29 (d, J=8.3 Hz, 2H), 7.12 (s, 1H), 6.65 (d, J=8.0 Hz, 1H), 6.52 (d, J=2.1 Hz, 1H), 6.39 (dd, J=8.1, 2.1 Hz, 1H), 3.37-3.26 (m, 1H), 3.04-2.88 (m, 2H), 2.60-2.49 (m, 1H), 1.95-1.81 (m, 4H), 1.81-1.72 (m, 1H), 1.52-1.34 (m, 4H), 1.27 (s, 1H);

$^{13}$C NMR (126 MHz, CDCl$_3$) δ (ppm) 163.2, 158.5, 150.2, 149.5, 144.0, 143.7, 131.4, 128.0, 127.4, 126.6, 121.7, 116.5, 116.2, 116.0, 108.6, 44.6, 40.7, 35.7, 34.5, 27.0, 26.3;

HRMS calcd for C$_{25}$H$_{26}$N$_3$O$_3$S [M+H]$^+$ 448.1689, found 444.1680.

Preparative Example 155

3-(3-chloro-4-hydroxy-5-methylphenyl)-2-cyano-N-(4-phenylthiazol-2-yl)propanamide

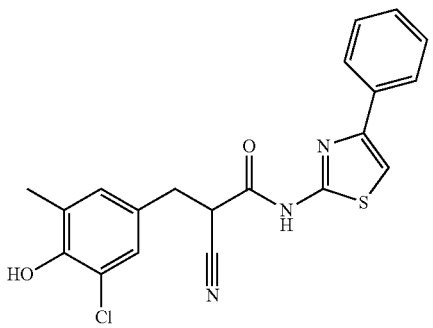 [SMILES: Cc1cc(CC(C#N)C(=O)Nc2nc(-c3ccccc3)cs2)cc(Cl)c1O]

The compound was prepared according to General procedure E from (E)-3-(3-chloro-4-hydroxy-5-methylphenyl)-2-cyano-N-(4-phenylthiazol-2-yl)acrylamide (120 mg, 0.3 mmol) and NaBH$_4$ (21 mg, 0.6 mmol) in EtOH (3 mL); the reaction time was 2 h. The product, purified by column chromatography (hexane:EtOAc; 7:3), was obtained as a white solid (80 mg, 70%).

$^1$H NMR (500 MHz, DMSO-d$_6$) δ (ppm) 12.75 (s, 1H), 9.09 (s, 1H), 7.95-7.87 (m, 2H), 7.72 (s, 1H), 7.48-7.41 (m, 2H), 7.38-7.30 (m, 1H), 7.19 (d, J=2.2 Hz, 1H), 7.02 (d, J=1.7 Hz, 1H), 4.29 (dd, J=9.6, 5.8 Hz, 1H), 3.25-3.01 (m, 2H), 2.17 (s, 3H);

$^{13}$C NMR (126 MHz, DMSO-d$_6$) δ (ppm) 163.9, 157.1, 150.0, 149.1, 134.0, 130.0, 128.7, 128.0, 127.9, 127.5, 126.9, 125.6, 120.3, 117.1, 108.9, 40.5, 34.3, 16.7;

HRMS calcd for C$_{20}$H$_{17}$ClN$_3$O$_2$S [M+H]$^+$ 398.0725, found 398.0720.

Preparative Example 156

3-(3-chloro-5-fluoro-4-hydroxyphenyl)-2-cyano-N-(4-phenylthiazol-2-yl)propanamide

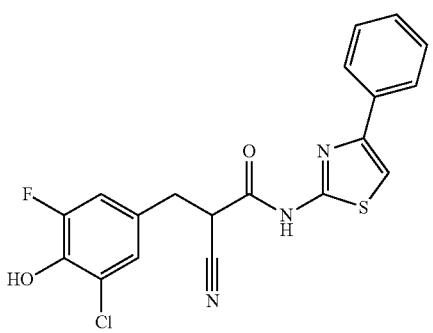 [SMILES: N#CC(Cc1cc(F)c(O)c(Cl)c1)C(=O)Nc1nc(-c2ccccc2)cs1]

The compound was prepared according to General procedure E from (E)-3-(3-chloro-5-fluoro-4-hydroxyphenyl)-2-cyano-N-(4-phenylthiazol-2-yl)acrylamide (95 mg, 0.22 mmol) and NaBH$_4$ (17 mg, 0.44 mmol) in EtOH (3 mL); the reaction time was 2 h. The product, purified by column chromatography (hexane:EtOAc; 7:3), was obtained as a white solid (55 mg, 60%).

$^1$H NMR (500 MHz, DMSO-d$_6$) δ (ppm) 12.77 (s, 1H), 10.40-10.28 (m, 1H), 7.93-7.88 (m, 2H), 7.72 (s, 1H), 7.48-7.41 (m, 2H), 7.36-7.32 (m, 1H), 7.26-7.21 (m, 1H), 7.17 (dd, J=11.3, 2.1 Hz, 1H), 4.34 (dd, J=9.5, 5.8 Hz, 1H), 3.29-3.09 (m, 2H);

$^{13}$C NMR (126 MHz, DMSO-d$_6$) δ (ppm) 163.7, 157.1, 151.6 (d, J=241.9 Hz), 149.1, 140.7 (d, J=16.3 Hz), 134.0, 128.8, 128.0, 127.9, 125.8 (d, J=3.0 Hz), 125.7, 121.9 (d, J=4.5 Hz), 117.0, 115.5 (d, J=19.4 Hz), 108.9, 40.3, 34.0;

$^{19}$F NMR (471 MHz, DMSO-d$_6$) δ (ppm) -131.37;

HRMS calcd for C$_{19}$H$_{14}$ClFN$_3$O$_2$S [M+H]$^+$ 402.0474, found 402.0471.

Preparative Example 157

2-cyano-3-(3,4-dihydroxyphenyl)-N-(4-(pyridin-2-yl)thiazol-2-yl)propanamide

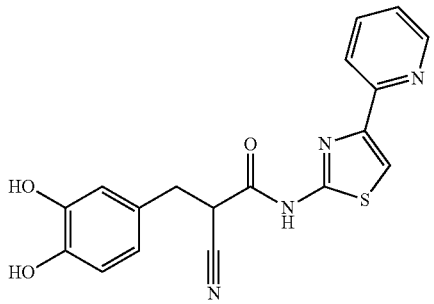 [SMILES: N#CC(Cc1ccc(O)c(O)c1)C(=O)Nc1nc(-c2ccccn2)cs1]

The compound was prepared according to General procedure E from (E)-2-cyano-3-(3,4-dihydroxyphenyl)-N-(4-(pyridin-2-yl)thiazol-2-yl)acrylamide (50 mg, 0.137 mmol) and NaBH$_4$ (10 mg, 0.274 mmol) in MeOH (3 mL) and THF (3 mL); the reaction time was 2 h. The product, purified by column chromatography (CH$_2$Cl$_2$:MeOH; 1:0 to 9.2:0.8), was obtained as a pale yellow solid (40 mg, 80%).

$^1$H NMR (500 MHz, DMSO-d$_6$) δ (ppm) 12.80 (s, 1H), 8.84 (d, J=15.47 Hz, 2H), 8.64-8.58 (m, 1H), 7.94 (d, J=7.82 Hz, 1H), 7.92-7.86 (m, 2H), 7.38-7.31 (m, 1H), 6.72 (d, J=2.14 Hz, 1H), 6.67 (d, J=8.01 Hz, 1H), 6.57 (dd, J=8.06, 2.13 Hz, 1H), 4.24 (dd, J=9.42, 5.84 Hz, 1H), 3.21-3.12 (m, 1H), 2.98 (dd, J=13.62, 9.47 Hz, 1H);

$^{13}$C NMR (126 MHz, DMSO-d$_6$) δ (ppm) 164.2, 157.5, 151.7, 149.5, 149.2, 145.1, 144.5, 137.3, 126.8, 122.9, 119.9, 119.8, 117.3, 116.3, 115.5, 112.4, 40.6, 34.9;

HRMS calcd for C$_{18}$H$_{15}$N$_4$O$_3$S [M+H]$^+$ 367.0859, found 367.0859.

Preparative Example 158

2-cyano-3-(3,4-dihydroxyphenyl)-N-(4-(6-methylpyridin-2-yl)thiazol-2-yl)propanamide

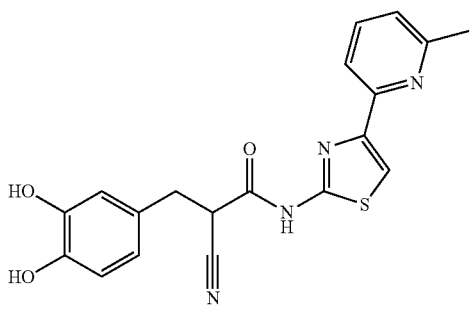 [SMILES: Cc1cccc(-c2csc(NC(=O)C(C#N)Cc3ccc(O)c(O)c3)n2)n1]

The compound was prepared according to General procedure E from (E)-2-cyano-3-(3,4-dihydroxyphenyl)-N-(4-(6-methylpyridin-2-yl)thiazol-2-yl)acrylamide (125 mg, 0.330 mmol) and NaBH$_4$ (25 mg, 0.660 mmol) in MeOH (8 mL) and THF (6 mL); the reaction time was 2 h. The product, purified by column chromatography (CH$_2$Cl$_2$:MeOH; 1:0 to 19:1), was obtained as a pale yellow solid (30 mg, 24%).

$^1$H NMR (500 MHz, DMSO-d$_6$) δ (ppm) 12.80 (s, 1H), 8.84 (s, 2H), 7.86 (s, 1H), 7.82-7.71 (m, 2H), 7.25-7.19 (m, 1H), 6.72 (d, J=2.14 Hz, 1H), 6.67 (d, J=7.97 Hz, 1H), 6.57 (dd, J=8.04, 2.13 Hz, 1H), 4.24 (dd, J=9.46, 5.85 Hz, 1H), 3.16 (dd, J=13.60, 5.88 Hz, 1H), 2.98 (dd, J=13.66, 9.44 Hz, 1H), 2.52 (s, 3H);

$^{13}$C NMR (126 MHz, DMSO-d$_6$) 3164.2, 157.8, 151.1, 149.4, 145.1, 144.5, 137.4, 126.8, 122.3, 119.8, 117.3, 117.1, 116.3, 115.5, 112.1, 40.6, 34.9, 24.1;

HRMS calcd for C$_{19}$H$_{17}$N$_4$O$_3$S [M+H]$^+$ 381.1016, found 381.1018.

Preparative Example 159

2-cyano-3-(3,4-dihydroxyphenyl)-N-(4-(2-(trifluoromethyl)phenyl)thiazol-2-yl)propanamide

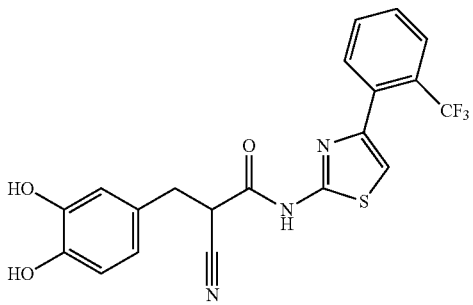 [SMILES: N#CC(Cc1ccc(O)c(O)c1)C(=O)Nc1nc(-c2ccccc2C(F)(F)F)cs1]

The compound was prepared according to General procedure E from (E)-2-cyano-3-(3,4-dihydroxyphenyl)-N-(4-(2-(trifluoromethyl)phenyl)thiazol-2-yl)acrylamide (65 mg, 0.15 mmol) and NaBH$_4$ (11 mg, 0.30 mmol) in EtOH (2 mL); the reaction time was 2 h. The product, purified by reverse phase column chromatography (H$_2$O:MeOH:AcOH; 60:40:0.05 to 5:95:0.05), was obtained as a white solid (20 mg, 30%).

$^1$H NMR (500 MHz, CDCl$_3$) δ (ppm) 7.78 (d, J=7.6 Hz, 1H), 7.62-7.50 (m, 3H), 7.11 (s, 1H), 6.66 (d, J=8.0 Hz, 1H), 6.61 (d, J=2.1 Hz, 1H), 6.54 (dd, J=8.1, 2.1 Hz, 1H), 3.54-3.41 (m, 1H), 3.18-3.00 (m, 2H);

$^{13}$C NMR (126 MHz, CDCl$_3$) δ (ppm) 162.8, 157.1, 147.2, 144.1, 143.9, 133.5, 132.1, 132.1, 129.2, 128.9 (q, J=31.0 Hz), 127.2, 126.9 (q, J=5.8 Hz), 124.1 (q, J=273.9 Hz), 121.8, 116.6, 116.3, 116.0, 113.4 (q, J=3.2 Hz), 40.9, 35.7;

$^{19}$F NMR (471 MHz, CDCl$_3$) δ (ppm) −57.74;

HRMS calcd for C$_{20}$H$_{15}$F$_3$N$_3$O$_3$S [M+H]$^+$ 434.0781, found 434.0785.

Preparative Example 160

2-cyano-N-(4-(3,4-dichlorophenyl)thiazol-2-yl)-3-(3,4-dihydroxyphenyl)propanamide

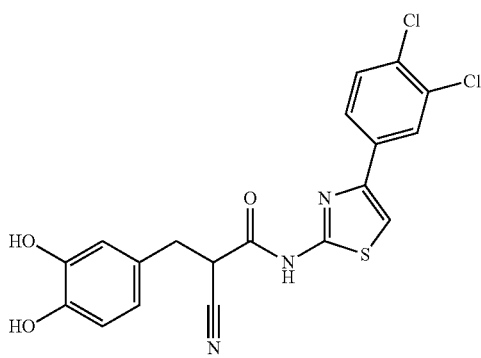 [SMILES: N#CC(Cc1ccc(O)c(O)c1)C(=O)Nc1nc(-c2ccc(Cl)c(Cl)c2)cs1]

The compound was prepared according to General procedure E from (E)-2-cyano-N-(4-(3,4-dichlorophenyl)thiazol-2-yl)-3-(3,4-dihydroxyphenyl)acrylamide (35 mg, 0.08 mmol) and NaBH$_4$ (6 mg, 0.16 mmol) in EtOH (2 mL); the reaction time was 2 h. The product, purified by reverse phase column chromatography (H$_2$O:MeOH:AcOH; 60:40:0.05 to 5:95:0.05), was obtained as a white solid (30 mg, 85%).

$^1$H NMR (500 MHz, DMSO-d$_6$) δ (ppm) 12.80 (s, 1H), 8.85 (s, 1H), 8.82 (s, 1H), 8.14 (d, J=2.0 Hz, 1H), 7.92 (s, 1H), 7.89 (dd, J=8.4, 2.1 Hz, 1H), 7.71 (dd, J=8.4, 1.2 Hz, 1H), 6.72 (d, J=2.1 Hz, 1H), 6.67 (d, J=8.0 Hz, 1H), 6.56 (dd, J=8.0, 2.1 Hz, 1H), 4.24 (dd, J=9.4, 5.9 Hz, 1H), 3.22-2.94 (m, 2H);

$^{13}$C NMR (126 MHz, DMSO-d$_6$) δ (ppm) 164.3, 157.6, 146.5, 145.1, 144.5, 134.6, 131.6, 131.0, 130.2, 127.3, 126.8, 125.7, 119.8, 117.2, 116.3, 115.5, 110.9, 40.6, 34.9;

HRMS calcd for C$_{19}$H$_{14}$Cl$_2$N$_3$O$_3$S [M+H]$^+$ 434.0127, found 434.0124.

Preparative Example 161

2-cyano-3-(3,4-dihydroxyphenyl)-N-(4-(o-tolyl)thiazol-2-yl)propanamide

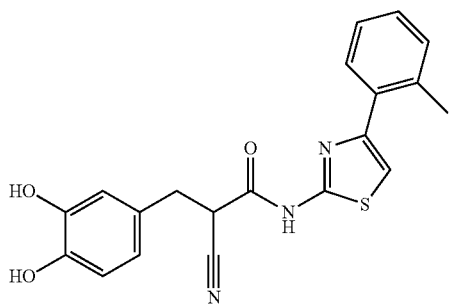 [SMILES: Cc1ccccc1-c1csc(NC(=O)C(C#N)Cc2ccc(O)c(O)c2)n1]

The compound was prepared according to General procedure E from (E)-2-cyano-3-(3,4-dihydroxyphenyl)-N-(4-(o-tolyl)thiazol-2-yl)acrylamide (60 mg, 0.16 mmol) and NaBH$_4$ (12 mg, 0.32 mmol) in EtOH (2 mL); the reaction time was 2 h. The product, purified by reverse phase column chromatography (H$_2$O:MeOH:AcOH; 60:40:0.05 to 5:95:0.05), was obtained as a white solid (50 mg, 85%).

$^1$H NMR (500 MHz, CDCl$_3$) δ (ppm) 7.46-7.42 (m, 1H), 7.38-7.32 (m, 1H), 7.30-7.23 (m, 2H), 6.98 (s, 1H), 6.67 (d, J=8.1 Hz, 1H), 6.60 (d, J=2.1 Hz, 1H), 6.49 (dd, J=8.1, 2.1 Hz, 1H), 3.08-3.03 (m, 1H), 3.02-2.91 (m, 2H), 2.35 (s, 3H);

$^{13}$C NMR (126 MHz, CDCl$_3$) δ (ppm) 163.4, 158.4, 148.5, 144.0, 144.0, 136.6, 133.0, 131.6, 129.9, 129.7, 127.2, 126.7, 121.9, 116.5, 116.3, 115.9, 111.8, 40.4, 35.7, 20.8;

HRMS calcd for C$_{20}$H$_{18}$N$_3$O$_3$S [M+H]$^+$ 380.1063, found 380.1069.

Preparative Example 162

N-(4-(3-chlorophenyl)thiazol-2-yl)-2-cyano-3-(3,4-dihydroxyphenyl)propanamide

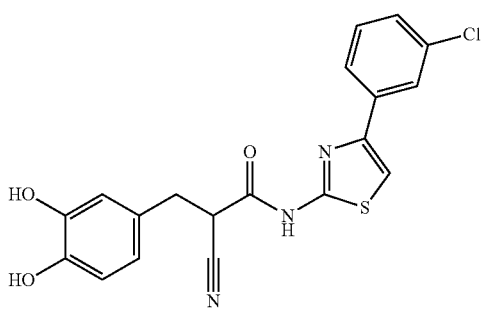 [SMILES: N#CC(Cc1ccc(O)c(O)c1)C(=O)Nc1nc(-c2cccc(Cl)c2)cs1]

The compound was prepared according to General procedure E from (E)-N-(4-(3-chlorophenyl)thiazol-2-yl)-2-cyano-3-(3,4-dihydroxyphenyl)acrylamide (82 mg, 0.206 mmol) and NaBH$_4$ (31 mg, 0.824 mmol) in MeOH (5 mL); the reaction time was 3 h. The product, purified by column chromatography on silica gel (hexane:EtOAc, 10:1 to 1:1), was obtained as a white solid (57 mg, 69% yield).

$^1$H NMR (500 MHz, DMSO-d$_6$) δ (ppm) 12.79 (s, 1H), 8.85 (s, 2H), 7.96 (t, J=1.9 Hz, 1H), 7.90-7.85 (m, 2H), 7.48 (t, J=7.9 Hz, 1H), 7.40 (m, J=8.0, 3.3 Hz, 1H), 6.72 (d, J=2.3 Hz, 1H), 6.67 (d, J=7.9 Hz, 1H), 6.56 (dd, J=8.1, 2.1 Hz, 1H), 4.24 (dd, J=9.5, 6.0 Hz, 1H), 3.16 (dd, J=13.6, 5.8 Hz, 1H), 2.98 (dd, J=13.7, 9.4 Hz, 1H);

$^{13}$C NMR (126 MHz, DMSO-d$_6$) δ (ppm) 164.2, 157.4, 147.5, 145.1, 144.5, 136.0, 133.6, 130.7, 127.6, 126.8, 125.4, 124.2, 119.8, 117.3, 116.4, 115.5, 110.3, 40.6, 34.9;

HRMS calcd for C$_{19}$H$_{15}$ClN$_3$O$_3$S [M+H]$^+$ 400.0517, found 400.0516.

Preparative Example 163

3-(3,5-bis(trifluoromethyl)phenyl)-2-cyano-N-(4-phenylthiazol-2-yl)propanamide

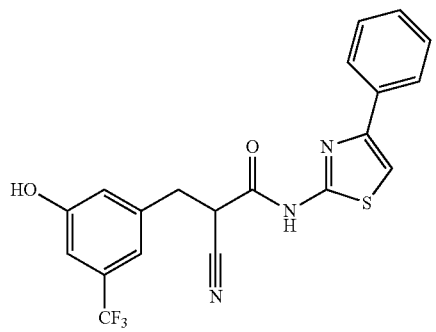 [SMILES: N#CC(Cc1cc(O)cc(C(F)(F)F)c1)C(=O)Nc1nc(-c2ccccc2)cs1]

The compound was prepared according to General procedure E from (E)-3-(3,5-bis(trifluoromethyl)phenyl)-2-cyano-N-(4-phenylthiazol-2-yl)acrylamide (140 mg, 0.29 mmol) and NaBH$_4$ (22 mg, 0.579 mmol) in MeOH (5 mL); the reaction time was 2 h. The product, purified by column chromatography on silica gel (hexane:EtOAc; 1:0 to 2:1), was obtained as a pale yellow solid (109 mg, 80%).

$^1$H NMR (500 MHz, DMSO-d$_6$) δ (ppm) 12.79 (s, 1H), 8.11 (d, J=1.6 Hz, 2H), 8.06 (s, 1H), 7.90 (dd, J=8.3, 1.3 Hz, 2H), 7.73 (s, 1H), 7.44 (d, J=7.9 Hz, 2H), 7.37-7.32 (m, 1H), 4.49 (dd, J=9.5, 5.7 Hz, 1H), 3.56 (dd, J=13.7, 5.7 Hz, 1H), 3.48 (dd, J=13.5, 9.5 Hz, 1H);

$^{13}$C NMR (126 MHz, DMSO-d$_6$) δ (ppm) 163.5, 157.1, 149.1, 139.8, 134.0, 130.3 (q, J=33.4 Hz), 130.3, 128.8, 127.9, 125.6, 124.3 (q J=273.4 Hz), 121.2, 116.7, 109.0, 39.8, 34.4;

$^{19}$F NMR (471 MHz, DMSO-d$_6$) δ (ppm) −61.4;

HRMS calcd for C$_2$H$_{14}$F$_6$N$_3$OS [M+H]$^+$ 470.0756, found 470.0759.

Preparative Example 164

2-cyano-3-(3,4-dihydroxyphenyl)-N-(4-(4-methylpyridin-2-yl)thiazol-2-yl)propanamide

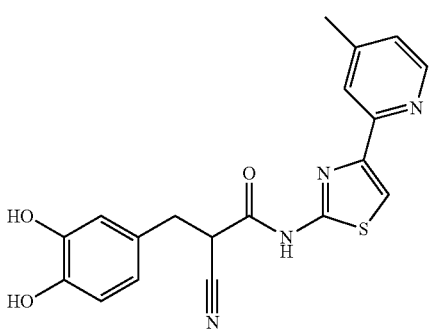 [SMILES: Cc1ccnc(-c2csc(NC(=O)C(C#N)Cc3ccc(O)c(O)c3)n2)c1]

The compound was prepared according to General procedure E from (E)-2-cyano-3-(3,4-dihydroxyphenyl)-N-(4-(4-methylpyridin-2-yl)thiazol-2-yl)acrylamide (37 mg, 0.1 mmol) and NaBH$_4$ (8 mg, 0.2 mmol) in EtOH (3 mL); the reaction time was 2 h. The product, purified by reverse phase column chromatography (H$_2$O:MeOH:AcOH; 60:40:0.05 to 5:95:0.05), was obtained as a white solid (30 mg, 80%).

$^1$H NMR (500 MHz, DMSO-d$_6$) δ (ppm) 12.77 (s, 1H), 8.84 (s, 2H), 8.46 (d, J=4.8 Hz, 1H), 7.86 (s, 1H), 7.78 (d, J=1.5 Hz, 1H), 7.18 (dd, J=5.1, 1.6 Hz, 1H), 6.72 (d, J=2.1 Hz, 1H), 6.67 (d, J=8.0 Hz, 1H), 6.56 (dd, J=8.1, 2.1 Hz, 1H), 4.22 (dd, J=9.4, 5.9 Hz, 1H), 3.21-2.94 (m, 2H), 2.38 (s, 3H);

$^{13}$C NMR (126 MHz, DMSO-d$_6$) δ (ppm) 164.3, 157.6, 151.7, 149.3, 149.3, 147.8, 145.1, 144.5, 126.9, 123.6, 120.8, 119.8, 117.3, 116.3, 115.5, 112.2, 40.7, 35.0, 20.7;

HRMS calcd for C$_{19}$H$_{17}$N$_4$O$_3$S [M+H]$^+$ 381.1016, found 381.1018.

Preparative Example 165

2-cyano-3-(3,4-dihydroxyphenyl)-N-(4-(5-methylpyridin-2-yl)thiazol-2-yl)propanamide

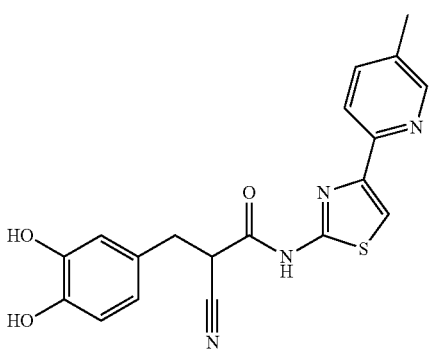 [SMILES: Cc1ccc(-c2csc(NC(=O)C(C#N)Cc3ccc(O)c(O)c3)n2)nc1]

The compound was prepared according to General procedure E from (E)-2-cyano-3-(3,4-dihydroxyphenyl)-N-(4-(5-methylpyridin-2-yl)thiazol-2-yl)acrylamide (46 mg, 0.12 mmol) and NaBH$_4$ (9 mg, 0.24 mmol) in EtOH (3 mL); the reaction time was 2 h. The product, purified by reverse phase column chromatography (H$_2$O:MeOH:AcOH; 60:40:0.05 to 5:95:0.05), was obtained as a white solid (30 mg, 65%).

$^1$H NMR (500 MHz, DMSO-d$_6$) δ (ppm) 12.77 (s, 1H), 8.85 (s, 1H), 8.82 (s, 1H), 8.45 (d, J=2.1 Hz, 1H), 7.84 (d, J=8.1 Hz, 1H), 7.82 (s, 1H), 7.70 (dd, J=8.2, 2.3 Hz, 1H), 6.72 (d, J=2.1 Hz, 1H), 6.67 (d, J=8.0 Hz, 1H), 6.56 (dd, J=8.1, 2.1 Hz, 1H), 4.22 (dd, J=9.4, 5.8 Hz, 1H), 3.21-2.93 (m, 2H), 2.33 (s, 3H);

$^{13}$C NMR (126 MHz, DMSO-d$_6$) δ (ppm) 164.3, 157.8, 149.8, 149.4, 149.3, 145.1, 144.5, 137.5, 132.1, 126.9, 119.8, 119.5, 117.4, 116.3, 115.5, 111.4, 40.7, 35.0, 17.7;

HRMS calcd for C$_{19}$H$_{17}$N$_4$O$_3$S [M+H]$^+$ 381.1016, found 381.1020.

Preparative Example 166

2-cyano-3-(3,4-dihydroxyphenyl)-N-(4-(4-isopropylphenyl)thiazol-2-yl)propanamide

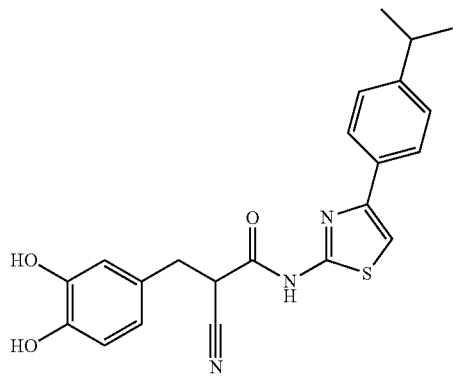 [SMILES: CC(C)c1ccc(-c2csc(NC(=O)C(C#N)Cc3ccc(O)c(O)c3)n2)cc1]

The compound was prepared according to General procedure E from (E)-2-cyano-3-(3,4-dihydroxyphenyl)-N-(4-(4-isopropylphenyl)thiazol-2-yl)acrylamide (95 mg, 0.234 mmol) and NaBH$_4$ (35 mg, 0.936 mmol) in MeOH (5 mL); the reaction time was 2 h. The product, purified by column chromatography on silica gel (hexane:EtOAc, 10:1 to 1:1), reverse phase column chromatography (MeOH:H$_2$O:AcOH; 50:50:0.05 to 92:8:0.05), preparative TLC (hexane:EtOAc, 1:1) and by reverse phase column chromatography (MeOH:H$_2$O:AcOH; 50:50:0.05 to 92:8:0.05), was obtained as a white solid (9 mg, 9% yield).

$^1$H NMR (500 MHz, CDCl$_3$) δ (ppm) 7.64 (d, J=8.3 Hz, 2H), 7.29 (d, J=8.3 Hz, 2H), 7.11 (s, 1H), 6.65 (d, J=8.1 Hz, 1H), 6.56 (d, J=2.1 Hz, 1H), 6.41 (dd, J=8.0, 2.2 Hz, 1H), 3.39 (dd, J=7.1 Hz, 1H), 3.05-2.86 (m, 3H), 1.26 (d, J=6.9 Hz, 6H);

$^{13}$C NMR (126 MHz, CDCl$_3$) δ (ppm) 163.3, 158.6, 150.2, 149.7, 144.0, 143.7, 131.0, 127.5, 127.3, 126.5, 121.6, 116.4, 116.2, 115.9, 108.4, 40.8, 35.7, 34.1, 24.0;

HRMS calcd for C$_{22}$H$_{22}$N$_3$O$_3$S [M+H]$^+$ 408.1376, found 408.1377.

Preparative Example 167

2-cyano-3-(3,4-dihydroxyphenyl)-N-(4-(4-methoxypyridin-2-yl)thiazol-2-yl)propanamide

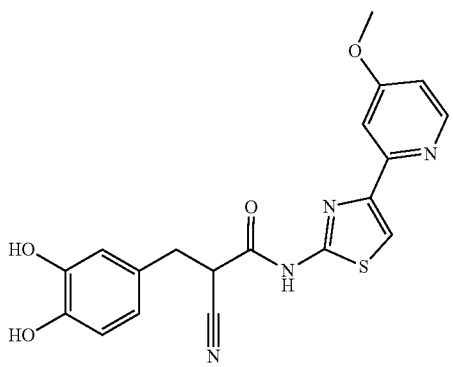 [SMILES: COc1ccnc(-c2csc(NC(=O)C(C#N)Cc3ccc(O)c(O)c3)n2)c1]

The compound was prepared according to General procedure E from (E)-2-cyano-3-(3,4-dihydroxyphenyl)-N-(4-(4-methoxypyridin-2-yl)thiazol-2-yl)acrylamide (40 mg, 0.1 mmol) and NaBH$_4$ (9 mg, 0.2 mmol) in EtOH (2 mL); the reaction time was 2 h. The product, purified by reverse phase column chromatography (H$_2$O:MeOH:AcOH; 60:40:0.05 to 5:95:0.05), was obtained as a white solid (26 mg, 65%).

$^1$H NMR (500 MHz, DMSO-d$_6$) δ (ppm) 12.80 (s, 1H), 8.85 (s, 1H), 8.82 (s, 1H), 8.42 (d, J=5.7 Hz, 1H), 7.89 (s, 1H), 7.48 (d, J=2.5 Hz, 1H), 6.93 (dd, J=5.7, 2.6 Hz, 1H), 6.72 (d, J=2.1 Hz, 1H), 6.67 (d, J=7.9 Hz, 1H), 6.56 (dd, J=8.0, 2.1 Hz, 1H), 4.23 (dd, J=9.4, 5.9 Hz, 1H), 3.88 (s, 3H), 3.22-2.93 (m, 2H);

$^{13}$C NMR (126 MHz, DMSO-d$_6$) δ (ppm) 166.1, 164.3, 157.5, 153.4, 150.9, 149.1, 145.1, 144.5, 126.8, 119.8, 117.3, 116.3, 115.5, 112.7, 109.3, 105.7, 55.3, 40.6, 35.0;

HRMS calcd for C$_{19}$H$_{17}$N$_4$O$_4$S [M+H]$^+$ 397.0965, found 397.0960.

Preparative Example 168

2-cyano-3-(3,4-dihydroxyphenyl)-N-(4-(5-methoxypyridin-2-yl)thiazol-2-yl)propanamide

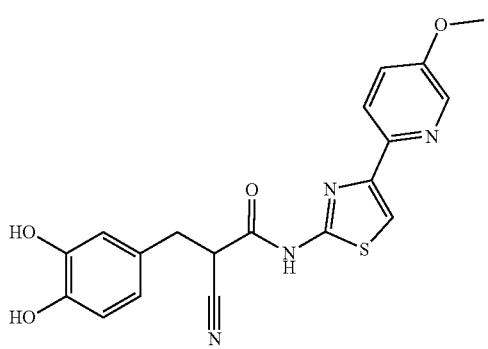 [SMILES: COc1ccc(-c2csc(NC(=O)C(C#N)Cc3ccc(O)c(O)c3)n2)nc1]

The compound was prepared according to General procedure E from (E)-2-cyano-3-(3,4-dihydroxyphenyl)-N-(4-(5-methoxypyridin-2-yl)thiazol-2-yl)acrylamide (50 mg, 0.13 mmol) and NaBH$_4$ (10 mg, 0.26 mmol) in EtOH (2 mL); the reaction time was 2 h. The product, purified by reverse phase column chromatography (H$_2$O:MeOH:AcOH; 60:40:0.05 to 5:95:0.05), was obtained as a white solid (40 mg, 80%).

$^1$H NMR (500 MHz, DMSO-d$_6$) δ (ppm) 12.75 (s, 1H), 8.85 (s, 1H), 8.82 (s, 1H), 8.33 (d, J=3.0 Hz, 1H), 7.89 (d, J=8.6 Hz, 1H), 7.71 (s, 1H), 7.48 (dd, J=8.7, 3.0 Hz, 1H), 6.72 (d, J=2.1 Hz, 1H), 6.67 (d, J=8.0 Hz, 1H), 6.56 (dd, J=8.0, 2.2 Hz, 1H), 4.23 (dd, J=9.4, 5.9 Hz, 1H), 3.87 (s, 3H), 3.19-2.93 (m, 2H);

$^{13}$C NMR (126 MHz, DMSO-d$_6$) δ (ppm) 164.2, 157.4, 154.8, 154.8, 149.1, 145.1, 144.5, 137.5, 126.9, 121.0, 120.6, 119.8, 117.3, 116.3, 115.5, 110.1, 55.6, 40.6, 35.0;

HRMS calcd for C$_{19}$H$_{17}$N$_4$O$_4$S [M+H]$^+$ 397.0965, found 397.0966.

Preparative Example 169

2-cyano-3-(3,5-di-tert-butyl-4-hydroxyphenyl)-N-(4-(pyridin-2-yl)thiazol-2-yl)propanamide

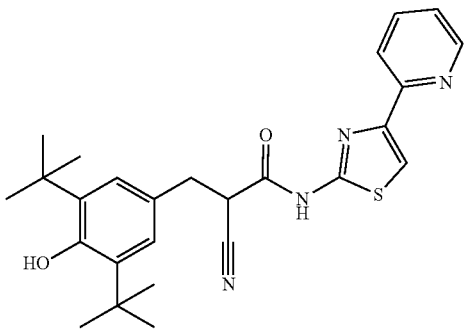 [SMILES: CC(C)(C)c1cc(CC(C#N)C(=O)Nc2nc(-c3ccccn3)cs2)cc(C(C)(C)C)c1O]

The compound was prepared according to General procedure E from (E)-2-cyano-3-(3,5-di-tert-butyl-4-hydroxyphenyl)-N-(4-(pyridin-2-yl)thiazol-2-yl)acrylamide (40 mg, 0.09 mmol) and NaBH$_4$ (8 mg, 0.18 mmol) in EtOH (3 mL); the reaction time was 2 h. The product, purified by reverse phase column chromatography (H$_2$O:MeOH:AcOH; 60:40:0.05 to 5:95:0.05), was obtained as a white solid (30 mg, 75%).

$^1$H NMR (500 MHz, DMSO-d$_6$) δ (ppm) 12.76 (s, 1H), 8.63-8.60 (m, 1H), 7.94-7.87 (m, 3H), 7.38-7.31 (m, 1H), 7.04 (s, 2H), 6.85 (s, 1H), 4.24 (dd, J=8.5, 6.1 Hz, 1H), 3.24-3.05 (m, 2H), 1.33 (s, 18H);

$^{13}$C NMR (126 MHz, DMSO-d$_6$) δ (ppm) 164.4, 157.5, 153.0, 151.8, 149.5, 149.3, 139.1, 137.3, 126.9, 125.4, 122.9, 119.9, 117.4, 112.4, 40.9, 35.9, 34.4, 30.2;

HRMS calcd for C$_{26}$H$_{31}$N$_4$O$_2$S [M+H]$^+$ 463.2162, found 463.2160.

Preparative Example 170

2-cyano-3-(3,4-dihydroxyphenyl)-N-(4-(6-methoxypyridin-2-yl)thiazol-2-yl)propanamide

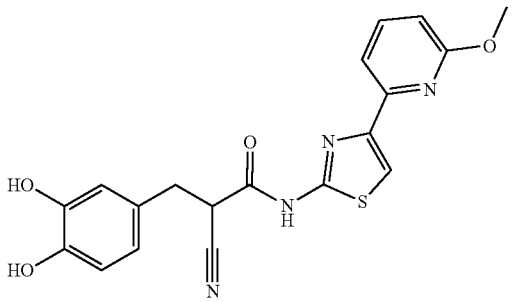 [SMILES: COc1cccc(-c2csc(NC(=O)C(C#N)Cc3ccc(O)c(O)c3)n2)n1]

The compound was prepared according to General procedure E from (E)-2-cyano-3-(3,4-dihydroxyphenyl)-N-(4-(6-methoxypyridin-2-yl)thiazol-2-yl)acrylamide (60 mg, 0.15 mmol) and NaBH$_4$ (12 mg, 0.3 mmol) in EtOH (3 mL); the reaction time was 2 h. The product, purified by reverse phase column chromatography (H$_2$O:MeOH:AcOH; 60:40:0.05 to 5:95:0.05), was obtained as a white solid (30 mg, 60%,).

$^1$H NMR (500 MHz, DMSO-d$_6$) δ (ppm) 12.78 (s, 1H), 8.85 (s, 1H), 8.82 (s, 1H), 7.89 (s, 1H), 7.82-7.76 (m, 1H), 7.52 (d, J=7.3 Hz, 1H), 6.77 (d, J=8.1 Hz, 1H), 6.72 (d, J=2.1 Hz, 1H), 6.67 (d, J=8.0 Hz, 1H), 6.56 (dd, J=8.1, 2.1 Hz, 1H), 4.24 (dd, J=9.5, 5.9 Hz, 1H), 3.94 (s, 3H), 3.21-2.92 (m, 2H);

$^{13}$C NMR (126 MHz, DMSO-d$_6$) δ (ppm) 164.2, 163.1, 157.4, 149.4, 149.1, 145.1, 144.5, 140.1, 126.8, 119.8, 117.3, 116.4, 115.5, 112.9, 112.5, 109.9, 52.9, 40.6, 35.0;

HRMS calcd for C$_{19}$H$_{17}$N$_4$O$_4$S [M+H]$^+$ 397.0965, found 397.0965.

Preparative Example 171

2-cyano-N-(4-(2,4-dichlorophenyl)thiazol-2-yl)-3-(3,4-dihydroxyphenyl)propanamide

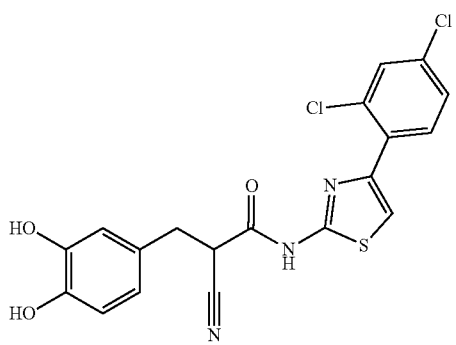 [SMILES: N#CC(Cc1ccc(O)c(O)c1)C(=O)Nc1nc(-c2ccc(Cl)cc2Cl)cs1]

The compound was prepared according to General procedure E from (E)-2-cyano-N-(4-(2,4-dichlorophenyl)thiazol-2-yl)-3-(3,4-dihydroxyphenyl)acrylamide (160 mg, 0.37 mmol) and NaBH$_4$ (27 mg, 0.74 mmol) in EtOH (5 mL); the reaction time was 2 h. The product, purified by reverse phase column chromatography (H$_2$O:MeOH:AcOH; 60:40:0.05 to 5:95:0.05), was obtained as a white solid (65 mg, 40%).

$^1$H NMR (500 MHz, DMSO-d$_6$) δ (ppm) 12.83 (s, 1H), 8.85 (s, 1H), 8.82 (s, 1H), 7.86 (d, J=8.5 Hz, 1H), 7.75 (s, 1H), 7.73 (d, J=2.2 Hz, 1H), 7.53 (dd, J=8.5, 2.2 Hz, 1H), 6.72 (d, J=2.1 Hz, 1H), 6.67 (d, J=8.0 Hz, 11H), 6.56 (dd, J=8.1, 2.1 Hz, 11H), 4.23 (dd, J=9.4, 5.9 Hz, 1H), 3.22-2.92 (m, 2H);

$^{13}$C NMR (126 MHz, DMSO-d$_6$) δ (ppm) 164.2, 156.6, 145.1, 144.7, 144.5, 133.0, 132.3, 131.8, 131.8, 129.8, 127.6, 126.8, 119.8, 117.3, 116.3, 115.5, 114.2, 40.6, 34.9;

HRMS calcd for C$_{19}$H$_{12}$Cl$_2$N$_3$O$_3$S [M+H]$^+$ 431.9971, found 431.9978.

Preparative Example 172

2-cyano-3-(3,4-dihydroxyphenyl)-N-(4-(3-fluoropyridin-2-yl)thiazol-2-yl)propanamide

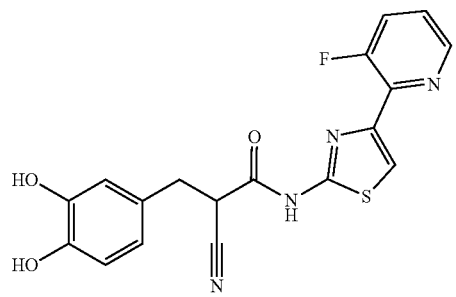 [SMILES: N#CC(Cc1ccc(O)c(O)c1)C(=O)Nc1nc(-c2ncccc2F)cs1]

The compound was prepared according to General procedure E from (E)-2-cyano-3-(3,4-dihydroxyphenyl)-N-(4-(3-fluoropyridin-2-yl)thiazol-2-yl)acrylamide (63 mg, 0.16 mmol) and NaBH$_4$ (12 mg, 0.33 mmol) in EtOH (3 mL); the reaction time was 2 h. The product, purified by reverse phase column chromatography (H$_2$O:MeOH:AcOH; 60:40:0.05 to 5:95:0.05), was obtained as a white solid (35 mg, 55%).

$^1$H NMR (500 MHz, DMSO-d$_6$) δ (ppm) 12.95 (s, 1H), 8.85 (s, 1H), 8.81 (s, 1H), 8.53-8.46 (m, 1H), 7.87 (s, 1H), 7.86-7.78 (m, 1H), 7.51-7.44 (m, 1H), 6.72 (d, J=2.1 Hz, 1H), 6.67 (d, J=7.9 Hz, 1H), 6.56 (dd, J=8.0, 2.1 Hz, 1H), 4.27-4.17 (m, 1H), 3.21-2.93 (m, 2H);

$^{13}$C NMR (126 MHz, DMSO-d$_6$) δ (ppm) 156.3 (d, J=261.6 Hz), 145.5 (d, J=5.1 Hz), 145.3 (d, J=4.7 Hz), 145.1, 144.5, 130.0 (d, J=10.4 Hz), 126.8, 124.8 (d, J=14.9 Hz), 124.7, 119.8, 117.3, 116.4, 115.7 (d, J=7.9 Hz), 115.5, 40.7, 35.0;

$^{19}$F NMR (471 MHz, DMSO-d$_6$) δ (ppm) −121.09;

HRMS calcd for C$_{18}$H$_{14}$FN$_4$O$_3$S [M+H]$^+$ 385.0865, found 385.0762.

Preparative Example 173

2-cyano-3-(3,4-dihydroxyphenyl)-N-(4-(2-fluoro-4-methoxyphenyl)thiazol-2-yl)propanamide

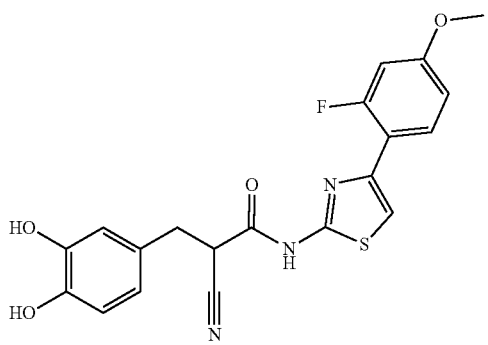 [SMILES: COc1ccc(-c2csc(NC(=O)C(C#N)Cc3ccc(O)c(O)c3)n2)c(F)c1]

The compound was prepared according to General procedure E from (E)-2-cyano-3-(3,4-dihydroxyphenyl)-N-(4-(2-fluoro-4-methoxyphenyl)thiazol-2-yl)acrylamide (80 mg, 0.2 mmol) and NaBH$_4$ (15 mg, 0.4 mmol) in EtOH (3 mL); the reaction time was 2 h. The product, purified by column chromatography (hexane:EtOAc; 3:1) followed by reverse phase column chromatography (H$_2$O:MeOH:AcOH; 60:40:0.05 to 5:95:0.05), was obtained as a white solid (45 mg, 55%).

$^1$H NMR (500 MHz, DMSO-d$_6$) δ (ppm) 12.75 (s, 1H), 8.85 (s, 1H), 8.83 (s, 1H), 7.96-7.88 (m, 1H), 7.44 (d, J=2.4 Hz, 1H), 6.95 (dd, J=13.5, 2.5 Hz, 1H), 6.90 (dd, J=8.7, 2.6 Hz, 1H), 6.72 (d, J=2.1 Hz, 1H), 6.67 (d, J=8.0 Hz, 1H), 6.56 (dd, J=8.1, 2.2 Hz, 1H), 4.23 (dd, J=9.4, 5.9 Hz, 1H), 3.28 (s, 3H), 3.19-2.95 (m, 2H);

$^{13}$C NMR (126 MHz, DMSO-d$_6$) δ (ppm) 164.1, 160.2 (d, J=248.8 Hz), 160.1 (d, J=11.3 Hz), 156.6, 145.1, 144.5, 143.0, 129.7 (d, J=5.0 Hz), 126.8, 119.8, 117.3, 116.4, 115.5, 114.4 (d, J=12.0 Hz), 110.9 (d, J=12.6 Hz), 110.7 (d, J=2.0 Hz), 102.1 (d, J=25.9 Hz), 55.7, 40.6, 34.9;

$^{19}$F NMR (471 MHz, DMSO-d$_6$) δ (ppm) −112.16;

HRMS calcd for C$_{20}$H$_{17}$FN$_3$O$_4$S [M+H]$^+$ 414.0918, found 414.0920.

Preparative Example 174

2-cyano-3-(3,4-dihydroxyphenyl)-N-(4-(4-(trifluoromethyl)pyridin-2-yl)thiazol-2-yl)propanamide

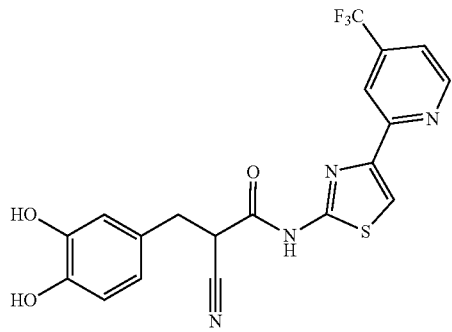 [SMILES: N#CC(Cc1ccc(O)c(O)c1)C(=O)Nc1nc(-c2cc(C(F)(F)F)ccn2)cs1]

The compound was prepared according to General procedure E from (E)-2-cyano-3-(3,4-dihydroxyphenyl)-N-(4-(4-(trifluoromethyl)pyridin-2-yl)thiazol-2-yl)acrylamide (60 mg, 0.138 mmol) and NaBH$_4$ (11 mg, 0.277 mmol) in MeOH (5 mL); the reaction time was 3 h. The product, purified by column chromatography (CH$_2$Cl$_2$:MeOH; 1:0. to 19:1), was obtained as an off-white solid (25 mg, 42%).

$^1$H NMR (500 MHz, DMSO-d$_6$) δ (ppm) 12.88 (s, 1H), 8.91 (dd, J=5.31, 2.52 Hz, 1H), 8.84 (dd, J=14.62, 2.59 Hz, 2H), 8.16 (s, 1H), 8.07 (d, J=2.62 Hz, 1H), 7.76-7.70 (m, 1H), 6.72 (t, J=2.39 Hz, 1H), 6.67 (dd, J=8.08, 2.61 Hz, 1H), 6.56 (dt, J=8.01, 2.51 Hz, 1H), 4.30-4.15 (m, 1H), 3.21-3.13 (m, 1H), 3.05-2.93 (m, 1H);

$^{13}$C NMR (126 MHz, CDCl$_3$) δ (ppm) 164.4, 158.0, 153.1, 151.4, 147.6, 145.1, 144.5, 137.8, 126.7, 124.0 (q, $^1J_{C-F}$=272.9 Hz), 119.8, 118.3, 117.2, 116.3, 115.5, 115.0, 114.3, 40.7, 34.9;

$^{19}$F NMR (471 MHz, DMSO-d$_6$) δ (ppm) −63.82;

HRMS calcd for C$_{19}$H$_{14}$F$_3$N$_4$O$_3$S [M+H]$^+$ 435.0733, found 435.0738.

Preparative Example 175

2-cyano-N-(4-(2,5-dichlorothiophen-3-yl)thiazol-2-yl)-3-(3,4-dihydroxyphenyl)propanamide

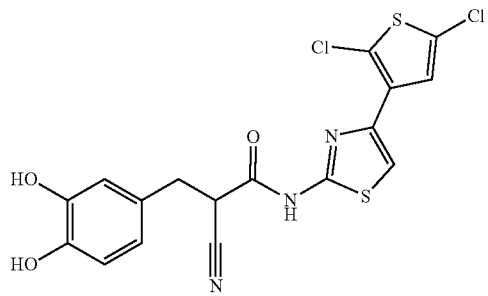 [SMILES: N#CC(Cc1ccc(O)c(O)c1)C(=O)Nc1nc(-c2cc(Cl)sc2Cl)cs1]

The compound was prepared according to General procedure E from (E)-2-cyano-N-(4-(2,5-dichlorothiophen-3-yl)thiazol-2-yl)-3-(3,4-dihydroxyphenyl) acrylamide (265 mg, 0.604 mmol) and NaBH$_4$ (46 mg, 1.20 mmol) in MeOH (8 mL); the reaction time was 2 h. The product, purified by column chromatography (hexane:EtOAc; 1:0 to 1:1), was obtained as a white solid (90 mg, 34%).

$^1$H NMR (500 MHz, DMSO-d$_6$) δ (ppm) 12.77 (s, 1H), 8.83 (d, J=12.72 Hz, 2H), 7.75 (s, 1H), 7.43 (s, 1H), 6.71 (d, J=2.14 Hz, 1H), 6.67 (d, J=8.01 Hz, 1H), 6.56 (dd, J=8.07, 2.12 Hz, 1H), 4.24 (dd, J=9.46, 5.83 Hz, 1H), 3.15 (dd, J=13.64, 5.82 Hz, 1H), 2.97 (dd, J=13.61, 9.50 Hz, 1H);

$^{13}$C NMR (126 MHz, DMSO-d$_6$) δ (ppm) 164.3, 156.9, 145.1, 144.5, 141.6, 132.2, 127.4, 126.8, 125.2, 121.0, 119.8, 117.2, 116.3, 115.5, 112.7, 40.6, 34.9;

HRMS calcd for C$_{17}$H$_{12}$Cl$_2$N$_3$O$_3$S$_2$[M+H]$^+$ 439.9692, found 439.9690.

Preparative Example 176

3-(3,4-bis((triisopropylsilyl)oxy)phenyl)-2-cyano-N-(4-phenylthiazol-2-yl)butanamide

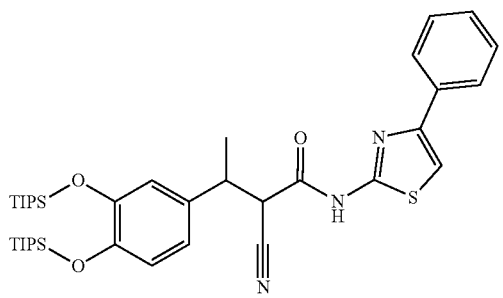

In THF (5 mL) was suspended CuCN (275 mg, 3.07 mmol) and the mixture was cooled to −5° C. MeLi (1.6 M in Et₂O, 3.7 mL, 5.9 mmol) was added to the solution and the mixture was stirred at 25° C. for 15 min. Then, a solution of (E)-3-(3,4-bis((triisopropylsilyl)oxy)phenyl)-2-cyano-N-(4-phenylthiazol-2-yl)acrylamide (0.74 g, 1.1 mmol) in THF (5 mL) was added and the resulting mixture was stirred at 25° C. for 16 h. The solution was poured into aqueous 1 M HCl (20 mL) and extracted with EtOAc (3×10 mL). The combined organic fractions were washed with brine, dried over MgSO₄, filtered, and the solvent was evaporated. The residue was purified by column chromatography (hexane:EtOAc; 10:1) to afford the product as a colorless solid (610 mg, 80%). The product contains two diastereoisomers in 1:1 ratio.

$^1$H NMR (500 MHz, CDCl₃) δ7.84-7.80 (m, 2H), 7.80-7.76 (m, 2H), 7.46-7.38 (m, 4H), 7.38-7.31 (m, 2H), 7.20 (s, 1H), 7.16 (s, 1H), 6.84-6.82 (m, 2H), 6.81 (d, J=8.2 Hz, 1H), 6.75 (d, J=8.2 Hz, 1H), 6.73-6.68 (m, 2H), 3.83 (d, J=5.4 Hz, 1H), 3.74 (d, J=5.4 Hz, 1H), 3.64-3.55 (m, 2H), 1.54 (d, J=7.1 Hz, 3H), 1.49 (d, J=7.0 Hz, 3H), 1.26 (ddq, J=29.0, 15.0, 7.4 Hz, 12H), 1.14-1.07 (m, 72H);

HRMS calcd for C₃₈H₅₆N₃O₃SSi₂ [M−H]⁻ 690.3586, found 690.3584.

Preparative Example 177

2-cyano-3-(3,4-dihydroxyphenyl)-N-(4-phenylthiazol-2-yl)butanamide

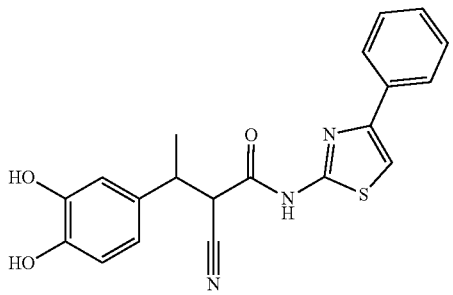 [SMILES: CC(c1ccc(O)c(O)c1)C(C#N)C(=O)Nc1nc(-c2ccccc2)cs1]

To a solution of 3-(3,4-bis((triisopropylsilyl)oxy)phenyl)-2-cyano-N-(4-phenylthiazol-2-yl)butanamide (96 mg, 0.14 mmol) in CH₂Cl₂ (2 mL) at −78° C., was added TBAF (1M in THF, 0.3 mL, 0.3 mmol) and the mixture was stirred at −78° C. for 1 h. The mixture was absorbed on the stationary phase and purified by reverse phase column chromatography (H₂O:MeOH:AcOH; 60:40:0.05 to 5:95:0.05). The product was obtained as a white solid (50 mg, 95%). The product contains two diastereoisomers in 1:1 ratio.

$^1$H NMR (500 MHz, DMSO-d₆) δ12.76 (s, 2H), 8.90-8.78 (m, 4H), 7.95-7.86 (m, 4H), 7.71 (s, 1H), 7.68 (s, 1H), 7.48-7.39 (m, 4H), 7.38-7.30 (m, 2H), 6.80 (d, J=2.0 Hz, 1H), 6.72-6.61 (m, 4H), 6.54 (dd, J=8.1, 2.2 Hz, 1H), 4.29-4.17 (m, 2H), 3.50-3.32 (m, 2H), 1.32 (d, J=7.0 Hz, 3H), 1.26 (d, J=7.0 Hz, 3H);

HRMS calcd for C₂₀H₁₈N₃O₃S [M+H]⁺ 380.1063, found 380.1069.

Preparative Example 178

3-(3,4-bis((2-(trimethylsilyl)ethoxy)methoxy)phenyl)-2-cyano-2-methyl-N-(4-phenylthiazol-2-yl)propanamide

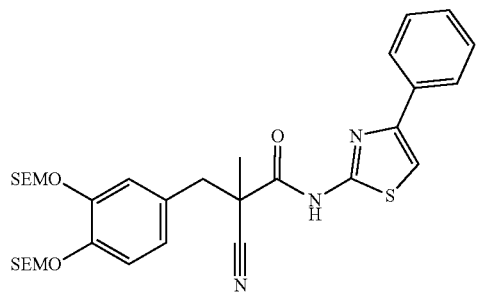

Ethyl 3-(3,4-bis((2-(trimethylsilyl)ethoxy)methoxy)phenyl)-2-cyano-2-methylpropanoate (74 mg, 0.14 mmol) and 4-phenylthiazol-2-amine (27 mg, 0.15 mmol) were dissolved in dry THF (2 mL) and the solution was cooled to −10° C. A solution of i-PrMgCl·LiCl (1.3 M in THF, 115 μL, 0.15 mmol) was added and the mixture was stirred at 25° C. for 30 min. The mixture was poured into water (10 mL) and extracted with EtOAc (3×10 mL). The organic fractions were combined, washed with brine (20 mL), dried over MgSO₄, filtered, and the solvent was evaporated in vacuo. The residue was purified by column chromatography (hexane:EtOAc; 10:1) to afford the product as a colorless wax (45 mg, 50%).

$^1$H NMR (500 MHz, CDCl₃) δ (ppm) 7.85-7.79 (m, 2H), 7.44-7.39 (m, 2H), 7.37-7.31 (m, 1H), 7.19 (s, 1H), 7.13 (s, 1H), 7.12 (d, J=11.0 Hz, 1H), 6.87 (dd, J=8.4, 2.1 Hz, 1H), 5.23 (d, J=1.2 Hz, 2H), 5.23-5.17 (m, 2H), 3.82-3.72 (m, 4H), 3.18 (dd, J=154.7, 13.6 Hz, 2H), 1.76 (s, 3H), 1.02-0.89 (m, 4H), −0.00 (s, 18H);

$^{13}$C NMR (126 MHz, CDCl₃) δ (ppm) 166.4, 150.6, 147.6, 134.2, 129.0, 128.4, 128.0, 126.3, 123.8, 120.6, 118.3, 116.7, 108.5, 94.1, 94.0, 66.6, 66.6, 46.8, 43.8, 23.8, 18.2, 18.2, −1.2;

HRMS calcd for C₃₂H₄₆N₃O₅SSi₂ [M+H]⁺ 640.2691, found 640.2686.

Preparative Example 179

2-cyano-3-(3,4-dihydroxyphenyl)-2-methyl-N-(4-phenylthiazol-2-yl)propanamide

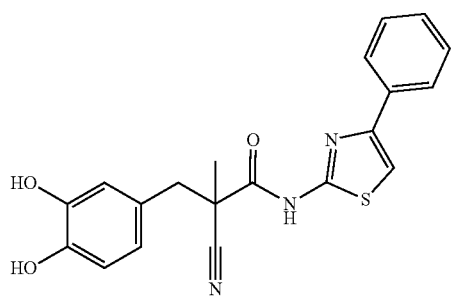 [SMILES: CC(C#N)(Cc1ccc(O)c(O)c1)C(=O)Nc1nc(-c2ccccc2)cs1]

A solution of 3-(3,4-bis((2-(trimethylsilyl)ethoxy)methoxy)phenyl)-2-cyano-2-methyl-N-(4-phenylthiazol-2-yl)propanamide (25 mg, 0.04 mmol) in $CH_2Cl_2$ (3 mL) was cooled to 0° C., TESCl (24 mg, 27 μL, 0.16 mmol) and MeOH (0.1 mL) were added and the reaction mixture was stirred at 25° C. for 1 h. The mixture was poured into water (10 mL) and extracted with EtOAc (3×10 mL). The organic fractions were combined, washed with brine (20 mL), dried over $MgSO_4$, filtered, and the solvent was evaporated in vacuo. The residue was purified by reverse phase column chromatography ($H_2O$:MeOH:AcOH; 60:40:0.05 to 5:95:0.05) to afford the product as a white solid (10 mg, 65%).

$^1$H NMR (500 MHz, $CDCl_3$) δ (ppm) 7.77-7.71 (m, 2H), 7.44-7.39 (m, 2H), 7.39-7.34 (m, 1H), 7.18 (s, 1H), 6.65 (d, J=2.1 Hz, 1H), 6.54 (d, J=8.0 Hz, 1H), 6.48 (dd, J=8.1, 2.1 Hz, 1H), 3.12 (d, J=13.6 Hz, 1H), 2.84 (d, J=13.7 Hz, 1H), 1.77 (s, 3H);

$^{13}$C NMR (126 MHz, $CDCl_3$) δ (ppm) 166.3, 157.6, 150.2, 144.2, 144.1, 133.8, 129.1, 128.8, 126.7, 125.9, 122.0, 120.6, 117.1, 115.6, 109.0, 47.2, 44.8, 23.1;

HRMS calcd for $C_{20}H_{18}N_3O_3S$ $[M+H]^+$ 380.1063, found 380.1060.

Assays:
HTS Assay
DNA Substrate Preparation

The DNA substrate is prepared by mixing the oligonucleotides listed below in a 1:1 ratio to reach a final concentration of 6 μM in a buffer containing 50 mM Tris pH 7.5, 100 mM NaCl and 8 mM $MgCl_2$.

The mixture is heat for 3 min at 65° C. and let to cool down slowly to RT. Then it is stored at −20° C.

```
Oligo 1:
                                        (SEQ ID NO. 1)
5' CY5 - CTAAGTTCGTCAGGATTCCAGC Oligo 2:
                                        (SEQ ID NO. 2)
5' CTCTATCACTGTTACAATGCTGGAATCCTGACGAACTTAG -

BBQ [650]
```

This substrate is a 5' overhang, which is a preferred substrate of MRE11. The CY5 fluorescent label is quenched by the quencher BBQ [650] and therefore it shows no or very low fluorescence. The fluorescence increases upon substrate cleavage by MRE11, when separation of the two labels occur.

Setup
The conditions of the assay are as follows:
Microplate type: 1536 Well Black Round Bottom Polystyrene Not Treated (Corning cat no. 3936)
Total reaction volume: 5 μL
MRE11 concentration in the reaction: 18 nM
DNA substrate concentration in the reaction: 40 nM
Number of compounds to test: 257
Inhibitor concentration range tested: 7 nM-50 μM
Multiplicates: 3
Concentration points: 13
Dilution step: 2.1

Each plate contains a series of high and low signal control wells, where no compound is added:
High signal: MRE11+DNA substrate
Low signal: DNA substrate only
These are used during data evaluation.
Two Extra Assay Controls:
1) To check whether unwinding of DNA by the compounds alone occurs.

The DNA substrate [CY5+BBQ(650)] is mixed with the compounds with no protein present.

This is done as a single measurement at 25 μM inhibitor concentration.
2) To check whether the compounds are able to quench the CY5.

The CY5 single stranded oligo is mixed with the compounds with no protein present. This is done as a single measurement at 25 μM inhibitor concentration.

The layout of the plates is created by the in-house software (CZ-Openscreen Prague) and this information is transferred to the robotic HTS station.

Assay Steps
1) Prepare 50 mL of master mix:
   16.7 mL 5× reaction buffer (150 mM Bis Tris pH 7; 5 mM DTT)
   1042 μL 400 mM $MnCl_2$
   32.3 mL $H_2O$
2) Fill the plates with 3 μL of master mix per well using MultiDrop (Thermo Scientific)
3) Transfer of compounds to the plates at the robotic station with the contactless Echo dispenser (Labcyte)
4) Measurement of autofluorescence with the EnVision reader (PerkinElmer)
5) Prepare 20 mL of 90 nM MRE11 in T+50 buffer (25 mM Tris-HCl pH7.5, 50 mM KCl 8.7% glycerol, 0.5 mM EDTA)
6) Add 1 μL of 90 nM MRE11 to the corresponding wells using MultiDrop
7) Preincubation at RT for 30 min
8) Prepare 20 mL of a 200 nM solution of 5' overhang DNA substrate: 480 μL 6 μM DNA+19.52 mL $H_2O$
9) Prepare 4 mL of a 200 nM solution of the single stranded DNA (oligo 1): 8 μL 100 μM DNA+4 mL $H_2O$
10) Add 1 μL of each 200 nM DNA solution to the corresponding wells with the MultiDrop
11) Fluorescence measurement with the EnVision reader every 45 minutes Fluorescence readout: $CY5\lambda_{ex/em}$=620/665 nm Analysis The reaction is started by the addition of DNA and the reaction time is counted from that moment, including a 15 min delay. Ten timepoints are measured:

|   | min | h |
|---|---|---|
| 1 | 15 | 0.3 |
| 2 | 60 | 1.0 |
| 3 | 105 | 1.8 |
| 4 | 150 | 2.5 |
| 5 | 195 | 3.3 |
| 6 | 240 | 4.0 |
| 7 | 285 | 4.8 |
| 8 | 330 | 5.5 |
| 9 | 375 | 6.3 |
| 10 | 420 | 7.0 |

The assay data analysis was performed at t=4 h. This corresponds to the time when the reaction is close to its maximum.

The data analysis was performed using the in-house software (CZ-Openscreen Prague) to obtain $IC_{50}$ for each compound.

HR Assay

DR-GFP U2OS cells (*Methods in Molecular Biology* 2012, 920, 379.) were transfected with 2.5 μg of I-SceI-expressing pCAGGS vector and treated with the inhibitors at 25 μM concentration. 72 hours after the transfection, the cells were trypsinized and resuspended in 3% BSA in PBS. GFP fluorescence detection was carried out using a BD FACSVerse flow cytometer and data analyzed with FlowJo software.

RPA Assay

U2OS cells were pre-treated for 1 h with MRE11 inhibitors followed by addition of 1 uM camptothecin for 1 h. Cells were lysed in SDS-PAGE loading buffer, sonicated and boiled at 70° C. for 10 min. Equal amounts of protein (50-100 μg) were analysed by Tris-glycine gel electrophoresis Expression levels were quantified using Multi Gauge software and expressed relative to loading control. Phosphorylated RPA32 S4/S8 (A300-245A, Bethyl Laboratories) 1:1000 dilution was used.

Results

Table 1 summarizes the inhibitory activities of indicated compounds tested in the in vitro HIS nuclease assay ($IC_{50}$), HR assay (inhibition of HR@25 μM) and RPA assay (% of inhibition of RPA phosphorylation at [10 μM] or [25 μM] (concentration of the inhibitor)).

HIS nuclease assay: ($IC_{50}$)
A: $IC_{50}$<2 μM
B: 2 μM<$IC_{50}$<10 μM
C: 10 μM<$IC_{50}$<90 μM
HR assay: inhibition of HR@25 μM
A: HR inhibition>75%
B: 75%>HR inhibition>50%
C: 50%>HR inhibition

TABLE 1

| compound | $IC_{50}$ (μM) | HR assay | RPA assay |
|---|---|---|---|
| Preparative Example 128<br>3-(4-acetamidophenyl)-2-cyano-N-(4-phenylthiazol-2-yl)propanamide | N.A. | B | N.A. |
| Preparative Example 129<br>N-(4-(4-bromophenyl)thiazol-2-yl)-2-cyano-3-(3,4-dihydroxyphenyl)propanamide | B | A | 60% at 10 μM |
| Preparative Example 130<br>2-cyano-3-(3,4-dihydroxyphenyl)-N-(4-phenylthiazol-2-yl)propanamide | B | B | N.A. |
| Preparative Example 131<br>2-cyano-N-(4-(4-cyanophenyl)thiazol-2-yl)-3-(3,4-dihydroxyphenyl)propanamide | B | B | N.A. |
| Preparative Example 132<br>2-cyano-3-(3,4-dihydroxyphenyl)-N-(4-(4-(trifluoromethyl)phenyl)thiazol-2-yl)propanamide | B | A | N.A. |
| Preparative Example 133<br>2-cyano-3-(3,4-dihydroxyphenyl)-N-(4-(p-tolyl)thiazol-2-yl)propanamide | B | C | N.A. |
| Preparative Example 134<br>2-cyano-3-(3,5-dichloro-4-hydroxyphenyl)-N-(4,5-diphenylthiazol-2-yl)propanamide | B | C | N.A. |
| Preparative Example 135<br>2-cyano-3-(3,4-dihydroxyphenyl)-N-(4-phenyl-5-(p-tolyl)thiazol-2-yl)propanamide | A | A | N.A. |
| Preparative Example 136<br>2-cyano-3-(3,4-dihydroxyphenyl)-N-(4-(4-(trifluoromethoxy)phenyl)thiazol-2-yl)propanamide | B | A | 40% at 10 μM |
| Preparative Example 137<br>2-cyano-3-(3,5-dichloro-4-hydroxyphenyl)-N-(4-(4-(trifluoromethoxy)phenyl)thiazol-2-yl)propanamide | B | C | N.A. |
| Preparative Example 138<br>N-(4-([1,1'-biphenyl]-3-yl)thiazol-2-yl)-2-cyano-3-(3,4-dihydroxyphenyl)propanamide | B | A | N.A. |
| Preparative Example 139<br>2-cyano-3-(3,5-di-tert-butyl-4-hydroxyphenyl)-N-(4-phenylthiazol-2-yl)propanamide | N.A. | A | 70% at 10 μM |
| Preparative Example 140<br>N-(4-(4-(tert-butyl)phenyl)thiazol-2-yl)-2-cyano-3-(3,4-dihydroxyphenyl)propanamide | B | A | 40% at 10 μM |
| Preparative Example 141<br>2-(3,4-dihydroxybenzyl)-$N^1$-(4-phenylthiazol-2-yl)malonamide | B | B | N.A. |
| Preparative Example 142<br>3-(1H-benzo[d]imidazol-6-yl)-2-cyano-N-(4-phenylthiazol-2-yl)propanamide | C | C | N.A. |

TABLE 1-continued

| compound | IC$_{50}$ (μM) | HR assay | RPA assay |
|---|---|---|---|
| Preparative Example 143<br>2-cyano-3-(3,5-dichloro-4-hydroxyphenyl)-N-(4-(naphthalen-2-yl)thiazol-2-yl)propanamide | B | C | N.A. |
| Preparative Example 145<br>2-cyano-3-(3,4-dihydroxyphenyl)-N-(4-(thiophen-3-yl)thiazol-2-yl)propanamide | B | C | N.A. |
| Preparative Example 146<br>2-cyano-N-(5-cyclohexyl-4-phenylthiazol-2-yl)-3-(3,4-dihydroxyphenyl)propanamide | B | A | N.A. |
| Preparative Example 147<br>2-cyano-3-(4-hydroxy-3,5-dimethylphenyl)-N-(4-phenylthiazol-2-yl)propanamide | C | B | N.A. |
| Preparative Example 148<br>3-(2-bromo-3,4-dihydroxyphenyl)-2-cyano-N-(4-phenylthiazol-2-yl)propanamide | A | A | 90% at 25 μM |
| Preparative Example 149<br>N-(4-(4-(tert-butyl)phenyl)thiazol-2-yl)-2-cyano-3-(4-hydroxy-3,5-dimethylphenyl)propanamide | C | A | N.A. |
| Preparative Example 150<br>N-(4-(4-(tert-butyl)phenyl)thiazol-2-yl)-2-cyano-3-(3,5-di-tert-butyl-4-hydroxyphenyl)propanamide | N.A. | A | N.A. |
| Preparative Example 151<br>2-cyano-3-(3-cyano-4-hydroxyphenyl)-N-(4-phenylthiazol-2-yl)propanamide | C | C | N.A. |
| Preparative Example 152<br>2-cyano-3-(3,4-dihydroxyphenyl)-N-(4-(5-methylthiophen-3-yl)thiazol-2-yl)propanamide (SH-1413) | B | C | N.A. |
| Preparative Example 153<br>2-cyano-3-(3,4-dihydroxyphenyl)-N-(4-(5,6,7,8-tetrahydronaphthalen-2-yl)thiazol-2-yl)propanamide | B | A | N.A. |
| Preparative Example 154<br>2-cyano-N-(4-(4-cyclohexylphenyl)thiazol-2-yl)-3-(3,4-dihydroxyphenyl)propanamide | B | A | N.A. |
| Preparative Example 155<br>3-(3-chloro-4-hydroxy-5-methylphenyl)-2-cyano-N-(4-phenylthiazol-2-yl)propanamide | C | C | N.A. |
| Preparative Example 156<br>3-(3-chloro-5-fluoro-4-hydroxyphenyl)-2-cyano-N-(4-phenylthiazol-2-yl)propanamide | B | C | N.A. |
| Preparative Example 157<br>2-cyano-3-(3,4-dihydroxyphenyl)-N-(4-(pyridin-2-yl)thiazol-2-yl)propanamide | B | A | N.A. |
| Preparative Example 158<br>2-cyano-3-(3,4-dihydroxyphenyl)-N-(4-(6-methylpyridin-2-yl)thiazol-2-yl)propanamide | B | A | N.A. |
| Preparative Example 159<br>2-cyano-3-(3,4-dihydroxyphenyl)-N-(4-(2-(trifluoromethyl)phenyl)thiazol-2-yl)propanamide | B | C | N.A. |
| Preparative Example 160<br>2-cyano-N-(4-(3,4-dichlorophenyl)thiazol-2-yl)-3-(3,4-dihydroxyphenyl)propanamide | A | B | N.A. |
| Preparative Example 161<br>2-cyano-3-(3,4-dihydroxyphenyl)-N-(4-(o-tolyl)thiazol-2-yl)propanamide | B | B | N.A. |
| Preparative Example 162<br>N-(4-(3-chlorophenyl)thiazol-2-yl)-2-cyano-3-(3,4-dihydroxyphenyl)propanamide | B | B | N.A. |
| Preparative Example 163<br>3-(3,5-bis(trifluoromethyl)phenyl)-2-cyano-N-(4-phenylthiazol-2-yl)propanamide | N.A. | A | N.A. |
| Preparative Example 164<br>2-cyano-3-(3,4-dihydroxyphenyl)-N-(4-(4-methylpyridin-2-yl)thiazol-2-yl)propanamide | B | A | N.A. |
| Preparative Example 165<br>2-cyano-3-(3,4-dihydroxyphenyl)-N-(4-(5-methylpyridin-2-yl)thiazol-2-yl)propanamide | A | A | N.A. |
| Preparative Example 166<br>2-cyano-3-(3,4-dihydroxyphenyl)-N-(4-(4-isopropylphenyl)thiazol-2-yl)propanamide | B | A | N.A. |
| Preparative Example 167<br>2-cyano-3-(3,4-dihydroxyphenyl)-N-(4-(4-methoxypyridin-2-yl)thiazol-2-yl)propanamide | A | A | N.A. |
| Preparative Example 168<br>2-cyano-3-(3,4-dihydroxyphenyl)-N-(4-(5-methoxypyridin-2-yl)thiazol-2-yl)propanamide | A | A | N.A. |
| Preparative Example 169<br>2-cyano-3-(3,5-di-tert-butyl-4-hydroxyphenyl)-N-(4-(pyridin-2-yl)thiazol-2-yl)propanamide | C | A | N.A. |

TABLE 1-continued

| compound | IC$_{50}$ (μM) | HR assay | RPA assay |
|---|---|---|---|
| Preparative Example 170<br>2-cyano-3-(3,4-dihydroxyphenyl)-N-(4-(6-methoxypyridin-2-yl)thiazol-2-yl)propanamide | B | B | N.A. |
| Preparative Example 171<br>2-cyano-N-(4-(2,4-dichlorophenyl)thiazol-2-yl)-3-(3,4-dihydroxyphenyl)propanamide | A | A | N.A. |
| Preparative Example 172<br>2-cyano-3-(3,4-dihydroxyphenyl)-N-(4-(3-fluoropyridin-2-yl)thiazol-2-yl)propanamide | A | A | N.A. |
| Preparative Example 173<br>2-cyano-3-(3,4-dihydroxyphenyl)-N-(4-(2-fluoro-4-methoxyphenyl)thiazol-2-yl)propanamide | A | A | N.A. |
| Preparative Example 174<br>2-cyano-3-(3,4-dihydroxyphenyl)-N-(4-(4-(trifluoromethyl)pyridin-2-yl)thiazol-2-yl)propanamide | A | A | N.A. |
| Preparative Example 175<br>2-cyano-N-(4-(2,5-dichlorothiophen-3-yl)thiazol-2-yl)-3-(3,4-dihydroxyphenyl) propanamide | B | B | N.A. |
| Preparative Example 177<br>2-cyano-3-(3,4-dihydroxyphenyl)-N-(4-phenylthiazol-2-yl)butanamide | N.A. | B | N.A. |
| Preparative Example 179<br>2-cyano-3-(3,4-dihydroxyphenyl)-2-methyl-N-(4-phenylthiazol-2-yl)propanamide | C | C | N.A. |

The invention claimed is:

1. A compound of general formula (1):

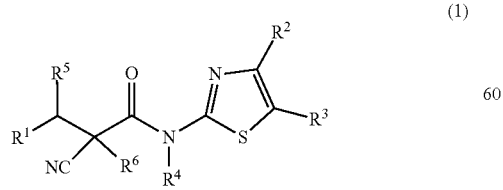

or pharmaceutically acceptable salts, or solvates thereof, wherein:

$R^1$ is selected from the group consisting of alkyl; aryl; cycloalkyl; heterocyclyl; and heteroaryl;

wherein each of the alkyl, aryl, cycloalkyl, heterocyclyl, heteroaryl, can be unsubstituted or optionally substituted with one or more moieties which can be the same or different, each moiety being independently selected from the group consisting of F, Cl, Br, I, OH, CN, N$_3$, =O, O(C$_1$-C$_6$-alkyl), =S, SH, S(C$_1$-C$_6$-alkyl), S(O)C$_1$-C$_6$-alkyl, S(O)$_2$C$_1$-C$_6$-alkyl, CF$_3$, C$_2$F$_5$, OCF$_3$, OC$_2$F$_5$, NH$_2$, NH(C$_1$-C$_6$-alkyl), N(C$_1$-C$_6$-alkyl)$_2$, =N—OH, =N—O(C$_1$-C$_6$-alkyl), NO$_2$, COOH, COO(C$_1$-C$_6$-alkyl), CO(C$_1$-C$_6$-alkyl), CONH$_2$, CONH(C$_1$-C$_6$-alkyl), CON(C$_1$-C$_6$-alkyl)$_2$, (C$_1$-C$_6$-alkyl)-S(O)$_2$—NH—, (C$_1$-C$_6$-alkyl)-S(O)$_2$—N(C$_1$-C$_6$-alkyl)-, (C$_1$-C$_6$-alkyl)-NH —$(SO)_2$—, $(C_1\text{-}C_6\text{-alkyl})_2$N—$(SO)_2$—, $(C_1\text{-}C_6\text{-alkyl})$-CO—NH—, $(C_1\text{-}C_6\text{-alkyl})$-CO—N($C_1\text{-}C_6\text{-alkyl}$)-, $(C_1\text{-}C_6\text{-alkyl})$-OCO—NH—, $(C_1\text{-}C_6\text{-alkyl})$-OCO—N($C_1\text{-}C_6\text{-alkyl}$)-, $(C_1\text{-}C_6\text{-alkyl})$-CO—NH—CO—, $(C_1\text{-}C_6\text{-alkyl})$-CO—N($C_1\text{-}C_6\text{-alkyl}$)-CO—, $NH_2$—CO—NH—, $(C_1\text{-}C_6\text{-alkyl})$-NH—CO—NH—, $(C_1\text{-}C_6\text{-alkyl})_2$N—CO—NH—, $NH_2$—CO—N($C_1\text{-}C_6\text{-alkyl}$)-, $(C_1\text{-}C_6\text{-alkyl})$-NH—CO—N($C_1\text{-}C_6\text{-alkyl}$)-, $(C_1\text{-}C_6\text{-alkyl})_2$N—CO—N($C_1\text{-}C_6\text{-alkyl}$)-, $NH_2$—$S(O)_2$—NH—, $(C_1\text{-}C_6\text{-alkyl})$-NH—$S(O)_2$—NH—, $(C_1\text{-}C_6\text{-alkyl})_2$N—$S(O)_2$—NH—, $NH_2$—$S(O)_2$—N($C_1\text{-}C_6\text{-alkyl}$)-, $(C_1\text{-}C_6\text{-alkyl})$-NH—$S(O)_2$—N($C_1\text{-}C_6\text{-alkyl}$)-, $(C_1\text{-}C_6\text{-alkyl})_2$N—$S(O)_2$—N($C_1\text{-}C_6\text{-alkyl}$)-, $C_1\text{-}C_6$-alkyl, O—$C_1\text{-}C_6$-alkyl, O-phenyl, phenyl;

whereas the $C_1\text{-}C_6$-alkyl, O-phenyl, phenyl in these moieties can optionally be further substituted by one or more substituents selected independently from: F, Cl, Br, $C_1\text{-}C_6$-alkyl, OH, O—$C_1\text{-}C_6$-alkyl, SH, $SCH_3$, $S(O)C_1\text{-}C_6$-alkyl, $S(O)_2C_1\text{-}C_6$-alkyl, $CF_3$, $OCF_3$, $NH_2$, NH($C_1\text{-}C_6$-alkyl), N($C_1\text{-}C_6$-alkyl)$_2$, $NO_2$, COOH, COO($C_1\text{-}C_6$-alkyl), $CONH_2$, CONH($C_1\text{-}C_6$-alkyl), CON($C_1\text{-}C_6$-alkyl)$_2$, $NHC(O)C_1\text{-}C_6$-alkyl, or $NHC(O)NH_2$;

$R^2$ is selected from the group consisting of aryl; heteroaryl; heterocyclyl;

wherein each of the aryl, heterocyclyl, heteroaryl, can be unsubstituted or optionally substituted with one or more moieties which can be the same or different, each moiety being independently selected from the group consisting of F, Cl, Br, I, OH, CN, $N_3$, =O, O($C_1\text{-}C_6$-alkyl), =S, SH, S($C_1\text{-}C_6$-alkyl), $S(O)C_1\text{-}C_6$-alkyl, $S(O)_2C_1\text{-}C_6$-alkyl, $CF_3$, $C_2F_5$, $OCF_3$, $OC_2F_5$, $NH_2$, NH($C_1\text{-}C_6$-alkyl), N($C_1\text{-}C_6$-alkyl)$_2$, =N—OH, =N—O($C_1\text{-}C_6$-alkyl), $NO_2$, COOH, COO($C_1\text{-}C_6$-alkyl), CO($C_1\text{-}C_6$-alkyl), $CONH_2$, CONH($C_1\text{-}C_6$-alkyl), CON($C_1\text{-}C_6$-alkyl)$_2$, $(C_1\text{-}C_6\text{-alkyl})$-$S(O)_2$—NH—, $(C_1\text{-}C_6\text{-alkyl})$-$S(O)_2$—N($C_1\text{-}C_6\text{-alkyl}$)-, $(C_1\text{-}C_6\text{-alkyl})$-NH—$(SO)_2$—, $(C_1\text{-}C_6\text{-alkyl})_2$N—$(SO)_2$—, $(C_1\text{-}C_6\text{-alkyl})$-CO—NH—, $(C_1\text{-}C_6\text{-alkyl})$-CO—N($C_1\text{-}C_6\text{-alkyl}$)-, $(C_1\text{-}C_6\text{-alkyl})$-OCO—NH—, $(C_1\text{-}C_6\text{-alkyl})$-OCO—N($C_1\text{-}C_6\text{-alkyl}$)-, $(C_1\text{-}C_6\text{-alkyl})$-CO—NH—CO—, $(C_1\text{-}C_6\text{-alkyl})$-CO—N($C_1\text{-}C_6\text{-alkyl}$)-CO—, $NH_2$—CO—NH—, $(C_1\text{-}C_6\text{-alkyl})$-NH—CO—NH—, $(C_1\text{-}C_6\text{-alkyl})_2$N—CO—NH—, $NH_2$—CO—N($C_1\text{-}C_6\text{-alkyl}$)-, $(C_1\text{-}C_6\text{-alkyl})$-NH—CO—N($C_1\text{-}C_6\text{-alkyl}$)-, $(C_1\text{-}C_6\text{-alkyl})_2$N—CO—N($C_1\text{-}C_6\text{-alkyl}$)-, $NH_2$—$S(O)_2$—NH—, $(C_1\text{-}C_6\text{-alkyl})$-NH—$S(O)_2$—NH—, $(C_1\text{-}C_6\text{-alkyl})_2$N—$S(O)_2$—NH—, $NH_2$—$S(O)_2$—N($C_1\text{-}C_6\text{-alkyl}$)-, $(C_1\text{-}C_6\text{-alkyl})$-NH—$S(O)_2$—N($C_1\text{-}C_6\text{-alkyl}$)-, $(C_1\text{-}C_6\text{-alkyl})_2$N—$S(O)_2$—N($C_1\text{-}C_6\text{-alkyl}$)-, $C_1\text{-}C_6$-alkyl, O—$C_1\text{-}C_6$-alkyl, O-phenyl, phenyl, heterocyclyl, heteroaryl;

whereas the $C_1\text{-}C_6$-alkyl, O-phenyl, phenyl, heterocyclyl, heteroaryl in these moieties can optionally be further substituted by one or more substituents selected independently from: F, Cl, Br, $C_1\text{-}C_6$-alkyl, OH, O—$C_1\text{-}C_6$-alkyl, SH, $SCH_3$, $S(O)C_1\text{-}C_6$-alkyl, $S(O)_2C_1\text{-}C_6$-alkyl, $CF_3$, $OCF_3$, $NH_2$, NH($C_1\text{-}C_6$-alkyl), N($C_1\text{-}C_6$-alkyl)$_2$, $NO_2$, COOH, COO($C_1\text{-}C_6$-alkyl), $CONH_2$, CONH($C_1\text{-}C_6$-alkyl), CON($C_1\text{-}C_6$-alkyl)$_2$, $NHC(O)C_1\text{-}C_6$-alkyl, or $NHC(O)NH_2$, $R^3$ is selected from the group consisting of H; aryl; cycloalkyl; halogen; alkyl; and heteroaryl, wherein each of the aryl, cycloalkyl, alkyl or heteroaryl can be unsubstituted or optionally substituted with one or more moieties which can be the same or different, each moiety being independently selected from the group consisting of F, Cl, Br, I, OH, CN, $N_3$, =O, O($C_1\text{-}C_6$-alkyl), =S, SH, S($C_1\text{-}C_6$-alkyl), $S(O)C_1\text{-}C_6$-alkyl, $S(O)_2C_1\text{-}C_6$-alkyl, $CF_3$, $C_2F_5$, $OCF_3$, $OC_2F_5$, $NH_2$, NH($C_1\text{-}C_6$-alkyl), N($C_1\text{-}C_6$-alkyl)$_2$, =N—OH, =N—O($C_1\text{-}C_6$-alkyl), $NO_2$, COOH, COO($C_1\text{-}C_6$-alkyl), CO($C_1\text{-}C_6$-alkyl), $CONH_2$, CONH($C_1\text{-}C_6$-alkyl), CON($C_1\text{-}C_6$-alkyl)$_2$, $(C_1\text{-}C_6\text{-alkyl})$-$S(O)_2$—NH—, $(C_1\text{-}C_6\text{-alkyl})$-$S(O)_2$—N($C_1\text{-}C_6\text{-alkyl}$)-, $(C_1\text{-}C_6\text{-alkyl})$-NH—$(SO)_2$—, $(C_1\text{-}C_6\text{-alkyl})_2$N—$(SO)_2$—, $(C_1\text{-}C_6\text{-alkyl})$-CO—NH—, $(C_1\text{-}C_6\text{-alkyl})$-CO—N($C_1\text{-}C_6\text{-alkyl}$)-, $(C_1\text{-}C_6\text{-alkyl})$-OCO—NH—, $(C_1\text{-}C_6\text{-alkyl})$-OCO—N($C_1\text{-}C_6\text{-alkyl}$)-, $(C_1\text{-}C_6\text{-alkyl})$-CO—NH—CO—, $(C_1\text{-}C_6\text{-alkyl})$-CO—N($C_1\text{-}C_6\text{-alkyl}$)-CO—, $NH_2$—CO—NH—, $(C_1\text{-}C_6\text{-alkyl})$-NH—CO—NH—, $(C_1\text{-}C_6\text{-alkyl})_2$N—CO—NH—, $NH_2$—CO—N($C_1\text{-}C_6\text{-alkyl}$)-, $(C_1\text{-}C_6\text{-alkyl})$-NH—CO—N($C_1\text{-}C_6\text{-alkyl}$)-, $(C_1\text{-}C_6\text{-alkyl})_2$N—CO—N($C_1\text{-}C_6\text{-alkyl}$)-, $NH_2$—$S(O)_2$—NH—, $(C_1\text{-}C_6\text{-alkyl})$-NH—$S(O)_2$—NH—, $(C_1\text{-}C_6\text{-alkyl})_2$N—$S(O)_2$—NH—, $NH_2$—$S(O)_2$—N($C_1\text{-}C_6\text{-alkyl}$)-, $(C_1\text{-}C_6\text{-alkyl})$-NH—$S(O)_2$—N($C_1\text{-}C_6\text{-alkyl}$)-, $(C_1\text{-}C_6\text{-alkyl})_2$N—$S(O)_2$—N($C_1\text{-}C_6\text{-alkyl}$)-, $C_1\text{-}C_6$-alkyl, O—$C_1\text{-}C_6$-alkyl, O-phenyl, phenyl;

whereas the $C_1\text{-}C_6$-alkyl, O-phenyl, phenyl in these moieties can optionally be further substituted by one or more substituents selected independently from: alkyl, O-phenyl, phenyl being optionally substituted by F, Cl, Br, $C_1\text{-}C_6$-alkyl, OH, O—$C_1\text{-}C_6$-alkyl, SH, $SCH_3$, $S(O)C_1\text{-}C_6$-alkyl, $S(O)_2C_1\text{-}C_6$-alkyl, $CF_3$, $OCF_3$, $NH_2$, NH($C_1\text{-}C_6$-alkyl), N($C_1\text{-}C_6$-alkyl)$_2$, $NO_2$, COOH, COO($C_1\text{-}C_6$-alkyl), $CONH_2$, CONH($C_1\text{-}C_6$-alkyl), CON($C_1\text{-}C_6$-alkyl)$_2$, $NHC(O)C_1\text{-}C_6$-alkyl, or $NHC(O)NH_2$, $R^4$ is selected from the group consisting of H and $C_1\text{-}C_6$-alkyl;

$R^5$ is selected from the group consisting of H; $C_1\text{-}C_6$-alkyl; and aryl;

$R^6$ is selected from the group consisting of H and $C_1\text{-}C_6$-alkyl;

or $R^5$ and $R^6$ together with the carbon atoms connecting these two substituents may form a cyclopropyl ring, unsubstituted or optionally substituted with alkyl, O-phenyl, phenyl being optionally substituted by F, Cl, Br, $C_1\text{-}C_6$-alkyl, OH, O—$C_1\text{-}C_6$-alkyl, SH, $SCH_3$, $S(O)C_1\text{-}C_6$-alkyl, $S(O)_2C_1\text{-}C_6$-alkyl, $CF_3$, $OCF_3$, $NH_2$, NH($C_1\text{-}C_6$-alkyl), N($C_1\text{-}C_6$-alkyl)$_2$, $NO_2$, COOH, COO($C_1\text{-}C_6$-alkyl), $CONH_2$, CONH($C_1\text{-}C_6$-alkyl), CON($C_1\text{-}C_6$-alkyl)$_2$, $NHC(O)C_1\text{-}C_6$-alkyl, or $NHC(O)NH_2$.

2. The compound according to claim 1, wherein $R^1$ is selected from $C_6\text{-}C_{12}$ aryl and heteroaryl having 5 to 12 ring atoms, wherein the aryl or heteroaryl is substituted with one to three OH groups, and the aryl or heteroaryl may optionally be further substituted by one or more substituents, independently selected from the group consisting of F, Cl, Br, $C_1\text{-}C_6$ alkyl, O($C_1\text{-}C_4$ alkyl), phenyl, O-phenyl, $NH_2$, N($C_1\text{-}C_4$ alkyl)$_2$, $NO_2$, NHCO($C_1\text{-}C_4$ alkyl), $CF_3$, $OCF_3$, CN, $S(O)_2C_1\text{-}C_6$-alkyl, $SO_2$NH($C_1\text{-}C_6$-alkyl), and $SO_2$N($C_1\text{-}C_6$-alkyl)$_2$.

3. The compound according to claim 1, wherein $R^1$ is selected from $C_6\text{-}C_{12}$ aryl and heteroaryl having 5 to 12 ring atoms, wherein the aryl or heteroaryl is substituted with two OH groups or one OH group and one group selected from CN, Cl, Br, F, and the aryl or heteroaryl may optionally be further substituted by one or more substituents, independently selected from the group consisting of F, Cl, Br, $C_1$-$C_6$ alkyl, $O(C_1$-$C_4$ alkyl), phenyl, O-phenyl, $NH_2$, $N(C_1$-$C_4$ alkyl)$_2$, $NO_2$, $NHCO(C_1$-$C_4$ alkyl), $CF_3$, $OCF_3$, CN, $S(O)_2C_1$-$C_6$-alkyl, $SO_2NH(C_1$-$C_6$-alkyl), and $SO_2N(C_1$-$C_6$-alkyl)$_2$.

4. The compound according to claim 1, wherein $R^2$ is selected from $C_6$-$C_{12}$ aryl and heteroaryl having 5 to 12 ring atoms, which may optionally be substituted by one or more substituents, independently selected from the group consisting of F, Cl, Br, $C_1$-$C_4$ linear or branched alkyl, $C_3$-$C_5$ cycloalkyl, $O(C_1$-$C_4$ alkyl), phenyl, O-phenyl, $NH_2$, $N(C_1$-$C_4$ alkyl)$_2$, $NO_2$, $NHCO(C_1$-$C_4$ alkyl), $CF_3$, $OCF_3$, CN, $S(O)_2C_1$-$C_6$-alkyl, $SO_2NH(C_1$-$C_6$-alkyl), and $SO_2N(C_1$-$C_6$-alkyl)$_2$.

5. The compound according to claim 1, wherein $R^2$ is substituted by at least one substituent selected from F, Cl, Br, OH, $C_1$-$C_6$ alkyl, O—$C_1$-$C_6$ alkyl, $CF_3$, $OCF_3$, phenyl, morpholinyl; or $R^2$ is substituted by at least one substituent selected from $S(O)_2C_1$-$C_6$-alkyl, $SO_2NH(C_1$-$C_6$-alkyl), $SO_2N(C_1$-$C_6$-alkyl)$_2$; or $R^2$ is substituted by at least one substituent selected from $NHC(O)NH(C_1$-$C_6$-alkyl), $NHC(O)N(C_1$-$C_6$-alkyl)$_2$, $NHSO_2(C_1$-$C_6$-alkyl), $N(C_1$-$C_6$-alkyl) $SO_2(C_1$-$C_6$-alkyl).

6. The compound according to claim 1, wherein $R^3$ is selected from H, phenyl, methyl, ethyl, propyl, isopropyl, butyl, isobutyl, tert-butyl, F, Cl, Br, cyclopropyl, cyclobutyl, cyclopentyl, cyclohexyl, tetrahydropyranyl, tetrahydrofuranyl, piperidinyl, which are unsubstituted or substituted by one or more substituents, independently selected from the group consisting of F, Cl, Br, OH, $C_1$-$C_6$ alkyl, phenyl, $NH_2$, $N(C_1$-$C_4$ alkyl)$_2$, $NO_2$, $NHCO(C_1$-$C_4$ alkyl), $CF_3$, $OCF_3$, CN, $SO_2NH(C_1$-$C_6$-alkyl), $SO_2N(C_1$-$C_6$-alkyl)$_2$, $S(O)_2C_1$-$C_6$-alkyl.

7. The compound according to claim 1, wherein $R^4$ is selected from H, methyl, ethyl, and isopropyl.

8. The compound according to claim 1, wherein $R^5$ is selected from H, phenyl.

9. The compound according to claim 1, wherein $R^6$ is selected from H, methyl, ethyl, and isopropyl.

10. A method of treatment of MRE11-related cancer, MRE11-related premature aging and/or MRE11-related neurological diseases, the method comprising the step of administering the compound of general formula (1):

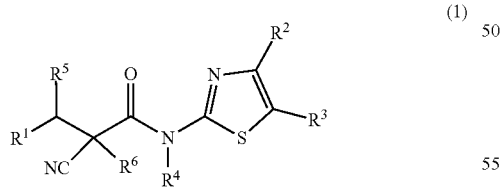

(1)

or pharmaceutically acceptable salts, or solvates thereof, wherein:

$R^1$ is selected from the group consisting of alkyl; aryl; cycloalkyl; heterocyclyl; and heteroaryl;
   wherein each of the alkyl, aryl, cycloalkyl, heterocyclyl, heteroaryl, can be unsubstituted or optionally substituted with one or more moieties which can be the same or different, each moiety being independently selected from the group consisting of F, Cl, Br, I, OH, CN, $N_3$, =O, $O(C_1$-$C_6$-alkyl), =S, SH, $S(C_1$-$C_6$-alkyl), $S(O)C_1$-$C_6$-alkyl, $S(O)_2C_1$-$C_6$-alkyl, $CF_3$, $C_2F_5$, $OCF_3$, $OC_2F_5$, $NH_2$, $NH(C_1$-$C_6$-alkyl), $N(C_1$-$C_6$-alkyl)$_2$, =N—OH, =N—O($C_1$-$C_6$-alkyl), $NO_2$, COOH, $COO(C_1$-$C_6$-alkyl), $CO(C_1$-$C_6$-alkyl), $CONH_2$, $CONH(C_1$-$C_6$-alkyl), $CON(C_1$-$C_6$-alkyl)$_2$, $(C_1$-$C_6$-alkyl)-$S(O)_2$—NH—, $(C_1$-$C_6$-alkyl)-$S(O)_2$—$N(C_1$-$C_6$-alkyl)-, $(C_1$-$C_6$-alkyl)-NH—$(SO)_2$—, $(C_1$-$C_6$-alkyl)$_2$N—$(SO)_2$—, $(C_1$-$C_6$-alkyl)-CO—NH—, $(C_1$-$C_6$-alkyl)-CO—$N(C_1$-$C_6$-alkyl)-, $(C_1$-$C_6$-alkyl)-OCO—NH—, $(C_1$-$C_6$-alkyl)-OCO—$N(C_1$-$C_6$-alkyl)-, $(C_1$-$C_6$-alkyl)-CO—NH—CO—, $(C_1$-$C_6$-alkyl)-CO—$N(C_1$-$C_6$-alkyl)-CO—, $NH_2$—CO—NH—, $(C_1$-$C_6$-alkyl)-NH—CO—NH—, $(C_1$-$C_6$-alkyl)$_2$N—CO—NH—, $NH_2$—CO—$N(C_1$-$C_6$-alkyl)-, $(C_1$-$C_6$-alkyl)-NH—CO—$N(C_1$-$C_6$-alkyl)-, $(C_1$-$C_6$-alkyl)$_2$N—CO—$N(C_1$-$C_6$-alkyl)-, $NH_2$—$S(O)_2$—NH—, $(C_1$-$C_6$-alkyl)-NH—$S(O)_2$—NH—, $(C_1$-$C_6$-alkyl)$_2$N—$S(O)_2$—NH—, $NH_2$—$S(O)_2$—$N(C_1$-$C_6$-alkyl)-, $(C_1$-$C_6$-alkyl)-NH—$S(O)_2$—$N(C_1$-$C_6$-alkyl)-, $(C_1$-$C_6$-alkyl)$_2$N—$S(O)_2$—$N(C_1$-$C_6$-alkyl)-, $C_1$-$C_6$-alkyl, O—$C_1$-$C_6$-alkyl, O-phenyl, phenyl;
   whereas the $C_1$-$C_6$-alkyl, O-phenyl, phenyl in these moieties can optionally be further substituted by one or more substituents selected independently from: F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$, $NO_2$, COOH, $COO(C_1$-$C_6$-alkyl), $CONH_2$, $CONH(C_1$-$C_6$-alkyl), $CON(C_1$-$C_6$-alkyl)$_2$, $NHC(O)C_1$-$C_6$-alkyl, or $NHC(O)NH_2$;

$R^2$ is selected from the group consisting of aryl; heteroaryl; heterocyclyl; alkyl and cycloalkyl;
   wherein each of the aryl, heterocyclyl, heteroaryl, alkyl, cycloalkyl can be unsubstituted or optionally substituted with one or more moieties which can be the same or different, each moiety being independently selected from the group consisting of F, Cl, Br, I, OH, CN, $N_3$, =O, $O(C_1$-$C_6$-alkyl), =S, SH, $S(C_1$-$C_6$-alkyl), $S(O)C_1$-$C_6$-alkyl, $S(O)_2C_1$-$C_6$-alkyl, $CF_3$, $C_2F_5$, $OCF_3$, $OC_2F_5$, $NH_2$, $NH(C_1$-$C_6$-alkyl), $N(C_1$-$C_6$-alkyl)$_2$, =N—OH, =N—O($C_1$-$C_6$-alkyl), $NO_2$, COOH, $COO(C_1$-$C_6$-alkyl), $CO(C_1$-$C_6$-alkyl), $CONH_2$, $CONH(C_1$-$C_6$-alkyl), $CON(C_1$-$C_6$-alkyl)$_2$, $(C_1$-$C_6$-alkyl)-$S(O)_2$—NH—, $(C_1$-$C_6$-alkyl)-$S(O)_2$—$N(C_1$-$C_6$-alkyl)-, $(C_1$-$C_6$-alkyl)-NH—$(SO)_2$—, $(C_1$-$C_6$-alkyl)$_2$N—$(SO)_2$—, $(C_1$-$C_6$-alkyl)-CO—NH—, $(C_1$-$C_6$-alkyl)-CO—$N(C_1$-$C_6$-alkyl)-, $(C_1$-$C_6$-alkyl)-OCO—NH—, $(C_1$-$C_6$-alkyl)-OCO—$N(C_1$-$C_6$-alkyl)-, $(C_1$-$C_6$-alkyl)-CO—NH—CO—, $(C_1$-$C_6$-alkyl)-CO—$N(C_1$-$C_6$-alkyl)-CO—, $NH_2$—CO—NH—, $(C_1$-$C_6$-alkyl)-NH—CO—NH—, $(C_1$-$C_6$-alkyl)$_2$N—CO—NH—, $NH_2$—CO—$N(C_1$-$C_6$-alkyl)-, $(C_1$-$C_6$-alkyl)-NH—CO—$N(C_1$-$C_6$-alkyl)-, $(C_1$-$C_6$-alkyl)$_2$N—CO—$N(C_1$-$C_6$-alkyl)-, $NH_2$—$S(O)_2$—NH—, $(C_1$-$C_6$-alkyl)-NH—$S(O)_2$—NH—, $(C_1$-$C_6$-alkyl)$_2$N—$S(O)_2$—NH—, $NH_2$—$S(O)_2$—$N(C_1$-$C_6$-alkyl)-, $(C_1$-$C_6$-alkyl)-NH—$S(O)_2$—$N(C_1$-$C_6$-alkyl)-, $(C_1$-$C_6$-alkyl)$_2$N—$S(O)_2$—$N(C_1$-$C_6$-alkyl)-, $C_1$-$C_6$-alkyl, O—$C_1$-$C_6$-alkyl, O-phenyl, phenyl, heterocyclyl, heteroaryl;
   whereas the $C_1$-$C_6$-alkyl, O-phenyl, phenyl, heterocyclyl, heteroaryl in these moieties can optionally be further substituted by one or more substituents selected independently from: F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, NH($C_1$-$C_6$-alkyl), N($C_1$-$C_6$-alkyl)$_2$, NO$_2$, COOH, COO($C_1$-$C_6$-alkyl), CONH$_2$, CONH($C_1$-$C_6$-alkyl), CON($C_1$-$C_6$-alkyl)$_2$, NHC(O)$C_1$-$C_6$-alkyl, or NHC(O)NH$_2$, R$^3$ is selected from the group consisting of H; aryl; cycloalkyl; halogen; alkyl; and heteroaryl, wherein each of the aryl, cycloalkyl, alkyl or heteroaryl can be unsubstituted or optionally substituted with one or more moieties which can be the same or different, each moiety being independently selected from the group consisting of F, Cl, Br, I, OH, CN, N$_3$, =O, O($C_1$-$C_6$-alkyl), =S, SH, S($C_1$-$C_6$-alkyl), S(O)$C_1$-$C_6$-alkyl, S(O)$_2$$C_1$-$C_6$-alkyl, CF$_3$, C$_2$F$_5$, OCF$_3$, OC$_2$F$_5$, NH$_2$, NH($C_1$-$C_6$-alkyl), N($C_1$-$C_6$-alkyl)$_2$, =N—OH, =N—O($C_1$-$C_6$-alkyl), NO$_2$, COOH, COO($C_1$-$C_6$-alkyl), CO($C_1$-$C_6$-alkyl), CONH$_2$, CONH($C_1$-$C_6$-alkyl), CON($C_1$-$C_6$-alkyl)$_2$, ($C_1$-$C_6$-alkyl)-S(O)$_2$—NH—, ($C_1$-$C_6$-alkyl)-S(O)$_2$—N($C_1$-$C_6$-alkyl)-, ($C_1$-$C_6$-alkyl)-NH—(SO)$_2$—, ($C_1$-$C_6$-alkyl)$_2$N—(SO)$_2$—, ($C_1$-$C_6$-alkyl)-CO—NH—, ($C_1$-$C_6$-alkyl)-CO—N($C_1$-$C_6$-alkyl)-, ($C_1$-$C_6$-alkyl)-OCO—NH—, ($C_1$-$C_6$-alkyl)-OCO—N($C_1$-$C_6$-alkyl)-, ($C_1$-$C_6$-alkyl)-CO—NH—CO—, ($C_1$-$C_6$-alkyl)-CO—N($C_1$-$C_6$-alkyl)-CO—, NH$_2$—CO—NH—, ($C_1$-$C_6$-alkyl)-NH—CO—NH—, ($C_1$-$C_6$-alkyl)$_2$N—CO—NH—, NH$_2$—CO—N($C_1$-$C_6$-alkyl)-, ($C_1$-$C_6$-alkyl)-NH—CO—N($C_1$-$C_6$-alkyl)-, ($C_1$-$C_6$-alkyl)$_2$N—CO—N($C_1$-$C_6$-alkyl)-, NH$_2$—S(O)$_2$—NH—, ($C_1$-$C_6$-alkyl)-NH—S(O)$_2$—NH—, ($C_1$-$C_6$-alkyl)$_2$N—S(O)$_2$—NH—, NH$_2$—S(O)$_2$—N($C_1$-$C_6$-alkyl)-, ($C_1$-$C_6$-alkyl)-NH—S(O)$_2$—N($C_1$-$C_6$-alkyl)-, ($C_1$-$C_6$-alkyl)$_2$N—S(O)$_2$—N($C_1$-$C_6$-alkyl)-, $C_1$-$C_6$-alkyl, O—$C_1$-$C_6$-alkyl, O-phenyl, phenyl;

whereas the $C_1$-$C_6$-alkyl, O-phenyl, phenyl in these moieties can optionally be further substituted by one or more substituents selected independently from: alkyl, O-phenyl, phenyl being optionally substituted by F, Cl, Br, $C_1$-$C_6$-alkyl, OH, O—$C_1$-$C_6$-alkyl, SH, SCH$_3$, S(O)$C_1$-$C_6$-alkyl, S(O)$_2$$C_1$-$C_6$-alkyl, CF$_3$, OCF$_3$, NH$_2$, NH($C_1$-$C_6$-alkyl), N($C_1$-$C_6$-alkyl)$_2$, NO$_2$, COOH, COO($C_1$-$C_6$-alkyl), CONH$_2$, CONH($C_1$-$C_6$-alkyl), CON($C_1$-$C_6$-alkyl)$_2$, NHC(O)$C_1$-$C_6$-alkyl, or NHC(O)NH$_2$, R$^2$ and R$^3$ together with the carbon atoms to which they are bound may also form an aliphatic or aromatic ring structure;

R$^4$ is selected from the group consisting of H and $C_1$-$C_6$-alkyl;

R$^5$ is selected from the group consisting of H; $C_1$-$C_6$-alkyl; and aryl;

R$^6$ is selected from the group consisting of H and $C_1$-$C_6$-alkyl;

or R$^5$ and R$^6$ together with the carbon atoms connecting these two substituents may form a cyclopropyl ring, unsubstituted or optionally substituted with alkyl, O-phenyl, phenyl being optionally substituted by F, Cl, Br, $C_1$-$C_6$-alkyl, OH, O—$C_1$-$C_6$-alkyl, SH, SCH$_3$, S(O)$C_1$-$C_6$-alkyl, S(O)$_2$$C_1$-$C_6$-alkyl, CF$_3$, OCF$_3$, NH$_2$, NH($C_1$-$C_6$-alkyl), N($C_1$-$C_6$-alkyl)$_2$, COOH, COO($C_1$-$C_6$-alkyl), CONH$_2$, CONH($C_1$-$C_6$-alkyl), CON($C_1$-$C_6$-alkyl)$_2$, NHC(O)$C_1$-$C_6$-alkyl, or NHC(O)NH$_2$ to a subject in need thereof.

11. A method of treatment of breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia, the method comprising the step of administering the compound according to claim 1 to a subject in need thereof.

12. A pharmaceutical composition comprising at least one compound of formula (1) according to claim 1 and at least one pharmaceutically acceptable auxiliary compound selected from the group consisting of pharmaceutically acceptable carriers, diluents, fillers, preservatives, stabilisers, binders, wetting agents, emulsifiers, buffers.

13. The compound according to claim 1, wherein R$^1$ is selected from $C_6$-$C_{12}$ aryl and heteroaryl having 5 to 12 ring atoms, wherein the aryl or heteroaryl is substituted with two OH groups, and the aryl or heteroaryl may optionally be further substituted by one or more substituents, independently selected from the group consisting of F, Cl, Br, $C_1$-$C_6$ alkyl, O($C_1$-$C_4$ alkyl), phenyl, O-phenyl, NH$_2$, N($C_1$-$C_4$ alkyl)$_2$, NO$_2$, NHCO($C_1$-$C_4$ alkyl), CF$_3$, OCF$_3$, CN, S(O)$_2$$C_1$-$C_6$-alkyl, SO$_2$NH($C_1$-$C_6$-alkyl), SO$_2$N($C_1$-$C_6$-alkyl)$_2$.

14. The compound according to claim 1, wherein R$^1$ is 3,4-dihydroxyphenyl.

* * * * *